US007361491B2

(12) United States Patent
Liu et al.

(10) Patent No.: US 7,361,491 B2
(45) Date of Patent: Apr. 22, 2008

(54) DNA MOLECULES ENCODING HUMAN NHL, A DNA HELICASE

(75) Inventors: Xiaomei Liu, Lansdale, PA (US); Chang Bai, Norristown, PA (US); Michael L. Metzker, Houston, TX (US)

(73) Assignee: Merck & Co., Inc., Rahway, NJ (US)

( * ) Notice: Subject to any disclaimer, the term of this patent is extended or adjusted under 35 U.S.C. 154(b) by 418 days.

(21) Appl. No.: 10/859,792

(22) Filed: Jun. 3, 2004

(65) Prior Publication Data

US 2005/0136425 A1 Jun. 23, 2005

Related U.S. Application Data

(62) Division of application No. 10/148,806, filed as application No. PCT/US00/33065 on Dec. 7, 2000, now Pat. No. 6,762,042.

(60) Provisional application No. 60/196,970, filed on Dec. 9, 1999.

(51) Int. Cl.

| | |
|---|---|
| *C12N 9/10* | (2006.01) |
| *C12N 9/12* | (2006.01) |
| *C12N 9/00* | (2006.01) |

(52) U.S. Cl. ....................... 435/193; 435/183; 435/194

(58) Field of Classification Search ..................... None
See application file for complete search history.

(56) References Cited

U.S. PATENT DOCUMENTS

| | | | |
|---|---|---|---|
| 5,466,576 | A | 11/1995 | Schulz et al. |
| 5,843,737 | A | 12/1998 | Chen et al. |
| 5,888,792 | A | 3/1999 | Bandman et al. |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*

Ngo, Thomas et al. "Computational Complexity, Protein Structure Prediction, and the Levintnal Paradox" in The Protein Folding Problem and Tertiary Structure Prediction, 1994, Merz et al. (ed.), Birkhauser, Boston, MA, pp. 433 and 492-495.

Genbank Accession No. AL080127, Wambutt, R. et al. Direct Submission, (1999).

Genback Accession No. AB029011, Kikuno, R. et al. "Prediction of the coding sequences of unidentified human gene. XIV. The complete sequences of 100 new cDNA clones from brain which code for large protens in vitro", (1999).

Bai, Chang et al. "Overexpression of M68/DcR3 in human gastrointestinal tract tumors independent of gene amplification and its location in a four-gene cluster". PNAS, vol. 97, No. 3, Feb. 1, 2000, pp. 1230-1235.

Zhou, J.-Q. et al. "Piflp Helicase, a Catalytic Inhibitor of Telomerase in Yeast". Science, vol. 289, Aug. 4, 2000, pp. 771-774.

Naumovski, Louie et al. "RAD3 Gene of *Saccharomyces cerevisiae*: Nucleotide Sequence of Wild-Type and Mutant Alleles, Transcript Mapping, and Aspects of Gene Regulation". Molecular and Cellular Biology, Jan. 1985, pp. 17-26.

Reynolds, Paul et al. "The nucleotide sequence of the RAD3 gene of *Saccharomyces cerevisia*: a potential adenine nucleotide binding amino acid sequence and a nonessential acidic carboxyl terminal region". Nucleic Acid Research, vol. 13, No. 7, 1985, pp. 2357-2372.

Weber, Christine A. et al. "ERCC2: cDNA cloning and molecular characterization of a human nucleotide excision repair gene with high homology to yeast RAD3", The EMBO Journal, vol. 9, No. 5, 1990, pp. 1437-1447.

Tuteja, Narendra et al. "Inhibition of DN Unwinding and ATPase Activities of Human DNA Helicase II by Chemotherapeutic Agents", Biochemical and Biophysical Research COMM., vol. 236, 1997, pp. 636-640.

Lun, Lapman et al. "Antihelicase action of CI-958, a new drug for prostate cancer". Cancer Chemother Pharmacol, vol. 42, 1998, pp. 447-453.

* cited by examiner

*Primary Examiner*—Richard Hutson
(74) *Attorney, Agent, or Firm*—Vineet Kohli; David A. Muthard

(57) ABSTRACT

The present invention disclosed isolated nucleic acid molecules (polynucleotides) which encode NHL, a putative DNA helicase. The present invention in turn relates to recombinant vectors and recombinant hosts which contain a DNA fragment encoding NHL, substantially purified forms of associated NHL, associated mutant proteins, and methods associated with identifying compounds which modulate NHL, which will be useful in the treatment of various neoplastic disorders. Both a genomic clone containing regulatory and intron sequences, as well as the exon structure and open reading frame of human NHL are disclosed.

2 Claims, 12 Drawing Sheets

AGTCAGCCCT GCTGCCAGCC AGTGCCGGGT GCTGGGGACT CAGGGAGGCC CGCCGGGACC ACTGCGGGAC
AGTGAGCCGA GCAGAAGCTG GAACGCAGGA GAGGAAGGAG AGGGGGCGGT CAGGGCTCTC AGGAGCCGGG
TCCTGGGCAA GGCGCAGCCG TTTTCAAATT TTCAGGAAAG CGGTCGGCTC ACACTCGAGC AGTAAAAAGA
TGCCTCTGGG GAGGAGGCCC GTGCAGCTCT CCGGGCAATG GTGGTGGCTC GGCCTAGAGA GGCGGTAGTG
GAACGCAGAC CCTGGTGGGG GAATGACATC AAGGGAGGAG ACGGGCGGGA CCCCAGATTT CTGCCTGTGG
GCGATGGAAG TGAGGTTCAC TGGCCAGCGG AGCCGGACAC AGAACGCGCA AAACGCCGTG TAGGCCTGGA
GGAGCCGAAG AGCAGGCGGA CCCCCTCCGC GGGGGAACAG TTTCCGCCGG GAGCACAAAG CAACGGACCG
GAAGTGGGGG GCGGAAGTGC AGTGGGCTCA GCGCCGACTG CGCGCCTCTG CCCGCGAAAA CTCTGAGCTG
GCTGACAGCT GGGGACGGGT GGCGGCCCTC GACTGGAGTC GGTTGAGTTC CTGAGGGACC CCGGTTCTGG
AAGGTTCGCC GCGGAGACAA GTGAGCAGTC TGTGCCATAG GGATTCTCGA AGAGAACAGC GTTGTGTCCC
AGTGCACATG CTCGCATCGC TTACCAGGAG TGCCCGAGAC CCTAAGATGT TCGGAGTGGT TTTTTCGCAC
AGACCCGAAT AGCCTGCCCC TCAGCCACGC TCTGTGCCCT TCTGAGAACA GGCTGATATG CCCAAGATAG
TCCTGAATGG TGTGACCGTA GACTTCCCTT TCCAGCCCTA CAAATGCCAA CAGGAGTACA TGACCAAGGT
CCTGGAATGT CTGCAGCAGA AGGTGAATGG CATCCTGGAG AGCCCTACGG GTACAGGGAA GACGCTGTGC
CTGCTGTGCA CCACGCTGGC CTGGCGAGAA CACCTCCGAG ACGGCATCTC TGCCCGCAAG ATTGCCGAGA
GGGCGCAAGG AGAGCTTTTC CCGGATCGGG CCTTGTCATC CTGGGGCAAC GCTGCTGCTG CTGCTGGAGA
CCCCATAGCT TGCTACACGG ACATCCCAAA GATTATTTAC GCCTCCAGGA CCCACTCGCA ACTCACACAG
GTCATCAACG AGCTTCGGAA CACCTCCTAC CGGCCTAAGG TGTGTGTGCT GGGCTCCCGG GAGCAGCTGT
GCATCCATCC TGAGGTGAAG AAACAAGAGA GTAACCATCT ACAGATCCAC TTGTGCCGTA AGAAGGTGGC
AAGTCGCTCC TGTCATTTCT ACAACAACGT AGAAGAAAAA AGCCTGGAGC AGGAGCTGGC CAGCCCCATC
CTGGACATTG AGGACTTGGT CAAGAGCGGA AGCAAGCACA GGGTGTGCCC TTACTACCTG TCCCGGAACC
TGAAGCAGCA AGCCGACATC ATATTCATGC CGTACAATTA CTTGTTGGAT GCCAAGAGCC GCAGAGCACA
CAACATTGAC CTGAAGGGGA CAGTCGTGAT CTTTGACGAA GCTCACAACG TGGAGAAGAT GTGTGAAGAA
TCGGCATCCT TTGACCTGAC TCCCCATGAC CTGGCTTCAG GACTGGACGT CATAGACCAG GTGCTGGAGG
AGCAGACCAA GGCAGCGCAG CAGGGTGAGC CCCACCCGGA GTTCAGCGCG GACTCCCCCA GCCCAGGGCT
GAACATGGAG CTGGAAGACA TTGCAAAGCT GAAGATGATC CTGCTGCGCC TGGAGGGGGC CATCGATGCT
GTTGAGCTGC CTGGAGACGA CAGCGGTGTC ACCAAGCCAG GGAGCTACAT CTTTGAGCTG TTTGCTGAAG
CCCAGATCAC GTTTCAGACC AAGGGCTGCA TCCTGGACTC GCTGGACCAG ATCATCCAGC ACCTGGCAGG
ACGTGCTGGA GTGTTCACCA ACACGGCCGG ACTGCAGAAG CTGGCGGACA TTATCCAGAT TGTGTTCAGT
GTGGACCCCT CCGAGGGCAG CCCTGGTTCC CCAGCAGGGC TGGGGGCCTT ACAGTCCTAT AAGGTGCACA
TCCATCCTGA TGCTGGTCAC CGGAGGACGG CTCAGCGGTC TGATGCCTGG AGCACCACTG CAGCCAGAAA
GCGAGGGAAG GTGCTGAGCT ACTGGTGCTT CAGTCCCGGC CACAGCATGC ACGAGCTGGT CCGCCAGGGC
GTCCGCTCCC TCATCCTTAC CAGCGGCACG CTGGCCCCGG TGTCCTCCTT TGCTCTGGAG ATGCAGATCC
CTTTCCCAGT CTGCCTGGAG AACCCACACA TCATCGACAA GCACCAGATC TGGGTGGGGG TCGTCCCCAG
AGGCCCCGAT GGAGCCCAGT TGAGCTCCGC GTTTGACAGA CGGTTTTCCG AGGAGTGCTT ATCCTCCCTG
GGGAAGGCTC TGGGCAACAT CGCCCGCGTG GTGCCCTATG GGCTCCTGAT CTTCTTCCCT TCCTATCCTG
TCATGGAGAA GAGCCTGGAG TTCTGGCGGG CCCGCGACTT GGCCAGGAAG ATGGAGGCGC TGAAGCCGCT
GTTTGTGGAG CCCAGGAGCA AAGGCAGCTT CTCCGAGACC ATCAGTGCTT ACTATGCAAG GGTTGCCGCC
CCTGGGTCCA CCGGCGCCAC CTTCCTGGCG GTCTGCCGGG GCAAGGCCAG CGAGGGGCTG GACTTCTCAG
ACACGAATGG CCGTGGTGTG ATTGTCACGG GCCTCCCGTA CCCCCCACGC ATGGACCCCC GGGTTGTCCT
CAAGATGCAG TTCCTGGATG AGATGAAGGG CCAGGGTGGG GCTGGGGGCC AGTTCCTCTC TGGGCAGGAG
TGGTACCGGC AGCAGGCGTC CAGGGCTGTG AACCAGGCCA TCGGGCGAGT GATCCGGCAC CGCCAGGACT
ACGGAGCTGT CTTCCTCTGT GACCACAGGT TCGCCTTTGC CGACGCAAGA GCCCAACTGC CCTCCTGGGT
GCGTCCCCAC GTCAGGGTGT ATGACAACTT TGGCCATGTC ATCCGAGACG TGGCCCAGTT CTTCCGTGTT
GCCGAGCGAA CTATGCCAGC GCCGGCCCCC CGGGCTACAG CACCCAGTGT GCGTGGAGAA GATGCTGTCA
GCGAGGCCAA GTCGCCTGGC CCCTTCTTCT CCACCAGGAA AGCTAAGAGT CTGGACCTGC ATGTCCCCAG
CCTGAAGCAG AGGTCCTCAG GGTCACCAGC TGCCGGGGAC CCCGAGAGTA GCCTGTGTGT GGAGTATGAG
CAGGAGCCAG TTCCTGCCCG GCAGAGGCCC AGGGGGCTGC TGGCCGCCCT GGAGCACAGC GAACAGCGGG

FIG. 1A

CGGGGAGCCC TGGCGAGGAG CAGGCCCACA GCTGCTCCAC CCTGTCCCTC CTGTCTGAGA
AGAGGCCGGC AGAAGAACCG CGAGGAGGGA GGAAGAAGAT CCGGCTGGTC AGCCACCCGG
AGGAGCCCGT GGCTGGTGCA CAGACGGACA GGGCCAAGCT CTTCATGGTG GCCGTGAAGC
AGGAGTTGAG CCAAGCCAAC TTTGCCACCT TCACCCAGGC CCTGCAGGAC TACAAGGGTT
CCGATGACTT CGCCGCCCTG GCCGCCTGTC TCGGCCCCCT CTTTGCTGAG GACCCCAAGA
AGCACAACCT GCTCCAAGGC TTCTACCAGT TTGTGCGGCC CCACCATAAG CAGCAGTTTG
AGGAGGTCTG TATCCAGCTG ACAGGACGAG GCTGTGGCTA TCGGCCTGAG CACAGCATTC
CCCGAAGGCA GCGGGCACAG CCGGTCCTGG ACCCCACTGG AAGAACGGCG CCGGATCCCA
AGCTGACCGT GTCCACGGCT GCAGCCCAGC AGCTGGACCC CCAAGAGCAC CTGAACCAGG
GCAGGCCCCA CCTGTCGCCC AGGCCACCCC CAACAGGAGA CCCTGGCAGC CAACCACAGT
GGGGGTCTGG AGTGCCCAGA GCAGGGAAGC AGGGCCAGCA CGCCGTGAGC GCCTACCTGG
CTGATGCCCG CAGGGCCCTG GGGTCCGCGG GCTGTAGCCA ACTCTTGGCA GCGCTGACAG
CCTATAAGCA AGACGACGAC CTCGACAAGG TGCTGGCTGT GTTGGCCGCC CTGACCACTG
CAAAGCCAGA GGACTTCCCC CTGCTGCACA GGTTCAGCAT GTTTGTGCGT CCACACCACA
AGCAGCGCTT CTCACAGACG TGCACAGACC TGACCGGCCG GCCCTACCCG GGCATGGAGC
CACCGGGACC CCAGGAGGAG AGGCTTGCCG TGCCTCCTGT GCTTACCCAC AGGGCTCCCC
AACCAGGCCC CTCACGGTCC GAGAAGACCG GGAAGACCCA GAGCAAGATC TCGTCCTTCC
TTAGACAGAG GCCAGCAGGG ACTGTGGGGG CGGGCGGTGA GGATGCAGGT CCCAGCCAGT
CCTCAGGACC TCCCCACGGG CCTGCAGCAT CTGAGTGGGG CCTCTAGGAT GTGCCCAGCC
TGCCACACCG CCTCCAGGAA GCAGAGCGTC ATGCAGGTCT TCTGGCCAGA GCCCCAGTGA
GTGCCCACGG AGGCCCCCAG CACACCCAAC GTGGCTTGAT CACCTGCCTG TCCAGCTCTG
GTGGGCCAAG AACCCACCCA ACAGAATAGG CCAGCCCATG CCAGCCGGCT TGGCCCGCTG
CAGGCCTCAG GCAGGCGGGG CCCATGGTTG GTCCCTGCGG TGGGACCGGA TCTGGGCCTG
CCTCTGAGAA GCCCTGAGCT ACCTTGGGGT CTGGGGTGGG TTTCTGGGAA AGTGCTTCCC
CAGAACTTCC CTGGCTCCTG GCCTGTGAGT GGTGCCACAG GGGCACCCCA GCTGAGCCCC
TCACCGGGAA GGAGGAGACC CCCGTGGGCA CGTGTCCACT TTTAATCAGG GGACAGGGCT
CTCTAATAAA GCTGCTGGCA GTGCCC (SEQ ID NO:1).

FIG. 1B

MPKIVLNGVT VDFPFQPYKC QQEYMTKVLE CLQQKVNGIL ESPTGTGKTL CLLCTTLAWR
EHLRDGISAR KIAERAQGEL FPDRALSSWG NAAAAAGDPI ACYTDIPKII YASRTHSQLT
QVINELRNTS YRPKVCVLGS REQLCIHPEV KKQESNHLQI HLCRKKVASR SCHFYNNVEE
KSLEQELASP ILDIEDLVKS GSKHRVCPYY LSRNLKQQAD IIFMPYNYLL DAKSRRAHNI
DLKGTVVIFD EAHNVEKMCE ESASFDLTPH DLASGLDVID QVLEEQTKAA QQGEPHPEFS
ADSPSPGLNM ELEDIAKLKM ILLRLEGAID AVELPGDDSG VTKPGSYIFE LFAEAQITFQ
TKGCILDSLD QIIQHLAGRA GVFTNTAGLQ KLADIIQIVF SVDPSEGSPG SPAGLGALQS
YKVHIHPDAG HRRTAQRSDA WSTTAARKRG KVLSYWCFSP GHSMHELVRQ GVRSLILTSG
TLAPVSSFAL EMQIPFPVCL ENPHIIDKHQ IWVGVVPRGP DGAQLSSAFD RRFSEECLSS
LGKALGNIAR VVPYGLLIFF PSYPVMEKSL EFWRARDLAR KMEALKPLFV EPRSKGSFSE
TISAYYARVA APGSTGATFL AVCRGKASEG LDFSDTNGRG VIVTGLPYPP RMDPRVVLKM
QFLDEMKGQG GAGGQFLSGQ EWYRQQASRA VNQAIGRVIR HRQDYGAVFL CDHRFAFADA
RAQLPSWVRP HVRVYDNFGH VIRDVAQFFR VAERTMPAPA PRATAPSVRG EDAVSEAKSP
GPFFSTRKAK SLDLHVPSLK QRSSGSPAAG DPESSLCVEY EQEPVPARQR PRGLLAALEH
SEQRAGSPGE EQAHSCSTLS LLSEKRPAEE PRGGRKKIRL VSHPEEPVAG AQTDRAKLFM
VAVKQELSQA NFATFTQALQ DYKGSDDFAA LAACLGPLFA EDPKKHNLLQ GFYQFVRPHH
KQQFEEVCIQ LTGRGCGYRP EHSIPRRQRA QPVLDPTGRT APDPKLTVST AAAQQLDPQE
HLNQGRPHLS PRPPPTGDPG SQPQWGSGVP RAGKQGQHAV SAYLADARRA LGSAGCSQLL
AALTAYKQDD DLDKVLAVLA ALTTAKPEDF PLLHRFSMFV RPHHKQRFSQ TCTDLTGRPY
PGMEPPGPQE ERLAVPPVLT HRAPQPGPSR SEKTGKTQSK ISSFLRQRPA GTVGAGGEDA
GPSQSSGPPH GPAASEWGL* (SEQ ID NO:2).

FIG.2

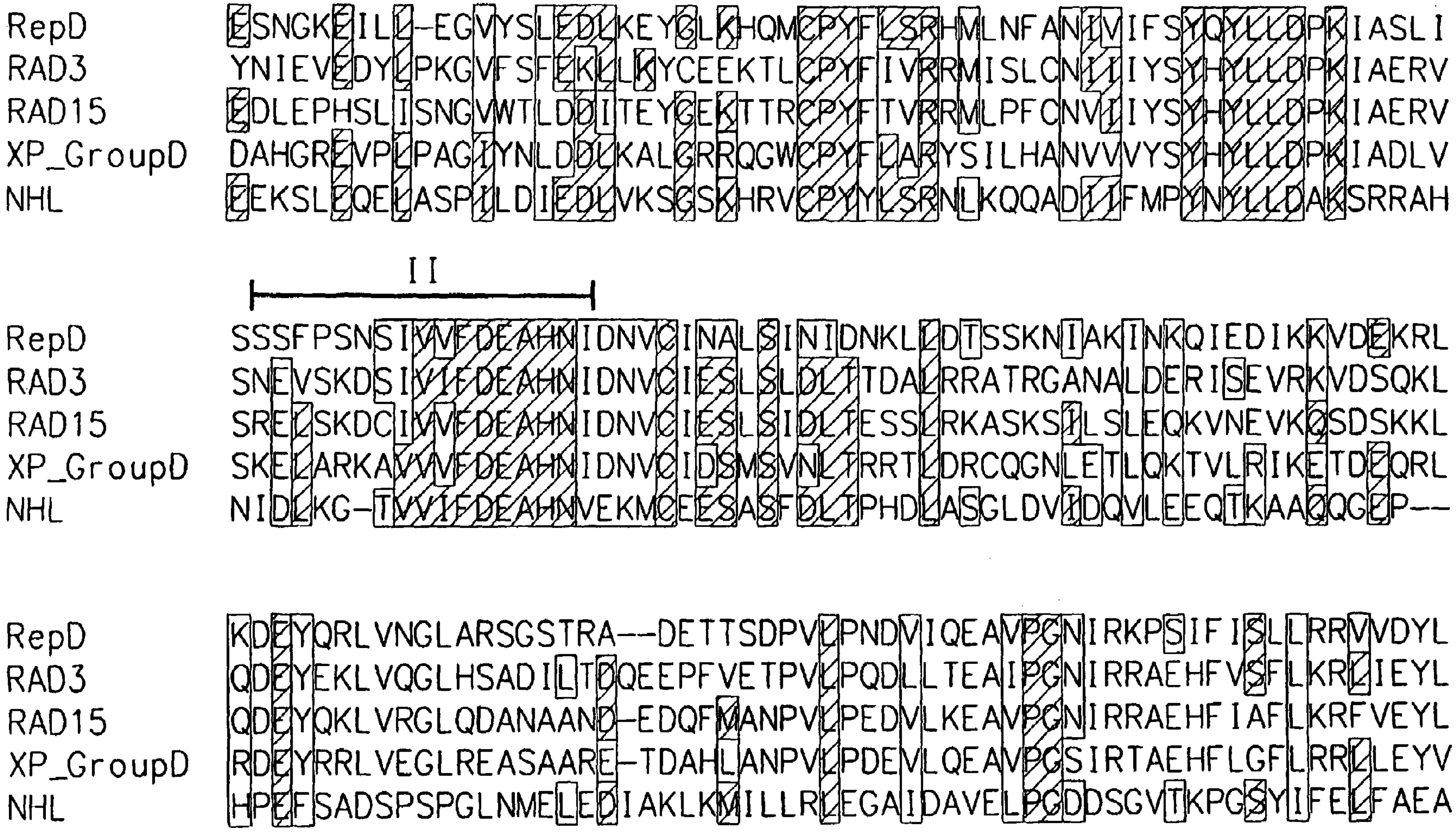

FIG. 3B

```
RepD    ESNGKEIL-EGVYSLEDLKEYQLSRHMLNFANIFSYQLLDPKIASLI
RAD3    YNIEVEDYFPKGVFSFEKLLKYCEEKTLQPYFIVRMISLCNIYSHLLDPKIAERV
RAD15   DLEPHSLISNGVWTLDQITEYGEKTTRCPYFTVRMLPFCNVLIYSHLLDPKIAERV
XP_GroupD DAHGREVPLPAGIYNLDQKALGRRQGWCPYFLARYSILHANVVYSHLLDPKIADLV
NHL     EKSLQEIASPILDIEDLVKSGSKHRVCPYMYSRNLKQQADLFMPINLLDAKSRRAH

                                 II
RepD    SSSFPSNSIWFDEAHKIDNVQINALSINIDNKLDISSKNIAKINKQIEDIKKVDEKRL
RAD3    SNEVSKDSIWFDEAHKIDNVQIESLSLDLTDALRRATRGANALDERISEVRKVDSQKL
RAD15   SREISKDCIWFDEAHKIDNVQIESLSIDLFESSIRKASKSILSLEQKVNEVKQSDSKKL
XP_GroupD SKELARKAVWFDEAHKIDNVQIDSMSVNLRRTLDRCQGNLETLQKTVLRIKETDEQRL
NHL     NIDLKG-TVVIFDEAHKVEKMQEESASFDLTPHDLASGLDVIDQVLEEQIKAAQGEP--

RepD    KDEYQRLVNGLARSGSTRA--DETTSDPVQPNDVIQEAVPGNIRKPSIFISLLRRMVDYL
RAD3    QDEYEKLVQGLHSADILTQEEPFVETPVLPQDLLTEAIPGNIRRAEHFVSFLKRLIEYL
RAD15   QDEYQKLVRGLQDANAAND-EDQFMANPVLPEDVLKEAVPGNIRRAEHFIAFLKRFVEYL
XP_GroupD RDEYRRLVEGLREASAARE--TDAHLANPVLPDEVLQEAVPGSIRTAEHFLGFLRRLLEYV
NHL     HPEFSADSPSPGLNMELEDIAKLKMILLREGAIDAVELPCDDSGVIKPGSYIFELFAEA

```

```
REPD       KSRLKSQMLLSESPLAFLQGLY--HATQISSRTLRFCSSRLSSLLRTLRINDVNQFSG-I
RAD3       KTRMKVLHVISETPKSFLQHLK--QLTFIERKPLRFCSERLSLLVRTLEVTEVEDFTA-L
RAD15      KTRMKVLHVIAETPTSFLQHVK--DITFIDKKPLRFCAERLTSLVRALQISLVEDFHS-L
XP_GroupD  KWRLRVQHVVQESPPAFLSGLA--QRVCIQRKPLRFCAERLRSLLHTLEITDLADFSP-L
NHL        QITFQTKGCILDSLDQIIQHLAGRAGVFTNTAGLQKLADIIQIVFSVDPSEGSPGSPAGL

REPD       SLIADFATLVGTYN--NGFLIIIEPYYQRQNNTYDQIFQFCCLDASIGMKPIFDK-YRSV
RAD3       KDIATFATLISTYE--EGFLLIIEPYEIENAAVPNPIMRFTCLDASIAIKPVFER-FSSV
RAD15      QQVVAFATLVATYE--RGFILILEPFETENATVPNPILRFSCLDASIAIKPVFER-FRSV
XP_GroupD  TLLANFATLVSTYA--KGFTIIIEPFDDRTPTIANPILHFSCMDASLAIKPVFER-FQSV
NHL        GALQSYKVHIHPDAGHRRTAQRSDAWSTTAARKRGKVLSYWCFSPGHSMHELVRQGVRSL

                III
REPD       VITSGTLSPLDIYTKMLNFRPTVVERLTMSLNRNCICPCILTRGSDQISISTKFDVRSDT
RAD3       IITSGTISPLDMYPRMLNFKTVLQKSYAMTLAKKSFLPMIITKGSDQVAISSRFEIRNDP
RAD15      IITSGTLSPLDMYPKMLQFNTVMQESYGMSLARNCFLPMVVTRGSDQVAISSKFEARNDP
XP_GroupD  IITSGTLSPLDIYPKILDFHPVTMATFTMTLARVCLCPMIIGRGNDQVAISSKFETREDI
NHL        ILTSGTLAPVSSFALEMQIPFPVCLENPHIIDKHQIWVGVVPRGPDGAQLSSAFDRRFSE
```

FIG. 3C

```
REPD        NRLDKRNKLPQWILQFC-QPQHLNLSTDMAISLSKTFLREMGQPFSREEQLGKSLWSLEH
RAD3        SR--KRSQLPKWIAQGL-SDADLNLSTDMAISNTKQFLRTMAQPTDPKDQEGVSVWSYED
RAD15       GRSDKRTKLPKWIQQYI-TEGATNLSTDMSLALAKKFLRTMAQPFTASDQEGISWWSLDD
XP_GroupD   ARGDKRGKLPRWIQEHL-TDANLNLTVDEGVQVAKYFLRQMAQPFHREDQLGLSLLSLEQ
NHL         AFADARAQLPSWVRPHVRVYDNFGHVIRDVAQFFRVAERTMPAPAPRATAPSVRGEDAVS

REPD        VEKQSTSKPPQQQNSAINSTITTSTTTTTTTSTISETHLT (SEQ ID NO:35)
RAD3        LIKHQNS--RKDQGGFIENENKEGEQDEDEDEDIEMQ (SEQ ID NO:36)
RAD15       LLIHQK---KALKSAAIEQSKHEDEMDIDVVET (SEQ ID NO:37)
XP_GroupD   LESEETL--KRIEQIAQQL (SEQ ID NO:38)
NHL         EAKSPGPFFSTRKAKSLDLHVPSLKQRSSGSPAAGDPESSLCVEYEQEPVPARQRPRGLL
```

FIG. 3E

```
NHL    AALEHSEQRAGSPGEEQAHSCSTLSLLSEKRPAEEPRGGRKKIRLVSHPEEPVAGAQTDR
NHL    AKLFMVAVKQELSQANFATFTQALQDYKGSDDFAALAACLGPLFAEDPKKHNLLQGFYQF
NHL    VRPHHKQQFEEVCIQLTGRGCGYRPEHSIPRRQRAQPVLDPTGRTAPDPKLTVSTAAAQQ
NHL    LDPQEHLNQGRPHLSPRPPPTGDPGSQPQWGSGVPRAGKQGQHAVSAYLADARRALGSAG
NHL    CSQLLAALTAYKQDDDLDKVLAVLAALTTAKPEDFPLLHRFSMFVRPHHKQRFSQTCTDL
NHL    TGRPYPGMEPPGPQEERLAVPPVLTHRAPQPGPSRSEKTGKTQSKISSFLRQRPAGTVGA
NHL    GGEDAGPSQSSGPPHGPAASEWGL (SEQ ID NO:2)
```

FIG. 3F

SEQUENCE LISTING

```
<160> NUMBER OF SEQ ID NOS: 38

<210> SEQ ID NO 1
<211> LENGTH: 4946
<212> TYPE: DNA
<213> ORGANISM: Homo sapien
<220> FEATURE:
<221> NAME/KEY: CDS
<222> LOCATION: (828)...(4487)

<400> SEQUENCE: 1

agtcagccct gctgccagcc agtgccgggt gctggggact cagggaggcc cgccgggacc      60

actgcgggac agtgagccga gcagaagctg gaacgcagga gaggaaggag agggggcggt     120

cagggctctc aggagccggg tcctgggcaa ggcgcagccg ttttcaaatt ttcaggaaag     180

cggtcggctc acactcgagc agtaaaaaga tgcctctggg gaggaggccc gtgcagctct     240

ccgggcaatg gtggtggctc ggcctagaga ggcggtagtg gaacgcagac cctggtgggg     300

gaatgacatc aagggaggag acgggcggga ccccagattt ctgcctgtgg gcgatggaag     360

tgaggttcac tggccagcgg agccggacac agaacgcgca aaacgccgtg taggcctgga     420

ggagccgaag agcaggcgga ccccctccgc gggggaacag tttccgccgg gagcacaaag     480

caacggaccg gaagtggggg gcggaagtgc agtgggctca gcgccgactg cgcgcctctg     540

cccgcgaaaa ctctgagctg gctgacagct ggggacgggt ggcggccctc gactggagtc     600

ggttgagttc ctgagggacc ccggttctgg aaggttcgcc gcggagacaa gtgagcagtc     660

tgtgccatag ggattctcga agagaacagc gttgtgtccc agtgcacatg ctcgcatcgc     720

ttaccaggag tgcccgagac cctaagatgt tcggagtggt tttttcgcac agacccgaat     780

agcctgcccc tcagccacgc tctgtgccct tctgagaaca ggctgat atg ccc aag       836
                                                    Met Pro Lys
                                                     1

ata gtc ctg aat ggt gtg acc gta gac ttc cct ttc cag ccc tac aaa       884
Ile Val Leu Asn Gly Val Thr Val Asp Phe Pro Phe Gln Pro Tyr Lys
     5                  10                  15

tgc caa cag gag tac atg acc aag gtc ctg gaa tgt ctg cag cag aag       932
Cys Gln Gln Glu Tyr Met Thr Lys Val Leu Glu Cys Leu Gln Gln Lys
 20                  25                  30                  35

gtg aat ggc atc ctg gag agc cct acg ggt aca ggg aag acg ctg tgc       980
Val Asn Gly Ile Leu Glu Ser Pro Thr Gly Thr Gly Lys Thr Leu Cys
                40                  45                  50

ctg ctg tgc acc acg ctg gcc tgg cga gaa cac ctc cga gac ggc atc      1028
Leu Leu Cys Thr Thr Leu Ala Trp Arg Glu His Leu Arg Asp Gly Ile
            55                  60                  65

tct gcc cgc aag att gcc gag agg gcg caa gga gag ctt ttc ccg gat      1076
Ser Ala Arg Lys Ile Ala Glu Arg Ala Gln Gly Glu Leu Phe Pro Asp
        70                  75                  80

cgg gcc ttg tca tcc tgg ggc aac gct gct gct gct gct gga gac ccc      1124
Arg Ala Leu Ser Ser Trp Gly Asn Ala Ala Ala Ala Ala Gly Asp Pro
     85                  90                  95

ata gct tgc tac acg gac atc cca aag att att tac gcc tcc agg acc      1172
Ile Ala Cys Tyr Thr Asp Ile Pro Lys Ile Ile Tyr Ala Ser Arg Thr
100                 105                 110                 115
```

-continued

```
cac tcg caa ctc aca cag gtc atc aac gag ctt cgg aac acc tcc tac      1220
His Ser Gln Leu Thr Gln Val Ile Asn Glu Leu Arg Asn Thr Ser Tyr
                120                 125                 130

cgg cct aag gtg tgt gtg ctg ggc tcc cgg gag cag ctg tgc atc cat      1268
Arg Pro Lys Val Cys Val Leu Gly Ser Arg Glu Gln Leu Cys Ile His
            135                 140                 145

cct gag gtg aag aaa caa gag agt aac cat cta cag atc cac ttg tgc      1316
Pro Glu Val Lys Lys Gln Glu Ser Asn His Leu Gln Ile His Leu Cys
        150                 155                 160

cgt aag aag gtg gca agt cgc tcc tgt cat ttc tac aac aac gta gaa      1364
Arg Lys Lys Val Ala Ser Arg Ser Cys His Phe Tyr Asn Asn Val Glu
    165                 170                 175

gaa aaa agc ctg gag cag gag ctg gcc agc ccc atc ctg gac att gag      1412
Glu Lys Ser Leu Glu Gln Glu Leu Ala Ser Pro Ile Leu Asp Ile Glu
180                 185                 190                 195

gac ttg gtc aag agc gga agc aag cac agg gtg tgc cct tac tac ctg      1460
Asp Leu Val Lys Ser Gly Ser Lys His Arg Val Cys Pro Tyr Tyr Leu
                200                 205                 210

tcc cgg aac ctg aag cag caa gcc gac atc ata ttc atg ccg tac aat      1508
Ser Arg Asn Leu Lys Gln Gln Ala Asp Ile Ile Phe Met Pro Tyr Asn
            215                 220                 225

tac ttg ttg gat gcc aag agc cgc aga gca cac aac att gac ctg aag      1556
Tyr Leu Leu Asp Ala Lys Ser Arg Arg Ala His Asn Ile Asp Leu Lys
        230                 235                 240

ggg aca gtc gtg atc ttt gac gaa gct cac aac gtg gag aag atg tgt      1604
Gly Thr Val Val Ile Phe Asp Glu Ala His Asn Val Glu Lys Met Cys
    245                 250                 255

gaa gaa tcg gca tcc ttt gac ctg act ccc cat gac ctg gct tca gga      1652
Glu Glu Ser Ala Ser Phe Asp Leu Thr Pro His Asp Leu Ala Ser Gly
260                 265                 270                 275

ctg gac gtc ata gac cag gtg ctg gag gag cag acc aag gca gcg cag      1700
Leu Asp Val Ile Asp Gln Val Leu Glu Glu Gln Thr Lys Ala Ala Gln
                280                 285                 290

cag ggt gag ccc cac ccg gag ttc agc gcg gac tcc ccc agc cca ggg      1748
Gln Gly Glu Pro His Pro Glu Phe Ser Ala Asp Ser Pro Ser Pro Gly
            295                 300                 305

ctg aac atg gag ctg gaa gac att gca aag ctg aag atg atc ctg ctg      1796
Leu Asn Met Glu Leu Glu Asp Ile Ala Lys Leu Lys Met Ile Leu Leu
        310                 315                 320

cgc ctg gag ggg gcc atc gat gct gtt gag ctg cct gga gac gac agc      1844
Arg Leu Glu Gly Ala Ile Asp Ala Val Glu Leu Pro Gly Asp Asp Ser
    325                 330                 335

ggt gtc acc aag cca ggg agc tac atc ttt gag ctg ttt gct gaa gcc      1892
Gly Val Thr Lys Pro Gly Ser Tyr Ile Phe Glu Leu Phe Ala Glu Ala
340                 345                 350                 355

cag atc acg ttt cag acc aag ggc tgc atc ctg gac tcg ctg gac cag      1940
Gln Ile Thr Phe Gln Thr Lys Gly Cys Ile Leu Asp Ser Leu Asp Gln
                360                 365                 370

atc atc cag cac ctg gca gga cgt gct gga gtg ttc acc aac acg gcc      1988
Ile Ile Gln His Leu Ala Gly Arg Ala Gly Val Phe Thr Asn Thr Ala
            375                 380                 385

gga ctg cag aag ctg gcg gac att atc cag att gtg ttc agt gtg gac      2036
Gly Leu Gln Lys Leu Ala Asp Ile Ile Gln Ile Val Phe Ser Val Asp
        390                 395                 400

ccc tcc gag ggc agc cct ggt tcc cca gca ggg ctg ggg gcc tta cag      2084
Pro Ser Glu Gly Ser Pro Gly Ser Pro Ala Gly Leu Gly Ala Leu Gln
    405                 410                 415

tcc tat aag gtg cac atc cat cct gat gct ggt cac cgg agg acg gct      2132
Ser Tyr Lys Val His Ile His Pro Asp Ala Gly His Arg Arg Thr Ala
420                 425                 430                 435
```

-continued

```
cag cgg tct gat gcc tgg agc acc act gca gcc aga aag cga ggg aag      2180
Gln Arg Ser Asp Ala Trp Ser Thr Thr Ala Ala Arg Lys Arg Gly Lys
            440                 445                 450

gtg ctg agc tac tgg tgc ttc agt ccc ggc cac agc atg cac gag ctg      2228
Val Leu Ser Tyr Trp Cys Phe Ser Pro Gly His Ser Met His Glu Leu
        455                 460                 465

gtc cgc cag ggc gtc cgc tcc ctc atc ctt acc agc ggc acg ctg gcc      2276
Val Arg Gln Gly Val Arg Ser Leu Ile Leu Thr Ser Gly Thr Leu Ala
    470                 475                 480

ccg gtg tcc tcc ttt gct ctg gag atg cag atc cct ttc cca gtc tgc      2324
Pro Val Ser Ser Phe Ala Leu Glu Met Gln Ile Pro Phe Pro Val Cys
485                 490                 495

ctg gag aac cca cac atc atc gac aag cac cag atc tgg gtg ggg gtc      2372
Leu Glu Asn Pro His Ile Ile Asp Lys His Gln Ile Trp Val Gly Val
500                 505                 510                 515

gtc ccc aga ggc ccc gat gga gcc cag ttg agc tcc gcg ttt gac aga      2420
Val Pro Arg Gly Pro Asp Gly Ala Gln Leu Ser Ser Ala Phe Asp Arg
            520                 525                 530

cgg ttt tcc gag gag tgc tta tcc tcc ctg ggg aag gct ctg ggc aac      2468
Arg Phe Ser Glu Glu Cys Leu Ser Ser Leu Gly Lys Ala Leu Gly Asn
        535                 540                 545

atc gcc cgc gtg gtg ccc tat ggg ctc ctg atc ttc ttc cct tcc tat      2516
Ile Ala Arg Val Val Pro Tyr Gly Leu Leu Ile Phe Phe Pro Ser Tyr
    550                 555                 560

cct gtc atg gag aag agc ctg gag ttc tgg cgg gcc cgc gac ttg gcc      2564
Pro Val Met Glu Lys Ser Leu Glu Phe Trp Arg Ala Arg Asp Leu Ala
565                 570                 575

agg aag atg gag gcg ctg aag ccg ctg ttt gtg gag ccc agg agc aaa      2612
Arg Lys Met Glu Ala Leu Lys Pro Leu Phe Val Glu Pro Arg Ser Lys
580                 585                 590                 595

ggc agc ttc tcc gag acc atc agt gct tac tat gca agg gtt gcc gcc      2660
Gly Ser Phe Ser Glu Thr Ile Ser Ala Tyr Tyr Ala Arg Val Ala Ala
            600                 605                 610

cct ggg tcc acc ggc gcc acc ttc ctg gcg gtc tgc cgg ggc aag gcc      2708
Pro Gly Ser Thr Gly Ala Thr Phe Leu Ala Val Cys Arg Gly Lys Ala
        615                 620                 625

agc gag ggg ctg gac ttc tca gac acg aat ggc cgt ggt gtg att gtc      2756
Ser Glu Gly Leu Asp Phe Ser Asp Thr Asn Gly Arg Gly Val Ile Val
    630                 635                 640

acg ggc ctc ccg tac ccc cca cgc atg gac ccc cgg gtt gtc ctc aag      2804
Thr Gly Leu Pro Tyr Pro Pro Arg Met Asp Pro Arg Val Val Leu Lys
645                 650                 655

atg cag ttc ctg gat gag atg aag ggc cag ggt ggg gct ggg ggc cag      2852
Met Gln Phe Leu Asp Glu Met Lys Gly Gln Gly Gly Ala Gly Gly Gln
660                 665                 670                 675

ttc ctc tct ggg cag gag tgg tac cgg cag cag gcg tcc agg gct gtg      2900
Phe Leu Ser Gly Gln Glu Trp Tyr Arg Gln Gln Ala Ser Arg Ala Val
            680                 685                 690

aac cag gcc atc ggg cga gtg atc cgg cac cgc cag gac tac gga gct      2948
Asn Gln Ala Ile Gly Arg Val Ile Arg His Arg Gln Asp Tyr Gly Ala
        695                 700                 705

gtc ttc ctc tgt gac cac agg ttc gcc ttt gcc gac gca aga gcc caa      2996
Val Phe Leu Cys Asp His Arg Phe Ala Phe Ala Asp Ala Arg Ala Gln
    710                 715                 720

ctg ccc tcc tgg gtg cgt ccc cac gtc agg gtg tat gac aac ttt ggc      3044
Leu Pro Ser Trp Val Arg Pro His Val Arg Val Tyr Asp Asn Phe Gly
725                 730                 735

cat gtc atc cga gac gtg gcc cag ttc ttc cgt gtt gcc gag cga act      3092
His Val Ile Arg Asp Val Ala Gln Phe Phe Arg Val Ala Glu Arg Thr
```

-continued

```
740                 745                 750                 755

atg cca gcg ccg gcc ccc cgg gct aca gca ccc agt gtg cgt gga gaa     3140
Met Pro Ala Pro Ala Pro Arg Ala Thr Ala Pro Ser Val Arg Gly Glu
                760                 765                 770

gat gct gtc agc gag gcc aag tcg cct ggc ccc ttc ttc tcc acc agg     3188
Asp Ala Val Ser Glu Ala Lys Ser Pro Gly Pro Phe Phe Ser Thr Arg
            775                 780                 785

aaa gct aag agt ctg gac ctg cat gtc ccc agc ctg aag cag agg tcc     3236
Lys Ala Lys Ser Leu Asp Leu His Val Pro Ser Leu Lys Gln Arg Ser
        790                 795                 800

tca ggg tca cca gct gcc ggg gac ccc gag agt agc ctg tgt gtg gag     3284
Ser Gly Ser Pro Ala Ala Gly Asp Pro Glu Ser Ser Leu Cys Val Glu
    805                 810                 815

tat gag cag gag cca gtt cct gcc cgg cag agg ccc agg ggg ctg ctg     3332
Tyr Glu Gln Glu Pro Val Pro Ala Arg Gln Arg Pro Arg Gly Leu Leu
820                 825                 830                 835

gcc gcc ctg gag cac agc gaa cag cgg gcg ggg agc cct ggc gag gag     3380
Ala Ala Leu Glu His Ser Glu Gln Arg Ala Gly Ser Pro Gly Glu Glu
                840                 845                 850

cag gcc cac agc tgc tcc acc ctg tcc ctc ctg tct gag aag agg ccg     3428
Gln Ala His Ser Cys Ser Thr Leu Ser Leu Leu Ser Glu Lys Arg Pro
            855                 860                 865

gca gaa gaa ccg cga gga ggg agg aag aag atc cgg ctg gtc agc cac     3476
Ala Glu Glu Pro Arg Gly Gly Arg Lys Lys Ile Arg Leu Val Ser His
        870                 875                 880

ccg gag gag ccc gtg gct ggt gca cag acg gac agg gcc aag ctc ttc     3524
Pro Glu Glu Pro Val Ala Gly Ala Gln Thr Asp Arg Ala Lys Leu Phe
    885                 890                 895

atg gtg gcc gtg aag cag gag ttg agc caa gcc aac ttt gcc acc ttc     3572
Met Val Ala Val Lys Gln Glu Leu Ser Gln Ala Asn Phe Ala Thr Phe
900                 905                 910                 915

acc cag gcc ctg cag gac tac aag ggt tcc gat gac ttc gcc gcc ctg     3620
Thr Gln Ala Leu Gln Asp Tyr Lys Gly Ser Asp Asp Phe Ala Ala Leu
                920                 925                 930

gcc gcc tgt ctc ggc ccc ctc ttt gct gag gac ccc aag aag cac aac     3668
Ala Ala Cys Leu Gly Pro Leu Phe Ala Glu Asp Pro Lys Lys His Asn
            935                 940                 945

ctg ctc caa ggc ttc tac cag ttt gtg cgg ccc cac cat aag cag cag     3716
Leu Leu Gln Gly Phe Tyr Gln Phe Val Arg Pro His His Lys Gln Gln
        950                 955                 960

ttt gag gag gtc tgt atc cag ctg aca gga cga ggc tgt ggc tat cgg     3764
Phe Glu Glu Val Cys Ile Gln Leu Thr Gly Arg Gly Cys Gly Tyr Arg
    965                 970                 975

cct gag cac agc att ccc cga agg cag cgg gca cag ccg gtc ctg gac     3812
Pro Glu His Ser Ile Pro Arg Arg Gln Arg Ala Gln Pro Val Leu Asp
 980                 985                 990                 995

ccc act gga aga acg gcg ccg gat ccc aag ctg acc gtg tcc acg gct     3860
Pro Thr Gly Arg Thr Ala Pro Asp Pro Lys Leu Thr Val Ser Thr Ala
                1000                1005                1010

gca gcc cag cag ctg gac ccc caa gag cac ctg aac cag ggc agg ccc     3908
Ala Ala Gln Gln Leu Asp Pro Gln Glu His Leu Asn Gln Gly Arg Pro
            1015                1020                1025

cac ctg tcg ccc agg cca ccc cca aca gga gac cct ggc agc caa cca     3956
His Leu Ser Pro Arg Pro Pro Pro Thr Gly Asp Pro Gly Ser Gln Pro
        1030                1035                1040

cag tgg ggg tct gga gtg ccc aga gca ggg aag cag ggc cag cac gcc     4004
Gln Trp Gly Ser Gly Val Pro Arg Ala Gly Lys Gln Gly Gln His Ala
    1045                1050                1055

gtg agc gcc tac ctg gct gat gcc cgc agg gcc ctg ggg tcc gcg ggc     4052
```

-continued

```
Val Ser Ala Tyr Leu Ala Asp Ala Arg Arg Ala Leu Gly Ser Ala Gly
1060                1065                1070                1075

tgt agc caa ctc ttg gca gcg ctg aca gcc tat aag caa gac gac gac     4100
Cys Ser Gln Leu Leu Ala Ala Leu Thr Ala Tyr Lys Gln Asp Asp Asp
                1080                1085                1090

ctc gac aag gtg ctg gct gtg ttg gcc gcc ctg acc act gca aag cca     4148
Leu Asp Lys Val Leu Ala Val Leu Ala Ala Leu Thr Thr Ala Lys Pro
            1095                1100                1105

gag gac ttc ccc ctg ctg cac agg ttc agc atg ttt gtg cgt cca cac     4196
Glu Asp Phe Pro Leu Leu His Arg Phe Ser Met Phe Val Arg Pro His
        1110                1115                1120

cac aag cag cgc ttc tca cag acg tgc aca gac ctg acc ggc cgg ccc     4244
His Lys Gln Arg Phe Ser Gln Thr Cys Thr Asp Leu Thr Gly Arg Pro
    1125                1130                1135

tac ccg ggc atg gag cca ccg gga ccc cag gag gag agg ctt gcc gtg     4292
Tyr Pro Gly Met Glu Pro Pro Gly Pro Gln Glu Glu Arg Leu Ala Val
1140                1145                1150                1155

cct cct gtg ctt acc cac agg gct ccc caa cca ggc ccc tca cgg tcc     4340
Pro Pro Val Leu Thr His Arg Ala Pro Gln Pro Gly Pro Ser Arg Ser
                1160                1165                1170

gag aag acc ggg aag acc cag agc aag atc tcg tcc ttc ctt aga cag     4388
Glu Lys Thr Gly Lys Thr Gln Ser Lys Ile Ser Ser Phe Leu Arg Gln
            1175                1180                1185

agg cca gca ggg act gtg ggg gcg ggc ggt gag gat gca ggt ccc agc     4436
Arg Pro Ala Gly Thr Val Gly Ala Gly Gly Glu Asp Ala Gly Pro Ser
        1190                1195                1200

cag tcc tca gga cct ccc cac ggg cct gca gca tct gag tgg ggc ctc     4484
Gln Ser Ser Gly Pro Pro His Gly Pro Ala Ala Ser Glu Trp Gly Leu
    1205                1210                1215

tag gatgtgccca gcctgccaca ccgcctccag gaagcagagc gtcatgcagg          4537
 *

tcttctggcc agagccccag tgagtgccca cggaggcccc cagcacaccc aacgtggctt   4597

gatcacctgc ctgtccagct ctggtgggcc aagaacccac ccaacagaat aggccagccc   4657

atgccagccg gcttggcccg ctgcaggcct caggcaggcg gggcccatgg ttggtccctg   4717

cggtgggacc ggatctgggc ctgcctctga gaagccctga gctaccttgg ggtctggggt   4777

gggtttctgg gaaagtgctt ccccagaact tccctggctc ctggcctgtg agtggtgcca   4837

caggggcacc ccagctgagc ccctcaccgg gaaggaggag acccccgtgg gcacgtgtcc   4897

acttttaatc aggggacagg gctctctaat aaagctgctg gcagtgccc               4946


<210> SEQ ID NO 2
<211> LENGTH: 1219
<212> TYPE: PRT
<213> ORGANISM: Homo sapien

<400> SEQUENCE: 2

Met Pro Lys Ile Val Leu Asn Gly Val Thr Val Asp Phe Pro Phe Gln
 1               5                  10                  15

Pro Tyr Lys Cys Gln Gln Glu Tyr Met Thr Lys Val Leu Glu Cys Leu
            20                  25                  30

Gln Gln Lys Val Asn Gly Ile Leu Glu Ser Pro Thr Gly Thr Gly Lys
        35                  40                  45

Thr Leu Cys Leu Leu Cys Thr Thr Leu Ala Trp Arg Glu His Leu Arg
    50                  55                  60

Asp Gly Ile Ser Ala Arg Lys Ile Ala Glu Arg Ala Gln Gly Glu Leu
65                  70                  75                  80
```

-continued

```
Phe Pro Asp Arg Ala Leu Ser Ser Trp Gly Asn Ala Ala Ala Ala Ala
                85                  90                  95

Gly Asp Pro Ile Ala Cys Tyr Thr Asp Ile Pro Lys Ile Ile Tyr Ala
            100                 105                 110

Ser Arg Thr His Ser Gln Leu Thr Gln Val Ile Asn Glu Leu Arg Asn
        115                 120                 125

Thr Ser Tyr Arg Pro Lys Val Cys Val Leu Gly Ser Arg Glu Gln Leu
    130                 135                 140

Cys Ile His Pro Glu Val Lys Lys Gln Glu Ser Asn His Leu Gln Ile
145                 150                 155                 160

His Leu Cys Arg Lys Lys Val Ala Ser Arg Ser Cys His Phe Tyr Asn
                165                 170                 175

Asn Val Glu Glu Lys Ser Leu Glu Gln Glu Leu Ala Ser Pro Ile Leu
            180                 185                 190

Asp Ile Glu Asp Leu Val Lys Ser Gly Ser Lys His Arg Val Cys Pro
        195                 200                 205

Tyr Tyr Leu Ser Arg Asn Leu Lys Gln Gln Ala Asp Ile Ile Phe Met
    210                 215                 220

Pro Tyr Asn Tyr Leu Leu Asp Ala Lys Ser Arg Arg Ala His Asn Ile
225                 230                 235                 240

Asp Leu Lys Gly Thr Val Val Ile Phe Asp Glu Ala His Asn Val Glu
                245                 250                 255

Lys Met Cys Glu Glu Ser Ala Ser Phe Asp Leu Thr Pro His Asp Leu
            260                 265                 270

Ala Ser Gly Leu Asp Val Ile Asp Gln Val Leu Glu Glu Gln Thr Lys
        275                 280                 285

Ala Ala Gln Gln Gly Glu Pro His Pro Glu Phe Ser Ala Asp Ser Pro
    290                 295                 300

Ser Pro Gly Leu Asn Met Glu Leu Glu Asp Ile Ala Lys Leu Lys Met
305                 310                 315                 320

Ile Leu Leu Arg Leu Glu Gly Ala Ile Asp Ala Val Glu Leu Pro Gly
                325                 330                 335

Asp Asp Ser Gly Val Thr Lys Pro Gly Ser Tyr Ile Phe Glu Leu Phe
            340                 345                 350

Ala Glu Ala Gln Ile Thr Phe Gln Thr Lys Gly Cys Ile Leu Asp Ser
        355                 360                 365

Leu Asp Gln Ile Ile Gln His Leu Ala Gly Arg Ala Gly Val Phe Thr
    370                 375                 380

Asn Thr Ala Gly Leu Gln Lys Leu Ala Asp Ile Ile Gln Ile Val Phe
385                 390                 395                 400

Ser Val Asp Pro Ser Glu Gly Ser Pro Gly Ser Pro Ala Gly Leu Gly
                405                 410                 415

Ala Leu Gln Ser Tyr Lys Val His Ile His Pro Asp Ala Gly His Arg
            420                 425                 430

Arg Thr Ala Gln Arg Ser Asp Ala Trp Ser Thr Thr Ala Ala Arg Lys
        435                 440                 445

Arg Gly Lys Val Leu Ser Tyr Trp Cys Phe Ser Pro Gly His Ser Met
    450                 455                 460

His Glu Leu Val Arg Gln Gly Val Arg Ser Leu Ile Leu Thr Ser Gly
465                 470                 475                 480

Thr Leu Ala Pro Val Ser Ser Phe Ala Leu Glu Met Gln Ile Pro Phe
                485                 490                 495

Pro Val Cys Leu Glu Asn Pro His Ile Ile Asp Lys His Gln Ile Trp
```

-continued

```
            500                 505                 510

Val Gly Val Val Pro Arg Gly Pro Asp Gly Ala Gln Leu Ser Ser Ala
        515                 520                 525

Phe Asp Arg Arg Phe Ser Glu Glu Cys Leu Ser Ser Leu Gly Lys Ala
    530                 535                 540

Leu Gly Asn Ile Ala Arg Val Val Pro Tyr Gly Leu Leu Ile Phe Phe
545                 550                 555                 560

Pro Ser Tyr Pro Val Met Glu Lys Ser Leu Glu Phe Trp Arg Ala Arg
                565                 570                 575

Asp Leu Ala Arg Lys Met Glu Ala Leu Lys Pro Leu Phe Val Glu Pro
            580                 585                 590

Arg Ser Lys Gly Ser Phe Ser Glu Thr Ile Ser Ala Tyr Tyr Ala Arg
        595                 600                 605

Val Ala Ala Pro Gly Ser Thr Gly Ala Thr Phe Leu Ala Val Cys Arg
    610                 615                 620

Gly Lys Ala Ser Glu Gly Leu Asp Phe Ser Asp Thr Asn Gly Arg Gly
625                 630                 635                 640

Val Ile Val Thr Gly Leu Pro Tyr Pro Pro Arg Met Asp Pro Arg Val
                645                 650                 655

Val Leu Lys Met Gln Phe Leu Asp Glu Met Lys Gly Gln Gly Gly Ala
            660                 665                 670

Gly Gly Gln Phe Leu Ser Gly Gln Glu Trp Tyr Arg Gln Gln Ala Ser
        675                 680                 685

Arg Ala Val Asn Gln Ala Ile Gly Arg Val Ile Arg His Arg Gln Asp
    690                 695                 700

Tyr Gly Ala Val Phe Leu Cys Asp His Arg Phe Ala Phe Ala Asp Ala
705                 710                 715                 720

Arg Ala Gln Leu Pro Ser Trp Val Arg Pro His Val Arg Val Tyr Asp
                725                 730                 735

Asn Phe Gly His Val Ile Arg Asp Val Ala Gln Phe Phe Arg Val Ala
            740                 745                 750

Glu Arg Thr Met Pro Ala Pro Ala Pro Arg Ala Thr Ala Pro Ser Val
        755                 760                 765

Arg Gly Glu Asp Ala Val Ser Glu Ala Lys Ser Pro Gly Pro Phe Phe
    770                 775                 780

Ser Thr Arg Lys Ala Lys Ser Leu Asp Leu His Val Pro Ser Leu Lys
785                 790                 795                 800

Gln Arg Ser Ser Gly Ser Pro Ala Ala Gly Asp Pro Glu Ser Ser Leu
                805                 810                 815

Cys Val Glu Tyr Glu Gln Glu Pro Val Pro Ala Arg Gln Arg Pro Arg
            820                 825                 830

Gly Leu Leu Ala Ala Leu Glu His Ser Glu Gln Arg Ala Gly Ser Pro
        835                 840                 845

Gly Glu Glu Gln Ala His Ser Cys Ser Thr Leu Ser Leu Leu Ser Glu
    850                 855                 860

Lys Arg Pro Ala Glu Glu Pro Arg Gly Gly Arg Lys Lys Ile Arg Leu
865                 870                 875                 880

Val Ser His Pro Glu Glu Pro Val Ala Gly Ala Gln Thr Asp Arg Ala
                885                 890                 895

Lys Leu Phe Met Val Ala Val Lys Gln Glu Leu Ser Gln Ala Asn Phe
            900                 905                 910

Ala Thr Phe Thr Gln Ala Leu Gln Asp Tyr Lys Gly Ser Asp Asp Phe
        915                 920                 925
```

-continued

```
Ala Ala Leu Ala Ala Cys Leu Gly Pro Leu Phe Ala Glu Asp Pro Lys
    930                 935                 940

Lys His Asn Leu Leu Gln Gly Phe Tyr Gln Phe Val Arg Pro His His
945                 950                 955                 960

Lys Gln Gln Phe Glu Glu Val Cys Ile Gln Leu Thr Gly Arg Gly Cys
                965                 970                 975

Gly Tyr Arg Pro Glu His Ser Ile Pro Arg Arg Gln Arg Ala Gln Pro
            980                 985                 990

Val Leu Asp Pro Thr Gly Arg Thr Ala Pro Asp Pro Lys Leu Thr Val
        995                 1000                1005

Ser Thr Ala Ala Ala Gln Gln Leu Asp Pro Gln Glu His Leu Asn Gln
    1010                1015                1020

Gly Arg Pro His Leu Ser Pro Arg Pro Pro Pro Thr Gly Asp Pro Gly
1025                1030                1035                1040

Ser Gln Pro Gln Trp Gly Ser Gly Val Pro Arg Ala Gly Lys Gln Gly
                1045                1050                1055

Gln His Ala Val Ser Ala Tyr Leu Ala Asp Ala Arg Arg Ala Leu Gly
            1060                1065                1070

Ser Ala Gly Cys Ser Gln Leu Leu Ala Ala Leu Thr Ala Tyr Lys Gln
        1075                1080                1085

Asp Asp Asp Leu Asp Lys Val Leu Ala Val Leu Ala Ala Leu Thr Thr
    1090                1095                1100

Ala Lys Pro Glu Asp Phe Pro Leu Leu His Arg Phe Ser Met Phe Val
1105                1110                1115                1120

Arg Pro His His Lys Gln Arg Phe Ser Gln Thr Cys Thr Asp Leu Thr
                1125                1130                1135

Gly Arg Pro Tyr Pro Gly Met Glu Pro Pro Gly Pro Gln Glu Glu Arg
            1140                1145                1150

Leu Ala Val Pro Pro Val Leu Thr His Arg Ala Pro Gln Pro Gly Pro
        1155                1160                1165

Ser Arg Ser Glu Lys Thr Gly Lys Thr Gln Ser Lys Ile Ser Ser Phe
    1170                1175                1180

Leu Arg Gln Arg Pro Ala Gly Thr Val Gly Ala Gly Gly Glu Asp Ala
1185                1190                1195                1200

Gly Pro Ser Gln Ser Ser Gly Pro Pro His Gly Pro Ala Ala Ser Glu
                1205                1210                1215

Trp Gly Leu
```

<210> SEQ ID NO 3
<211> LENGTH: 114793
<212> TYPE: DNA
<213> ORGANISM: Homo sapien

<400> SEQUENCE: 3

```
tgaagagctt tgaccaagag gctgtgacga ggccctacga ggactctggc tctcctcctg     60

ctaagcacac ccaggcaggt gtcctggcag atgaggacca catgcagagc ctcggccagc    120

ccaccaatgc ccggatatgc aagtgagccc agcctggacc ccccggcgag gcccagcagc    180

accagcccag gcccgaaaac cttaagaaat gaccagtgtc tgctgcttta agccaccaag    240

ctctgcggtg gtttgttagg ctgcaagcat ggctaattca gaaactgcca gaaacaagca    300

ctgctgtccc cagcctggga cacacagcac cgcctctgcg tggggagagg gcacaggcta    360

agggcacaaa tgccatccca gacccggctc ttgtgtgtgg aaggggccac tgtgccatga    420
```

-continued

```
ggcagaggaa accttggcag gaccttatgc cacagcaatt taaaagagaa gaaacaggct    480
gggcgtggtg gctcatgcct ataatcccag cactttggga ggccaaggtg gtggatcact    540
tgaggtcagg agttcaagac cagcctggcc aatatggtga aaccctgtct ctacgaaaaa    600
tacaaaattt aggcaggcgt ggtggcgggt gcctgtaatc cctgctattc aggaggctga    660
ggcaagagat ttacttgaac ccaggaggtg gaggctgctg cagtgagctg agatcatgcc    720
actgcactcc agcctgtgtg acggagtgag acttggtctc aaaaaaaaaa aaggaaacac    780
atctgactag tgtgatctcg caaggaacat tccagacaca gtggagctag aaggttcttc    840
tccaaacaag gaatccccag gggatcaaat tgttttgcat cggccagaca tggtggctca    900
agcctgtaac cccagtgctt cgggaggctg aggtgggagg actgcttgag tccaggagtt    960
caagactagc ttgggcaaca cagtgagagc ccattagcca ggcgtggtgg cacatgcctg   1020
cagtcccagc actgtactaa aaatctacac ggggccgggc atggtggcac atgcctgtag   1080
agtcccagct actcaggagg ctgaggcagg acgattcctt gaacccagga ggtcacggct   1140
gccatgagcc gtgactgtgc cactgcactc cagtctgtgc aacagaacga gactctgttt   1200
cgaaaaacaa aaaatcattt catgtctcca gtttctccac tggcaaaaga ctctgtcaag   1260
gtaaaaaatg gttctgaccc acagaaatct aagaaaggaa aaaatataaa aaatagaaaa   1320
tttaaaaaag agatggtctc agaataaaga ccaacctggg ctatggttgt cactcttccc   1380
tcacacctta gaaagctttc tggccgcatc tggccaaagg gccaccctgc cccatcttgg   1440
atcagtgagg tgccttcgaa caagccacct gccctggagc ccgtcctgtc ttgtctgcca   1500
ccgcacgctc agtaggggag gggaagtcgc taggttttag ttcaccagtc tctggatcaa   1560
gacgtgccat aaccaagaag ccccagccac acccagaccc gatgtggcca caaggggtga   1620
gctgggaagg cccaggaaaa ggcgggaggc ggacgaatgg aaatgtcatt ctgtggccac   1680
agaaatgatc tcaacgtttt gtaacttcct accaagaggc agtcttagct ctgcccttga   1740
accagcactt ggtgatgtcg cttgcgtcaa tcaaggcaac agaagtgagc aggaggccca   1800
ctttcctctg caactgtggg cttacggggc aaagaagtcc aggcctccag gtggaggatc   1860
acagaccggg caaagcagag gagagccacc cagccgagcc tacctgtgcc tcagactgcc   1920
tccctccaga gacccctgtg gccaaggcca cccagaccag caggtccttg ccaagctgtc   1980
agctgacgac aggggttggt gaggccggcc cagaccagca gaaccacgaa ccaaccaaca   2040
gaattaaaaa taataacaac tatgtcttgt cttaagccac taagttttgg atggtttctt   2100
tctttctttt tctttttttt tttcggagac gcagtctcac tctgttgccc aggctggagt   2160
gcagtggcgc aatcttggct cactgcaagc tctgcccccc ggattcacgc cattcccctg   2220
cctcagcctc ctgagtaact gggactacag gtgcctgcca ttgggtgttt tcttaaacag   2280
caaaagaaaa ctgacacaat cataaacaga gcaagcaaga gaacttggca attatttcct   2340
ctctacttct cactgttctt caaagagtta actcaagcat aagatgtgag caaattcttt   2400
taacatccta gaaaaaaagc tcctactcag tgttcataaa gcaaagctaa cctacaggag   2460
ccaccttcca cagtgaccac aggaaaccaa gacagcaagt gggacaccag cctccagggc   2520
actgcgccag ccgtgcgcct gtgtctgcca ctgccctggt ccgtcactgc caccagccgg   2580
caagacaccc acagaggaga gctctaagcc acaactgtgt acgaagacaa ctgtgcagga   2640
ttttattact acaacatttt tgttttcttt tttttttttt tttgagactg agtctcgctc   2700
tgtcacccag gctggagtgc agtggcacaa tctcggctca ctgtaacctc catctccctg   2760
gttcaagcaa ttctcctgct gcagcctccc aactggatta caggcgcccg ccaccacgcc   2820
```

-continued

```
tggctaattt ttgtactttt agtagagatg gggtttcacc atgttggcca gactggtctc   2880
aaattcctga caagtgatcc acccaccctg gcctcccaaa gtgctgggat tacaggtgtg   2940
agccactgcg cctggcccat ttttgtttat caataaaaat gtacttaatg ttgaactctc   3000
cacatttcaa atgggtaact ccagtgtcct tgatgctcct gcgacatgtt cgtgagactt   3060
ctcttgggtg tgagagtcta gcatgtgggt ggtctggaca ggagggggag ggaagagtgc   3120
agagccgggc agggtaaaga gaccccctag gatgtgaagg ccgccctgca tttgtcagac   3180
tgggcaacac ccactccatc agatggaccc tggtatgggc ggcaagccac ctaggtgccg   3240
aggcaagaga ccgagggcac gagctgttcc ggtgtaataa aatgcataaa ataagaatag   3300
ttatactaga tatagatcat aaatatgatt atatatgaat atcattcatc attagtttgt   3360
agcaattact ctttattcca atattataat aatccttgcc taagcataac ctaggaaaaa   3420
ctaggaaatc ataacctagg aaaaactagg ccatacagag ataggagctg aggggacata   3480
gtgagaactg accagaagac aagagtgcga gccttctgtt atgcctggac agggccacca   3540
gagggctcct tggtctagcg gtaacgccag catctgggaa gacgcccgtt gccaagtgga   3600
ccgtggtcta gcggtagcct cagtgtcaag gaaaaacacc cgctacttag caaaccagga   3660
aagagagtct ccctttcccc gggggagttt agagaagact ctactcctcc acctcttgcg   3720
gagggcctga catcagtcag gcccgcccgc agttatccgg aggcctaacc gtctccctgt   3780
gatgctgtgc ttcagtggtc acgctcctag tccgccttca tgttccatcc tgtgcacctg   3840
gctctgcctt ctagatagca gcagcaaatt agtgaaagta ctgaaagtct ctgataagca   3900
gaaataatgg cgtaagcggt ctctctctct ctctcctctc tctctgcctc agctgccagg   3960
aagggaaggg ccccctggcc agtgggcacg tgacccacat gaccttacct atcactggac   4020
atggttcaca ctccttaccc tgccgctttg tcttgtatcc aataaatagc gcaacctggc   4080
attcggggcc gctaccagtc tccgcgtctt ggtggtagtg gtcccccagg cccagctgtc   4140
tttttctttt atctttgtct tgtgtcttta tttctacact ctctcatctc cgcatacgag   4200
gagaaaaccc accaaccctg tggggctggt ccctacaccc tggctttgta gactggagcc   4260
taggcacgac tcagctgctg tagtgaattg cgatcctcca aacccagcaa ggcacctgca   4320
ggacatctgg cccagtctcc tcgttgagcc agttcacgaa aaagagactt ttctgagtga   4380
catgctaatg ggcaatatga ggactaaatg ggatggtctc caacttggac aaaccaacag   4440
taaaagccac tttgcgggga aagaaacttt tcctttttttc tttttttttga gacaggatct   4500
caccctgtca cccaggctgc agtgcagtgg catgaccttg gctcactgca gcctcaacct   4560
ctctcaggct caagcaatcc tcccgcctca acctcccatg cagctgggac cataggtgca   4620
tgccaccaca cccaaataat ttttatattt tttgtagaga cgaggtttca ctatgttgct   4680
cgggctggtc tcaactcctg ggctcaagca accctcccac ctcagcctcc caaagtgctc   4740
agattacagg caggagccac caggcctggc caacatagga agaaatttaa atttgaattg   4800
aatattagaa gagatgaaaa ttcatcaaca tggaaagaca aagatcatta actaaagcca   4860
aaccagaatg gaagctgtgt gtacagtggg gtctcatgct gggaacgcga ggggcacgtg   4920
cagggctcca cggtgtggcg acgccccatg ctccctttgt gggggttcat ccagcggaac   4980
atgaggacct ggggtgcttt tcaacatgta cgtgagttta ataataaaaa ggtttaagga   5040
aagaaaaatt catatgtttc tatataaaca gaacatctgg aaagatctat tctaaggtgt   5100
tgacagtagg aatctctagg tagtagtaat atggcctttt tgaatttttg cttatcagta   5160
```

-continued

```
ttttctaatt ttctttttct ttctaaataa ttctagctat gaaataattt tctaccatat   5220
atattttgta ataaaaatgg ttatatttaa ttttttaaag gctgtacaaa cttcctgata   5280
aaatggcaaa ttagacacac acatgtgggc cgggtacagt ggctcgcgcc tgtaattcca   5340
gcactttggg aggctgaggc aggcagatca cctaaggtca ggagtttgag accagcctgg   5400
ccaacatggt gaaaccccgt ctctactaaa tatacaaaaa tgagctggat gtggtggcac   5460
acacctatag tgccagctac ttgggaagct gaggcaggaa aattgcttca acccgggagg   5520
cagaggttgt agtgagccga gatcatgcca ctgcactcca gcctaggcaa caagagcgag   5580
actccaactc aaaaaaaaat aaaaataaca cacacgtgaa taggctcctc atggaagtca   5640
tcacaacaat gcagagggaa gagcttccaa agtgtaaacc cagaagcgag gagcaggagg   5700
gtgcgcgcag acgcagagag cagcaaggtg cagactgaga ggcggaggct ggccgtgggg   5760
agatgactga tgctcagttt ataccccaaa tccgtaaatc tagaggcctg gcacatcaac   5820
tacctctgcc agcaggaatg agggaaagga gggcaaccaa aagatgtccc accctcaccc   5880
atccagctac ctgccatcct cagccccact ggcagaagac cctgagaggt ggaggcaggc   5940
ccctgcctac aggaccctga gagctagggg aaggcgttat cctgaactgt gtcccccgta   6000
aaattcatat gttgaaggcc tcatccccag tgtgactgta tttaaagatg gggtcttcag   6060
gagataattt aaatgaggtc atataagttg gccctcatcc agtaagactt tgaccttctg   6120
gtggtttttt ttttttgga gactgggtct cactctatca ctcaggttgg agtacagtgg   6180
cacgatcacg gctcactgct gtctccaact cctgggctca ggtgatcctc ctgcttcagc   6240
ctcctgagta gctgggacta caggtgctta ccaccgcacc cagctggtgg tgcattgtgt   6300
tttttgtaga gatggggttt tgccatgtcg cccaggctgg tcctgaactg ggctcaagtg   6360
atctgtctcc ctcggcctcc tgcagtgctg gaattacagg tatgagccac cgcgcctggc   6420
cgaccgtgac cttctaagaa gtgaaagaga aagatctttc tctctccctc cctctccatc   6480
atgaggacac agcaagaagt cggccatctg caaggtagaa agcgagtcct cccaacagct   6540
gaacctggca gaccctgatc ttggacttca gccttcagag ctgtaagaaa ataactctct   6600
gctgttcagg ccacgcggtc tacggcagcc cgagcagact aagacacacg ccatctgggg   6660
agtcagacca gatcaggaag aaaggcctag agctcaggat actgaaggtc ccaacccggt   6720
gctggaccag accaccccgg cagccgcggc cacggagtca cggctcgggt gaggtgacct   6780
ggacaccatc ccggcagccg cggccacgga gtcacggctc gggtgaggtg acctggacac   6840
catcccggca gccgcggcca cggtgtcacg gctcggatga gatgactcgg acaccacccc   6900
ggcagccgcg gccacggtgt cagggctcag gtgaggagag ttggatatgg gactgggcct   6960
accccgaggc tgcttccacc cagacgcctg ggtgggtgac acgaaagctg ggctcagttg   7020
ggatcagagc agcctctccc caggtcagaa atgaccctgg gctcctcaca gtagccctag   7080
ggcaccatga gaaagctacg tggacttctc tgaccaaggg tcactgctgc cacactactc   7140
attgcaggcc atgtcagggc tcagctgagg agacgtggac accaccccag cagccgcggc   7200
cacggcgtcc caagggaggg acttgggcac tgcctctctg ggcaagagtg gggaggtgtg   7260
gggtgggaga tgtctggaaa catcatggac acatgccggg aaaacacgga agctgtgcac   7320
caaggtgctg acaaaggaaa aaggagaatg gaggtgtgaa catccagcta gcaggtccca   7380
ctcagaaact cctgcatttc cagacatggc caccagctct gtggatgaga caggggagga   7440
cagggtacct cacaccagga acccacacag gtccatgtct tgctctgtga tcacacaaca   7500
gcctccacca ccctgacatg caggagggag gtcaaagcct cgggtccaac aacaggctcc   7560
```

-continued

```
acagcaaggg aagaaaggca ggaaggaact cagggccagg tcctcccagg cagcagctgc   7620
ctgcacgctg tccaccaagg gaggtctgac ctacaccgca caggggttgg cagtctagag   7680
tcgtcctctg tcaaacggtg agaaagtcaa aagctcatgc tcagtgatat gctaggtcag   7740
catgaagatg ccacacatga gacacagcaa ggatgagacc aacgggaaga ctgccccaga   7800
ccagagcccc agagccctct ggggaggaag aataaggatg gcagcctggg actgcccggg   7860
gctgactctg cctttatttc accccagcag aggcaggagt gacaccggct cacagcagga   7920
gcagctctgc cacctcctag cagttccacc tacgggcagc aaaacaaagc tggcagtttg   7980
ggcaaatgtt agcgtttttg ccaactaaca tttgaatcgg acatctggta cagagatgag   8040
gaagaaaaca ctcacagttt catgaagact gtcaagaaaa tcactgactc ttcacttcat   8100
ttatgaaagg ccagctctct gacatcccta ccactccctc tcacatgaga aatcacggcc   8160
tttcaggacg tggagccacg tggccatgca ggtacgggag gcctccccgc agctgcagct   8220
gggtcttctg gtccccgtgc catttctgct tttcttcgct ctctacttac acacacattt   8280
gagtccagtc tcagaagaac tggaactaga aaaatcctga cacttgtccc ttactacgtt   8340
aatgccagct gtgccaagga cagcccaacc caagccccca tcagccccaa tggcaccgag   8400
gcccgagctt acccgtgagg ggccaagttg gtcgtcacca acacggtctt cacccccctcc   8460
acaccactgc cgtccactgc agtgtccgga gttgtcacaa ccaccacctc ctccatgtgc   8520
acactcacgt cgggagtcgc catggctcag cggaagggga cgcccaggcc agcagcgtca   8580
gtcctccagg gtcccaagtc ctggaggaag caaggcaggg cacagggatg gagtcatctc   8640
cacatccaca caacatagca ctcacaaagg catctctaat cagctccaaa gacccaccct   8700
tgagtcccag actgctacct cctgacaaaa acgagcggca acagaagggc tactccaggc   8760
tctggttccg agggcggtgt aagcgcactc cacccgtttt tcccactgga taagccgaaa   8820
cccttgggta gaaagcacag agccactccc tccacgtggg gctcagagca ggaggacagg   8880
aggggcctgg aattccaagc aacttccctg gacgcaggct cccggcttgc cagttcttcc   8940
gtctctcctg gcctgaactc aaagccagcc ccaatccctg aactgagttt caggtgcaga   9000
aagcactcca agaagtcctc gctggtctgt ggaacgggaa gggaaaccca ttcaagacag   9060
aaagagagga gggaaacgcc ctgggttttt ttgggttttt gggttttttt tgagacggag   9120
tctcgctctg tcgcccaggc tggaatgcag tggcacgacc tcggctcact gcaagctcca   9180
cctcctgggt tcaagtgatt ctcctgcctc agcctctcca attgctggga ttacaggttt   9240
caccatgttg cccaggctgg tctcaaactc ctgacctcag gtgatccact cacctcggcc   9300
tcccaaagtg ctgggattgc aggtgtgagg caccatgcct ggcctgcccc gggtttaaaa   9360
attattatta ttttgtcttt cctggctttg ccttcagcaa gtccaacccc tgctaaaacc   9420
cggtgataat ggctgtcctg gcccaaaaag cttggagaca ggggaatctt cctcctgact   9480
aaaggaatgg tggcccaaga gtgtgggggc tccctgttgc cctctcactc tccatcccct   9540
acctagcaca gggaacacaa aagcccctgg tttccagcca gagggcaacg agcctggagt   9600
cagagtgtgg gggaggcgac aagaggagag gggagaagag aggatggcac acagctgtgt   9660
gtgagcgcct gggtcgtccc aagacagtct ctacgtggtc ctgaccctaa agggcaaagg   9720
gaagaaaact gacctacagg ataggccact gcccaggtct cagatgggcc ccagtggcgc   9780
atatgggaca gatccacagt gcactggaaa gtctctaaaa taaactggcc taagaacaca   9840
gacacaggaa cggggtgcaa aatttgcagc ctgaacctaa ccaggtcgat ttcttgctat   9900
```

-continued

```
gaaaaaaaaa agtctacatt ctctgtgaaa cttaaaacaa gacctagagt ccatagcaca   9960
gtagtcaaag catccagaac acgatcaaac ttcctggcaa agggtagtct ggttgattct  10020
caaaggaaca aatacacaag agaagctggc tcttgaacgc agaatccaga gactttcagg  10080
tgctatcgga ccagctccaa gaggaaagca aacattgtca accaagtgga aagaaaatct  10140
tggtatagaa acaggagtta taaccaaaca gaaatgtgaa aattaaaaac gacaaccaaa  10200
agaaaataca caaagctggg atagtctcag ctactcggaa ggcggggctg gaggatcgtt  10260
tgagcctagg agattgaggc tgcaatgagc tgtgatcaca ccaccgcact ccagtctggg  10320
caacagagtg agaactctct caaaaaacga aaaagaaaga aagtagaaca gaagtgacca  10380
ggggctgggg gagggagtac agggagttgt tctttaatga gtacagaatt tctgtttggg  10440
atgatgaaaa gctctggaaa tggacggcgg tgatggctgc acaatcactg tggctgttct  10500
gaatggtgct gaaccacaca tttaaaaaca gttaaaatgg gctgggcgtg gtggctcacg  10560
cctgtaatcc cagcactttg ggaggcggat cgcctgaggt caggagttcg agaccatcct  10620
ggccaacaca gtgaaatcct gtcttgacta aaaatactaa aaattagcca ggcatggtgg  10680
caggcacctg tagtcccagc tacttgggag gctggggcag gagacctgct tgaacccagg  10740
aggcagaggt tgcagtgagc cgagatcgtg ccactgcact ccagcctggg caacaagagc  10800
gaaactccat ctcaaaaaaa aaaaaaaaaa aaaaaaaaaa aagtttaaaa tggttaaatt  10860
ttatgttatg tatattttac cgtaataaaa acactgtaat gctactataa tagaatgact  10920
cattaggatt agatatagac tagaaagtac agaatataaa aactttttaa acaaagaaaa  10980
atttcatgg  ccaggcatgg tgtcacacct gtaatcccag gactttggga ggccaaggca  11040
agaggaatgc ttgagctcag gggtttgaga ccagcctggg caacacagca acaccccatc  11100
tctgctaaat aaataataaa aaatagccag gcatggtggt gtgcacgcct gtagttgcag  11160
ctactctgga ggctgaggca ggaggatcac ttaagcccag gaggtcaagg ctgcagtgag  11220
ccatggttgt gccactgcgc tccagcctgg gcaacagatc aagaccttgt cacaaaaaaa  11280
agaaagaaag aaaagaaaaa agaaagaaaa taaaatcttc cagaactttt aaaatcatca  11340
ttgttaatat aaaaataaca tcacctgccc ctaggactgt aacaaacaag tgtgtctaag  11400
gacaggagtg ggtccacccc aacctggcac gcagtggtcc cctgcggaga gtctggccct  11460
gcactcacta agaggaggca ctcatagccc agccaggcct ctgcaattat gccttcaatg  11520
ccagaactaa ctcacccaaa ctgaacaatc gatcacaaaa tgtgccttca ggtctcaagg  11580
ttcttgctaa atcttactca accgacattt tccagcatgg gaacattttt ctgaatgtct  11640
tagggagagg aagtccgcaa gagaacaaaa ggtcctcagg ccaccctagc ttcttttcct  11700
ccattccaca ggctgtcttt tgtctgggta tgcactggac caggggctc  tacttcttcc  11760
tacctgggca tgggtctcca cacaactcca aggtaaaggg ccacaggcaa gataaagggg  11820
agaaaagaaa gctacgattt cctgggccac caatcgcaaa tggcagccag tctctgaagt  11880
aacccttgac cagagatcca aggaaccaag aaatgtaggt gatctgaaca gaggggatgg  11940
tggttaaaca ccatgaagga aagacccatt ctcaaagaaa aggaagcaaa aagaaaccgt  12000
ggggagctgg gtaccacccg cagcaaagac cccgcacgcg ttactgacgc cagcctggcc  12060
tgggagagca gtgagtgtgg cggacggtga gtggcgggga gggctgtggt aggtttaggg  12120
taagaagggg cagcgcccag agcccagaga acaccagtga gggctccaca ggaacactac  12180
tcaaagtatt cacggaacac atctaaacac aagcactaag gactaagtgc gagggacaag  12240
aaaatattcc ccgtttcctg tttcaggagg gtatcgaaaa tgagtgatgg aaggaaaatg  12300
```

-continued tattgtttaa atgaggaaaa aaaattttta caaattaaga acatcctgga acatgatgag 12360
ccgtttactg tcactcaatt taaatggtgg ccatctagga cagagcgcct aaggggaaag 12420
ggggctcaca ggtgaacccc tccagctgct ggtgggcaat ttcccattag ggcatcaggg 12480
tctctgaaga ctgtcttcag atgcttttta gccaggaaag ttacaatgat gaattcgttt 12540
acactggcgg aattacttcg tatttctcaa atataatgtt ttcactagca taactttgtt 12600
gttgtagact taggcttcaa aataaagaac tttaaacaaa catgaataaa aagccacttt 12660
aggccgggcg cggtggctca cacttgtaat cccagcactt tgggaggccg cggcgggtgg 12720
atcataaggt cagaagttca aagaccagcc tgatcaatac ggtgaaaccc cgtctctact 12780
aaaaatacaa aaattagccg ggcgcggtgg caggtgcctg taatctcagc tacttgggag 12840
gctgaggcag gagaatcgct tgaacctggg cagcagaggt tgcagtgagc caagatcatg 12900
ccactgcact caagcctggg tgacagagtg agactctctc ttaaaaaaaa aaagccactt 12960
taaaatttta ctcaggccag gtgtggtggc tcacgcccat aatcctagca ctttgggagg 13020
ccgaggcgag cagatcacct gaggtcagga gttagaccag cctggccaac atggtaaaac 13080
cttgtctcta ctgaaaacac aaaaaattagc tgggcgtggt ggtgtgccca tgtaatccca 13140
gctactcagg aggctgaagt gagagaactg cttgaacccg ggaggcagag gctgcagtgt 13200
gccaagactg caccactaca cttcagcctg ggcgacagag caagaccctg tctcagaaaa 13260
aaaaaaaatt caaaaatttg gccaggcgtg gtggctcacg cctgtaatcc catcactttg 13320
gaaggccgag gcgggtggat cacctgaggt caggaattca agaccagcct ggccaccatg 13380
atgaaaccct gtctctacta aaaatacaaa aaaaaaaaaa caaattggcc gggcatggtg 13440
gcgggtgcct gtaatcccac ctacttggga ggctgaggca ggagaatctc tcgaactccg 13500
gaggcagagg ttgcagcgag ccaagattgt gccactgcac tccagcctag acaacagagc 13560
gagactctgt ctcaaaaaaa aaaaaattaa aattaaaaaa taaaaatttc atttaaaata 13620
ctactgatct cccgtgctga cttctcgggg tttaactctc actgaggaga cgctgctttc 13680
ataagggtaa gctcagcagg ggcaactaaa gtcatttaag cagagagctg caaagaggca 13740
acagcctcac tgcaggcagg ggtcctcgtc acagcttcag ggctttgcag aggattacgc 13800
aatgtacacg cacaaaactg aattccagcc tctccattgg caactgcata catacatata 13860
ttcttttttt gagacggagt ctcgctctgt agcccaggtt ggactgcagt ggcccgatct 13920
cggctcaatg caagctctgc ctcccgggtt caagcgattc tcttgcctca gcctcctgag 13980
tagctgggat tacaggcgcc caccaccacg cccggctaat tttgtattt ttagtagaga 14040
cggggtttca ccatgttggc caggacagtc tcgatctcct gacctcgtga tccgcccgcc 14100
tctgcctccc aaagtgctgg gattacaggc gtgagccact gagcctggcc tccaatggca 14160
actatattaa aggttcaaag caatatgcac aaaagttacc tcacagaaaa tagtgcaagt 14220
ccttgataca atgctcttta gacacagaag aagcactata gaatagagca cctcgcccta 14280
ttgccttccc aagggcgagc accccctcct ctctccacag ctccttcttt gtttttttga 14340
gatggagtct cgctctgtca cccaggctgg agtgcaatgg caaaatcttg gctcactgca 14400
acctccgcct cccgggttga agtgattctc ctgcctcagc ctcccgagta gctgggacta 14460
caggcaccca acacgcctag ctaatttttg catttttggt agagacgggg tttcatcatg 14520
ttggccaggc tggtctcgaa ctcctgacct ccagtgatcc tcccaccttg acctcccata 14580
gtgctgggat tataggtgtg agccactaca cctggcctct ccacagcccc ttctgtgttg 14640

-continued

```
aagccaagac ccacccagct ttgatcccaa ggcttgggtt ccccactagt gtgaagtgag  14700
tttccaaatt attaggtaaa tcagatatga gaaaatattt tattttactt tttttttttt  14760
gagacgcaat cttgctccgt cacccaggct ggagtgcaat ggcaccatct ccactcactg  14820
caacctctgc cttctgggtt caagcaattc tcctgcctca gcctcccaac tagctgggat  14880
tacaagtgca caccaccacg cccggctaac ttttgtattt ttagtagaga cagggtttca  14940
ccgtgttagc caggctgctc tcaaactcct gacctcatga tccgcccacg tcgggctccc  15000
aaagtggtgg gattacaggt gtgagccatc acacctggcc caagaaaata tttttaaact  15060
agtattcttg accggcacgg tcaacactga tgtaattgaa actgttgtat ttgaagtgtt  15120
agcaaagaaa gagaattctg gttcaacaga aaagtcagtc acgacttttc agtcacgcat  15180
gaattacaca gtaaccaaat agataacatg ccatgactga cgacgggccc acaacaaatc  15240
agctccgacc aacagggtcc acaccaccat gggtctacac agatccaggt cccgcctgtg  15300
agcctacagt gacgcgggcc cctgtggggt ggtccctgca ggtcaggtcc ctgagagtgg  15360
gtcccagtgg ggtgatccct gcgggtcgcg tccctgcgag ttgggtgcct gccgggtggc  15420
ccctgcgggt cgggtgcctg cggggtggtc cctatgggtc gcgtccctgc gggtcgggtg  15480
cctgcggggt ggcccctggg aatcgcgtcc ctgcgggtcg ggtgcctgcg gggtggcccc  15540
tggggatcgc gtccctgcgg gtcgggtgcc tgcggggtgg cccctgggga tcgcgtccct  15600
gcgggtcggg tgcctgcggg gtggtccttg tgggtcgcgt ccctgtgggg tggtccctgt  15660
gggtcgcgtc cctgtggggt ggcccctgcg ggtcgcgtgg tggcccctgc gggtcgggtg  15720
cctgcggggt ggtccctgtg ggtcgcgtcc ctgcgggtcg ggtgcctgcg gggtggtccc  15780
tgcgggtcgc accccctgcgg cgtggtcccc ccgggatggg tccaccgagg aggccgctgg  15840
aggccgagcc cgcgcccgcc cgcggcgcca agatggaggc aggaagcgcc gccgcccgcg  15900
cccgccaccg cccgcgccgc ccgcctgacg ccgccgttgc gcctgacgcc gccgcccgcg  15960
cggccgcccc tcccccggcc ctcccctccc cccgccgtaa cgtcctgacg ctccgcaggg  16020
acccctgact ggacggcggc gcgtgagcgg agcgagaggc ctcgccgcgg gggggccgcg  16080
ggctcgccgg cgccgcttac ctggggccgc gccgggcctg cttaggcacc cggcgggggc  16140
ggcggcgtcg ggagctgcgg cggcggcggg cggcggcggc ggccgcgggc ttcgctcctt  16200
gttggggatt cggcggcggc ggcggcgcgg gcgcgcgctt cctagtgacg caggcggcgg  16260
ggccgcgcac gcacggggct gggagggccg gacacttatt tggcgctcgc ggaggaggaa  16320
ggcggggccg tgaaataagg cccgacgggc cccggggcgc gtgcgcggac cgacactgtc  16380
agctcctaac gccgcaggtt cctcctggtc cccgaggccc ccggtcgggc gttgcctgcc  16440
ccgcgcgggc ggccgggccg agggacgatg gtcagtggac ggacggcgcc agggagcagt  16500
gcccacgcgc ggcagggcgg taccttcagg cctccaggta cgggcgctcc tcgcccggac  16560
gctgctgtgt gtgaatgggc gcgaggggac tcccctgcgg ggcggacgcc tgaacacgag  16620
gctgtggagg aggacgctgt agggtgcgcg gactcacgcg gaacatgcca gaggctcagc  16680
cagccacggc gctcccagcg tggagggcga ggggcatccg ggagcggccg ggagggctcg  16740
gtcacccctc aagctgtcac cccagtccca caaccagcac ccccgatccta tcgcagtccc  16800
acagccgaca ccccgatccc acccctgccc aacagccggc acccacccca atcccatagc  16860
taacaccccg gtcccaccgc tgtcccacgg ccggcacccc gatcccaccc cagtcccgca  16920
gctggcaccc cgatcccacc ccagcccaac agctggcacc caccccgatc ccaccgctgt  16980
cccacagccg gcaccccgat cccaccccag tcccgcagcc ggcaccccga tcccacagcc  17040
```

-continued

```
ggcactcacc ccgatcgcat agcatagctg ataccccgat cccaccccag tcccatagcc  17100
agcaccccga tcccacccca gtcccatagc cagcacctcg atcccataga tgacaccccg  17160
atcacgcccc agtcctatag cccgcacccc gatcccaccc gagtcccgca gccggcaccc  17220
catcccaccc atgtcccaca gtcggcaccc cgatcccact cggatccggc agccagcttg  17280
gatcctgtgg ccctcctcca gcccccaggg ctcatttata tgttttattg gcagaggctg  17340
gggctggctc tgttggcctc tgtgctgggt ttcttcctct gcaccgcagg actggctctc  17400
ctgacctctc caggtgtcat cgaacaccct tgtgcttgct gtcacccgct gcctgtctgc  17460
aggatcccgg attccgtatc aggggaccga aattagtcgg aaaataggaa gcaggtgctc  17520
gcttggatgg aaccctgacc ctgtgctcac acttgtagga ggagggctct gcaggccgcc  17580
tcccggaacg ggaggttccc aagccactgc acttcggagg ggctgtaatt agagttgcac  17640
attcattcag ttcccagtaa agtagaacgt gctccagcca gtgaggaaaa ggtgttttta  17700
aaaattagat tggccgagtg cggtggctca tgccttttac ctcaacactt tgggagacaa  17760
aggtgggagg atcacctgtg gccaggagtt caagaccagc ctgggcaaca gagcctgtct  17820
ctggggaaga ataaaaaaaa aaattgagcc tttgtcagtg ctactatttt attatctggt  17880
aaatatgaga gggttcacgc ggtctatgtg tgtcatttat ctgagtttgc ctatcgtcac  17940
gttttggaaa taaatgtcaa taaagtcgaa gaggagtgct gagggggggcc tggggatggg  18000
agggtggcta catcatgcct gtgtgttgcg caagcccacc gaggtcggcc tggggtgagc  18060
cctggggcct gttctgcctc cttcactctg gggctccaag agacaaactg ggcaacaaga  18120
gagaaactcc atctaaaaaa aaagaaaaat cacctccaag ataacttagc tttcttctgc  18180
tggcataaca aattatctca aacttagtcg cttaaaaatg caaatttagg ctgagtgcgg  18240
aggctcacgc ccataatcct agcactttgg gaggccaagg caggattgct tgaggccagg  18300
agttcgagac caacatggcc agaactgtct ctttttaaaa aatgcaaatg tgtccggcac  18360
ggtggctcac gcctataatc ccagcacttt gtgaggccaa ggcgggcaga tcacgaggtc  18420
aggagataga gaccatcctg gctaacactg tgaaaccccc tctctactaa aaatacaaaa  18480
aattagcctg gcgtggtggc aggcgcctgt agtcccagct actcgggagg ctgaggcagg  18540
agaatggcgt gaacccagga agcggagctt gcagtgagcc gagatggcgc cactgcactc  18600
cagcctaggc aacagagcaa gactccgtct caaaaaataa ataaataaaa ctgcaaatgt  18660
attctctaac tgttctgtag gtcggaagtc cagcccagcc tcactccgcc aaaatcaggg  18720
tgtctgcagg gccgattgct tttggagctc caggggagaa gctgttctgg cctttccagt  18780
ttctggaagc acttgagccc cttgtctcgt ggcctatccc acacctgaaa gccagccaaa  18840
gccagttgag tcctcaccct gttggccccg acactgatct cctgcctccc tcatctgctg  18900
tcaaggcccc ttgtgatgac atggggccac cagctggccc agggcacctc ctgtcagagt  18960
ccgccgacca gtgaccttca ttccatctgt cgctgtaatt cccctttgct tggaaccaac  19020
gttcacagat cccaggggtt aggatgtgaa tatcttgggc agggctgtgg gggggctatt  19080
cttccttcta aaatatttat catttttgtt ttggggattt ttttggtttg gtttttttttg  19140
agacagagtc tcgctctgtc gcccaggttg gagtgcaatg gtgcaatctc agctcactgc  19200
aacctctgcc tccgggcaga cgtgagccac tgcaccaggc ctgtttttgt ttttgtttgt  19260
tttgttttgt ttttgagatg gagtctcggc cgggcgcggt ggctcacgcc tgtaatccca  19320
gcactttggg aggccgaggc gggcggatca cgaggtcagg agatcgagac catcctggct  19380
```

-continued

```
aacacggtga aaccccgtct ctactaaaaa tacaaaaaat tagccgggcg tggtagcggg  19440
cgcctgtagt cccagctact cgggaggctg aggcaggaga atggcgtgaa cccgggaggc  19500
ggagcttgca gtgagccgag atcgcgccac tgcactccag cctgggcgac agagcgagac  19560
tccgtctcaa aaaaaaaaaa aaaaaaaaaa aaaaaaagag atggagtctc actttgtcac  19620
ccaggctgga gtgtagtggc gggattatag gtacgcgcca tcatgcccag ttactttttg  19680
tatttttagt agagacaggg ttttaccatg ttggtcagac tggtctcaaa ctcctgatct  19740
caggtaatcc acccgcctca gcctcccaaa gtgctgggat tacagacgtg agccaccgtg  19800
tctggccata tttattaact acaaagggaa agatgataat ttttttttt gagatggagt  19860
ctcactctgt cacccaggct ggagtacaat agcgtgatct tggctcactg aaacctctgc  19920
ctcccaggtt caagcgattc tcctgcctca gcctcccaac tagctgggat tacaggcgca  19980
cgctaccaag cccagctaat tttgtattt ttagtagaaa cggagtttca ccatgttggt  20040
gaggctggtc tcgaactcct gaccttgtga tctgcccacc tcggcctccc aaagtgctgg  20100
gattataggc atgagccact gcaaccggct gaaagatggt aattttaaag tagagaaact  20160
gggttggctg ggcatggtgg cttatgcctg taagctcagc actttggaag tccaaggcaa  20220
gaggatcgct tgagtccagg agtttgagac cagcctggac aatatagcaa gaccccatct  20280
ccgcaaaagc taaaaagtta gccaggtgtg gcggcacatg cctgtagtcc cagctactca  20340
ggaggctgac gtgggaggat cacttgagac caggaggtca aggctgaagt gagctgttat  20400
tgtgccactg cactcagcct gggcaacaga gcgagagtct gtctccaaag gtaaaaaaag  20460
gtccaggcac agtggctcac acctgtaatc tcagcacttt gggaggccga ggcgggcaga  20520
ttcgttgagg tcaggagttc aaaacgagcc tggctaaatg gtgaaacccc gtctctacta  20580
aaaatacaaa aaaattagcc aggcatggtg acgggcgcct gtaatctcag ctacttggga  20640
gactgaggca ggagaatcat gtaaacccag gaggctgagg ttgcagcgag ccaagatcat  20700
gccactgcac ttcagcctgg gcgacagagc aagactgtct caaaacaaaa caaaagaatc  20760
ttgagtcctg agttcctcta agggaaattc caggcacctc gccacccttg acaggcaaag  20820
gaacaatctg atgaggaaga agatagaaac agcttaaaca atagtctccc ggccgggggc  20880
agtggctcac gcctgtaatc tgagcacttt gggaggccga ggcgggtgga tcacaaggtc  20940
aagagatcaa gaccatcctg gctaacatgg tgaaaccccg tctctactaa aaatacaaaa  21000
aattagccgg gcgtggtggt gggtgcctgt agtcccagct actcgggagg ctgaggcagg  21060
agaatggcgt gaacccagga ggcggagctt tcagtgagct gagatcgcgc ctctgcactc  21120
cagcctgggc gacagagcct cgagactcca tctcaaaaaa aaaaaaaaat tagctgggtg  21180
tggtggctca cacctgtaat cccagctacg tggcaggctg aggcaggaga atcgcttgaa  21240
cctgggaggc ggaggttgta gggagctgag atcgcaccac tgcactccag cctgggcaac  21300
agagcgagac tctgtctcaa aaaaaaaaaa aaaaaacaaa aaaacaatag tctcccaagt  21360
aagtcagagt cacaaggtgt tttgattccc tgtggaaact aaaatataac agcttaacat  21420
atgttcttga gttatttttc agaaacttgg acatccacca ggtggaaaat gctgagctag  21480
gaacagtggc tataatttca gccttttgag aggccaaggt ggaaggatca cttgaggcca  21540
ggagttagag accagcctgg ccaacatggt gaaaccccgt ctctagtaaa aatacaaata  21600
ttagctgggc atggtggtgc aacctgaaat cccagctact tgggagacct agctgggagg  21660
atcgcttgaa cctggtagga ggagtttgca gtgagctgaa attgtgccac tgcactctag  21720
cctgggcaac agagtgagac tctgtctcaa aaaataaata aataaaaaga gaaaaaagtg  21780
```

-continued ttgcctgcag gccgggcaca gtggctcacg cctgtaatcc caacactttg ggaggccgag 21840
atgggcagat cacctgaggt caggagtgca agaacagcct ggccaacatg gtgaaacccc 21900
atctctacta aaaatacaaa agttagctgg gtgtgtacat gtagtctcag ctacttggga 21960
agctgaggca ggagaatctc ttcaaccggg gaggtggagg ttgcgatgag ctgagatcac 22020
gccaccacac tccatccagc ctgggtgaca gagtgagact ccatctcaaa gcaaaaaaag 22080
aaacataggt gggacccttg gtgtgtcctt agggcatgat ggttgaggta tactgctggt 22140
cctgtcatgt aaaagaaaac gagccgactc tgtgtctact ggagaaagca ctgcatatat 22200
cagccacagt caatacctcg cttctgcagg gacggtggct gccagagtgg gaggctttgg 22260
tagcacccat gtcgtggaat cacaatgttg tcgatagctc tggggtcttg tacaaaatgc 22320
cagatcctcc catttggttt ccttatggga aggatcgcag tactataata catgggcttg 22380
tgcaagggat cattataccc ttttctcttt ttttgctttt ctttgagaca gagtttcact 22440
ctcgtcaccc aggctggagt gcaatggcgc gatcttggct cactgcaacc tccacctcct 22500
gggttcaagt gattttcctg gctcagcctt ctgagtagct gggattacac atgcccgcca 22560
ccaggcctga cttatttttg tatttttagt agagacaggg tttcaccaag ttggtcaggc 22620
tggtcttgaa ctcctgacct caggtgatcc acccacctcg gcctcccaaa gtgttgggat 22680
ttcaggcata agccaccagg cccagccttt ctttcttttt aaaattaatc tttgtttaaa 22740
aatactctca ttttttattt aattgtagca ctcctagatc ccgaaagcag atacactctt 22800
gttatgggtc tgattctttt cattgcttca cgccttagag gatattgtcc aatactggat 22860
aaaagtttac tcaggtctac ttccacttta acggggatgg ctgaatatct cttccacttg 22920
gctgtttgtt tataatgaac tgacaaacat acaaattttc ttgagttctg tgagacattc 22980
tagtaaatca tctaacctga agagcaggtt gtgagaaccc ctgatttaga aagcccagtg 23040
gtcataaata taagtggctc tggactggct cccggggtct gaagtgtggg cagtcggtta 23100
ggattgagcc cttgtaattt gtaggatctg acacacactc caggaaggca gtgtcagaat 23160
ttacctgtat tatattggac acccagttag cgtttggaga attggttgct ggtatagaaa 23220
aataccaaat attttatgtc aggggagtga aagaaaaaac aaaaacccgg ccgggcgcgg 23280
tggctcacgc ctgtcatccc agcactttgg gaggccgaga cgggcggatc acgaggtcag 23340
gagatcgaga ccatcctggc taacacggtg aaaccccatc tctactaaaa atacaaaaat 23400
tagccgggcg tggtggcgcg cgcctgtagt cccagctact cgggaggctg aggcaggaga 23460
atggcgtgaa cccgggaggc ggagcttgca gtgagcccag atcgcgccac cgcactccag 23520
cctgggcgac agagcgagac tccgtctcaa aaaaaaaaaa caaaaaaaaa aaacaaaaaa 23580
aaaaaaccca tacactttaa ggaaagcaac tgacagcatt tgttaccagt gataaaattt 23640
gagctttgaa gtaagaataa caattttgcc attgtgcccg ggccaagaaa aaaaaaagaa 23700
ttttgccatt gtgaaaggct tcccagtact ttctgatgag cttgacggtg atattaacaa 23760
ataacttttt tttttttttt ttgagatggg gtcttgctct gtcacccagg ctggagtgca 23820
gtggttcaat ctcagctcac tgcaacctcc gcctcccagg ttcaagcgat tctcctgcct 23880
caacgtccca agtcgctgga ctacaggtgt gcgccaccac gtccagataa tttttgtatt 23940
tttagtagag atggggtttc accatgttgc ccagactggt ctcaaactcg tgacctcagg 24000
cgacccgccc acctcggcct cccaaaggtg ggaggccttg ctgggattag aggtatgagc 24060
cgctgcacct ggcctcttgt ccttgtgttt tgcagtgatg caatgaccat gtcttacatt 24120

-continued

```
tgcaaccaga aaaaaaggtt agtgtaacaa tgtttatcct gtttttccca gagtagacat  24180
tatgaagatt aaaaaaattt gaaagtgttt tgaatataat aaactatgct atacacacaa  24240
cattttggtg actagaaata caagtttatt gtttgttgtt tgttgagaca gggccctgct  24300
ctgtctccca ggctgggtgg cacaatcatg gctcactaca gtcttgaact cctgggctta  24360
agcgatcctc ccacctcagc ctccagagta gctgggactg caaacgagca ccaccacgcc  24420
tggctaatat ttgtattttt tgtagagatg gggtttcacc atgttgccca gactggtctc  24480
aaactcctgg gctcaagcaa tgctcctgcc tcggcctccc aaagtgctgg gatcacaagt  24540
atgagccact gcacccggct gagtttctgt tgttttaagc cgcttcattt gtggtacttc  24600
ttacagcagt cccaggaaac tgagcaactg cagaacatca aaattgtttt tcttcagcaa  24660
aaggagaagc acttgtggtt ggcaccagct tttcctgtgc tcacttctgc atggccgcac  24720
ctttgcccga cacgagtgca cagcaggctg tgggggagca actggttgag tcaggcctcc  24780
acttgtgccg tatccccacc tgctttgctg gacacccctg tttggggggc acccactgct  24840
gccccagaca ccaagcaagc accagctgtg tccaaaactt acagtcactg tcttggcccg  24900
ttttgtgctg ctgtaacaga atgccacaga ctgggtaatt taatacagaa cagaaattta  24960
tttcctcaaa gttttggagg ctgggaagtc caagagcaag gggccatcag gtcagggcct  25020
ggtctctgct tccacgatgg caccttgacc accgtgtcct cacgtggtca gagagagccc  25080
actcccagga gccctttttaa tagagcagaa cactgctgcg ctgcggttaa gtttccaaca  25140
cgtgaacttc ggaggtgaca cattcagatc atagcagtca ctctaggcag agtgtctgat  25200
gtggttttaa aatacgttca cagactggcc gggcactgta gctcacgtct gtaatcccaa  25260
cagtttggga ggccaaggtg ggtggatcac ctgaggtcag gagttcaaga ccagcctcac  25320
caacatggtg aaaccccatc tctactaaaa atacaaaatt agccaggtgg tgcatgcctg  25380
taatcccagc tactcgggag gccgaggctg gagaatcgct tgaatccagg aggtggaggt  25440
tacagtgagt cgagatcatg ccattgcact ccagcctggg caacaagagc gaaactctgt  25500
ctcaaaaaat aaaataaaat aaaatacatt cacaaggccg ggcactgtgg ctcacgcctg  25560
taatcccagc tacttgggag actgaggcag gagaatcgct tataacctgg gaggtggagg  25620
ttgcagtgag ctgagatcac accgctacac tctagcttgg gcaacaagag tgaaactccg  25680
tctcaaaaaa gtaaaataag gccctgcagg catggtggcc cacacctgta atcccagcac  25740
tttaggaggc caaggcggtc ggatcacgag gtcaggagtt cgagaccagc ctggccaaca  25800
tgatgaaacc ccgtctctac tagcctagcc aacatgggga aaccctgtct ctactaaaaa  25860
tacaaaaatt agccgggcat ggtggtgcgt gcctgtaatc ccagctactc aggaggctga  25920
ggcaggagaa tcgcttgaac ccaggaagca gagggtgcag tgagccaaga ttgcgccgct  25980
gctctctagc ctgggcgaca gagcgagact ccatctctaa ataaataaat aaaataagaa  26040
aataaaatat gttcacaaat cctttgacat tcctcacctc aaaagctgga acccaactcc  26100
ctcctaagca tgagtcttct cagtgactca cttctaacag cagaacttac atggttcccc  26160
acacccagag gacattgggt tcctcccaat atccccccac ccagcgaccc ccacccaggt  26220
cgctggcttt gggtccccca gagccatgtt tcaaggacac tcaggcagcc cctggatgtc  26280
catgtggtaa ggaatgaagg cctcctgcct gcagcctcgg gagggagcat tctcagaaga  26340
ggatgcccca cctcctgccc agccttcaga tggccaggac ctcgtccaac gtcctgactg  26400
caacatcatg agagactccg agccagaaac ccccaggttt tgtactcctg acttatggga  26460
actgacagat aatgttcgtt gttaattaag gggtgacttg tcacacacaa taggtcacta  26520
```

-continued

```
aacagctctg tctggcctcc caggaggagc ctgcctttcc ttttcttcat gggaaaagtg  26580
cgatcagttt gtgaaggaat gtccgccccc acttgatgcc agaggctcca catggtgact  26640
gtcataaact ccatctgccc tcagtgcctt gccagcaccc ggcctgcgat cagcttggtc  26700
ttgcgggagg ccaaggccca cgtgtgtttg tgtgtggtgt ctgtgtctgc gtgcccatgc  26760
atgcccaggg tacagggatg ccatatacaa attctttcaa tgttgtatgt ggcatgtgtg  26820
tgtctgtatg cccaggatac agggatgcta tatacaaact ctgtttttc gtttttttt  26880
ttttgagaca gagtcttgct gtttcgccca ggccggactg cagtggcgct atctcggctc  26940
actgcaagct ccacctcccg ggttcacgcc atcctcctgc ctcagcctcc tgagtagctg  27000
gaactacagg cgcccgccac cacacccggc taattttttg tatttttagt agagacgggg  27060
tttcaccatg ttagccagga tggtcttgat ctcctgacct cgtgatccac ccgcctcagc  27120
ctcccaaagt gctgggatta caggcatgag ccaccacgcc tggcctacaa actctttctt  27180
ttttttttt tttttttga gatggagtct cactgtcttc caggctggag tgcagtgatg  27240
cgatctcagc tcactgcaag ctccacctcc cgggttcatg ccattctcct gcctcagcct  27300
cccaagtagc tgggactaca ggcacacacc accacgccca gctaattttt tgtgttttta  27360
gcagagatgg ggtttcacca tgttagccag gatggtctcg atctcctgac ctcgtgatcc  27420
gcccgcctcg gcctcccaaa gtgctgggat tacaggcgtg agccactgcg cccagcctgc  27480
aaactctttc aatgtctttc ttttctctct cctgccatct tctcccttgc agatttcttt  27540
tgtctctacg tcttccccag ctgagtccga ggtcctgact tgcccacgct ccctggactg  27600
gaggagaggt gatagcaaga gctccttcaa gcccaggaat gccaccaggg ctgccccggg  27660
agaggaggaa gctgggtctc tcggggttgt ggggaccaga cacccttcta agacatggac  27720
tcagcacaga aagtctagac atccactaca aacacatctc cctcctaaca gggggcccct  27780
gggcacccca agtggctgtt tggtgggaca ggcatgtcca tcagtcagaa tatctttatt  27840
ttttattttt tattttttat ttttgagaga gtttcactgg agtgcaatgg cacgatctca  27900
gctccctaca acctccgcct cccaggttca agcgattctc ctgcctcagc ctgccacgta  27960
gctgggatta caggtgtgag ccaccacacc cagctaattt ttttttttt tttttgagat  28020
ggagtctcga ggctctgtcg cccaggctgg agtgcagagg cgcgatctca gctcactgaa  28080
agctccgcct cctgggttca cgccattctc ctgcctcagc ctcccgagta gctgggatta  28140
caggcatgag ccaccgcgcc cggccaattt tgtattttta gtagagacag ggtttcacca  28200
tgttggtcag gctggtcttg aactcctgac ctcaggtgat ccacctccct cggcctccca  28260
aagtgctggg attacaggcc tgagccacca cgcccagccc agaatgtctt cttacttttt  28320
attactctgt cccccatcct gggtccagac ctgtgaccgt gaacaaccgg ctgcccaggg  28380
gtgaatgggg tgagtggggt gagtccacag aacagtgggg tgcagcccca ggggtctcgt  28440
agcacctgcc cccaggtcag gaagtcccac agcctagagg ctccagcctc agatgcatac  28500
atatgtaggc cctgcccttt cctcctgagc ggcgggccac agagtcctga acaacaggaa  28560
gcccctgagg agggctccgc cctgagggag ggcaggggag cccccgccag ccccacccac  28620
agcagcgggc cctgccaccc cccaccctga cacctcaccc cttggattcc agagaggaaa  28680
gtgggcttgt gtgtagttta catgctcata tcttaaaatc accgttgtca atagaacaat  28740
tcataataat gatgataaaa taagatttat aaccagcttc agtctggaga tacacacaga  28800
gcagatcttc actcccagac agggagcccg cagctgcccc cgaccccaca ggtgcaggac  28860
```

-continued

```
acacacagac agttcaacca tgtcttaaac acacaggtgt ttatttaatt gttcatttga  28920
ttgaattttt aagttcactt tactacgtgg atgagatggg tgcatattac agtaggcttt  28980
cgctatgagc gctgccacca tgaggaatat cccagccctc agttctgctt ccctttctga  29040
gtcccacaaa agccagatgt ggacagcctt gggttcccat cccagctggc tgctccttct  29100
ggggctgtct tggtggggag agggagatgg ggcagtgggt ccctgctgac cctgagccc  29160
tgcaggggtc aggatcctcc cgtggtccct gggtgtggct ctggaagaca ctggcagtgc  29220
ccggccaagg cctcccgcag gatggaagtt gagggccctg gctctgggtc ctaagagaac  29280
tcagccgccc ccttcacact ttacagcaag gggccaggca gcagctttgg gatggggctt  29340
ccgtggagaa gtgggggatg ctgcagtggt acaaagacag cctcccccac cgccatcctc  29400
cagctgaccg tcctccaagg ccagcactgg gcgtccaagg gaaagaagga actcagccca  29460
gagggtgtgg gcaggagagg cctggagtca ggcctccacc cacagccccc tctgggtgcc  29520
aagtgggaag ggtgttgggg ctggcttggg aaccttaccc gctgcccttc caacacctgg  29580
atctgtgggc agcggtccca caaaatcccc cttggggctc cctgaggagg acttgtggct  29640
gccgcttcca ccagggcaga gggcacagga ggggccagca ctccaaaggg ctctagggtg  29700
ggtctttcaa ggacatctgc aaagccctgg tggggagggg cctgggccag aggctctttg  29760
gaactcttgc acttctgagt gggggactgt ccatgctgcc cacaacctct agaccatgca  29820
gcctgctcat gggtccctgg cagagaatgc ccactcccca gcagactcag ggcaggcccc  29880
caactgcagg cttccaggaa ggcccagggt gtccacctca cgccaggtgg tctcagagga  29940
cccctgtgca accacattaa ggaaagctgc agcccccacc cacccgcctg ccagttcaac  30000
aagcaccggc tgcacacgca ggctcccagg caccatcacc cccctccccc gtcgcccctc  30060
cctcacgggg agccccttcc ccctggaaag acagcaggta ctgtagcctc gcctgctggc  30120
caggggcgcc ggctcagagg acctgccctg acctgcacgt gctgaccaga cagcccagcg  30180
taaggacccg cgatcccacg ccaccgccct gggtttacca cggtcaccac cacctctctc  30240
acagggcccc cgggggaccc agccgcgccc ggcctggtgt ctgcaccgag ggaccgcgtc  30300
tcacgcccgg cggctcctgc aggggaagcc gtggtcagcg actcaccacg aggacagggc  30360
agggcggctg agtgcggaag agaagcatga agctgggggc gggggtgggg gaggaggaac  30420
aaaagttgca tctagacaga ggtgaacgaa acaaaaccaa aacccgaacg tgttccgtcg  30480
caggatgggc gccgcccgtc ccgggccctt agcccgacat ctcttctcgc tgctccttgt  30540
tcctgcgcac ctcggccgcg tgcagctcct gcaggacagg gggcgggagg gcctgagggc  30600
gggggtggct tggggcgact ccgggaaccc ccaggcgcgc aggccgtggc gccctggcac  30660
ccgcccggcc tcatccgggc tggccttcgg caggaccctg actgagttga gggggcggga  30720
gcaccgggga ggcgcagagc aaggccaggg accaaggacg ggtttcctgg gagctggctg  30780
ggccccgctt ctagctcgta ccggagccga gcttccttca gggcactttc aatataatga  30840
atttagccat ctattactgc ggctagttac tgtcccgcca ggaccagact ctggacctgc  30900
ctcgtgcgct gctggggacg cccagtaaac acgggaggag cccccgaccc ccaccccagc  30960
tcagcgcctc ggagtccccg gccccgctct gcgcccctcc gagctccgcc ctagccccgc  31020
ccccgcccag tgccccgccc cctgcctgct gctagccctg cccccgcccc ggcccctgcc  31080
cgctccgagc tccgccctgg ccccgccccg gcccctgccc gctccgagct ccgccctggc  31140
cccgcccccc gcccagtgcc ccgccccctg cctgctgcta gccctgcccc cgccccggcc  31200
cctgcccgct ccgagctccg ccccggcccc gccccggccc ctgcccgctc cgagctccgc  31260
```

-continued

```
cctggccccg cccccgccca gtgccccgcc ccctgactgc tgctagccct gcccccgccc  31320
cggcccctgc ccgctccgag ctccgccccg gccccgcccc ggcccctgcc cgctccgagc  31380
tccgccccgg ccccgccccg gcccctgccc gctccgagct tcgccccggc cccgccccgg  31440
cccctgcccg ctccgagctc cgccccggcc ccgcccccgc accttctcgc gcagccgctc  31500
gcgcagtgcg gccaggtgtg cctcgcggat ctccttgctg agctccatct tgtagttgag  31560
cttctcctcc gcctggcggc tgaagttgtt attctcctcc agcgccttgt gcagcacctc  31620
gcgctcgtgc tcgcgccgct ccgccagctg cttcagcacc tgcgcctcct gcgtctgtgc  31680
ggggccggcg ggcgcgcgtg agcggcaacc ccgggccctg cccggccgga ctcctccctg  31740
ctctccgcct cccgcccagc gcccgctcgc ctcacctggc gcctccacct gcccaggcct  31800
cggtgggcgc cgggaccccc gggcgctgcc ctgggaaccc tcgcctgcca tccggcctgt  31860
ggtcggggca gggccagggg gtcgcgatcc gccgccccg cccccgtccc tgcctcgcgc  31920
gcgggtcccg cggtcctggc tgcgcccagg gcccccgcca taccctgccg ccactgcaca  31980
ccctgccctg cgcgtctgcc cctccaagga ccagcagcaa gaaaccctaa acttgtgggc  32040
ggtctctgag ctttgtctct tcctcggaca tccgcccact gagcagagta gctgcttgtt  32100
acacaccggg ttcccagctc ccaattaggt gcccaggagc ggagggtccc cagggatgct  32160
gggggagggg ccggctggtg accccctggga ggagagcggg gcagcaggac ccgcacccac  32220
atgccagtcc ctactagtca gccctgtgaa ccctggtctc tggcctcacc gggaagggaa  32280
cggagccgct tcccctgccc aatgcgttgg cctccagggt ggcaccccca aaaggacatt  32340
tttatctctg tttcagtctc agaggggctg gtgggagggg aggctgcagg gaggggacct  32400
ggagcccaca cccacctctc ccagggcccc tccgccctcc agcaagcctc agggtcttca  32460
cacatgaggc ccttcctcca gcttccctgt ctgggagagg gatgccccac ccgacgtccc  32520
cagggcccat ctggggacca ccccctagca tcctgctggc cctgacaagg gtgcctccca  32580
ccctcaccag aggctcctgc tccttccagg tggccgcctc ggaacccttc ctcctctcca  32640
tccctttctt tttttgttct tgtttgtttt ttgaaatgga gtctcaccct gtcgcccggg  32700
ctgaggagtg cagtggcgca gtctcggctc actgcatcct ccacttcttg ggttcaagca  32760
attcccctgc ctcagactcc ctagtaggtg ggattacagg tgtgcaccac cacacctggc  32820
taattttgta tttttagtac agatggggtt tcaccatgtt ggccaggctg atcttgaact  32880
tccaacctca agtgatctgc ctgcctcagc ttcccaaagt tctgggatta caggcgtgag  32940
ccaccacacc cggcctctcc ccatcccatt cttatctctc agaaagaggc ccagggagcc  33000
acagcccctc ctgctccagg ccaaggcact gaccaagcct gtccgggagc accctgcttc  33060
ttgcaggccc tgtccccgtg ggccgcctcc gttgaaactc ctgggggtg ggggatggag  33120
gactccttgc cttcctccgc tcctcggctg cctccagccg cttttgcagc tcctccaggg  33180
aggtgtcctt cttcttgggt ggggaggaga gcatagggct ctctggggac aggtcagaag  33240
gggacttgag gatgacctcg aagctctggc ctgaggcccg cttgtccagc tgcttcacct  33300
ccatgtctgc agggcaagac cagagtagag cttcagaggc ccggccaggg catggcgtgg  33360
gctgagcggg atgctcccag cacacatcca accccagggc tgggcgagag ggggtggctg  33420
ctcccgcagg aatcccaggc ttcagccccc aggatgggcc ccttccccct agaacctccc  33480
tctccagagg cagccaggac gggagttcag agagactgcc ggaggccggg ggaaaaggtg  33540
aggtgggcag gcaccgcagg gaagggcagg cggcagccag gcactcaccc ccgtactggt  33600
```

-continued

```
agacggtatt ggggtgcggc tgtgtgtaga agcaggagca gatgagcgac agcaccgaca  33660
gctccttcat cttctccttg taggctgtgg gcacaaggct gggctgagca agcaccactg  33720
gggcctgccc acctgggccc ccgttttccc tccccatggc tgcctctatc atgtctctgt  33780
gagacacgga gctgcccagc acgctctctt gtgtgtctcc acaccgccgg cccccttcgtc  33840
tctccagctc tctcgcttcc agacgtcggc actgtctccg tggtgtgtcc cctgccttct  33900
gtctctctcg ccctctgcct ctccccgctt ttcctctctc tcggcattaa tgtctgtctc  33960
atcttccaca ctgacttgtt tctccatcct tctcctgcct gctgtggtct gaatgtttcc  34020
attacccaaa actcatgtgt tgaaatcgta accccaaggt gccggtgtgc ggaggtgagg  34080
cattcggagg gaattaggcc atgaggatag agccctccta agtggcccca gagtggggct  34140
tcagagaact ccctcacctt ccatcatgtg aggacacagc cagaagacgc cacccgtcta  34200
tgtaccagga ggcgagacct ctccaggcac cgactctgcc ggcaccttga tcctggactt  34260
tctggcctcc agagcgatgg gaaataagtt cctgtcgtct ataaaccact cagtctcagg  34320
tacctgccca gactgacaaa gtggctaccc ctgcctgtct gggtctctgt ttaccttctg  34380
tgtgtctgac tctgtcactg tcattgtatc tttctgtgtc tctgggggta gcccctgact  34440
ctgtctttct ccctgagtgc atctttctgt gattccttgt cactgtgtgt ctttctgact  34500
cttacctccc tctgtcccgc tacttctctc tcccctcctc ctccttccca ctcctcgcca  34560
gctcaagcag gcaagattta ctcatgacgg gaccagcaca gatgcaaacc ctctgtgggc  34620
aggactttct tgggctgtaa acctggatga agccctcaga ccctcctttt tccttcccaa  34680
tgattgtgtg gtcaccttga gatgaaacca ggccctctcc aggcacatgc tctctgtcta  34740
tctagggctg ggcttgggcc actgatgcca ccaaggagca agggagggaa gctgtccgtt  34800
cagcaccaca gccagccctc ttgcccattc aggtcaatca agtgcccacc agccagtgtc  34860
cctgctgccc aacccaaacc agaagcaagc cgggctcctg tggccctgtg ccctgtcagg  34920
ggaagaggaa ggcgcctgct gtcacagtga aaataattta gctcttttgg tctattcagg  34980
gcgaacctca ttcctaagca gacacgctgg cccggtttct cactagtgct cgataatcct  35040
tttggctggg tgcagtggct catttaactg taatcccagc actttgggag gccaaggcag  35100
gtggaacacc tgaggtcagg agtttgagac cagcctgacc aacatggtga aacccgatct  35160
ctactaaaaa tataaaaatt agccaggcgt ggtggcaggc acctgtaatc ctagctactt  35220
gggaggctga ggcaggagaa tcgcttgaac ctgggaggcg gaggttgcag tgagccgagg  35280
tcgcgccatc gcactccagc ctgggtgaca gtgtgagact ccgtctcaaa acagaaagaa  35340
aaagagagag aggaagaaag gaaggaggga gggagggagg aaaagaagaa aggaaaggaa  35400
aggaagacag acaaggcaga agtaatcaag cctttcatgg tgagctgggt cttctggtga  35460
cagtgcagag aatggtctgt cctgacttaa atttcctggt gacctacact tttctggaca  35520
gagcagcaca gagcccaaga gggtgtaagg aggagcagaa aggaatccca gggtgggcag  35580
gcccgtgcga gagcctttgg gggaaggaat gagactttga gccgggaagc gaggcaaagc  35640
tacctgtctt ggtcattgtc ttcagggagg gagatggagg gggaccaggt gggggagcct  35700
cacaggggac tttggtctga cttgtcaagt tttctttttt tctttttgag atggagtctt  35760
gcactgttgc ccaggctgca gtgcagtggt gcgatctcgg ctcaccgcaa gctccgcctc  35820
ctgggttcac accattctcc tgcctcagcc tcccgagtag ctgggaccac aggcaccgcc  35880
accacaccca gctaattttt tgtattttta gtagagacgg ggtttcacta tattagccag  35940
gatagtctcg atctcctgac ctcgtgatcc gcccgcctcg acctcccaaa gtgctgggat  36000
```

-continued

```
tacaggtgtg agccactgtg cctggcctac tttatttttt agaaacagga ctgtgctctg  36060
ttgcccatgc tggagtgtag ggtgcagctg tgcggttcac tgcagccttg aacttctggg  36120
cttgacggat cctgccatct tagcagctgg gactacaggt gcatgccagc acaccagttt  36180
tctttttttt tttatctctg ctcactgcaa ttccgcctcc tgggttctag cgattctcct  36240
gcctcagcct cccaagtagc agggattaca cgcacatgcc accacacccg gctaattttt  36300
gtatttttag tagagacagg gtttcactat gttggtcagg ctggtcttga gccaccgcgc  36360
ccgcccggcc tacacaccag cttaaaaaaa agaaaaaaat agctgggcgt ggtggctcat  36420
gcctgtaatc ccagcacttt gggaggctga ggcaggcaga tcacctgagg tcaggagttc  36480
aagaccaacc tggccaacat ggcgaaaccc tgtctctact acaaatataa aaatcagcca  36540
ggcgtggtgg cgggctcctc taattccagc tacttgggag gctgaggcag gagaatcact  36600
tgaacccggg aggtggaggt tgaagtgagc caagatcgag ctactgcact ccagcctggg  36660
agcaagactc ccgtctcaaa aaaaaaaaaa aaatttgtag tggtatggag gccgggcatg  36720
gtggctcacg cctgtaatcc cagaactttg aggggccaag gcgggcagat catgaggtca  36780
ggagttcgag accagcctga ccaacatgat gaaaccctgt ctctactaaa aataacaaaa  36840
attagccagg catggtggcg ggcacgtgta gtcccagcta ctcgggagac tgagacggga  36900
gaatcgcttg aacccaggag gcagaggttg cagtgagctg agatcacgcc actgcactcc  36960
agcctgggtg acagagtgag actctgtctc aaaaacaaac acaaacaaac atatatatat  37020
atacatgtat atatataata tatatatacg tatatataca cgtgtatata tataatatat  37080
atacgtatat atacacgtgt atatataata tatatacgta tatatgtata tattaatata  37140
tatacgtata tatacacgtg tatatattaa tatatatacg tatatataca cgtgtgtata  37200
tattaatata tatacgtata tatgtgtgtg tgtgtatata tatatgtata tatatatata  37260
tatatacata tatatataca gagagagaga gagtagtgat aggtcttgct gtcttgtcca  37320
ggctgatctt gaactcccgg cctcaagaga ccctcccacc tcagcctccc aaagcactag  37380
gattataggt gtaagccaca gtacctagcc tattaaaaat taatgttaaa caagaggatg  37440
tgatgaggga gttagagggt gtgccagcca tgtgttccac agcagcaggt caggagacat  37500
tggggacatt tagaggagct gaagaggtgg ccaaccctgt gctcaggagg acgggggagg  37560
gagagagcaa gagggagttt gggctggggc agaacgtacc tgggtcctga gaggataaga  37620
aggtagggac ttggcccctc caggcctgac tctgccagca accagctccc tatcagcaga  37680
ctccaggccc ctacccttca gctcatcctt ccttatcaca catccaaaac tctgaatgtg  37740
gccgggcgca gtggctcacg cctgtaatcc cagaactttg ggaggctgag gcaggaggat  37800
cgcttgagaa caagagtttg agaccagcct aggcaacatg gtgaaacccc atctctacta  37860
aaaatataaa aattagctgg gtgtggtggc acatgcctgt tgccccagct actcaggagg  37920
ctgaggcagg agaatcactt gagcctggaa ggcggaagtt gtagtgagca gagattgtgc  37980
cactgcgttc cagcctgggc aacacagcga gactctgtct caaaaaacaa aaactggaat  38040
gtgtttacca taaaggccag aaaatgtgat taacagctgc tcaaagcccc tgtctgccct  38100
aagcctgaaa ttttcaccga aaaaaagatc tgtaggctca tacagaggaa ggacaaacac  38160
cagggaggct ctcttccagt ttgcttcacc tcagcaagca gacggctggc agcaatttgg  38220
gggcaggtgt gagcacctgc atcatcagga aagaaggggc acggtgggga cgcaggtcag  38280
acctctcaca ggtcttggct ctgcccagga gacacgtgtc caactgagag gtgaggaact  38340
```

-continued

```
gggttctgca gctgcagaca caggtgcggc tcagcatctg atggccacgg agacccccctg  38400
gcttggcttc tcccagctgg tggcccatga ggagcttcta tcccaagaga ctgtccctca  38460
aggagcaagt gggaccaggt acccacagga cggagcctgg gagtgaggcc tgccctgtgg  38520
tctggctaca gggaggaagg gcagattgga gggggcagga cagcaggtca ggaattggcc  38580
aactctggag agagcaagca aggggaagtc tgcgcacagg gcagggctgg tcaggggcga  38640
ggcagggcat tggaccagta ttttcagagc tggtgaggct taaagagcat gtctactgcc  38700
tcttattaca gagagaggat gccgaggccc agacccatcc aggccacctc tccacagaca  38760
cagctggtgc cagggaagcc cctcccagag cctcaaggca ttgctccctc tctctctctc  38820
tttttgtttt tttggagacg gagtctcact ctgtctccca ggctggagtg cagtggtaca  38880
atctcggctc acggcaagct ccgcctcccg gattcacgcc attctcctgc ctcagcctcc  38940
cgaatagctg ggactacagg cgcccgccac cacgcccagc taattttttg tatttttagt  39000
agagacgggg tttcactgtg ttagccagga tggtctcgat ctcctgacct tgtgatccgc  39060
ccgtctcagc ctcccaaagt gctgggatta caggtgtgag ccaccgcgcc tggacttttt  39120
ttttttttta agacggggtc tcactctgtc acccaggctg gagtgcagtg gcgcgatgtc  39180
ggctcactgc aacctctgcc tccccagttc aagtgattct cctgcctcag cctcccaagt  39240
agctagaatt acaggcacat gccaccatgc ccagctaatt ttctgtattt ttagtagaga  39300
tgaggtttca ccatgttggc caggctggtc ttgaactcct gacctccggt gatctgccca  39360
cctcagcctc ccaaagtgct gggatgacag gcgtgagccc ccgcgcctgg ccccccgcag  39420
tgctgggatt acaggcgtga gcccccgcgc ccggcccctc cctctctttg actcccttct  39480
ttctcaccgc cccctcccca ccatccttcc ccttcactga cttcagggag ttaaaaacaa  39540
ttctcgcagt gagctgggct tgttttgtct ccctgcttct ctttgtacta aacattagat  39600
accgaggaaa tgcggattgg cctttggatg attcatgagc aggagtcaga aaaaggcacc  39660
aggttggcct caagcagcag ggtatagtag tgcccgctcc cagggtcaca cctcacgccc  39720
acccctcccg ccgtccaggt ggatggtgcc cactcccagg gtcacacctc acgcccaccc  39780
ctcccgccgt ccaggtggat ggtgcccact cccagggtca cacctcacgc ccacccctcc  39840
cgtcgcccag gtggatggtg cccactccca gggtcacacc tcacgcccgc ccctcccacc  39900
cacccgggtg gatggtgccc gctcccaggg tcacacctga cgcccacccg ggtggatggt  39960
gcccgctccc agggtcacac ctcacgccca cccctcccgc ccgcccgggt ggatggtgcc  40020
cgctcccagg gtcacacctc acgcccaccc ctcccgccgt ccaggtggat ggtgcccact  40080
cccagggtca cacctcacgc ccacccctcc cgccgcccag gtggatggtg cccactccca  40140
gggtcacacc tcacacccac ccctcccgcc cacccgggtg gatgccctta tcagctctcc  40200
ttctccttct ctttcgtctt cttcgtcttc ctcctcttct ttcttctttt tttttttttt  40260
tagaaagagt ttctactctt gctgcccagg ctggagtgca atggcacaat ctcagctcac  40320
tgcaacctcc ctctccccgg gtcaagcaat tatcctgcct cagtctccca gattgctggg  40380
atcacaggag tgtgtcacca cacctggcta attttgtact tttagcagag aggggggatt  40440
tcaccatgtt ggccaggcta gtctcgaact cttgacctca gtttatccac cggcctcagc  40500
ctctcaaagt gctgggatta caggcatgag ccaccctatc tgcctcactt ctacagagga  40560
ggaatgaagg ctcagagagg gcaagcattc cacccagcat cacacagagt gccgggtgag  40620
agcccagtca tgagcctggg cctgactgca ggctcctgtt gggagctcgc ggaggtgggg  40680
gatctgtcca gaactgagag gccaggggac cacagtggcc tctgacccct ggagggccct  40740
```

-continued

```
ggaggctgct gccggctccc cccgggggca gatggaggtc actgtcaccc aggctgcttc  40800
tcatggtgcc aggagcacag catggcagga gccaccagcc gatttgcctt tccctgggca  40860
ggaaactcag aaatgtggct accacagtca ggctgcttga cgtgcggtga gcactcatct  40920
cttagcaggc aagcggccaa gcacctttcc tgaaatattg aggcctcaga acaagcccca  40980
ggagaggtgc cagcaccgtc atctctaccc agataaggag acccaggtcc tgagaggtta  41040
ggcagctcgg acaacaccac acagctggag gaggtcagac tctgggttgc agaaggagaa  41100
tgtgagcaga ggccacaaaa gagcgaggag ccagtgccca gatgccgaga tgccctcgcc  41160
ctcccagctc agccccagga accgagccca tggggaggga ccgtcaggga aaggctgtca  41220
ggaagggcag gaggcggccc tggagaggac ggcgctgccc tcaggggcag gaggggagtc  41280
ccctccgctg agagcccccc cacccccagt atccccgggg gtgtccagga ggaggcggag  41340
ggaggaagcg cagatggaca ggactcccag atagggtggg gaggtgtggc cggtgacaca  41400
cacggtcccc tcctggcagg tgctgaagtc acctggagcc tccaagcccg tggggcctga  41460
ggggcggggt caggtcgggc acgcgtgggt gggcggagtt ctgcgccccg ggccaaggcg  41520
cccgagttga accagtcagc tcgggagagg gaccgcggcg acctgtcccg ggggcgtaag  41580
aaaaggtggg agggagtgcg gctcgtgaac gggggcggcg atgggaagga ggtgcggccc  41640
ttcgtcctgt cctcccaaac gtcgagtgaa aaacgaagcg ggttctgcgg cctcgcggcg  41700
gagcagagcg tttcgggaag ggcgggccca gcgtcctcgc gcccgaggtc gcccggcagc  41760
tcccctgcgt ccagaatccg ccccccgccc gggcctgcgc ccgcccctcc gcctgagctc  41820
cgcgcgggac gggccgggag gccggggtgg gcgctacctt cgaaggcggt gggtccgccc  41880
cgcgggaggt ggaggggcgg gaggggcgga gccctctggt ctccggaggg tttggggatc  41940
gcagtcgccc ctcccccatc cagaccccgc ggcgcaaagg gcagtggctt ttctggccag  42000
agcaggtggc gcgggcgtcg caaagggtgg tccccgaggc cgcagcggtg tggggggagg  42060
gcgcggtccc cctcactccg ggctccgccg tgtctggccc gccccccctcc ttcagcgccc  42120
cctccagccc ctgtgctgca ctggcgcggg gagcgccggg ttcccggctg gggctttggc  42180
agagggtccc accctctccc cgcctcccca cgaaggctct ggcggaccca gatctcgggt  42240
cgccggacgc cccagggacc ccgcccgcac atcgcgagcg cgcccacccg gtcgcgagcc  42300
cacgcccggg tctgggagcc accctgcggc agtcgcgccc tgcgtggcac gctgctcccc  42360
caggggcgag gcgcccccgc ccgacgtccc ggtcccgagc gctccccggc gcggcgcctc  42420
gcagcccagc gccccaccag ccccgccggc gccgcagacc ccagcctcgg gcgggtcggg  42480
cccaggcttg caacgcgcag ggtaggagaa gggaaattgg cgtccgctgc cggccgctgc  42540
cccaggcgag gccagacgag gcctctgctc agatcccgcc gccccacaaa gcccgtggcc  42600
ccggagccta ccggaaatgg tgctggccat ggtgctggcg gcggttgggc ctgcggaggc  42660
tggagaggcg caagtggcgg ccggagctgc agacggctgg tgctgcagtg ccggggaggg  42720
gaggggagag gagtggaggg agcgagggcg ggcgggaggc gggcgcggcg ggagagagag  42780
agggagggag acagagggag agagagagag ggttggggga aggagcgggg ggaggaggga  42840
gggagggttg ggggaaggag agagagagag agagagactg cgggggcggg ggaaggaggg  42900
agggaggaag ggagggagga agagagagag gagcaagcgc ctggctgcgg aaggggccgc  42960
ggctctcagg gggagagggc ggaggagggg ggctacccga actgcaacaa gacccccccac  43020
cctccaaccg ctcacagcgg gacagctgct tctccaactt ggctttgtga ggcctgagag  43080
```

-continued

```
tggggtgggg gtggagatga gcccccattc cccagggcag gcggggcagg ggcaatgccg  43140
gaggagcagg tcccacccat ggggtggggc cgcagagctc ttcgccgcca aggccgctgt  43200
aggctgggct ggcgccaaca gggtccaggt ctgtgcctgc catcggagag gatgccacag  43260
ccacaggggt gggcgctggc ctggaggcct ccaaggggca tctcctgtga gcccagggga  43320
tgggcaggat ctgagcggag aagagtgaaa gtggaggagt gaggccagaa caaaggcttt  43380
gccgtgaaag aggtggtttc ccgcctgggc tcagaccttc actcactgtg tggcccaggc  43440
caagggcaag cgtctgacct cgctgggcct ttgtttctca ggggtaagat gaaacaatga  43500
tgcccccaga cgatggagag gaggggtgcc agggttgtgc gcacttagtg agtggggggc  43560
aacctatcct gcctccccct ctcctcataa ctcccaaagg gaaagcctgg taggcaaacg  43620
gagcgtcttt gccattgcag ggatgaagcc accgaggcag ggagaaaagt gctttgccct  43680
acaagcaact aagtcatagg gccaggagca aaaccctgaa aacctcagga gacttgcaga  43740
gccatgaggc tggctcagca acacaaaagc caggggcaag cctcagctct agcagtgcgg  43800
tgggagcacc caaggccagt cacatcctag ggtggcctgg agagtcctga cccctgacgt  43860
gcaagccggc atcatccccg ggactgtgag tctggtgggg gtgatgccca ggaatgtgac  43920
attgtgtggc ccagaggtac ccttaagact ggaggatcac caggcgggcc ctgacctcat  43980
cacaggagcc ctttaaaagc agtttccttt gcctggttga agaaatcgga gggatcaaac  44040
caaagaaggt tttctgttgt tgagatgagg gggccacgtg gcaaggatct gagaactgct  44100
cccagccaac agccagcaag acaacaagac cttaactgca aggaagtgag ttctgccaac  44160
aagaagagaa tgggcttgga ggcaggtttg accccagggc ctccacacaa gaactgagcc  44220
caactgccca cttggtttca gccttgggtt actaagaatt aggaggtaat gaatgagagt  44280
tgttttaagc tgttggtttt gtggtgattt gctatgaagc catatcaaac taatatacac  44340
acagaggtgt tggcccctgg gccattccta ggaagccagc tctgcgaagg aggaagaagg  44400
gcagagaggc acacagagct gcccaccaca gcagctgtgt cctccctgtt ggccaccaca  44460
gtagcagttg gggatggtca gcatccttca ggcagactcc agccccgggt gctggagctc  44520
aggtgctagg gatcaagaga agtagccctc tctgggacct ccagagtctt ctcatgtggg  44580
tggggtagga cccacccagt caggctcaga gcaccgcaat gcctcacact cattgtgact  44640
ctggccaggc cctctctgag cctctgtgtc ctcatctgga gcacagggac caggtgtgtg  44700
gaagcccgtg gcatagtgcc aggaacacag tagatgtgca cagtgtgcac tagcaggaac  44760
acacaacagg ggtactgact gtcagcacct aggcaggcac acgcaatggg gtactgactg  44820
tcagccatac tgactgtcag cgtgctagca ggcatacaca acagctgtac tgacagcaca  44880
ctagcaggca catgccatag gtgtactgac tctcagtgca ctggcaggca cacgcaatag  44940
gagtaatgac agcatgctgg caggcacaca atagctgtac tgactgtttg ccccaatata  45000
gtgccaggtc ttggagcaga ttttgacttc tcaccaagat caaatgcaga aagtgcacga  45060
gcatttcaaa gatgtttttc acatgcacat tagtgctagt taaaaaaatg ttttgactgg  45120
gtgcagtggc tcacaactgt aatcccaaca ctttgggggg ccgaggtggg cagatcacct  45180
gaggtcagga gtttgagacc agcctggcca acatggtgaa accccatcta ccctaaaaat  45240
acaaaaatta gccaggtgtg gtggcaggtg cctgtaatct cagctacttt ggaggctgaa  45300
gcaggagaat cacttgaatc caggaggcag aggttgcagt gagccgagat cccaccactg  45360
cactccagcc tgggcaacaa tatcaagact ccacctcaaa aaaaaaaatg tttttcataa  45420
agtgtgactt ttatcagacc tctgcattct tgaaattaac tctggcttgg ctgggcgtgg  45480
```

-continued

```
tggcccacac ctgtaatctt aacactttgg gaggctgagg tgggcagatc acgaggtcag  45540
gagttcaaga ccagcctgac caacatgatg aaaccccatc tctactaaaa atacaaaaat  45600
tagccgggcg tggtggcatg cacctgtaat cccagctact caggaggctg aggcaggaga  45660
atcgcttgaa cccaggaggt ggaggttgca gggagccgag atcgcaccac tctattccag  45720
cctgggcgac agagcaagac tctgtctcaa aaaaaaaaaa gaaagaaaga aattaactct  45780
ggctcctaga aggagcccta tatctcagca ggacactcag tcattcaaca gacatctgtc  45840
aagcacctgc tgtatgctgg agctgtgggt acgtcagcaa ttagaggaag agggcagggg  45900
tacaggagtt cctgaccacc ccaggccagc acgctcctat agcagctggc aaggagcaga  45960
tgactcagac ttcagctcag tccacaggac agccttttct ggccactgct ctcaggagat  46020
gagatgtgtg gctgcaaaag gtaaactcct ggctcctgag caggctctgg gcaatctgct  46080
caacgctctg tgcctcactt tctcacccag aaagtgtgga caatgagagg acttatctgg  46140
ctgggcgcgg tggctcacgc ctgtaatccc agcactttgg gaggccgagg cgggtggatc  46200
acctgaggtc aggagttcaa gacctgcctg gccaacacgg tcaaactcca tctctactaa  46260
aaatataaaa aattagccgg gcttagtggt gcacacctgt aatcccagct acttgagagg  46320
ctgaggcagg agaatcactt gaacccagga ggtggaggtt gcagtgagcc aagattgtgc  46380
cactgcactc cagcctgggc aaaaagccaa aactctgtct caaagaaaaa agaatcatgg  46440
cagaaggtga agtctatgtt agtcccagtt cccaggtcgt acatggcggc aggagaaaga  46500
gagagagaag gggaaactgc cacttttaaa ccatcgggtc tcctgagcac tcactgtcag  46560
aacagcctgg aggaaactga ccgcatgatc caaccacctc cctccaggtc cctccctcca  46620
cacgtgggga ttacaattcg aggtgagact tgggtggaga cacagagccg aaccatatca  46680
gcatgtatgg ggggcactga aacttgtgct tggtgcccat tcattcaacg agtgtgtgtg  46740
gctggtctcc tcatcttcaa ctccctgccg agtctcagat aggcagcctg cagttccttc  46800
accacaacag gcacatgggg ctgggtgcca gtgagtgctg gggcttctcc gagcactatc  46860
tcacacccag gagcgtgggc acgcatggca ttcgcatgtg ccgtcagtgg acattaaaca  46920
cagccatgaa gaagccacga agaagtgctg cctgccggcc gtgcgcggtc acgcagcgcc  46980
aactccctcc tggggccttc tggggccttc tggggcatgg gagctggggc cgcctgagac  47040
aaacatccgt gacgctgggc tgaccccaca gaacggtgcg ggcctcgctc ttggagtcag  47100
ccctgctgcc agccagtgcc gggtgctggg gactcaggga ggcccgccgg gaccactgcg  47160
ggacagtgag ccgagcagaa gctggaacgc aggagaggaa ggagaggggg cggtcagggc  47220
tctcaggagc cgggtcctgg gcaaggcgca gccgttttca aattttcagg aaagcggtcg  47280
gctcacactc gagcagtaaa aagatgcctc tggggaggag gcccgtgcag ctctccgggc  47340
aatggtggtg gctcggccta gagaggcggt agtggaacgc agaccctggt gggggaatga  47400
catcaaggga ggagacgggc gggaccccag atttctgcct gtgggcgatg gaagtgaggt  47460
tcactggcca gcggagccgg acacagaacg cgcaaaacgc cgtgtaggcc tggaggagcc  47520
gaagagcagg cggacccccct ccgcgggggga acagtttccg ccgggagcac aaagcaacgg  47580
accggaagtg gggggcggaa gtgcagtggg ctcagcgccg actgcgcgcc tctgcccgcg  47640
aaaactctga gctggctgac agctggggac gggtggcggc cctcgactgg agtcggttga  47700
gttcctgagg gaccccggtt ctggaaggtt cgccgcggag acaagtgagc agtgagtcgc  47760
agtgacccta caagtggttc ttttacccga gcggctcgta ggcgcgttgc ggtttttcga  47820
```

-continued

```
aactacagct cccggcaggc cccaagccgc cctcggggcc gcgggtcggc ggattggccg  47880
cgctgcattt tgggacctgt agtttcctgc gctcgtggcg ctggcgccgc ggcgttggct  47940
gagcccttga ccggggctgg agggaagggc cgacattcag tgtgtccgcg tctgttctgt  48000
tagtcccagt tcccgggcgg gattgaggct tagagaagtt gagtgatttg ctgagggctg  48060
cacgggttgg catcccggca tgctctttcg ctactttggc tgcatctggt tgcccacccg  48120
ggcggatggg gaatggactc cagccagcca ggagggcaga gggctggaga ggcagggccg  48180
gaggttcaga ccctccgctc tgacgttgcg cctggtgagg ccgggagggg tgccgcttgc  48240
ctcttcagcc ctcacgctct tgtggaagtc gcggaattac tgcaggcgga acttgcagca  48300
ctgtgggcgt cttttccaga gaaggacgga gttgtggggc gggaggataa ggcaaggccc  48360
agccacttcg catcttcgcc ccgccagctc ctcgagatgg gatataccag ggttgctctc  48420
caaccctctc cgcaggaggg actgatggaa acgcctggga aagtagcccg gtacccacaa  48480
aggctgtcta caaacagagt cttactgtct ttcccaggtc tgtgccatag ggattctcga  48540
agagaacagc gttgtgtccc agtgcacatg ctcgcatcgc ttaccaggag tgcccgagac  48600
cctaagatgt tcggagtggt tttttcgcac agacccgaat agcctgcccc tcagccacgc  48660
tctgtgccct tctgagaaca ggctgatatg cccaagatag tcctgaatgg tgtgaccgta  48720
gacttccctt tccagcccta caaatgccaa caggagtaca tgaccaaggt cctggaatgt  48780
ctgcagcagg tagagcacag gccccgagga aaggactgcg ggtgggtgga gcttcagcca  48840
ggacggggtg tgcttccctc tcccggccca ttccagccag gcccctccgg gccagaggca  48900
gcgtctgtca taaaaagggc tggtgttcca ggtggggtca gagagaggat tgacaagtaa  48960
aaacgatcgt cctttgaagg gggccggccc ctccacacct gtgggtattt ctcatcaggc  49020
gggacgagag actgagaaaa tgaataagac acagagacaa agtatagaga gaaaagtggg  49080
cccaggggac cggcgctcag catacagagg acctgcaccg gcaccagtct ctgagtttcc  49140
tcagtattca ttaattacta ttttcactat ctcagcaaga ggaatgcggc aggacagcaa  49200
ggtgatagtg gggagaaggt cagcaagaaa acgtgagcaa aggaatctgg gtcacaaata  49260
agttcaaggg aaggtactat gcctggatgt gcacgtaggc tagttttatg cttttctcca  49320
cccaaacatc tcggtggagt aaagagtaac agagcagcat tgctgccaat atgtctcgcc  49380
tcctgccaca gggcggcttt tctcctatct cagaattgaa caaatgtaca atcgggtttt  49440
ataccgaaac attcagttcc caggggcagg caggagacag tggccttcct ctatctcgac  49500
tgcaagaggc tttcctcttt tactaatcct cagcacagac ccttcacggg tgttgggctg  49560
ggggactgtc aggtctttcc catcccacga ggccatattt cagactatca catggagaga  49620
aaccttgggc aatacccggc tttccagggc agaggtccct gcggctttcc gcagtgcatc  49680
gtgcccctgg tttatcgaga ctggagaatg gcgatgactt ttaccaagca tactgcctgt  49740
aaacatattg ttaacaaggc atgttctgca cagctctaga tcccttaaac cttgattcca  49800
tacaacacat gtttctgtga gctcaaggct ggggcaaagt tacagattaa cagcatctta  49860
gggcaaagca attgttcagg gtacaggtca aaatggagtg tgttatgtct tccctttcta  49920
catagacaca gtaacagtct gatctctctt ttccctacag tccttgaggg tgacagactt  49980
aggagtgcct tgggggcctc tctgaggagc agctgatatt cacgggtcag gaggaagcat  50040
ttccattaga ggggcagccg gtggccagcc tcacttggaa ggtctttgaa cctcgggggt  50100
gcagggaggt ggcagtggtg caggttgcct tctcctgggt tccttgaggt gccctcttgt  50160
acccggctca cacccttccc ctccccgagt ttcctgctca ggttcccgtc tgagagcttg  50220
```

-continued

```
tatgtaggac gtcagatagg acagcataaa tgtttggatc cagaaacgca gaacagtttc  50280
ctattttgag acttgacacc taattagtca tcttactatt taagctgaaa aatagtgtcg  50340
tgttttgggt aacgttctgc aaatcgtttg ctaatggcgg ctgagttgct tcacgccctt  50400
tagggcaaga gtgggacttg cctgtggact tctccgcggt cccacagggc tctcgccacc  50460
tggcagtggc ctctgcatct gcaaagagct gcccgctggc tgccgaagct tgtctcaggg  50520
cagcttgtgt ggcctcgcct cttcctggct tccccgtaac ccttgctccg aactccgttc  50580
agaaggtgaa tggcatcctg gagagcccta cgggtacagg gaagacgctg tgcctgctgt  50640
gcaccacgct ggcctggcga gaacacctcc gagacggcat ctctgcccgc aagattgccg  50700
agagggcgca aggagagctt ttcccggatc gggccttgtc atcctggggc aacgctgctg  50760
ctgctgctgg agaccccata ggtgacccta gttcccaggc ctctcctggc ctcctgtggg  50820
gatggttggc aagggatggc gctgagggtg gggtgggccc atggggactc ctgccgtctc  50880
tcaagcagaa ctcaaggaga attttttagc tgctgtataa tttctcgcca tcgtgggtgt  50940
aaacctaggg ttgggctttt ttgctgaatt agggcacggc agatgcccac ttcacccatt  51000
tttgataaac cagtatctgg ggtgtcagat tcttggctgt ctgcagggcc gagttagccg  51060
aatgccacct gcctttgata cgtgagaacg ttgtctgaga accgtgactt ctgtgcttgc  51120
ttgtgtctgg tcagcttgct acacggacat cccaaagatt atttacgcct ccaggaccca  51180
ctcgcaactc acacaggtca tcaacgagct tcggaacacc tcctaccggt gggtcagacg  51240
agtttacacc tgtctcgggg tcctcaagag aaccagcttg gcatggtgct gagtccacag  51300
ccccatgctg tgctgtggtg gagggtggtg gtctttctag acgctccccc gaagtgtgca  51360
gagcgctggt gcccaggggt ggggtgcggc ctgggctgcc tccaatgccc attacttgtg  51420
aggaagcagc tttgcatctg tgtgctgacc ttgggcgggc gtcctgagct cctcgcaggt  51480
gctgttgtag cagctgtgca gtaggtcagg gctggccccc agtgcagctt tgcacatgaa  51540
gtaggaggag gccctgctgc ttgtcagagc ccagcagagt cttggtgttc tgtcgggttc  51600
ctgtggccgg accagtggca gggtgctgtg gaagctgtcg aatctcctcc ctctgtccag  51660
tacccccgct cgtcttctag ctccctccta cgcccgggcc acgtttcagt tatgctcact  51720
tcctctgacc gccgaggctc ctgcgtgtct ccatacagct cacgctgcag ggccacgctg  51780
tgggtgttgg agacagctcc tcctcgaccc acggtgctct ctcccaccag gcctaaggtg  51840
tgtgtgctgg gctcccggga gcagctgtgc atccatcctg aggtgaagaa acaagagagt  51900
aaccatctac aggtaggctc ctgggctccc gctccggctc agtgtccgac aggcgagtgc  51960
tgctgggtgt ccagagcccc aggctgcgct cccgctgggc tagggtttga agttcactgg  52020
gggactgcag gggaggacct ggtgggggtg gggactggct tcggtccttt cttggccgtg  52080
cttcagctgc gcactctgcc cttcctccca cagatccact tgtgccgtaa gaaggtggca  52140
agtcgctcct gtcatttcta caacaacgta gaaggtacaa gcagctgggt gggaccaggg  52200
tcgggttgga gtgtgtgcag cctctcaggg tggagctcag tggtgtcaca gcctggttgt  52260
gcttgcccgg tggggcggcc agtgcggcca tgtacctggg ccctgtcttc tgactcgggg  52320
ccacccatgt tagacttctg tgtggaagag ctcacacagt ggtctgagac agccagccgg  52380
caagactgcc tctggctggt gcctggggcc ttggattttg ggaaggctcc ctccatttcc  52440
tgatgagagg gtctccctgc acctaacctg ctggtgcaaa cagtaggggt tttgctgaac  52500
accggctttc tcttcgggga ctttgttgct tgcccagcag caggtgctcc agtgaccggc  52560
```

-continued

```
cctcatacca tcttgggagg gtgtcctgga agccgtgtct ggcctcccgc gaccctgccc  52620
cgtgtgtctt tttcctgtgc tgaccttgct gcggaaaatt atggccctga gtgtgactcc  52680
aggctgagtc ctgtgggtcc aacacgggat gccttggggc ctcttctgga gacgggatgt  52740
gagtgacagg agccggccgg ggcagcttgc cctgtgactg cacgtggcca cagcctgtga  52800
gggccggggg tgcttctcca cccacgtggc tgcccctcgg gtatgtcaag ggcttctggg  52860
gctcatcacg gggtcctaga gacagtggca gggtgcaccc ccgttggctg cccttacagt  52920
ttctgtgacc tgagggtggc atctgtgcag tcggcgcggt ctgtgcttct gtgggatcag  52980
ggttccctct gtttcctgcc tcagttgggg ctcaagcctc aggtgaggtg gccccggagc  53040
actcagaagg catcggcggt cctgtgggct gctttctgca ctcacgtttg ctgagtgctc  53100
agtgtgccag gactgaggac cctgaagctg ctcttgtatt tagggcggcg ctcccctggc  53160
agagactgag ccaggtggtc ccgcatgacc cactaccagg cgtttctggg ccctggccct  53220
tggagggaca gggtgggcgg aacatgggcc tgcagggagg ctcccgctta ctggaggcat  53280
gtgctgtgtt gctggagaca tcctctgtgt tgcttcttgt tcgctgtggt ttttggtctg  53340
gtggcaccaa ggaccctcag tcatcttgat gtgtggttgt ccaggccttt ttgttggtcc  53400
taagaagggg ctctgccttt gtgcccccag gttccctgac aggagctgcc ggctcgtccc  53460
ggtgatgcct gcaggacgtg actctgggac ggggggttgg gcagatgtgc tgatggaaat  53520
tctcaagcag gcgtcatttc cgaggtcctc acctggattt ccaggacagg agtgcctgct  53580
gggtgtcccc agtcccatgc agcgggggtc cttgggatag catggaacgc tgagcatggg  53640
cctggccggc cgtggtcctg gacaagggca gtgccccggt ggctgctggg cctgggacct  53700
ggtggggacg ctgggcctgg tacctggtgg ggatgctggg cctgggacct ggtggggagg  53760
cctctgactg cctcctggtg ctgcttccgt ctgtgttagg cctctgggta ttggggcccc  53820
catctgtctc ctcctccagg cctgtggact cagaccagga agacacaggc cagcccctgc  53880
ctgtccccct tggcttgggc tctcactgcc cgacctggcg ggaggttgcc tagccgtgaa  53940
ccttcgcacc ctgtctgcca ccggacaggc tgtgaggggg tgtctgcagc acctgcaccg  54000
gcctgagcat cttcagagtg ggctgcagct cctggagggg tctgagagga agggaggcag  54060
gtattttggg cgaatgagga gacagctgga gagctggcac ccttcctggc ctgcgtcctg  54120
tgaggactct ggttggggac agcaagcttg gggtcagcct ggggcagagc ctctgggacg  54180
gccccgcccc tcgtgcccct tcccctcgca gctcctgtcc tcgccccgcc ctcagctctc  54240
cgccaggcaa ggtttggcaa gtgccgctgt gcggcagtgc ctgctgattg gctggtctgt  54300
tgctatggtg ctgcccaggg gtgtgctttt cctcccctgc cttccctgct atccctggga  54360
gtatctgggg ttgggtcatc gctggtgtgt gtgagtgtgt gtgtgtgtgt atgtgcacgt  54420
gtgcatatgt gtgcgcttct ggcctctgca gctgagtcct ggccctcggg gggcctggca  54480
cctcctgggg acaggcacaa agcagccatg atggagtcgg gagctggggg aggccccatt  54540
gccccacgtg gctgccctgt gactctgggg tgcttgttag aagaggtatc tggttctgtc  54600
tgtgtttaag caactcccta aggaattctt gtggttccag tttgggggc ctgtactgta  54660
gaggcaaggg aggggcagga catcccccag actctgactt ctgaagcctt ttctgcccgg  54720
ggcctctccg ccagtacagg cagtgtcctt tgccagggct gccatgctgc agaggggagt  54780
gggccactgt ttagcccagg aaaacctggc tctcccttag ctggaagttc tgggcctgtt  54840
gtggttggca gggaagctga gtgacggtgc taatcacagg ggcacctgca ggggtttgtg  54900
ggagatgcct ctgtgggttg gggcgatagg ctgagggct gttcttccct gccctgagga  54960
```

-continued

```
gggctgagtg tagccgccac tcctgtcctg tcttgggctg tctcggagag gatgcgtaga  55020
accctcggga tcctgctggc ctccgtctgg tccaccctga acctcaggcc ttctgggggc  55080
agaggaggat tccctcagga tcactcgggt gggggcctct cttgggcacc tgagaccctc  55140
agtgggtgct ttgtggcgcg ttcacggttg gtgggggacg cccagccctg cccgccgtgt  55200
aggagccgtt ctgtcctggg catccccctg tggtctggga cttagtggac cctgagggtg  55260
tgtgtttacc cctgcctcac acctgcagaa aaaagcctgg agcaggagct ggccagcccc  55320
atcctggaca ttgaggactt ggtcaagagc ggaagcaagc acaggtgaga cccctcagtg  55380
aggccacgac cactgtcctt ccatggccca gctctcctgt gacctgtgga ggcccggata  55440
tatttcttca cttttctttg ttccttttta aattatgaaa ctaaccacca ttcagtacga  55500
aaaagtttaa gcagctctga ggaagataga gtaaaaaatt gtctccctct tccctggccc  55560
tcagccatcc ccggtggcca ccgtggagtg tggacggagc cctgcaggcc tgtgtctgtg  55620
cggaagcacg cgcagttttg tctgcacaga ctgtcctgca gttggctgtt ttcactcagc  55680
gttgtgggta tagcttccca tgctggtgct ggcagctcgg ccttgttctt ttgaggacag  55740
cagatgtctc ctatgtctac ctcttacagc ttcagagatt caagttataa taaagctctt  55800
cttatattga gggggaaacc tccctccccc ttttttttga aacagggtct cgctctgcta  55860
cccaggctgc agtgcagtgt cacagtcttg gctcactgca gcctcagcct cccaggctca  55920
agcgattttc ccacctcagc ctcccaagta gccgggactg caggcacgca ccaccatgcc  55980
tggttaattt ttgtattttt tgtacagaca gggtctcact ctgttgctca ggccagtctc  56040
ctgagctcga gagttccacc tgccttggcc tcccaaagtg ctgggattac aggcgtgaga  56100
ccccatgcct ggccagctct tttttttttt tttttttttt ttgagacgga gtctcgctct  56160
gtcgcccagg ctggagtgca gtggtgcgat ctcggctcac tgcaagctcc gcctcccgag  56220
ttcacgccat tctcctgcct cagcctcccg agtagctggg actacaggtg cccgccacca  56280
cgtctggcta attttctgta tttttagtag agacggggtt tcaccgtgtt agccaggatg  56340
gtctcgatct tctgaccttg tgatccgccc acctcggcct cccaaagtgc tgggattaca  56400
ggagtgagcc accgcgcccg gcccagctct gctttttctt agtggttctg cgttgtgttt  56460
gtttctatcc aggaataggg ttggttttac ttttccatcg agtttttaaa gagacgacga  56520
tttacatggt cggaaactca cgaggactcc ccatcccttg gtcggaaact cacatggact  56580
ccccatccct tggtcagaaa ctcacgtgga ctcccatcca tcccaggcag cagcttccca  56640
cctgggccct acgtgcagga tgagggctcc ttccgggtca gaagacatgg cggcctcggg  56700
gcaccgtccc ctgcatgggg tgctcacagg atcttctcct ctctccttcc cagggtgtgc  56760
ccttactacc tgtcccggaa cctgaagcag caagccgaca tcatattcat gccgtacaat  56820
tacttgttgg atgccaaggt gggggctcag tcctgtagct gacgactcct gatgtccagg  56880
ggtgtccctg ggcttgggaa cagctgtccg agcctttgct gcttcagggc cttagatcag  56940
caggcctggg tgggaggact cacctctgtc actgggcagg ggctcaacct ggccagacac  57000
acttgtgagc agccccaggc cacaggtcag ttttctgagc agtctgggag cgggcaggct  57060
ggtgggagtg aggagagacc tccaggctgt ggtccatagg ccagtgcccg ctcttgatcc  57120
tgacagctca ggttctctcc ttcacgtcag gccatgggag gcaccgagaa cacaggaagc  57180
ccactgactc ccctcttccc agcgcgtgcc cggccccaca ctcactcccc ctcccagcat  57240
gtgcccggct tcacactcac tcccctcttc ccagtgcatg cccggcccca cactcactcc  57300
```

-continued

```
ccccacagca tgtgcccggc ctgacactca ctcccctcct cccagtgtgt gcccagcccc  57360
actcccttcc gccccgtgtg cccagcccca cgctcactcc ccccgccagc atgtgcccgg  57420
ccccacactc aactcccctc ctcccagtgt gtgcccggcc ctgctgccct cctccccatg  57480
tgccctgctt ttgtgcccca cactttttac ttagtgcagg tgggatcaca cgccacgggt  57540
caatggtttg tgtgttcacg tgacgatggc gtggtgacgt ttccagatcc cgtcgttggt  57600
tcgctcattc tcggggtgta tatttattga gagctcatca tgctgggtgc tattccaggc  57660
atagcaagac tggcttcact cacatggagc tttgattcta gtggtgggga caggtggaca  57720
gcaaaagagt aagcacgtga gctgacgata ctgaagggaa atagagcaga gggaggaggc  57780
ggagaccgag ccaagcgggc ccaagtgcga tgtcggcggg aggtggggaa tgctggtggg  57840
tctgagggga gcctcagcag gtgcagcaga gcaagggaag aggtgagtgg gggcggctgg  57900
ggggccgact cctgggaagc tgtagcagaa ccccacagag agctggtgag gtttgccgtg  57960
gttgtgggtg actcggtgct ttgagccctg gctgcccctg ggaaccatct ggagagcttc  58020
taacccaacc aggcccctcc ctgggacagt tatatcacag ctggtaagcc gagtctaaca  58080
ctttcacgga aacgcagaag atctaaaaca gcaagatgac cgtgaagaag aacagagctg  58140
gaggactcac ctcgctggtt tcaagactcc tctaaagctg caggagtgga ggtggagatg  58200
gcccagctca ggcacaggcc tgcaggccat ggagaaggca gcaagctcaa gctgacccac  58260
acgcatgtgg tcattgtttt ttttttcagt tggaatctca ctctgtcacc caggttggag  58320
tgcagtggca ccatctcggc tcactgcagc ccccgcccct aggttctagc gattctccca  58380
catcagcctc ccgagtagct gggattacag gcgtgcgcca ccatgcctgg cccttggtga  58440
ttgtttttttg acaaacatgc caatttaatt gagagaggaa atgaaggttg atttctggtt  58500
ttctgaaaaa atggtgctaa gaacagctgg atatctgttc ggaaaacagt gaatcttaac  58560
tcttgtttta ccctgtataa acctaaatgt aaaagctaaa ctaaaagtta tagaaaggaa  58620
catgggggag gtctttgcaa ctttggggta ggcagagatt tcttagtatg gatacacaag  58680
gcactagcca tgaagaaaaa cattaaaatt tagacttcac caaaatttaa agcttcaact  58740
ctgtggaaga gttgagaaaa tgaaaaagca gttaaagaaa gggagaaaat acttctttca  58800
aaggacttaa aaaatttttt cagccctcct ctgatttgaa aggacctttg accagagtat  58860
gtaaaattct cccataacta agcaaacaac ccacttaacc actgggaagg gatctggaca  58920
gacgtttcac caagatgggt ggaatggcca gttaaccact gggagagcat ccggacagac  58980
gtttcgccaa gatgggtgga atggccagtt aaccactggg agagcatccg gacagacgtt  59040
tcgccaagat gggtggaatg gccagttaac cactgggaga gcatccggac agacgtttcg  59100
ccaagatggg tggaatggcc agttaaccac tgggagagca tccggacaga cgtttcgcca  59160
agatgggtgg aatggccagt taaccactgg gagagcatcc ggacagacgt ttcgccaaga  59220
tgggtggaat ggccagttaa ccactgggag agcatccgga cagacgtttc gccaagatgg  59280
gtggaatggc cagttaacca ctgggagagc atccggacag acgtttcgcc aagatgggtg  59340
gaatggccag ttaaccactg ggagagcatc cggacagacg tttcgccaag atgggtggaa  59400
tggccagtta accactggga gagcatccgg acagacgttt cgccaagatg ggtggaatgg  59460
ccagttaacc actgggagag catccggaca gacgtttcgc caagatgggt ggaatggcca  59520
gttaaccact gggagagcat ccggacagac gtttcaccaa ggtggatgga atgaccagtt  59580
gagcacatgg aaagtcgccc agcatctcca gtcataggag aaggcagatt aaagccacgg  59640
ggagccgaca ctgtggtccc actggcatgg ctgaaattca gaagccctga gtgtggcatg  59700
```

-continued

```
aggatgtgga acagctggat ctcatccatc gctgtgaagt tgtgtagcca ctccacaaac  59760
gtgtggcaaa cagccgagcc gggagaaggg aagacgtgtt caaagattca tatgtggcca  59820
ggctcagtgg ctcacgcctg taatcccaga actttagggg ccaaggctgg gggatcgctt  59880
aagcccagga gtttgagacc agcctaggca acatagggag accccatctc aaaaaaaaaa  59940
aaaaagaaaa aagaaaagac ttcagtgtgc aggtttacca gagttttgtt tgcagttgcc  60000
aaaactggga agcagcccgc gtgagcccat ccacaggtga atggacagac cgtggtaccc  60060
gaacactaac agcagccacg ggcgtggact gtggtcacac agcagcaggg agccgatgag  60120
tctcggacat gctaacccag agaggcccat tgaggaggac ctactgtttt ttgtgttttt  60180
gtttttgtt ttgaaatgga gtctcgctct gtggtgcagg ctggagtgca gtggtgtggt  60240
cttggctcac tgcagcttcc gcctcttggg ttcaaacagt tctcctgcct cagccttccg  60300
agtagctggg actacaggca cccgccacca cacccggcta atttttgtat tttcagtaga  60360
gacggcagtt cgccatgttg gccaggctgg tcccaaactc ctgaccttgt catccactca  60420
ctttggcctc ccaaagtgct gaggttgcag gcatgaacca ccgcacccgg ctggacctac  60480
tgttttattc catttatgtg acactctatt aatagaaaag gcaggggtgg ggctggtggt  60540
tatatggtgc acataactgc cagaactcag tacacttaaa atgaacatct taatgtgtga  60600
aatttttttt tttgagacgg ggtcttgctc tgtcacccag gctagagtgc agtggtgcga  60660
tctccactca ctgcaagctc tgcctcctgg gttcacgcca ttctcctgcc tcagcctccc  60720
gagtagctgg gactacaggc gcccgccacc acgcctggct aatttttttt tttttttgt  60780
atttttagta gagacggggt ttcacagtgt tcgccaggct ggtctcgatc tcctgacctc  60840
gtgatccgcc tgcctcggcc tccgaaagtg ctgggcttgc aggcgtgagc caccatgccc  60900
ggccaatgtg tgaaaattta aaagtaccaa agctggaccc caccccagat tgctcccatg  60960
acactctgtg ggtgggacct gggagttggg ttttgttttg ttttgttttg tttttgagat  61020
gaagtctcac tctgtcgcct aggctggagt gcagtgacac aatctcggct cacattaacc  61080
tctgcctccc agatgaaagc gattctcctg cctcagcctt ctgagtagct gggattacag  61140
gcacacacca ccaccccctg ctaatttttg tatttttagt agagacgggg ttttaccatg  61200
ttggccaggc tggtcttgaa ctcctgacct cgtgatccgc ccgcctcggc ctcccaaagt  61260
gctgggatta caggcgtgag ccaccgcgcc tggctgggag ttgggtttgt aaatctccct  61320
gagtggggct ggggcaggga actgctgggt ctgggtcttc ctggctcctc tggtctgtgg  61380
cttcctgact gcggtggccg gggctcccca gggcatcgtg gccgtctgtc ttgctgagcg  61440
tggcacgtgc ctttccatgc tgtggaggag cgtctcccgg tatggcgaac tgctggttag  61500
ggtggggcgg tgttgccagg tcatccaggt ctggcctctg ctctcgacat cgccggcgct  61560
gttgctcatc tgcgcttgtg atgttcgatg cctgctgcac atgtcttggc ttccctcttt  61620
cccggcctct gtgagctcca gcgctgcgtc ccttctcttc ctcctgtaga gccgcagagc  61680
acacaacatt gacctgaagg ggacagtcgt gatctttgac gaagctcaca acgtggtgag  61740
tctccgctgg cctcctaaac acctcctatt gcttctggcc tttttgtcaa gagccacgca  61800
aacctttctg gaggggctct ggccaaactc ctgaagccct aggtgcccag gactggggac  61860
tgagcacacc aggagcttct gccacccccct cccgccctga tccgatgcct ctgctggggc  61920
tggagactgg ccagctgggc cagggacctg cccgtcaggc gcagggcccc cacaggccgc  61980
tcaccagacc ctttccctcc agccagctcg gggtcagcct gggccagggc tgtctcctct  62040
```

-continued

```
gccctcggca gcagcaggct tgtggtcttg cctgcagtgt ctctgccctt ccggccacat  62100
ggcttgagac tgaggcagga gaatcgcttg aaccttggag gcagaggctg cagtgagcca  62160
ggatcacacc actgcattcc agcctgggtg acaaagcggg attctgtgtc aaaaaaaaaa  62220
atgttgactg ggcgcgctag ctcatgccta taatcccagc actttgggag gctgaggtgg  62280
gcggatcacg aggtcaagag atcaagacca tcctggccaa catagtgaaa caccgtctct  62340
actaaaaata caaaaaaatt agctgggcgt ggtggcgtgt gcctatagtc ccagctactc  62400
aggaggctga ggcaggagaa tcactcgaac ccaggaggta gaggttgcaa tgagccaaga  62460
tcacaccact gtactccagc ctggtgacag agcaagactc cgtctcaaaa aaaataaaat  62520
caaaaagaat aattggcaat tccagtgaaa taattgtttg tttgtttgtt gagacagggt  62580
ctccttctgt cgtccaggct ggagttcagt ggtatgatct tggcccactg caacctccac  62640
ctcctgggct caagccatcc tcccacctca gcctcccgag tagccgggac tacaggtgca  62700
caccaccacg cccggctaat ttttgtattt tttgtagagg cggggtttcc cagcgttgcc  62760
caggctggtc ttgaacccct gagctcaagt gatctgccca ccttggcctc ccaaagtgct  62820
gggattacag gtgtgagcca ccgcgcccgg cctgaaacaa tcgtttctaa atattggtgt  62880
gggccacaca gtcatgtttg gacctacttg tggcctttta cagaccccag gccaaggctt  62940
tgggaacttg gctgtcagcc tcctgtgcct tctgcacccc caccccattt ctgctttctg  63000
gaacccccga tcctgtcctg ttctgtggtg attcgggtgt gcttgggctc taggagaaga  63060
tgtgtgaaga atcggcatcc tttgacctga ctccccatga cctggcttca ggactggacg  63120
tcatagacca ggtgctggag gagcagacca aggcagcgca gcagggtgag ccccacccgg  63180
agttcagcgc ggactccccc agcccaggtg cgttcatagc cagactgctt ggtcctgagg  63240
cctgcgctgc tgcagggtga gccccacccg gagttcagca cggactcccc cagcccaggt  63300
gcgttcatag ccaggctgct tggtcctgag gcccgtgcta ctgcagtggg cagcctgccc  63360
tgtggctgtg tgtggtcggc ctgggcacca tctattcagg ctggcactgc agggcatccg  63420
cttctctcag aggcttcttg ggtgtgaatt cttcagggtc ctgtagcctg tggaagggct  63480
ggtattgttc agtagttctg gtattttcca aagacctatg tcttctccca gccagtatca  63540
acttggcctc tactgtgtaa aactggaaaa ctctactttg tgaagctgag ttgggagcat  63600
cgcttgaggc caggagtttg agaccagcct gggcaacatg gcggaacctc gcccctgcca  63660
aaaaattagc caggtgtggt ggtgtgctcc tgtggtccaa gcttttctgg aggccgaagt  63720
gggaggcgtg cttgagcctg ggaggcagag cttccggtgc cccagatgac tccactgcac  63780
tccagcctgg gcggcagagt gaggccatct caaaaaaaaa aaaaaggaaa actaaatata  63840
ttcactgtaa gggcattttg catctttaaa tgacccacaa atctggcatg catcagctgc  63900
tctgcctgta ggttccttcc cagtgtttgt ccagaggtgt atttccacac agcgctagtc  63960
acggcatatg tggaaaacgt ggaaaccctt catggatgtt gtcagttggt ctatattttc  64020
tttctttttt tttttttga gatggagttt cacttttgtt gcccaggctg gagtgcaatg  64080
gcgcgatctt ggctcactgc aacctccgcc tcctgggttc aagcaattct cctgcctcag  64140
cctcccaagt agctgggatc acaggcgtgc accaccacgc ccagctaatt ttgtattttt  64200
agtagagatg gtttctccgt gttggccagg ctggtctcga actcctgacc tcacgtgatc  64260
cacccgcttc ggcctcccaa agtgctggga ttacaggcgt gagccgccac gcccggcctt  64320
tgtccatatt ttctacatgg cttctgtaaa cagctgacta ggagtctgtg tgaatatctt  64380
cataggttct gctgtgacac tacttgctcg tgagcatctc caggtgtaaa cagcatcagc  64440
```

-continued

```
ttcccccatt ttcctttaaa atcgcacatg tggacggaca ccacggggac cctggaccct  64500
ggggagcccc gtcctcaccc ttctcaccag gatggctgct tggtagagag tgagtttgca  64560
aagttggcat ttgtttagta cagaagttat caggtgttct ggctttagaa tccctttata  64620
tatatatata tatacatata tttaagtgac agggtctcac tctgttgccc aggctggaat  64680
gtggtggtac aatcaaagtt ccctgtagcc tcggcctcct gggctcatgg gatcttcccg  64740
tctcagcgtc ttaaagcgcc gggaccacag gtgtgcacca ctgccaccgg ctctcaagat  64800
tgccacgcag ggagttgcag tgggggaagg ggttcctggg actttgaacg ctccacctcc  64860
ctcctctcca cagtccccca accccacctc tctaacgggg tggacggccg cctctttcca  64920
tccttcgctt ggcgcagggt ggggagagtg acaggtctcc ttccctcatc tcggcagctg  64980
ccatttcatc gcttacataa cgtgggagaa acatccaccc acccccaggc ctgtgtgaac  65040
atcaccacgg ggccttctcc actcttcagt tttgttagtt acttgatgtg cagggctttt  65100
tgttgtaact agtgggggac gtgtggtggg gtgggcttct gccatctcat tcaggaccag  65160
aacttcagtt ttcatcccta tctgttcccc caccccttttg gagatggggt ctcactctgt  65220
cacccaggct ggagagcggt ggtgccatca cggctcactg cagcctccac ctcctgcagc  65280
ctccacctct tgggctcaag tgatcctcct gcctcggcct cccaagctcc tgggactaca  65340
ggcgtgtgcc actgtgcttg gcagggtcca ttcttttcct cacactttat ttattgaaga  65400
gcccaggccg tttaccctgc agagtcggaa tctgtacagg aggggcagcc acacgagttc  65460
cccggtttac tctgaactta ggtggcttga gggccccagt tagactgcgg ccaccgtttg  65520
ccgggctcca gatgggacgt cctttctatc agaaggctca cagtatctcc tttcccgttt  65580
cttcccatgt gaacattgtt gctgctgaac acctgaatat gttaatcact gggggcttgc  65640
aagatggcag tgtgctaatt ccatcatcta gtcagttagc aggaataact taggaccacg  65700
ccctgcacca tatcagctat gtggtgatcc cattcacaca ggaaaggtgg gacaaatgct  65760
gggggtgggc cgggtgtgct gtctcacacc tgtcatccca gcactttggg aggcccaggc  65820
aggcggatca cgaggtcaga gattgagacc atcctggcca acacggtgaa accccgtctc  65880
tactaaaaat acaaaaaaat tagccaggtg tggtggtgca tgcttgtaat cccagctact  65940
tgggaggctg aggcaggaga atcacttgaa cccaggaggc ggaggttgca gtgagccgag  66000
atcgcaccat tgcactccag cctggcaaca gagcgagact ccgtctcaaa aatcaatcag  66060
tcaatcaagt gtcatcactg aatgtttgtg tgtgaacgtg ggattggtc ctgccccatg  66120
ctccctcctg aatctcactc ctgacctcag ttgctgcacc ttgaggtgtt ttctgtgggc  66180
tcttgtgtcc tgaccccggc ggttgtggcc tctgctgtct gggagtcagg atttttcaca  66240
ctcatgtcct gctccagacc tggaatcagc caagtctcca agaagccctg ctttcttttc  66300
ctgcaagacg gtatttcaag acccgccgtg cggcagcggg ttggtcatgg ttactgggtt  66360
ggtcgttgtg actgggtgtt ttcgtggaga tacagccata cgcacaggtg tgttcacaaa  66420
tgttaattct aaaggtcaaa cacccggcca ggcataaggg ctcagcggta atcccagcac  66480
tttgggagac caagactggt ggatcacctg aggtcaggag tttaagacca gcctgagcaa  66540
cagggtgaaa ccccatctct actaaaaatg cgaaaattag ccgggcatgg tggcgcacac  66600
ctatagtccc agctagtcgg gagacagaca cgagaattgc ttgaacctgg gacatggagg  66660
ttgcagtgag cagagatggc gctgctgcac ccctgcctgg gtgacagagt gacaccctgt  66720
ctcaaaaatg aatagataaa taaagataaa acacctgctc ctcttggtgt ctccagtttg  66780
```

-continued

```
gatttggcct gtgtagcctc ttccttcgcc tgttggtgga tttggcctgc acggattctg  66840
tgtggcctct tccttcccct gttggtggat ttggcctgca cggattctgt gtggcctctt  66900
ccttcccctg ttggtggatt tggcctgcac ggattctgtg tggcctcttc cttcccctgt  66960
tggtggattt ggcctgcacg gattctgtgt ggcctcttcc ttcccctgtt ggtggatttg  67020
gcctgcacgg attctgtgtg gcctcttcct tcccctgttg gtggatttgg cctgcacgga  67080
ttctgtgtgg cctcttcctt cccatgttgg tggatttggc ctgcatggat tctgtgtggc  67140
ctcttccttt ccatgttggt gtcctttttt ccatgccagg aatcctggtt ctcaagggcg  67200
gggttgttgg cacgagcgtg atgcagactg cctttgctgc ctttctcttg cccagggctg  67260
aacatggagc tggaagacat tgcaaagctg aagagtaagt gttgccctcc ccgcctcctt  67320
gcagctgggt ggggcctcct ccttgcgagg aggtgggtga cacctcctcg acccacagtg  67380
atcctgctgc gcctggaggg ggccatcgat gctgttgagc tgcctggaga cgacagcggt  67440
gtcaccaagc cagggaggtg agaggcgggg agccagcccc ttcactgcag gcccagccta  67500
gagctagaaa cgggccatgg tgcagtcctg ggctgtcaca tcacgagtga ggcctgtttt  67560
caggcctgtt ttcccttttt gagacctggg aggagcacct gctttgcatg atctggttgc  67620
tgagatgttg agaggagcag cacacactcc cacgggacag cacacagccc cccacggaac  67680
ggcacacaca cccatggaac agcacacaca ctcccacgaa cagcacacac actcccacga  67740
acagcacaca cactcccacg gaacagcaca cacacccacg gaacggcaca cacacccacg  67800
gaacagcaca cacactccca cggaacagca cacacaccca cggaacggca cacactccca  67860
cggaacagca cactctccca cggaacagca cactctccca cggaacagca cacacactcc  67920
cacggaacag cacacacacc cacggaacgg cacacactcc cacggaacag cagactctcc  67980
cacggaacag cacacacact cccacagaca gcacacacac acccacggaa cagcacactc  68040
tcccacgcgg ggccgctggg tttcctgcag tttctcctcc tccaggcctt tccctggacc  68100
ctggtccagt ccgtcatttg agcacaggtg cctgttagaa cgagaccttc ttgttaggac  68160
gatgagtgtc ccagccacca cctcttttgg actccgggag gcctggaacg ttctgaacgc  68220
tccgtggggc tccagtcttc tccgcagcca gggcagcagg gtttgctgtc tgtcctgcag  68280
gcagatgagg agtcagggct ggggcctgtg tgggggctct cctgagcgcg cagccgccga  68340
ggtggagcgt gttctgcctg agcgccgacc tggtcggggg aatcccagtt gcttccaggt  68400
ggagccactg tcctcagcgt aatgctcaag gctctggcct ggctcctcgg ccaccctgca  68460
ccctcagggt cccctcctgt agcttctgct gccccatcac tgtcactctc caaagctttg  68520
gggactctgc ccagagccac cgcctcccag aagcccctga caacctcttg acgacccccct  68580
agtgacccca tccctcccct ctgacggcgg cccctgctct gaggcggctt cttttcctcg  68640
gtgctgttct cgtgctggcc aggcctcctc tccccacctg gaggctcctg agggcggagg  68700
cctctcacct ccaatgctgg cgtcccctgg agggctgaat ttgtttccga gggaaggaaa  68760
cttccacagt tgttgccttc agttccaaag ctgcagcctg atttcccccct ccaggctcga  68820
gcctgttttc ttctcggcag ctacatcttt gaccagtgtc gtcccccctc aggcccgagc  68880
ctgccttctt ctcctcagtt cccaaagctg cagtctggtc cccccgccag gctcgagcct  68940
gccttcttct cctcggcagc tacatctttg agctgtttgc tgaagcccag atcacgtttc  69000
agaccaaggg ctgcatcctg gactcgctgg accagatcat ccagcacctg gcaggacgtg  69060
agtgctggca cggggtcttt ggtgcgggca aatgtggcgt agggggtgca gcaggcctcc  69120
atcttggcag tcagggctcc cctggccgtc acctggccgt cagcaggaac aggcccacag  69180
```

-continued

```
aacctcatct tctgatcggg gcgtggaggc gttagtgcca cttgccagct gccgtagagc  69240
ctgtcccagt tctgcagctg gcggcttcgt cctacagcct catcccatta ttctgctttt  69300
gagaaagagc agcccaaggc cctagctggc ttgtggggcc tctggcttct ccacaccacc  69360
ccgagttctg cttctcagag ttgtggggtc cagaggcttt gcccagaggc ggtgtcccca  69420
tgggctgctc tggtttgaga cgccgggccc agcggggtct ctcctctgct gcgctcccgg  69480
gtgctgggga gggtggcttt tgctgcttca acccttaggc gaccatagag cctcttttca  69540
agtcccactg accccccttgg agactctgtc cctgcctggc ttctctcctg gctgctggga  69600
agagcaggcg aactgcccgc cctgaatgga tgctgcgctc caccctgggc cccccattgg  69660
gcaggagatg gagcttggca gtcgggctga gcgggctcat gctggaaggg ccggggctgg  69720
ggtcggggcc tcccctgcct gcagtgtggg tgtcagcgcc ctgctgccct ccaggtgctg  69780
gagtgttcac caacacggcc ggactgcaga agctggcgga cattatccag gtggggcctg  69840
ctcctctgtg gcatctcctt ccctgatgga agccgggcgg gtgccttctc ctgctgtatt  69900
agttaactga ttctagactt ggggatggga gaaaggcccc tacaccacct gtttctgatt  69960
ggcaaactct cggctccttt ccagtgccct aaacccacac tgggcctcct gcagggatgg  70020
gggaggacga ggtctggtgg cacatgccca gggtgatgct ggtgagggag gacgcaaagg  70080
acagtggggg ccggggagcc gctcctgccc tgtccgggcc ctcaggccag gggggaccca  70140
ctgctggcag ccccagcagc cccagctgca cgcagatgaa gagctctgga cacacgcggc  70200
ttcctgaaca gcttctccag ggacagacaa atggggaccc tgcaggttcc cggcaggggt  70260
gtccctggga gcccatgatt gggggtgcga ccctggcccc cttctcattg gccccgtcct  70320
gtcctgcaat gcccgtccca tgtgaggtct gcttctggct ccatgcctat ggcagcacct  70380
gctttccctg gcgtagaggt gcttgtccgg tttgtggagg gcacgcccca ttttgggtgc  70440
tctgggcacg ttgcctctcc ggggcctcgg tggctttttt agaagcagac tcagaagtcc  70500
ctgactgggg aagccaaggc acaggtggct gtgtggagcc ctgtgaggcc tcctctgtgc  70560
tgcccacgct gtacctgctg gccacacgag atcatggcag ggttaggcag ggctgcccag  70620
cgctatgaca gcttcatgag tgtccatctg gcctgtgggg tgcttgagct gggggaggcc  70680
gcagaagaac cctgggatgc atggctggcc tgtgcatgct gctgggcatg gagctgcaga  70740
tcccggaaca agcaggcact gccttctcct tcacagacgc agctctgagc gggggcgaga  70800
cctgggcagg gaccaggtgg ggtgggcaca gggtggtggg gcccaggctc agccctccct  70860
ccactgtggc cgtctctgtg gccagtgacg ccacagcctg tgtcttctct gtgcggtagc  70920
tggggctgga aggacagcac tgccttgtcc tcccaactcc tccccaaagg cacggtgggc  70980
atcccaggcc cagacccctc tgtctgtggc tcctgcctgc caagggctgc tgtgctgtcc  71040
cgcatggagt gtggttggct cttcaagcag gaggccgtgc acctatcagg cggacctgct  71100
tccatgtccc tgatgggtca ctgcaaagca cctccagcac atggccaggc gaggtagccc  71160
tgcagcccag ggcctggagg gcaggtgtga gctggcccgg gcctgtccct ccctggaata  71220
cagcttccca ggctcccact tatggagaag tctcctccac actatggaac tgaatcctag  71280
aatgtggctt ctgaggttcc tacactcgaa ctgaatcctg gaatgcggct tccaaggctt  71340
ccagctatgg agaagactcc acactctgga accgaatcct ggaacgcggc ctcccaggcc  71400
cccagctatg gagaagactc cacactctgg aaccgaatcc tggaacgcgg cctcccaggc  71460
ccccagctat ggagaagact ccacactctg gaaccggatc ctggaacgcg gcctcccagc  71520
```

-continued

```
ctcccactta aggagaagtc tccacactct ggaaccggat cctggaacgt ggcctcccag  71580
gcccccactt aaggagaaga ctccacactc tggaaccgaa tcctgcacac tccatcggtt  71640
tggaatttcc tttggctgct gctctaagta gccgctggtg gatgactcag cttctgccag  71700
ccctcgggtg cctggaggat gagggactgc acacagtgct cacccgcgtt ggctcctgag  71760
cccctgcagg tgtgggcggt gcccataggg ctggtgctgg gttgggcctg cagccctgag  71820
tcacaggtga ccctgggggc agagtggggc cagtggcccc aggaagagga tgtgggatgc  71880
acagctcagc tggaggcgaa ctccaggcag ggtcaggccg tgtgctcgga agtcagggct  71940
tagctggagg caaactctgg gcagtgctgg cccgtgttgg ggaaccagtt gcccctgggc  72000
ccccgtgaga ctgctgggtc ctcatccctc tctgcctgag gccggagctg ccctgggctg  72060
aggcacaggg ggatttgtgg tggtgttttt ttgagaaagg gtctcgcttt gtcaccccgg  72120
ctggagtgca ggggcttgat cacagctcac tgcagcctca acctcctggg cccaagtgat  72180
cctcttgcct cagccacccg aggagctgtg aacacaggtg tgcaccaccg cactcagcta  72240
atttttaaaa tttttttgta gagatgaggt cttgccatgt ttcccaggct ggtctcaaac  72300
tcctgggctc aggcagtctg cccgccttgg cctcccaaag tgctgggatt acaggcaaga  72360
gcttccatgc ctgcccagca gaaggctttt cgaaggaagc tgtttcctga ggcagactca  72420
gccctgctca tggcagccac cagcgtgggg gtgaacttgt tctgttactt ccatccccgt  72480
gggccaaatg ctttggtaaa acacaaggcc ctgtgtttag ctgtcttgac agtgaaaatg  72540
gctgggaagg aaggaaggaa cggaaggaaa tttctctctc cttctgtgcg tacccaggca  72600
cgtgcacatg catgcagagt acgcacacac gcacgcacgc ctgcacaaat ccacgcatgt  72660
tgccaagtct ctgtgttcca gccgtggtgt ctgccccccg gtgttctcta gttcggcttc  72720
tccgcatttc tgtgaatgat tccggcttct tggtgttccc agcagaactc cctcaagtct  72780
gcggcggggc tctgacggcg gtggcttggc tgacatggcc acattgctga gcctgttggg  72840
ggctttgcgt tcctgttctg gccgtttttg gctcgttttc caggaacggt cgtcacgcgc  72900
tcctctccta gtgcaggcat cattcctttc ccattgattt gcagggttct ctgtaagttc  72960
tgaggatccc atatacatat actctctgta agttctgagg atcccatata catattctct  73020
ctctaagttc tgaggatccc atatacatat tctctctcta agttctgagg atcccatgcc  73080
gacatacata ttctttcctt gtctcatgct ggtcattttt tccattttca tgacaggttt  73140
ggtgaacaca tgtttccttg tcagattttt gttctgagct tgtgcctccc gaccaagatg  73200
ctaaaccggg tcttgtgtat tctccaaact gcactgtaga gtgacggagc tttgtgtctg  73260
ggcctccatg ccttctgacg tcacctgtgg gggtgtgaaa ggcagactct accttgattt  73320
ttcccagcac gccacaccgg tggttctgtg cgctgaccga gcggctcggc ttccccccaac  73380
tccactgggc acctgccaca cttttcctca tgtttttgtt cactgtggtt ttgtcgtaag  73440
tcctggtgtt ggcctgaacc aatttctttt tgtttgtttt tgagacagag ttttgctctt  73500
gttgcccagg ctggagtgca gtggcgcgat ctcggctcac tgcaagctcc gcctcccggg  73560
ttcacgccat tctcctgcct cagcctccca aatacctggg attataggca cctgccacca  73620
cgcctggcta attttttgta tttttagtag agacgaggtt tcaccgtgtt agccaggatg  73680
gtctcgatct cctgacctcg tgatccgcct cccaaagtgc tgggattaca ggcatgagcc  73740
accgtgccca gcctgatatt tttagtagaa atggggtttt gccatgttgg ccaggctggt  73800
ctcgaactcc tgacctcagg tgatcctctc accttggcct cccagagtgc tgggattacg  73860
ggtgtgagcc accacgcccg gcctcttgtt cttttgaaac ctgccctgac gttttttcca  73920
```

-continued

```
tagtgcatct tggagtcagc gtgtctactt cctgtaaaaa tcttactgtg attttgacta  73980
gaatgtgttg aattcctgtt ttttttttga gtcagggtct ctctgttgcc caggctggag  74040
tgcagtggga ccatcacagc tcactgcagc ctcaacctcc tgggctcagg ggatcctctc  74100
agctcaacct cccaagtagc tgggaccaca ggcacatgcc accatgcccg gctaggtttt  74160
tttttttttt tttttggtga acaccctggg gttgcaccat gttgcccagg ctggtctcga  74220
actcctgggt tcgggcagtt tgctcctctc agcctcccgg agtgctggga ttacaggcct  74280
gagccactgc actaggccat gttgaatttc tagattaatt tggggccctc aggggcacag  74340
agaggagggc tgggccagtt ggcgggagga gaggcccctc gggctgccgc attttcagtg  74400
catggagatg gcctatgttg ggggaacaca gagctcaccg ggggtccctg cagggaggag  74460
aaagggtcag gcaggtgcca gctcctgtcc attggcctgg ggctgcatga tggcaggggc  74520
cggtgaaccg atgacccctg ggtgtcctgt gaccttctgt gtatgcggct gatgctgcag  74580
aaagtcgggt ggcctcaggc tcctgacggg gctgcacttc ctctgccttt cagattgtgt  74640
tcagtgtgga cccctccgag ggcagccctg gttccccagc agggctgggg gccttacagt  74700
cctataaggt aggggccacc tccaggaggc aggtggaggg cagcccttgt tccccggcag  74760
ggctgggggc cttacagtcc tataaggtgg gggccacctc caggaggcag gtggggctgg  74820
gggtcttctg gtcctaaaag gtaaggggct gcccccagga catgggcggg gcctccacac  74880
tcctggtcct gtcccctcca ggtgcacatc catcctgatg ctggtcaccg gaggacggct  74940
cagcggtctg atgcctggag caccactgca gccagaaagc gaggtacaga cctgggccca  75000
cacgctcccc gcccgcccgg gtgcagtgcc cggcaccacc atgccacagg ctaggcacat  75060
gcccagccgt ggatctcctg cccccatggg cctggccacc ttctccatat ccaggccaat  75120
ccagagcatt ctcctcactg tccctctgaa gattggagtt actgagagac gtaggagatg  75180
gcctgatggc accgtgacct gcccagagtc acctggttgg tggtggcaga gccacagccc  75240
agccaggcct ccctgctggg acacgctcgt ttatgccgag gccgtcagca cagagcctcc  75300
acagtgaggc acggctctgc ctgctgcctc cacgcagcgc ctggccgggc caagcctcag  75360
ggtcacatct gaagggggcc cggctggccc tgttgtccga agcccctggt gcgctcagcc  75420
ccgaggcccc acgtgccttc ttggcttcct gtgctccgtg gcgtcttcga gtcggtgctg  75480
ccggggacgc tgtgtggatg gggtctgtga gtgtgccctc ggctccgtgt ccggagccct  75540
gtggttcttg gggtgtatct ggccccaccc ccactgcgtg gtgtccaggg tggggcttca  75600
cggctgcagc tgcgggagct gctgcccctg ccttgtgctc cagtggggcc ttgcctctgg  75660
gcttggttcg tccctctctg gaacattctt tctcagctgc tgtccgaccc atggtggcat  75720
gacgtggccc tggctgaagc agcccttgtg cggttgctgt ggttgggtct gcctggccga  75780
gccggaaggg aagggctggg agggcgtcag ggtggcgtgg cttgaccccc gctcggtgat  75840
ggtcctgcag caaggcctct cccagcagga agcgtccatc ccggggggag gccggcgccc  75900
ctcacgcagt tggggttgcg ggaggcagtg cgtgcctgag gcagccggtg cacagattcc  75960
aagggcctgg aatctgtttg ttccattgac ctctgatgtc acttgacttc tcagaagcag  76020
ccactccctg cactgggcgt ttgtaggaaa tgagctcctg gaggaggggg tggggaagtt  76080
cccccattgc agggcacact cagccccagg aaggaaacgt gcctcgtccc tgctgactcc  76140
gaatcgcagt cagagtcgtt ctgcttgtgc cgtgttgaat tcccggcatc cggcatccag  76200
actcagcctc ctccccaggc cacggccgcc gtggccagtc ggtcaagccc ttctaggaac  76260
```

-continued

```
ttcctttgag ctggcgccct tgttcactgc tgacgccact cagaggcttg tgcacgtgtc  76320
ctgcttccag gcagagctgg gaactcgcac cccgtcttct gcacgcggcc gtggaatgtc  76380
gggatgccgg cgcttccttc ccgtgtgctc ttggcggggt gggcttcttg ccctgagccg  76440
catgtcacag tttctgcaga agtttagggt tggagtgggc tgacctctct gcaggtgtcc  76500
ccagcctctg cctggggtct gcctcctact cccaggaccc cctgtccccc agaggggccc  76560
caagctggca ggctcacact cagggcagcc tcctttgttc tgacttctgc acagtgggcc  76620
tgggtggctg cccgcggctc gcttgcttga tgccagtggg tggagagggt gatgggcaga  76680
gaggcaggtg gtcaggcccc cagtcccgtc ctcacactct gtgccctctg ccgccccccg  76740
ccccacaggg aaggtgctga gctactggtg cttcagtccc ggccacagca tgcacgagct  76800
ggtccgccag ggcgtccgct ccctcatcct taccagcggc acgctggccc cggtgtcctc  76860
ctttgctctg gagatgcaga tgtacgggcc acccctgcca gggcctgagc accggtgaca  76920
cctctgacat cagcggggtg gaagtggtgg gggtccccat gagccgggtg ctgggggtct  76980
cgggcctcga gggctaaagg ggtgctggtg cacttcccca ctgtctgctc cctctggcca  77040
cgctcagccc tttcccagtc tgcctggaga acccacacat catcgacaag caccagatct  77100
gggtgggggt cgtccccaga ggccccgatg gagcccagtt gagctccgcg tttgacagac  77160
ggtgagggcc tgtccctggg ccctgctggg gtgggaggtg gggagcact gaggcctgag  77220
gccctgagca gtggcctctc cggctctagg ttttccgagg agtgcttatc ctccctgggg  77280
aaggctctgg gtgagtgccc tgaatgcccc agctgtgcgc atcctggatc ctggacccct  77340
gctcccaaga gctggtaggg acccctgcag acatcctgcc cctgccttga ccccggcccc  77400
tgcacttcca ggcaacatcg cccgcgtggt gccctatggg ctcctgatct tcttcccttc  77460
ctatcctgtc atggagaaga gcctggagtt ctggcgggtg cgtctcccct gtgttctggg  77520
cggggtgggt gagggcaggg ctggagcatg aagcaggcag tggtcacagc tcctgcttgc  77580
cctcatcgga tcggcggcgt gaccagggct gccgtgtccc tgcctcttcc tcccacaggc  77640
ccgcgacttg gccaggaaga tggaggcgct gaagccgctg tttgtggagc ccaggagcaa  77700
aggcagcttc tccgaggtcg gcacttggcc ggggctctgg gcctgctgcc ccctcgtgcc  77760
tcccctgcct ctcacagctt ccccaaggct gaccactggc cctgaccatg ggctccggcg  77820
gctcccgctg cctcttcagg gctcctgcgt ttccttcctg gccctgagtg ttgcctctta  77880
tcttacaaag cccccagcac cgggtgggtg tggtaacagt ggccctcctg tctgagtagc  77940
cctagtcggc caccctggcc ctggggttcc ccgtgttttc tgggaagcac tgagcaggcg  78000
tggggtcagc ctgggatccg tgccaggaag aagcttccag aacccgattg gccttcctgg  78060
ctaggacgat ccttcatctt ggagcatgag acctgggtct ccctcatggg ggaggaaggg  78120
gctgggggg ggctccaggc tcagcctcac caactttcct tccagaccat cagtgcttac  78180
tatgcaaggg ttgccgcccc tgggtccacc ggcgccacct tcctggcggt ctgccggggc  78240
aaggtgagct ctccagggcc ctctgccctg acctggttgc ctgttccctg gtgggtgctt  78300
atggctcccc agcagactct gggccctggg ggctgcccgg tcccctcctt gggtcccacg  78360
agagcgactg ctggccctgc tgggagcgtg tcctgctctg ggcctgggca ggcaggatgg  78420
gagtttcctg gccacaagag ttggaggtgg cgtctgggag ctgtggaccc caagtggggt  78480
cctgacccac agatggagct tcctcccacc cctggttggg gacggagcct cggggaaggt  78540
ggctgggctg ggtgtgggca ccagggagag gagcccccac ggccccaggc agctccctgg  78600
tgtgtcccct aggccagcga ggggctggac ttctcagaca cgaatggccg tggtgtgatt  78660
```

-continued gtcacgggcc tcccgtaccc cccacgcatg gacccccggg ttgtcctcaa gatgcagttc 78720
ctggatgaga tgaagggcca gggtggggct gggggccagg tgagttacag cagggtgggg 78780
ctggggtaag gcggtctggt gactgagccc ccgccccgtg gccaagggag cccccgtgac 78840
cgagccgcct cgccccacag ttcctctctg ggcaggagtg gtaccggcag caggcgtcca 78900
gggctgtgaa ccaggccatc gggcgagtga tccggcaccg ccaggactac ggagctgtct 78960
tcctctgtga ccacaggtgc gtgcagtccg gtggcaggcg cggcgccagg ggacacgccc 79020
acaccccact gggcccctgg actctccttc cccacatgag gccccgtctc ctccagagcc 79080
tctccggcta ctcggggtca gcgtggggcc cctgcagcag atgagggtct tcacttcggt 79140
gaactgaacc cttgaagcgg ctgtgggcag ggcagcaggg ctatggccac cccccaggtt 79200
cgcctttgcc gacgcaagag cccaactgcc ctcctgggtg cgtccccacg tcagggtgta 79260
tgacaacttt ggccatgtca tccgagacgt ggcccagttc ttccgtgttg ccgagcgaac 79320
tgtgagttcc tgcccaggga ggggatgagg gtgttgtccc cagaggagcc agaaatgggt 79380
ccacccaccc ccatggttct gcagatgcca gcgccggccc cccgggctac agcacccagt 79440
gtgcgtggag aagatgctgt cagcgaggcc aagtcgcctg gccccttctt ctccaccagg 79500
aaagctaaga gtctggacct gcatgtcccc agcctgaagc agaggtcctc aggtgcggac 79560
gggcagcgct gggtgggcgg tgtgggggtg gcggagcggg cggcgtgggg cgggcagcac 79620
caggcgccca gggcggaggc gactcacctg gctttgtgcg cttcccctcc cacctccaaa 79680
ggctgcctct ccctcctagg gcagggcccc cacgggctgc aaccctcccc tacaggcaga 79740
gaacgcccca ggcaaggatg ccccccgagg ctgagactcc ccccaatagc agggaggaca 79800
cccacaggca ggaccccaag tgctgggact ctcccccaag aggggctttg ccacaggcag 79860
ggaccccagc tggggccccc cgtgggcttc actgcgcact cgggtgcccc tgcagggtca 79920
ccagctgccg gggaccccga gagtagcctg tgtgtggagt atgagcagga gccagttcct 79980
gcccggcaga ggcccagggg gctgctggcc gccctggagc acagcgaaca gcgggcgggg 80040
agccctggcg aggagcaggt acagttccag ggccttggga tggacacaga ccctctgtct 80100
cctgaggcca acccgacccc gcccatctgg cctcaggcac ctccccacac acccctgtaa 80160
atcccctgcc tggcaggcag gcgggcaagc gggcggggga tcccagctgc ctggctgtct 80220
gtgggtcctc caccccacct cacccacagg ctgctggctc ccaggtggtg catgccctgg 80280
ccctccgcgg gtgcccccca catcactttg gttctctggc gggtcagctt ggctcagtgc 80340
actcaaggtc gggtgcccct gccactggct gcgcttgagg ctggcctttc tccaggaatg 80400
tgctgcgggt ggaacccagg ttccttcttc cttggggcct tttgccccag aagcccataa 80460
ttcctcaggc caacccgaaa ttttctccct gcttcctgct gggagccatt cccctcttcc 80520
tgcccatccc tgcccttcag gcccctggag tgagctccag gtgcaggcac caggcacctg 80580
tgtccccttc ctgccagccc ctcgctgtgg tcggactgtc ttccctggac ctgctcttac 80640
aagtcaccac ctgcgagcct catgagccgc tggtgtgact tggacaggac caagttgtgg 80700
cactgtcacc ggggtgtgct gtgccccccct cccccgacct ccatcttggc tcagggctcc 80760
ttgggaccat cttccctgtg cgtccaggtg ctttgggacc ccagagtgtg tggttggggt 80820
ctgtgtgtgg ttgtgagctg tgtcctcctc aggcccacag ctgctccacc ctgtccctcc 80880
tgtctgagaa gaggccggca gaagaaccgc gaggagggag gaagaagatc cggctggtca 80940
gccacccggt gcgtgagctg tccctgcacc tgtgccgacc accatagaca cgcatgggaa 81000

-continued

```
cgcagccgtg ggtgccccca gccacggctg gtcccgatgg gaccagggaa tccaccccca  81060
ggagctgatg tccagggcag ctgtgatgct gacggccagg ggctcaagtg tgtggtttct  81120
tctgcagggg gctcatgagt cccagctgga atcaggcccc acccttgggc aggtttggca  81180
tggggcctgc agcactgggc ttggccctgg catttccctc aagtgtggat gcacacctgc  81240
ctcatgtgag ggacacagcc cattcctagc cttggatcaa agaacggagt tatagccgga  81300
gccaggaagc cccctgcctg ctggaaaacc ccaagtgtgg cggcctttgt ccatgtccct  81360
tggcttctgg gaagaactgg gtggtgccca ggcagggctg gtgccatcag gaagtgggtg  81420
gctgctgagg ggcctgggct ggcgagggcc tgggtgggga gtgcctgggc cgcccctgcc  81480
ttggtttcca cgtttccgtg ttggtctggg gtgtgtagag agatgggcac tgctcatccg  81540
gaagcccctc cttgtgcgct gccatcctgg gagcctcagc cgcatccgct gtggggcagg  81600
gggcttgagg gaggaggaga gagacgggcc atgcaggacc cctggcttga ggcagagcca  81660
atctaccctt tgcccattca ctgctctcag ttccctgcca gcctctcact gtgtgacctc  81720
agacgggccc agccccacag ctttcttccc gcagcccctc cctatgtcca tccagccagc  81780
cagtttctca ggcagcagcc ccacctcggc agtcactgtc ccagggaacg ctcaatgttc  81840
caaggaaggc tctgcagccc cagggaccag atgatgaggc tggccctgat ggagcctcgg  81900
gcctgtgtcc tgcaggagga gcccgtggct ggtgcacaga cggacagggc caagctcttc  81960
atggtggccg tgaagcagga gttgagccaa gccaactttg ccaccttcac ccaggccctg  82020
caggactaca agggttccga tgacttcgcc gccctggccg cctgtctcgg ccccctcttt  82080
gctgaggacc ccaagaagca caacctgctc caaggtgccc tggcttgcag aggccaccca  82140
ccctgagggc agtgctgccg ccgcgtgtgg ggtgggggcc atctgggtcc aaggtggtct  82200
ctgttctcta gagaaaaagg ggcagatggg gacagacgcc ccttcctcta caggcttcta  82260
ccagtttgtg cggccccacc ataagcagca gtttgaggag gtctgtatcc agctgacagg  82320
acgaggctgt ggctatcggc ctgagcacag cattccccga aggcagcggg cacagccggt  82380
cctggacccc actggtaaat ggggccccag gtgggaccct cagactcctg cgtggaaggc  82440
agtgtgggcc agagtcctgg gctgcttggg gtgggcatcc tcgggccctg cttggccccg  82500
cctctctgtt cccctatggg agtgatgggg gcctccacct ccaccaccag caccagcagc  82560
accacctcca ccttcaccac caccacctcc accaccacca cctccaccac ctccacctcc  82620
accacctcca ccacctccac cacctccacc accaccacca cctccaccac caccaccacc  82680
accacctcca ccaccaccac caccaccacc acctccacct ccaccacctc caccaccacc  82740
tccacctcca ccaccaccac cacctccacc tccaccacct ccacctccac ctccaccacc  82800
accacctcca ccaccaccac caccacctcc acctccacca gcagcagcat cacttgttgg  82860
ggagaccctg tgcaactcca tgcacagccc tgtccctgcc atagccccga cccctaagca  82920
cagccctgtc caactgccac acgtcccctg cctcccatgc atggtcctgg ggggtcaact  82980
gcacacgcca gggtcctagg gtcctagacc cctgtcctcc ctgtttctgc ctctgtttgg  83040
ggtggagtcc aagtctccag aggcggaagc atctgtgttc gtgtgttaat gaacagcccc  83100
tacagagttc ccctagttca cccagggggg aacctagcct gttgggacga ccccagatcc  83160
cttctgggct tggtactcac tgggatatcc tcatgcctgc acccagccta cggctctgag  83220
ctcctgagtg gggctttggc ctgcccgcca ctgttccagc ccccatccag caggctggtg  83280
tctcctctga tgcccccagc acccaggcgt gtacctgcct gggttttccc gccctggtct  83340
gaggtgggtg aggcctggcc tccctagcca gccctgcccc cccaccccag ggaactttcc  83400
```

-continued

```
agatgctccc gaccagcttt gtggctctac atctcttcat caggaagaac ggcgccggat  83460
cccaagctga ccgtgtccac ggctgcagcc cagcagctgg acccccaaga gcacctgaac  83520
cagggcaggc cccacctgtc gcccaggcca cccccaacag gtagctgact cctgaaccgt  83580
gtgcagccta cgacttggtg ggtccctcag tggcttcacg aggctaactc ttgagtgtgg  83640
ccggggctgc ccctgtgggg agccatctca tggtggggac tgctcccggt tctgcacccc  83700
gcagttgtcc tgagcagctc tccaggagtt cctggaggaa gggcgggcag ggcggtggga  83760
ctctcagtcc tccaccccag cgccactctg agccatgcta ctcccacacc aggagaccct  83820
ggcagccaac cacagtgggg gtctggagtg cccagagcag ggaagcaggg ccagcacgcc  83880
gtgagcgcct acctggctga tgcccgcagg gccctggggt ccgcgggctg tagccaactc  83940
ttggcagcgc tgacagccta taagcaagac gacgacctcg acaaggtgct ggctgtgttg  84000
gccgccctga ccactgcaaa gccagaggac ttccccctgc tgcacagcaa gtggccctgg  84060
cgtggggaac agccggtggg gtgggggca ggggacaaaa tgggggctgt gccgggtctg  84120
attgaagctc cccgcagggt tcagcatgtt tgtgcgtcca caccacaagc agcgcttctc  84180
acagacgtgc acagacctga ccggccggcc ctacccgggc atggagccac cgggacccca  84240
ggaggagagg cttgccgtgc ctcctgtgct tacccacagg gctccccaac caggtagggc  84300
acctgcctgg ctgctcctgg cagcgcccca accgcacgca gccctgggag tgagcagcaa  84360
agccccaggc ccccctcaga ctcaagtctc tgtctccagg cccctcacgg tccgagaaga  84420
ccgggaagac ccagagcaag atctcgtcct tccttagaca gaggccagca gggactgtgg  84480
gggcgggcgg tgaggatgca ggtcccagcc agtcctcagg acctccccac gggcctgcag  84540
catctgagtg gggtgagcct catgggagag acatcgctgg gcagcaggcc acgggagctc  84600
cgggcgggcc cctctcagca ggctgtgtgt gccagggctg tggggcagag gacgtggtgc  84660
ccttccagtg ccctgcctgt gacttccagc gctgccaagc ctgctggcaa cggcaccttc  84720
aggttggtgc ctggccacta cagttcctgc tgggtgtagc cccaggtgat gggctgaggg  84780
ggaaagggca ggcccttgtc ctggtggcaa cgcctggcag acgtgtgcag tgggccggtt  84840
gtctcacagg cctctaggat gtgcccagcc tgccacaccg cctccaggaa gcagagcgtc  84900
atgcaggtct tctggccaga gccccagtga gtgcccacgg aggcccccag cacacccaac  84960
gtggcttgat cacctgcctg tccagctctg gtgggccaag aacccaccca acagaatagg  85020
ccagcccatg ccagccggct tggcccgctg caggcctcag gcaggcgggg cccatggttg  85080
gtccctgcgg tgggaccgga tctgggcctg cctctgagaa gccctgagct accttggggt  85140
ctggggtggg tttctgggaa agtgcttccc cagaacttcc ctggctcctg gcctgtgagt  85200
ggtgccacag gggcacccca gctgagcccc tcaccgggaa ggaggagacc cccgtgggca  85260
cgtgtccact tttaatcagg ggacagggct ctctaataaa gctgctggca gtgcccagga  85320
cggtgtcttc gtggcctggg cttggtggtg ggagttgagg gacagggagt tggcagaggc  85380
ccctcccagc ctgccatgtg acactgtact tcctccacgg tgggctcagc cctgccctca  85440
tcctcacagc cgcagccaag ctgcagttgg taggggatcc accgacacac caggctgcct  85500
gggctggtct ctgggttggg agctgcccca ggtgctgagg agggcagctc cctggctggt  85560
gaggccccctc ccagaaccac ccttggactg agctctgggg agggatggta ccaggtgggt  85620
gaggggggct gcctggggag ggaggggttc ctatggggcg tggcgaggct ggcccagccc  85680
tctccccgcc catatatgta gggcagcagc aggatgggct tctggacttg ggcggcccct  85740
```

-continued

```
ccgcaggcgg accgggggca aaggaggtgg catgtcggtc aggcacagca gggtcctgtg  85800
tccgcgctga gccgcgctct ccctgctcca gcaaggacca tgagggcgct ggagggggca  85860
ggcctgtcgc tgctgtgcct ggtgttggcg ctgcctgccc tgctgccggt gccggctgta  85920
cgcggagtgg cagaaacacc cacctacccc tggcgggacg cagagacagg ggagcggctg  85980
gtgtgtgccc agtgcccccc aggcaccttt gtgcagcggc cgtgccgccg agacagcccc  86040
acgacgtgtg gcccgtgtcc accgcgccac tacacgcagt tctggaacta cctggagcgc  86100
tgccgctact gcaacgtcct ctgcggggag cgtgaggagg aggcacgggc ttgccacgcc  86160
acccacaacc gcgcctgccg ctgccgcacc ggcttcttcg cgcacgctgg tttctgcttg  86220
gagcacgcat cgtgtccacc tggtgccggc gtgattgccc cgggtgagag ctgggcgagg  86280
ggagggggcccc ccaggagtgg tggccggagg tgtggcaggg gtcaggttgc tggtcccagc  86340
cttgcaccct gagctaggac accagttccc ctgaccctgt tcttccctcc tggctgcagg  86400
cacccccagc cagaacacgc agtgccagcc gtgcccccca ggcaccttct cagccagcag  86460
ttccagctca gagcagtgcc agccccaccg caactgcacg gccctgggcc tggccctcaa  86520
tgtgccaggc tcttcctccc atgacacgct gtgcaccagc tgcactggct tccccctcag  86580
caccagggta ccaggtgagc cagaggcctg agggggcagc acactgcagg ccaggcccac  86640
ttgtgccctc actcctgccc ctgcacgtgc atctagcctg aggcatgcca gctggctctg  86700
ggaaggggcc acagtggatt tgaggggtca ggggtccctc cactagatcc ccaccaagtc  86760
tgccctctca ggggtggctg agaatttgga tctgagccag ggcacagcct cccctgggga  86820
gctctgggaa agtgggcagc aatctcctaa ctgcccgagg ggaaggtggc tggctcctct  86880
gacacggaga aaccgaggcc tgatggtaac tctcctaact gcctgagagg aaggtggctg  86940
cctcctctga catggggaaa ccgaggccca atgttaacca ctgttgagaa gtcacagggg  87000
gaagtgaccc ccttaacatc aagtcaggtc cggtccatct gcaggtccca actcgcccct  87060
tccgatggcc caggagcccc aagcccttgc ctgggccccc ttgcctcttg cagccaaggt  87120
ccgagtggcc actcctgccc cctaggcctt tgctccagct ctctgaccga aggctcctgc  87180
cccttctcca gtccccatcg ttgcactgcc ctctccagca cggctcactg cacagggatt  87240
tctctctcct gcaaaccccc cgagtggggc ccagaaagca gggtacctgg cagcccccgc  87300
cagtgtgtgt gggtgaaatg atcggaccgc tgcctcccca ccccactgca ggagctgagg  87360
agtgtgagcg tgccgtcatc gactttgtgg ctttccagga catctccatc aagaggctgc  87420
agcggctgct gcaggccctc gaggccccgg agggctgggg tccgacacca agggcgggcc  87480
gcgcggcctt gcagctgaag ctgcgtcggc ggctcacgga gctcctgggg gcgcaggacg  87540
gggcgctgct ggtgcggctg ctgcaggcgc tgcgcgtggc caggatgccc gggctggagc  87600
ggagcgtccg tgagcgcttc ctccctgtgc actgatcctg gccccctctt atttattcta  87660
catccttggc accccacttg cactgaaaga ggcttttttt taaatagaag aaatgaggtt  87720
tcttaaagct tatttttata aagctttttc ataaaactgg ttgtagttgc acagctactg  87780
ggagggcagc cggggacacc tgagccgccc gctgtgccca gatccctcag gctgcctgcc  87840
atcagaactg ctgcccgggg cttcccctac ctcagacaga ccctccctgg gaggatcagt  87900
ggggagtgcc acctctgccc ccagtggctg tggcacgtgg caggggcccc tgaagctcag  87960
cgagggtcag ggcctgggag ggtatcattg ctggaagaac aggatggggc tcaggccagc  88020
cctagtcgcc ggggcccaca ctaacccccc acttatgaat tcctcccact cccaactcac  88080
aggggatttc ccgagagggg acctgccaaa gacctcctcc aggcctccca tgcttcccgg  88140
```

-continued

```
gaagtgaagc ttctccccct ctggggcagg ctctgaagcc tcccgatgca cccagagcaa  88200
ccagggggct gcaccagcca ctcgcctccc cagcacggcc aggttcccgg ggctggaggt  88260
ccccccagg tcctgggaac caacctgcag aacacacaca gggtcccctg gagaggacgc  88320
ggggacttcc agggcccgac tcctgtgagt cacagccccg cagctgctgc gccaccccca  88380
ccctgactca tgccccttcc cagcagctcc tcccaggacc ccatgtcctt cccacatccg  88440
caggaaggga gtgcctggac tctccaggcc cacctgggga gcccctcacc tgcccaccag  88500
cccctgagca gcccagtaac accatcaccg tgtccaacag ccaggagcct ccaccctcca  88560
ggagggaagg gatggacaga gccacactcg ccgtctttat tttgcactca ccctgggtga  88620
cactgggcag gccgctcctg cccacagcca gactgaggaa gaacacagca ctcggcaggc  88680
ccagtggggt ccgtgcaggg aggaccccag gaccagcctt actcccgagc aggggacaca  88740
gggccccaca gagaacccct ccgggaggtt ctctcctggc tgggggaggg ctctggaccc  88800
ccacaaacac tccccaactt gcggggctgg ggcataaaaa cagccactcc cagcaggccc  88860
cctcagcttt ttgcatcagt cagctccctc ccgggggatt agggtgaggt gaagccaggc  88920
ccaggcgtgg ggtataggtc ttcccccgca ggcctcagcc ctgtcccgag gctgcatcac  88980
aatccagggc ccccgctggc ctttgggaac atggcctggg tcttcctcaa ggcaagatca  89040
gccccagacc acttccgggg tcacggggtc acagggcaga agccagatgg cagccatggc  89100
tgacgggcct cctcctcgat ggggcggaga cagccacggg gtctcccgag ggtcccacag  89160
ggctgtcctc atgcagccca agccagcctg agcactggag ccccaattcc caaccaggtc  89220
tccctcagac cccccagaaa gggcctcgaa aggccgccgc tgcgccctgt ggaaaggctg  89280
ccgctgcagg gcctgggcca gccgggctgc cagactcccc tccaaagcct ccggatgcct  89340
acgcttttcc agacatagag gaaagtttgt cttcgagaaa acaaagtaaa tagaagaacc  89400
ccaaagcaaa gcaaacccac cccccagatc agcagcatgg gagccaacag gaggccactc  89460
ctccagcacc aggggaccag ccgtcccgac ggcagcgcgg ctgcgcctac gtgatgtccc  89520
tctgccgcgg cggccggtgc acattccgca cgacacactt caccatccac tcgatgccct  89580
cgcgcacccc tttgctgtga agacagcggg tgtgaggcgg ggggtctcgg tccccaaagc  89640
ccccgcaggt gcagccccca ctcaccctgt gagggccgag caggcctggg tcaggcaatc  89700
gcgcctgccg atcttgctgg tgcagtcgct gaaggccgtc ttgatgtcag ggattgagag  89760
gcacgtctgg gggaggtaag gccgtgagga gcagccccca cgtctggccc tgtcctgcct  89820
gtgggcccgg gactctcaga agggcgtatg ccccttcaccc cagggaaaca gccagagctc  89880
caccagggtc ccagtgtctc ccacagagac cacagcagtg aggaccctgt gctcagcccg  89940
aggctgaaca tggctggtag tgcctgagac aaactagacg tccacacggc tccaaggagt  90000
ccaccccca tcccctccct gggggacacc ctgagccccg aggtggggcg ctgaggactg  90060
aggcctcctg ggcagtggcg gaggcaggtc ccaggggccc acacagccgg ggatgatgga  90120
gaggtgggag ccctgcatca gtgatggggg cagtctgcag tcatggtggc ttctgctcac  90180
aaccacctgc ccagtcttca aaaagcagcc ctcccctccc cttttcctcc gaggggagac  90240
ccctgccccg taccagatgt ccctcttgtc ggctgagatt gtaggggagg ccagccttac  90300
aggctggggg caacagagcc accccagaga aggcaggaag tgaagattca cccggccctc  90360
tggacgccgg gctgcttctg tgcaaagcca ctccaagaga acagctagaa ctcagcgtgg  90420
ccagtgctcc cgggggcagt ggcacctcag aggggtcttg aggggctgcc ctgggggtgg  90480
```

-continued ggctggcaca gatgccacct ccaagggtag caggaacagg taagggtcag agctgactcc 90540
caccagggcc ccagcatcac ttctttgagc tctgagtttc acctgggtgt ccccacagct 90600
tggccacaca ctcctgagac acggccgccc tcctggggag aggtgccctg catagcagga 90660
agaggcctct gggcgcctgc cctgaggtgg gagaacctcc agggctggca gcagcaggtc 90720
tggagaggaa ccaagcttgg gaagctgctg ggggcagggc aggccttgag aatggctctg 90780 tacccccctgg gcagtcactg ggcctggggt gtctgggtgc acacctactc cccttgctgt 90840
gggggaggct ggggactcgg gaagctgctg cgggaggcag gggtggggct cacctccaca 90900
tcctgcttgt tggccagcac caagacgggg acaccgcaca gcgcctcgct ggtcaccacc 90960
ttctctgggg agggcaggag aggcagcgcc tcacacccag catcctgcct ctgactgccc 91020
aggggcccac aggcgtggac actgtgacag ccactccctc tgcccccccc ccgtcaccca 91080
ctaggcagga gcacttctga ccagacactg agcctgcccc aggcacagag ctgcccaagc 91140
tggacctgcc cccactcacc atccatccct cccagagcag ccaggccgca ctcaccaaac 91200
gcctgcttgg actcagccag cctctcctcg tcggtggagt caatgacgta gatgacgccg 91260
tgacactccg cataatactg ggaggaagca ccaggagttg gggctcagtc cccaccctgc 91320
caagggccag cagagccagg cctgtgtcat ggccacagtg aggggctcac atgaggaagg 91380
ggcaagaggg cagcccccaa ctgcaagacc cttctgggat gcattctggg gttgcgggga 91440
gatctggtgg aggtgtcccc agacgctgct cctgagaacc tgccggcaac ctttggcctg 91500
atggtggcca aaggtgaaag acagggattg ggccaggcgt ggtggctcac acttattatc 91560
ccaacacttt gggaggcaga agcaggagga tcacctgagc ccacttcacg gccaacctgg 91620
gcaacacagt gagactccgt ctgtacaaaa gcttatggta atgtgcgcct gcagtcctag 91680
ctactcggga ggctgaggtg ggaggatggc ttgagcctgg gaggttgagg ctgtagtgag 91740
ctctgatcac accactgcac tccagcctgg gtgagaatga gagaccctgt ctcaaaaaaa 91800
agatagggtt tgggggctgg aggaacctag accacagcct ggcccgttga gggagtgcac 91860
ctgtggggct ctgtgccagc acctcgcaca gggagggagt gtggccatgc ggataagact 91920
gaccagcacc atctacgaag cgagccttcc ctgccaggac agggccagag tcactgagct 91980
cagacctctg cagcctgggc tggtcagtcc tgggctcgct ggcaacactc ctgggcaaga 92040
cagggcacag cccctgcagc ctcaggtaca agtgctgagc cctggaccag atgagtgcac 92100
ctctatctca atcagaaaaa aacacagcaa actccgcgtc cacgtggagc agacaacagc 92160
tcacatttgc cactttgcct ccaggctgtg ccagctctcc tgtccaggca tgagtgccca 92220
gagacctaga actggatgct gaccaggtag gacaagctgg tggtcagtgt gttaagacac 92280
acacacccga gagcatgaga agccaggagg cacagcccaa ctctccgaaa tccttagggt 92340
gtctgagcag ggagtaccag acaaccccat cccagtgcca gacaagcttg tgcacctgca 92400
cttcccacag aggagagaag cctgtgcacc tgcacttccc acagtggaaa ggaggaggcc 92460
caaggccagg cccccccacc cccaggaact tcccacagtg gagaggaggc ccaaggccag 92520
gcgccctcca gggttctgca ggtagcgagg cccccccacc cccaggaact tctctggcct 92580
acagacaggt cccacacaga ggccgccaac ccctcaaggg accctgcagt gtgccggctg 92640
tctgctgctg acacaaggga gcaggcggac cctaaggtgg agacctctgt ggcaggaggg 92700
gcggctctgt ggaggctgca gcaagcccag tgagagaatc tccacgtggc tcctggggct 92760
tctgagcagg gtggcagaag gttcatgtgc aaccgggtcc tggaccatgg gaccacgtgg 92820
ccagagccac ccatcacacc taccaggcac aaggtgcaca gcccagcagg gccgcagtgg 92880

-continued

```
acgggagcga cacctcaggg ctgagtgcgg gcaggaccca gagccccacg ccccagtgga  92940
ggcgtcacag cagtggtcat tgtggggtgc cccacaagga gggggaagag ggaggtgtcc  93000
cagcgtggct cctggctggc cagctgaccc cagtggagca gtcagaggga ctgtgggtct  93060
gagtttttct ccccagcagc aatgggagct ccccaactgc aaagtgccag ccagcctgag  93120
agactagtgt tacagcaaag aacccaggag ctgaggtcct ggcacatgcc acacatgtgg  93180
acaccaaccc agggtccagc cccaggacga ggccaattcg caatgacgcc cctttctgtg  93240
gtgctggctc tgcacaagga tgcaggatac aggaaccagg gtgggagcag gggcctccct  93300
tccggtccct cccagtgacc tagggggggtc cctgcagctg atcctcccag ctctgagctc  93360
agcagggtca ggggtcccgg ccactagagc agcacatact cagcagacac gctgaatgac  93420
gagccacagc tgcctcatgg gcatgacttg cacctcatgt ctaggagacc ctggtgggca  93480
ggagatgggg ctgccatccc acagctgtcc cacagctggg gacccaggga gccactggcc  93540
ccaccacggt ggtgtctgga gaagggctca gactgccagg aagtcgcacc ccagcagaag  93600
tggtagtgaa ttgggagggc actcaaggaa gggctgtgca gccccaagac cagcagcaag  93660
gatgggctac agtggccccc ttaagtctcc ctcttccagt ttcgccttaa gagaggccct  93720
caggaccttg gaggaacccc tctccaacgt ggaagtgtgg gtccacatag ggctgcagct  93780
gtggccagtg caggcatctc tggccccact gtattcttgc ttcatgttgg agaacactgc  93840
accagcagat ggtctcattt tggtttctgt gggacccact ttggctgcaa agagccacac  93900
tgccaggtca cacctgccca gggcagccca cactggggac ccaccaggcc atggtgtgaa  93960
gtcccggcca gcctggcccc acatggcaca gcatagccag ttctcctcca gggctccctg  94020
ctgggccaac cacagctctg cggatcctgc tgcctgagtc gacctctcct ctcccgtcct  94080
ccctgccttc ctggtgccga cccccagtgt gcatcctgta cctcgacctg tctcagcatc  94140
tgtgcctgag acaccggcct gtgacaagat catcatcatc tgtgtcactc cccaagcatg  94200
ctgcgcactg gacacacagg ccctgactca acttgtcctg tctgacttca gtggtcctac  94260
aggatctatc agagatcact tggccatggg agaaatgtct tcttggctag aagtcacagc  94320
aggaggggac actttggggg cgcctaggaa aggggaacta ggatcaaaaa agagatcagg  94380
acctgggcac tcagctctag agatggcatc agggcagcca aggcactggg gacaccccac  94440
acccactgtg ccagcctagg gcagggagcc cgaggaagcc acaggctctg ccctgctcag  94500
tgctggactc agtgcctggc ccaggctgag aaggagataa actgcagcct tgggggtgtg  94560
gggaaggggc accacactgg gatctcagaa atgcccaaaa cctgtgtcaa aataggagac  94620
tgccgctgtg agaccctgag gagtcttctg gtgatcatgg aagaacaaat gttaagctag  94680
aactgaagga acctcatcag gggagaggca gccatcctgc cgtccccaca tctggtcttt  94740
gccatttctg tgtcctgtgg tggtcagcag caaggtctct gagccgaaag gaggcactca  94800
ctttggagga gtgcagggtc cccaggtccc cacactttgt cttgtcctga ctgagaaaga  94860
aacagactgc cctgacctct ctgacttggc cagcgaggtt gcccttaggc tcaaacccaa  94920
gccagggttt gaacattccc agacacttgt aagatgttta ggttgttaac ataatgttca  94980
ggtttcaaaa cattgaaaga aactagcccc agccctgaac ccagatcccc cccggcttca  95040
ggcatgacca gtgaacacgc ccttctctca ctggtcacct gaggatgccg cactctgtca  95100
acaggttccc ctaatacatg ctctgatctg atcgccttgg catttagtga ttctttccct  95160
ggaattctcc actggcccca tcgcagggaa ctcccaagtg ggaaactccc ctaccaccac  95220
```

-continued

```
ttttggggca acttcagcta agggttcagc tgggacaaaa cagggagcca ctcgggaacc  95280
tgggacagga ccagagagaa aacccgaggg acagagtggg taaggaaagc tgctgaggaa  95340
gggcccaaag ggcactctgg aaagaagtgg cactggaggg ctggggtggg ggtggtcctg  95400
gccagggagt cttaccttgt cccacaaaga ctgcagctct tcctgccctc ctaagtccca  95460
gaacatgagc cgagcctttc ccacatccac agtgccgact ggggagagga ggaaacaggc  95520
aaggctcatg accttggtcc tcgacacacc cagtcccagc tctcccaggg gatggggcaa  95580
accatgctgg tgccactcaa atgagacttg agaggggccc gacagggctg tggccacggg  95640
ccagctggac tgtgaatatc acggcatcct caaggcccca aacccacagc ctgctattga  95700
gacccttact gtttaggccc acggtggtgg tgattttgga tagactcatc cccttgtagt  95760
tcttgttaaa tcgggttttc gactgctcca ggaaggtctg aggagagagg cagaggcgaa  95820
acacatcaag gaggggctat actggcttcc aaatatcctt actcaggtct gttctttaaa  95880
agacagaaac agaaacagag caacactctg ctcttcagga ggctggtggt gactatcctg  95940
ccgtctcagg tgaaatttgg cttccgtctg ggtagtgaac gtgcagctga cagcacaaaa  96000
ccgaaggggg cgccgccagg ccgtgggaaa ggtgcgcgca agggcgtggg cactcaccgt  96060
cttcccagca ttgtccaggc ccaggatcag gatgcagtac tcgtccttct gaaacatgta  96120
cttgtacaag cccgacagca gcgtgtacat cctgccctgg gcaccccaac ataggtcagt  96180
gtgcagccag aaagcacctc ccctcccccg ggcttctcca cggtggtcag tggcgcccca  96240
cgtccagccg accgctcagg acgagagcct gggggccatt cccgactcct cgtccctctc  96300
ccaccccgtc cctctgtaac ttctcccagg tcagccgcca ctgtgtcctg ctcacagcaa  96360
tgactgcgac ctctccgcat acacatcggt tccggcccct cccctgctcg cgggactacc  96420
cagccgggtg ttcacagtga gctcagccgc gctcccgccc tcccccgagg cttcgctccc  96480
acgcttcacg cgcgcggaac ggggaacaca ctcgctgcag ccccgcctgg gccacggcac  96540
cctcgagcgc cagccccgcg ccccacccgg gagcagcgag ccaccggcgc gctccccagg  96600
agcccctgca ggcgccgggt agggacgccc catcacccca tttcttaaaa cggggacggc  96660
cctgggggga gcggactaca gggcgggtga gcagcggcgc ggctgctcct ggagtgcacc  96720
tggaggcggc gcgcggctgg cagggaacga ctgcgaagga agaacctggg tcgcggcccc  96780
cggctacgtc cgccccaagc cgccgccgcc aggtctgagg ctccccgaca agcagccaaa  96840
gctggctcct gtcacacccg cgtcccacct cgagtcctgg gccgcccctc gggcctcgcg  96900
cctcaccgca cagcctgcgg cctacctgcg tccgccgcgc cctcggagcc gctgctgctg  96960
acccccgctg acctccgctg accccgcgct aaccccgcgc ggcgcctgac gggacgcggg  97020
ccggcctcag ggaatgagct gaaccgcgtc ccagcggcct ccgcgctccg cttcccggct  97080
gcccccgcgc gccaagcact tccggaagcg gcggcgctcg ggaggaagtg ccgatcggct  97140
gctggggcga aaagggggcg ccgggccgct ctagccggtg aggccggcgg gctctctgtg  97200
gctgcggctg ggaaaccgcg cggaggaggt gcccggccgg ggaccaggtg gccgcggttt  97260
gcggggacgc ggccctggcc agacagaaga gacgccgggc ggggggggcgc ggccggcctg  97320
gaaggcggcg ggcgcggcgg gtgggctcgg cggagggtga ggcggcgggg cgccccgcgg  97380
ggaaggggct ccggagtgac gcgggacccg gctagcggcg agcccacggc ggctcggaag  97440
ggaagcgcgg agcctgagcg ggggtacccg ggctgcgacc tctgcgctgg gagctgtgcc  97500
tctgagccgg tgtctccccg agggaaaggg gacgtgcccg tgcccgtgcc cgccctcagg  97560
ctgtggggtc ggtcccgaga cgcggggctc agctggcttc tcttcttgca gccctggtcc  97620
```

-continued agcgcctccc tctctcagca tggacgagga gagcctggag tcggccttgc agacctaccg 97680
tgcgcagctg cagcaggtgg agctggcctt gggcgccggc ctggattcgt ctgagcaggc 97740
tgacctgcgc cagctgcagg gggacctgaa ggagctcatc gagctcaccg aggccagcct 97800
ggtgtctgtc aggaagagca ggttgttggc cgcgctggac gaagagcgcc cgggccgcca 97860
ggaagatgct gagtaccagg ctttccggga ggccatcact gaggcggtgg aggcaccagc 97920
agcggcccgt gggtccggat cagagaccgt tcctaaagca gaggcggggc cagaatctgc 97980
ggcaggtggg caggaggagg aagagggaga ggacgaggaa gagctgagtg ggacaaaggt 98040
gagcgcgccc tactacagct cctggggcac tctggagtat cacaacgcca tggtggtggg 98100
aacggaagag gcggaggatg gctcggcggg tgtccgtgtg ctttacctgt accccactca 98160
caagtctctg aagccgtgcc cgttcttcct ggagggaaag tgccgcttta aggagaactg 98220
caggtaaagc cctttgttgt cagatgccaa ccttaggggc gtaaggggca cgcacacagg 98280
gtcgggtcag gatcggccct ccctttgctt tgcagttttg tctcagcttc ctggggcagg 98340
cgtgctttga cagctgtgtc tgtgttcagg cgtctacgtc ttccttctgg ggtgaatcaa 98400
gaagcatgga aggaggccag gcgcggtggc tcacgcctgt aatcccagca ctttaggaag 98460
ccgaggcggg cagatcacct gaggtcagga gttcaagacc acgctggtca acatggtgaa 98520
accccatctc cttaaaaaca caaaaatgaa ccggtcgtgg tggcgcgcac ctgtggtcct 98580
ggctactcag gaggctgagg caggagaatt ggttgaaccc aggaggccga gtttgcagtg 98640
agtggagatg cagccactgt actgcagccc gagcagcagt gcaaggctta tgtggaagag 98700
agtaggtctc cagcctatcg tcagtttttt tttggtggtt gttttaattt tttttgagac 98760
agggtcttac tttgtcaacc aggctggagt gcagtggcat agtcctggct cactgcagcc 98820
tggacctcct gggctcaacc gatcctcctg cctcagcccc cctaggagct gggctacaga 98880
ctcacgctac tacacccagc taatttttat attactataa tttttttatct tttttttgag 98940
acggagtctt gttctgttgc ccaggctgga gtgcagtggc gtgatctcgg ctcactgcaa 99000
gctccgcctc ccgggttcac gccattctcc tgcctcagcc tcccgagtag ctgggactac 99060
aggcgcccgc caccatgtct ggctaatttt ctgtattttt agtagagacg gggtttcacc 99120
atgttagcca ggatggtctc aatctcctga cctcgtgatc cgcccacctt ggcctcccaa 99180
agtgctggga tgacaagcgt gagccaccgc gcctggcctt ttttttttgg agacagagtt 99240
tcactctcct cacccaggct ggagtgtagt ggcgcaatct cagcttaccg caacctctgt 99300
ctcccgggtt gaagtaattc tctacctcag cgtccagagt agctggcatt acaggcgccc 99360
gccaccacac tcggctaatt ttttgtattt ttagtagagt cggagattca ccatcttggc 99420
caggctggtc ttgaactcct gacctcgtga tccacccacc ttggcctccc aaagtgctgg 99480
gatcacaggc gtgagccact gcgcctggcc ctgttgttag ttttattctc tagagttcaa 99540
cttttaaatt ttactttcat ggagattttc aaacataccc caaattagag agtttagcat 99600
aatcaccgcc cacggtccat catccaatgt cgtcatttat taatattttc ccagtctcat 99660
tttgtctgtt ctccctgccc tatttttttc tttcctgggc cattttaaag caaattccag 99720
aagttactgg tttttttccaa ttatgaatac ttcatagttg catctctaat ctaactgatt 99780
aggaaattac ttaaaaagta actttttgga agtccaagtc cgatgtgagg acaaaaaaga 99840
gtaacttctg tgtcataata ggtaacacat ttaatggtaa tacctcttcc atattcaaat 99900
atgaacaatt attactgtaa tgtctctatt tccctaagcg catagcttta tttttcctcc 99960

-continued

```
tttttacttt tctcttagaa gaaatattta ccaagccttc tagtaggtaa ttttcttttt 100020
tagccaatag ttcaggctga ccgtgtaacc atccctagtt ctagttctag ttctttgaat 100080
gtcttccttt tttttttttt ttgaaacagc gtcttgctgc tctgtcaccc aggctggagt 100140
gcagtggcac aatctcggct cactgcaatc tccgcctccc tggcccaagc catcctccca 100200
cctcagcctc cctaatagct gatactacaa gtgtgcactg ccacgcccag ctaatttttg 100260
tatttttgt agagacggga tttcaccata ttacccaggt ctcgaattcc tgatcccttt 100320
gatgagagat ctgacacatc cctgtggtgc tccctctgga ccaggcactg ctccaagggt 100380
ttcatatact ttcattcatc tgtgcaacag ccctgtaggt aggccctgca gtcacaccat 100440
ctgacagagg aggaaacagg agtagaagaa ctgagtggtc cagggcttca aggctcagag 100500
ggctccagtt gcccccagcc ctcgttccgt cccctgctcc acccagtgct gcttgccatg 100560
tcggcatcag gcctgatctg aaagcttccg gagcatctta cagacgtcca ccttgccacc 100620
attcaggact gataagttct cttggatttg cgttggacct tttttttttt tttaagatgg 100680
agtttcactg ttgttgccca ggctagagta caatggcacg acctccacct cctgggttca 100740
agggattctc ctgcctcagc ctcccaagta gctgggatta caggcgcctg tcaccacgtg 100800
gtgcccagct aatttttata tttttagtag aggcagggtt tcaccgtgtt ggccaggctg 100860
gtctcgaacc cttgacctca ggtgatcccg ccttggtttc ccaaagtgct gggattacag 100920
gcatgagcca ccacacccgg cccaggattt ctttatatat tctggatatc atcccttatg 100980
aagtatatag tttgcagata tttgctccca ttgtttgggt tgtcttttca cttgatatag 101040
tgtcctttga tgcacaaaca ttttaaattt tgatgcagtg caatttattg tttctttatt 101100
gcctatgttt ttgtcatcag gtttaagaaa ccacctcatc catagttatg aggattttca 101160
cctatgtttt cttctaagag ttctgtagtt ttagctgtta aatttaggtc tttgatccat 101220
tttgagttaa tttttgtata tgttattagg tgagggtcca ctttattctt ttgcatgtgg 101280
atttccagtt ttcccagcac catttgttta aaagactgct ttttctccac tgaatggtct 101340
tggcactttt gtccaaaatc aattggcaat atatgtaagg gtttatttct gagctctctc 101400
tcctgttcca ttggtgtata tgtgccagta ccacactgtt ctgattatta tagctttgtg 101460
ataagtttta aactcaggaa gtggtagtta ttcaccattt gctcctcttt ttcaagtttg 101520
ttttgtttct ggatcctttg caatttcata tgaattttag gatcggcttg tccaattctg 101580
cataaaagac agtttgaatt ttgatatgga ttgcatagaa tgtgtagatc tgtttggggc 101640
acattgtcat ctttacaata ttaagccttc tggctgggtg tggtggctga cgcctgtaat 101700
cccagtactt tgggaggctg aggcgggcat atcacttgag gtcaggagtt caagaccagc 101760
ctggccaacg tggtgaaacc ccgtctctac taaaaataaa aaacaaatta gtcggaggtg 101820
gtgcacacct gtaatcccag ctacaggaga gggtgaggca ggagaatcgc ttgaacctgg 101880
gaggaggagg ttgcagtgag ctgagatcat gccactgcac tccagcctgg gtaacagagg 101940
gagactccat cttaaacaac aacaataaca gaagaaaaaa acagtattaa gtcttccaat 102000
tcatgaatga aggatctgtc catttattta cgtctttaat ttctttcaac agtattttgt 102060
actgttcaag tcttgcacat tcttggttaa ataagtatta tttttgatgc ttctctaagg 102120
aattgttttt cttttccttt tttttttga gacagagtct tgctctgtca cccaggctgg 102180
agtgcagtgg cacaatcttg gctcactgca acctctgcct cccgggttca agcaattctt 102240
ctgctcagcc tcccaagtag ctgggatcac aggtgcctgc caccacaccc agctaatttt 102300
ttttttgag atggagtctt gctctgttgc ccaggctgga gtgaagtggc ccaatcttgg 102360
```

-continued ctcactgcaa gctccacctc ccgggttcac accattcttc cgcctcagcc tcctgagtcg 102420
ctgggaatac aggtgcctgc caccacgccc agctaatttt ttgtattttt agtagagatg 102480
gggtttcacc atgtagccag gatggtctcg aactcttgac ctcaggtgat ctgcctgcct 102540
cggcctccca aagtgctggg attacagatg tgagccactg tgcccggctc gagttgtttt 102600
ccttagttac attttcaggc tgtttgttgc tagtatatag aaatacaagc tgggcaccgt 102660
ggctcacgcc tgtaatccca gcactttggg aggccaaggc gggtggatca cctgtggtca 102720
ggagttcgag accagcctgg ccaacatggt gaaatccagc ctctattaaa aatacaaaaa 102780
ttagtctggc atggtggcag gtgcctgtaa tcccatctac tcaggaggct gaggcaagag 102840
aattgcttga acctgggagg cggaggttgc agtgagctga gatcgcgcca ttgcactcca 102900
gcttggggaa caagagtgag acttcatctc aaaaaaaaaa aaaaagaaat acagtggatt 102960
tttttatgtt aatcctgtat tgattgctga attggtttat tagtgctaat aggatttttt 103020
atgcactatt taggattttc gatatataca atcatatata ttcaatatat acaattaata 103080
tatatgtgaa tagagataat tgtagtcttt gtttctagtt tgcatggcat ttatttcttt 103140
ttcttgctta actgccttag ctagaacttc aagtacgatg ttgaataaaa gtgactagag 103200
cgggccgggg gtggtggctc acacctgtgt tcccagcact ttgggaggtg gaagtgggca 103260
gatcacttga gatcagcagt ttgagaccag cctggccaac acggcgaaac cccatctcta 103320
ctaaaaatac aaaaattagc tgggtgaggt gatgtgcacc tgtagtccca gctacttgag 103380
agggtgagac atgagaattg cttgaacctg gggggcggag gttgcagtga gccaagatca 103440
tgccactcca ctccagcctg gacgacagag caagaaccct gtctttaaaa aaaaaaaaaa 103500
aaaagtggct agaacaaaca tctttatctt gttcctgatc ttaggtggaa aacttttttg 103560
ttcctgatat taggtggaaa acttttagtc tttcactgtt gaatatgatg ttacttgtag 103620
gttttctgta gattcccttt atcgagttga ggaaattctc ttatattcat agtgtgttga 103680
gtgtttttta tcatgaaagg gtgttgattt tttttttaaa gatagggtct tgttctgtca 103740
cccaggctgg agggcagtgg catgatcatg gctcactgca acctcgaatt cctgggctca 103800
ggggatcctc ctacttcatc ctcctgagta ggtgagacta caggcatgag ccaccatgcc 103860
cagctaattt tttaattttt ctgtagaggt agggtcctgc tttgctgccc aggctggtct 103920
taaactccag ggctcaagca atcctgcctc agcctcccaa agtgctgaga ttacaggggt 103980
gagtcactgc actgcaccca gctgtgtggg atttttcaaa tgcttttttc ctttagatga 104040
tcatgtgtgg tttttttcct ttcattttgt taatgtggta tattgatttt cgtatgttga 104100
accatccttg aattcctcag ataaagcacg catattcatg gcgtattatc tctttattat 104160
tatttttttt gtagagatga gatttcactc tgttgcccaa gctggtctca aactcctggg 104220
ctaaagtgat cctcctgcct cagcctccga aagcgctggg attataggca tgagccactt 104280
ggccctatct tttttctttt tctttttttt ttttttttga gacagagtct cactctgtcg 104340
ccgggctgga gtgagtggcg cgatctcggc tcactgcaac ctccatctcc cgggttcaag 104400
caattctcct gcctcagcct cctgagtagc tgggactaca ggtgcccgcc actatgccca 104460
gctaattttt tgtgttttta gttgagacgg tgttttgcca tgttggacag gctggtcttg 104520
cactcctgac ctcgtgattc acccaccttg gcctcccgaa gtgctgggat tacaggcatg 104580
agccaccgca gcgagcctta tctttttaac agttaaaagt ttaaggcctt atcatgtaat 104640
aacattgctg gatttgattt gctgctgttt tgttgagaat atttgcatct gtattgataa 104700

-continued gggatattgg tctgtagttt tcttttcttg gcatgtcttt gtatagcttt gatgccagca 104760
taatattggc ctcatagaat gagttaggaa gtattcttta tattatggga agaggtaaaa 104820
agggattggt gttaattctt cttcaaatgt ttgatagaat tcaacagtga agtgatatat 104880
acaatcatat atatagagag agagagagag agagatggac ttttcttttg ttggaagttt 104940
attgactatt gattcaattt ccttattgaa attgactttt ctttttggaa gctaaaatgt 105000
ataactgtag tgaaagtttc tgaacttttc tttcattgga agttttttga ctactgattc 105060
tttatttgtt ataggtctat tcagattttc tgtttcttct tgagtcagtt tggtctcgct 105120
ctgtcgccca ggctggagtg cagtggtgcc atcttggctc actgcaactt ctacctcccg 105180
agttcaagtg attctcccac ctcagcctcc ccagtatctc ggactacagg cgcacgccag 105240
catacctggc taatttttgt atttttagta ggaacagcat ttcaccatgt tggccaggct 105300
ggtctcgaac tcctgacctc aggtgatcca cccgcctcgg cctcacaaag tgctgggact 105360
acagacataa gccaccgcgt ccagccttga gtcagtttag atagtttgca tgcatgtttc 105420
taggaatttg tccattttgt ttatgttatc taatctgtta ccatacaatt gttcatagta 105480
tccttttata gccctagtta tttctgtaag atcagtagta atagctccac tttctctctt 105540
ggttttagca atttgagtca tctcttttct tcttcttttt tttttttga gatggagtct 105600 cactgtgtca cccaggctgg agtgcagtgg catgatcttg gctcactgca acccctgcct 105660
cccaggttca agcaattctg ccttagcctc ctgagtagct gggattacag gtgtgagcca 105720
ccacacccag ctagttttgt tttgtttttt tgtttttgag acggagtctg tttctgtctc 105780
ccaggctgga gtgcagtggt gcaatctcac tcattgcaac ctccgactcc cagattccag 105840
caattctcct gcctcagcct cccgagtagc tggaactata ggcgtgcacc accacgcctg 105900
gctgattttt atatttttag tagagatggg atttcaccat gttggccagg ctggtcttgg 105960
actccctacc tgaggtgatc cgcccacctt ggcctcccaa agtgctggga ttataggcat 106020
gagccaccat gcccagccag tttttgtatt tttagtagag atggggtttc tccctgtcgg 106080
ccaggctggt cttgaaatcc tgacctcagg ttatccacca gccttggcct cccaaagtgc 106140
taggattaca ggcatgagcc accacgcatg gcctgtcttt tcttcttggt cattttcgct 106200
aaaggtttgt caattttgtt gatctttttt gttgctgatc tctattgttt tcccattctg 106260
tttcatttat ttccatttta acctttgttt cctttttttct gctggtttgg gtttaatttg 106320
ctcttttttt cccctaattt ttcaaggtat acagttaagt tattgatttg agatctcttt 106380
tttcttttct tttttttttt ttttttttt tttggttgct gttgagatgg agtctccctc 106440
tgtcacccag actggagtgc agtggcatga tctcagctca ctgcagcctc cgccgcccag 106500
gcgattctcc tgcctcagcc tcctgagtag acgtttcccg gccaaggtgt ttcttttttga 106560 atgtaagcat ttacagctac agatttccct ctaaacactg ctttcactgc attccataag 106620
attgtttttt gttgtttttt gttgttgttt tgttgtttga gacacagtct cactctgttg 106680
ccgtttggag agcagcgatg cgatcatagc tctgtagcct tgagctcctg gactcaatca 106740
gtcctcctgc ctcagcctcc caagtagctg ggactacagg tgtacaccac tgcacctaac 106800
taatttcttt tataagtttt tgcagaggcc aggcacagtg gctcacacct gtaatcccag 106860
cactttggga ggccaaggtg ggtggatcac ctaaggtcag gagttcgaga ccagcctggc 106920
cgacagggag aaaccccatc tctactaaaa atacaaaaat tagctgggcg tggtggcagg 106980
tgcctgtaat cccagctact caggaggctg aggcaggaga atcgcttgaa cctgggaggc 107040
agaggttgca gtgagccagg atcacaccat tgcactccag cctgggtaac aaaagcaaaa 107100

-continued ctccatctca agaaaagaaa aaaaaaagtt tttgcagaga cagggtatca ctttgttgcc 107160
caggctggtc tcaaactcct gacttgaagg agtcctactg cctcagcctc ccaaagtgct 107220
gagattatgg gcaagagcca ccgcaccctg ccacttggct gttttgttct gttgtatttc 107280
cattttcatt gatctcaaga catcctaatc tccctttttgt ttttttgttc gacttactgg 107340
ttattcaaga gtgtctttat ttctgcatat ttgtaaattt tccaaaaaag tttttctttc 107400
tttttttttt gagaaagggt cttgctctgt cgcccaggct ggagaatggt ggtgcacaat 107460
cttgcctcac tgcaacctct gcctcccggg ttcaagtgat cctcccacct cagccttccc 107520
agtagctggg attacaggca cacaccacca cacctggcta atttttgtat tttagtctta 107580
acgtgctggt cagactggtc tcgaattcct gacctcaggt gatctgcccg ccttggcctc 107640
ccaaagcact gggattacag gcgtgaaaca ccatgcccag cccccaattt ttttttttta 107700
atagagagaa ggtctcactc aagcccaggc tggtcttgaa ctcctgagct caagctgtca 107760
tccctcctcg gcctcccaag gtgctgagat tacaggtgtg agtcacagta cctggccttc 107820
tttcaagact ttaaaaatgc catcttggct gggcacggtg gctcacgcct gtaatcccag 107880
cactttggga ggccgaggtg ggcagatcac gaggtcagga gatcaagacc accctggcta 107940
acatggtgaa accctgtctc tactaaaaat acaaaaaatt aaccaggtgt ggtggcaggt 108000
gcctgtagtc ccagctactc gggaagctga agcaggagaa tggcgtgaac ccgggaggtg 108060
gagcttgcag tgagctgaga tcacaccact gtactccagc ctgggcaaca gtgcgagact 108120
ccgtctcaaa aaaaaaaaaa aaaatgtcat ctcactgcct tctggtccaa tagtttctga 108180
tgagaaattg gctgttaatc ttattgagga acatttatat attgactagt cacttgtctc 108240
ttgctgtttt aggagattct ctatctttgg gtttcagcag tttgattata atgtatcagt 108300
gtggatccct caatttataa gctacttgga gttcattgga cttcttggat gtgtaaattc 108360
atgtctttca ttaaatttgc aaagtttcag ctactattct ttgcatcttg aaatactagt 108420
tttgtttctt tctgtctgtt tgccgcttat ggaactttat gcatacattg atgtgcttca 108480
tggtgtagca caggtccctt gggctctagg catttttctt tgttcttttt ttctttctgc 108540
tcctcatttt ggataaattc agctgacctg tcctcaagtt cactgtttct ttcttcttcc 108600
ttctcaaatc tgctgttgaa acttctggtg aaattttcac tacagttact gtacttttta 108660
gctccaaagt ttctatttgg tttctttctg tagtaattat cactttacta gtattctcta 108720
tttggttaga catggttctt ttgttttcct ttagttcatt atccatggtt tcctttattt 108780
ttaaatttct ttttatttag ttattaattt tttttttttt tgaagcgggg tttcactctt 108840
gtcacccagg ctggcaggca acgtcacaat cttggctcac tacaacctcc gcctcctggg 108900
ttcaagtgat tctcctgcct cagcctccca agtagctggg attataggca tgtgccacca 108960
cacccaccta atttttggta tttttagtag aaactgggtt tcaccacatt ggccagactg 109020
gtcttaaact actaacctca ggtgatctgt ccgcctcagc ctcccaaaat gctgggatta 109080
cagatgtgag ccactgtgcc cagcctcttt ttttagtgta tttaaggtaa ttgattgaaa 109140
gtttttgtct agtcattcaa atgtctaggc ttcctcagga acagtttcta ttaatttctt 109200
tatttttaaa aaattttttt taattttctt tttttttag atggagtctc actctatagc 109260
ctaggctgga gtgcaatggc ttgatcttgg ctcactgcaa cctctgcctc ctgggttcaa 109320
gcgattctcc tgcttcagcc tcctgagtag ctgggactat aggtgcgtgc caccactcct 109380
ggctaatttt ttgtattttc agtagagaca tggttttgcc gtgttagcca ggatggtctc 109440

-continued gatctcgtga cctcatgatc ctcctgcctc ggcctcccaa agtgctggaa ttacaggtgt 109500
gagccaccgc gcccagccta ttttttattt tttgagacaa agtctccctc tctcacccag 109560
gctgtagtgc agtggcacaa ccctggcaca ctgcagcctt aaccgtccag gcttaagtga 109620
gtctcccacc ttagtctcct gagtagctag aactacaagc atgtgccacc atgcctggct 109680
ggttgtgttg ttactgtttt agacacaggg tcttgctaca tttctctgac tggtcttgaa 109740
ctcctgggct caagcagtca tcccaccttg gcctcccaag gtgttgagat tacaggtgtg 109800
agccaccgca cccggcctgt taatttcttt atttccggtg aatgggccac actttcttgt 109860
ttctttgcat gccttgtaat tttttgttga aacctgcaca atttgaagat gataatgtgg 109920
ttactttgaa aatcagatcc tccgccctct gcagggttca ttgttgctgt ttgttgtgga 109980
ttgtcgtttc tcgtttgttt agttactttc ctgacctttt taaataaaga ctatattctg 110040
tcaggggtgc ttgtttctgt tcttttaggt tagtggttag cttgtgcttt gaaagagatt 110100
tctttaaata tctagtggca aaaaggataa agaggccggg cgcagtggct cacgcctgta 110160
atgctaggac tttgggaagt ggaggcgggt ggatcacttg aggtcaggag tttaagatca 110220
gcctggccag tatggtgaaa ccctgtctct actaaaaata caaaaattaa ccgggcatgg 110280
tggcacctgc ctgtagtccc agctactggg aagactgagg caggagaatc gcttcaatcc 110340
agggggcgga ggttgcagtg agctgagatt gcgccattgc actccagcct gggcaacaga 110400
gcgagactct gtctcaaata aaaaaaaaaa aaaaaggata aagagtgtct tccatccttt 110460
ccaggttgcc tctgtactgg ggcaagtcct tcagtgtccg ccaggctgtt cacggctttt 110520
cctcagcctt tacttctcgc tcccatggag cctaaggatg aaccagaggt gaaagttgag 110580
ggcctcctca ggtgtttctg agcccctgtc tagccccagc tgtgtgcatg gccttctgga 110640
tttccaagca tgaacaggag ctttccaaag cccttagacc ttcatgtagc tcttttccca 110700
gcctcttcct tcctaggctt ttctgtcagc tctttgccca tctgttgttg tccctccccc 110760
acaacttcag gtagtatcta cctgtaaatg ccttcaggcc aggcgcggtg gctcatacct 110820
gttatcccag cactttggga ggccgaggcg ggtgaattgc ttgaggtcag gagttcgaga 110880
ccagcctggc caacatggtg aagccccgtc tctagtaaaa atacaaaaat tagctgggcg 110940
tggtgggtgc ctgtaatctc agctactcgg gaggctgaag caggagaatt gcttgagcct 111000
gggaggcgga ggttgcagtg agctgagatc gtgccattgc actccagcct gggcgacaga 111060
gtgagactcc atctcgggga aaaaaaaaaa aaaaaaatgc catcaacagc acgaccctgg 111120
aggctgcccc agccctgaga gagttcgagg gggtgaaaca aaggcaagcc cttcagggag 111180
acactagaaa gatccaaatg cataagcagg attccttgag aaaaggtctg tatcatccct 111240
tctgacacca gcaagccaca tcagaaatac aggttgcctt ccccatggct acatgtgagc 111300
tggtagtagt ggctgagcag aaatagccca gctgtcctcc tgaaatttag cagggtctta 111360
cttcattgag cagtcatctg gttcgtagac accagagtta cagaaaagtt tattgggagg 111420
ttttgacagt ttaatagaaa aaagtttatt gtgacagttt tgacagctga atagaaaaaa 111480
gtttactgtg acagttttga cagcagaata gttgctttgc tggagagacg gatctttgga 111540
gctgccaact ccatcatttt ggtgatatcc agctctgttg ctgaattttt agctatgctg 111600
ttttaagtta ttttcttagt ggttgctcta gagatgacaa tgtgcatctt taacttacca 111660
caatgtactt cagattatta ctaacttaac acttaaagta cagcattttt ttttttatgg 111720
agtttcactc tgtcacccag gctggagtgc aatggtgtga tctcggctca ctgcaacctc 111780
cgcctcccag gttcacgcca ttctcctgcc tcagcctcct gagtagctgg gactacaggc 111840

-continued acccccacca cacccggcta attttgtatt tttagtagag atgaggtttc accatgttgg 111900
tcaggctggt ctcgaactgc tgacctcagg tgatccgccc atcttggcct cccaaagtgc 111960
tgggattaca ggtgtgagcg actgcactga gcctaagtat ggcaacgtgt ctataacata 112020
gatctacttc cgttgtacta tgacatagtt ccccctccat tttcctatag cacagtccca 112080
acctcccttt tcctctgaca tagttccatc ctccctcctc ctatgacgtc ctcccttctc 112140
ctctggcata gctccatcct cccttctcct atgacacagc tccatcctcc cttctcctct 112200
gacacagctc catcctccct tctcctatga cacagctcca tcctcccttc tcctctgaca 112260
tagctccatc ctcccttctc ctatgtcata gctccatcct cccttctcct ctgacacagc 112320
tccatcctcc cttctcctct ggcatagctc catcctccct tctcctatga cacagctcca 112380
tcctcccttc tcctatgaca cagctccatc ctcccttctc ctatgacaca gctccatcct 112440
cccttctcct atgacacagc tccatcctcc cttctcctct ggcatagctc catcctccct 112500
tctcctctga catagctcca tcctcccttc tcctctgaca tagctccatc ctcccttctc 112560
ctctgacata gctccatcct cccttctcct ctgacatagc tccatcctcc cttctcctct 112620
gacatagctc catcctccct tctcctctga catagttcca tcctcccttg tcctctgaca 112680
tagctccatc ctcccttctc ctctgacata gctccatccc ctcttctcct tcatgtatta 112740
ttgccatata tacatttatg tatgttataa cttcagctct tcagcgttat aattattgct 112800
tcaaaagtat tttgaaagaa gttgcctgga ggcagtggct tatgccttta actccagcac 112860
ttttgggggc tgaggtgggc agatcgcctg agccagggag ttggagacca gcctgggcaa 112920
catgacgaaa cccatctcca ccaaaattac aaaaaattag tctggcatgg tggcacgcgc 112980
ctgtagtccc agctatttgg gggaggatcc cagctaaggt gggaggatca cttgagcctg 113040
ggaagtcaag gctgcagtga gctgagattg tgccactgca ctccagcctg ggtgcagatc 113100
ttatctcaga agtaaaggga ctaggaatgg tggcttttat ctctaatccc agcactttgg 113160
gaggctgagg tgagtggatc accggaggtc aggagtttaa gaccagcctg gccaacatgg 113220
tgaaaccccg tctctactaa aaatacaaaa agtagccggg tgtggtggtg ggtgtctgta 113280
atcccagcta ctcgggaggc tgaggcaaga gaatcgcttg aacctgggaa gcggaggttg 113340
cagtgagcaa gatcgcacca ctgcattaca gcctagatga cagagcgaga ctctgcctaa 113400
aaaaaaaaaa aaaaagaaaa gaaaagaaat taagatctag acactgtggt tcatgcctgt 113460
aatcccaaag ccttgggagg ccaaggcagg aggatcactt gaggccagga gttcaacacc 113520
agcctgggca acatagcgag actccatctc tatttaaaaa agaaagaaat tcaaagagaa 113580
aaaaagtata cttgtttttt tgtatcatcc atattttacc tttctttttt ttgccccttt 113640
ttctttcctg tgaatttgag ttactgtcta gtgtcatttc cttttagtct gaagaacttc 113700
atttagaatt tttttttttt tttgagacaa agtctcactg tgttgcccag gctggagtgc 113760
aatggtgcag tctcagatca ctgcaacctc tgcctccctg gttagagtga ttttcctgcc 113820
tcagcctccc aagtagctga gactgcaggc acctgccacc acccccagcc aatttttttg 113880
gtatttttag tagagacagg gtttcactat gttggccagg ctggtctcga attcatgacc 113940
tcatgatctg cctgtcctgg cctcccaaaa tgctgggatt accatgagcc accacgccca 114000
gcccatttag aatttctttt tttttttttt ttttgagatg gggtctcgct cttgtttccc 114060
aggctggagt gcagtggcac gatctcggct cactgcgagc tccgcctccc gggttcacgc 114120
cattctcctg cctcagcctc ccgagtagct gggattacag gcgcctgcca ccacgcccac 114180

-continued

```
ctaatttttt gtatttttag gagagatggg gtttcaccat gttagccagg atggtcttga 114240

tctcctgacc tcgtgatccg cccgccttgg cctcccaaag tgctgggatt acaggcgtga 114300

gccaccgcgc ccggctagaa tttcttgtag gacaggcttg ctagcaacca attcagtgtt 114360

tatttgggaa tgtctttatt tcagcttcat tttttgaagg atagtttagc tggctataga 114420

attattaatt gatcattctt ttcagtgttt aaaagtgtca tcatgctacc ttctgggttc 114480

cattgtttct gatgagaagt catctgtcaa attgtccctt tgtacttgaa gaattatctt 114540

tttttctctt gatgttttca agattttctc tttgtctttg gcctttagta gtttgtgatg 114600

tatctaggtg tggatctctt ggtgtgcatc gtatttgggc ttcagtaagc ctcttagatt 114660

catagattaa tgttttgttt tgttttacca aatttggaga gtttttactc atcatttcaa 114720

caaatttttt tcctgcccct ctctcatctc cttttgggag taccactgca tgtatgttgg 114780

tgtgcgttct cta                                                    114793


<210> SEQ ID NO 4
<211> LENGTH: 25
<212> TYPE: DNA
<213> ORGANISM: Artificial Sequence
<220> FEATURE:
<223> OTHER INFORMATION: oligonucleotide

<400> SEQUENCE: 4

cacaggttca gcatgtttgt gcgtc                                           25


<210> SEQ ID NO 5
<211> LENGTH: 25
<212> TYPE: DNA
<213> ORGANISM: Artificial Sequence
<220> FEATURE:
<223> OTHER INFORMATION: oligonucleotide

<400> SEQUENCE: 5

cacagtccct gctggcctct gtcta                                           25


<210> SEQ ID NO 6
<211> LENGTH: 25
<212> TYPE: DNA
<213> ORGANISM: Artificial Sequence
<220> FEATURE:
<223> OTHER INFORMATION: oligonucleotide

<400> SEQUENCE: 6

caggacatct ccatcaagag gctgc                                           25


<210> SEQ ID NO 7
<211> LENGTH: 25
<212> TYPE: DNA
<213> ORGANISM: Artificial Sequence
<220> FEATURE:
<223> OTHER INFORMATION: oligonucleotide

<400> SEQUENCE: 7

aataagaggg ggccaggatc agtgc                                           25


<210> SEQ ID NO 8
<211> LENGTH: 20
<212> TYPE: DNA
<213> ORGANISM: Artificial Sequence
<220> FEATURE:
<223> OTHER INFORMATION: oligonucleotide

<400> SEQUENCE: 8
```

-continued gtgaatggca tcctggagag 20

<210> SEQ ID NO 9
<211> LENGTH: 20
<212> TYPE: DNA
<213> ORGANISM: Artificial Sequence
<220> FEATURE:
<223> OTHER INFORMATION: oligonucleotide

<400> SEQUENCE: 9
gtctccaggc agctcaacag 20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
accctgtccc tcctgtctga 20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
agaccctaag atgttcggag 20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide

<400> SEQUENCE: 12
gatgacctgt gtgagttgcg 20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
cgcaactcac acaggtcatc 20

<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
ggagtcaggt caaaggatgc 20

<210> SEQ ID NO 15
<211> LENGTH: 20
<212> TYPE: DNA

-continued

<213> ORGANISM: Artificial Sequence
<220> FEATURE:
<223> OTHER INFORMATION: oligonucleotide

<400> SEQUENCE: 15
gcatcctttg acctgactcc 20

<210> SEQ ID NO 16
<211> LENGTH: 20
<212> TYPE: DNA
<213> ORGANISM: Artificial Sequence
<220> FEATURE:
<223> OTHER INFORMATION: oligonucleotide

<400> SEQUENCE: 16
ggtctgaaac gtgatctggg 20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
cccagatcac gtttcagacc 20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide

<400> SEQUENCE: 18
cgatgatgtg tgggttctcc 20

<210> SEQ ID NO 19
<211> LENGTH: 20
<212> TYPE: DNA
<213> ORGANISM: Artificial Sequence
<220> FEATURE:
<223> OTHER INFORMATION: oligonucleotide

<400> SEQUENCE: 19
ggagaaccca cacatcatcg 20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide

<400> SEQUENCE: 20
cgtgtctgag aagtccagcc 20

<210> SEQ ID NO 21
<211> LENGTH: 20
<212> TYPE: DNA
<213> ORGANISM: Artificial Sequence
<220> FEATURE:
<223> OTHER INFORMATION: oligonucleotide

<400> SEQUENCE: 21
ggctggactt ctcagacacg 20

-continued

<210> SEQ ID NO 22
<211> LENGTH: 20
<212> TYPE: DNA
<213> ORGANISM: Artificial Sequence
<220> FEATURE:
<223> OTHER INFORMATION: oligonucleotide

<400> SEQUENCE: 22
acagcatctt ctccacgcac 20

<210> SEQ ID NO 23
<211> LENGTH: 20
<212> TYPE: DNA
<213> ORGANISM: Artificial Sequence
<220> FEATURE:
<223> OTHER INFORMATION: oligonucleotide

<400> SEQUENCE: 23
agtcctctgg ctttgcagtg 20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24
tgtgcgtgga gaagatgctg 20

<210> SEQ ID NO 25
<211> LENGTH: 20
<212> TYPE: DNA
<213> ORGANISM: Artificial Sequence
<220> FEATURE:
<223> OTHER INFORMATION: oligonucleotide

<400> SEQUENCE: 25
ggctggaaag ggaagtctac 20

<210> SEQ ID NO 26
<211> LENGTH: 20
<212> TYPE: DNA
<213> ORGANISM: Artificial Sequence
<220> FEATURE:
<223> OTHER INFORMATION: oligonucleotide

<400> SEQUENCE: 26
tggttcaggt gctcttgggg 20

<210> SEQ ID NO 27
<211> LENGTH: 20
<212> TYPE: DNA
<213> ORGANISM: Artificial Sequence
<220> FEATURE:
<223> OTHER INFORMATION: oligonucleotide

<400> SEQUENCE: 27
cgtgaagcag gagttgagcc 20

<210> SEQ ID NO 28
<211> LENGTH: 20
<212> TYPE: DNA
<213> ORGANISM: Artificial Sequence
<220> FEATURE:

-continued

<223> OTHER INFORMATION: oligonucleotide

<400> SEQUENCE: 28
atcttgctct gggtcttccc 20

<210> SEQ ID NO 29
<211> LENGTH: 20
<212> TYPE: DNA
<213> ORGANISM: Artificial Sequence
<220> FEATURE:
<223> OTHER INFORMATION: oligonucleotide

<400> SEQUENCE: 29
cactgcaaag ccagaggact 20

<210> SEQ ID NO 30
<211> LENGTH: 20
<212> TYPE: DNA
<213> ORGANISM: Artificial Sequence
<220> FEATURE:
<223> OTHER INFORMATION: oligonucleotide

<400> SEQUENCE: 30
ataagcaaga cgacgacctc 20

<210> SEQ ID NO 31
<211> LENGTH: 20
<212> TYPE: DNA
<213> ORGANISM: Artificial Sequence
<220> FEATURE:
<223> OTHER INFORMATION: oligonucleotide

<400> SEQUENCE: 31
ctattctgtt gggtgggttc 20

<210> SEQ ID NO 32
<211> LENGTH: 20
<212> TYPE: DNA
<213> ORGANISM: Artificial Sequence
<220> FEATURE:
<223> OTHER INFORMATION: oligonucleotide

<400> SEQUENCE: 32
cgtgcctcct gtgcttaccc 20

<210> SEQ ID NO 33
<211> LENGTH: 20
<212> TYPE: DNA
<213> ORGANISM: Artificial Sequence
<220> FEATURE:
<223> OTHER INFORMATION: oligonucleotide

<400> SEQUENCE: 33
cagaccccaa ggtagctcag 20

<210> SEQ ID NO 34
<211> LENGTH: 20
<212> TYPE: DNA
<213> ORGANISM: Artificial Sequence
<220> FEATURE:
<223> OTHER INFORMATION: oligonucleotide

<400> SEQUENCE: 34
ggaagaccca gagcaagatc 20

-continued

<210> SEQ ID NO 35
<211> LENGTH: 780
<212> TYPE: PRT
<213> ORGANISM: Dictyostelium discoideum

<400> SEQUENCE: 35

```
Met Lys Phe Tyr Ile Glu Asp Leu Leu Val Tyr Phe Pro Tyr Ser Tyr
 1               5                  10                  15

Ile Tyr Pro Glu Gln Tyr Ser Tyr Met Val Ala Leu Lys Arg Ser Leu
            20                  25                  30

Asp Asn Gly Gly Pro Cys Ile Leu Glu Met Pro Ser Gly Thr Gly Lys
        35                  40                  45

Thr Val Ser Leu Leu Ser Leu Ile Ser Ser Tyr Gln Val Lys Asn Pro
    50                  55                  60

Ser Ile Lys Leu Ile Tyr Cys Ser Arg Thr Val Pro Glu Ile Glu Gln
65                  70                  75                  80

Ala Thr Glu Glu Ala Arg Arg Val Leu Gln Tyr Arg Asn Ser Glu Met
                85                  90                  95

Gly Glu Glu Ser Pro Lys Thr Leu Cys Met Ser Met Ser Ser Arg Arg
            100                 105                 110

Asn Leu Cys Ile Gln Pro Arg Val Ser Glu Glu Arg Asp Gly Lys Val
        115                 120                 125

Val Asp Ala Leu Cys Arg Glu Leu Thr Ser Ser Trp Asn Arg Glu Ser
    130                 135                 140

Pro Thr Ser Glu Lys Cys Lys Phe Phe Glu Asn Phe Glu Ser Asn Gly
145                 150                 155                 160

Lys Glu Ile Leu Leu Glu Gly Val Tyr Ser Leu Glu Asp Leu Lys Glu
                165                 170                 175

Tyr Gly Leu Lys His Gln Met Cys Pro Tyr Phe Leu Ser Arg His Met
            180                 185                 190

Leu Asn Phe Ala Asn Ile Val Ile Phe Ser Tyr Gln Tyr Leu Leu Asp
        195                 200                 205

Pro Lys Ile Ala Ser Leu Ile Ser Ser Ser Phe Pro Ser Asn Ser Ile
    210                 215                 220

Val Val Phe Asp Glu Ala His Asn Ile Asp Asn Val Cys Ile Asn Ala
225                 230                 235                 240

Leu Ser Ile Asn Ile Asp Asn Lys Leu Leu Asp Thr Ser Ser Lys Asn
                245                 250                 255

Ile Ala Lys Ile Asn Lys Gln Ile Glu Asp Ile Lys Lys Val Asp Glu
            260                 265                 270

Lys Arg Leu Lys Asp Glu Tyr Gln Arg Leu Val Asn Gly Leu Ala Arg
        275                 280                 285

Ser Gly Ser Thr Arg Ala Asp Glu Thr Thr Ser Asp Pro Val Leu Pro
    290                 295                 300

Asn Asp Val Ile Gln Glu Ala Val Pro Gly Asn Ile Arg Lys Pro Ser
305                 310                 315                 320

Ile Phe Ile Ser Leu Leu Arg Arg Val Val Asp Tyr Leu Arg Glu Pro
                325                 330                 335

Asp Lys Ser Arg Leu Lys Ser Gln Met Leu Leu Ser Glu Ser Pro Leu
            340                 345                 350

Ala Phe Leu Gln Gly Leu Tyr His Ala Thr Gln Ile Ser Ser Arg Thr
        355                 360                 365

Leu Arg Phe Cys Ser Ser Arg Leu Ser Ser Leu Leu Arg Thr Leu Arg
    370                 375                 380
```

-continued

```
Ile Asn Asp Val Asn Gln Phe Ser Gly Ile Ser Leu Ile Ala Asp Phe
385                 390                 395                 400

Ala Thr Leu Val Gly Thr Tyr Asn Asn Gly Phe Leu Ile Ile Ile Glu
                405                 410                 415

Pro Tyr Tyr Gln Arg Gln Asn Asn Thr Tyr Asp Gln Ile Phe Gln Phe
            420                 425                 430

Cys Cys Leu Asp Ala Ser Ile Gly Met Lys Pro Ile Phe Asp Lys Tyr
        435                 440                 445

Arg Ser Val Val Ile Thr Ser Gly Thr Leu Ser Pro Leu Asp Ile Tyr
    450                 455                 460

Thr Lys Met Leu Asn Phe Arg Pro Thr Val Val Glu Arg Leu Thr Met
465                 470                 475                 480

Ser Leu Asn Arg Asn Cys Ile Cys Pro Cys Ile Leu Thr Arg Gly Ser
                485                 490                 495

Asp Gln Ile Ser Ile Ser Thr Lys Phe Asp Val Arg Ser Asp Thr Ala
            500                 505                 510

Val Val Arg Asn Tyr Gly Ala Leu Leu Val Glu Val Ser Ala Ile Val
        515                 520                 525

Pro Asp Gly Ile Ile Cys Phe Phe Thr Ser Tyr Ser Tyr Met Glu Gln
    530                 535                 540

Ile Val Ser Val Trp Asn Glu Met Gly Leu Leu Asn Asn Ile Leu Thr
545                 550                 555                 560

Asn Lys Leu Ile Phe Val Glu Thr Ser Asp Pro Ala Glu Ser Ala Leu
                565                 570                 575

Ala Leu Gln Asn Tyr Lys Lys Ala Cys Asp Ser Gly Arg Gly Ala Val
            580                 585                 590

Leu Leu Ser Val Ala Arg Gly Lys Val Ser Glu Gly Ile Asp Phe Asp
        595                 600                 605

Asn Gln Tyr Gly Arg Cys Val Ile Leu Tyr Gly Ile Pro Tyr Ile Asn
    610                 615                 620

Thr Glu Ser Lys Val Leu Arg Ala Arg Leu Glu Phe Leu Arg Asp Arg
625                 630                 635                 640

Tyr Gln Ile Arg Glu Asn Glu Phe Leu Thr Phe Asp Ala Met Arg Thr
                645                 650                 655

Ala Ser Gln Cys Val Gly Arg Val Ile Arg Gly Lys Ser Asp Tyr Gly
            660                 665                 670

Ile Met Ile Phe Ala Asp Lys Arg Tyr Asn Arg Leu Asp Lys Arg Asn
        675                 680                 685

Lys Leu Pro Gln Trp Ile Leu Gln Phe Cys Gln Pro Gln His Leu Asn
    690                 695                 700

Leu Ser Thr Asp Met Ala Ile Ser Leu Ser Lys Thr Phe Leu Arg Glu
705                 710                 715                 720

Met Gly Gln Pro Phe Ser Arg Glu Glu Gln Leu Gly Lys Ser Leu Trp
                725                 730                 735

Ser Leu Glu His Val Glu Lys Gln Ser Thr Ser Lys Pro Pro Gln Gln
            740                 745                 750

Gln Asn Ser Ala Ile Asn Ser Thr Ile Thr Thr Ser Thr Thr Thr Thr
        755                 760                 765

Thr Thr Thr Ser Thr Ile Ser Glu Thr His Leu Thr
    770                 775                 780
```

<210> SEQ ID NO 36
<211> LENGTH: 778
<212> TYPE: PRT

-continued

<213> ORGANISM: S. cerevisiae

<400> SEQUENCE: 36

```
Met Lys Phe Tyr Ile Asp Asp Leu Pro Val Leu Phe Pro Tyr Pro Lys
 1               5                  10                  15

Ile Tyr Pro Glu Gln Tyr Asn Tyr Met Cys Asp Ile Lys Lys Thr Leu
            20                  25                  30

Asp Val Gly Gly Asn Ser Ile Leu Glu Met Pro Ser Gly Thr Gly Lys
        35                  40                  45

Thr Val Ser Leu Leu Ser Leu Thr Ile Ala Tyr Gln Met His Tyr Pro
    50                  55                  60

Glu His Arg Lys Ile Ile Tyr Cys Ser Arg Thr Met Ser Glu Ile Glu
65                  70                  75                  80

Lys Ala Leu Val Glu Leu Glu Asn Leu Met Asp Tyr Arg Thr Lys Glu
                85                  90                  95

Leu Gly Tyr Gln Glu Asp Phe Arg Gly Leu Gly Leu Thr Ser Arg Lys
            100                 105                 110

Asn Leu Cys Leu His Pro Glu Val Ser Lys Glu Arg Lys Gly Thr Val
        115                 120                 125

Val Asp Glu Lys Cys Arg Arg Met Thr Asn Gly Gln Ala Lys Arg Lys
    130                 135                 140

Leu Glu Glu Asp Pro Glu Ala Asn Val Glu Leu Cys Glu Tyr His Glu
145                 150                 155                 160

Asn Leu Tyr Asn Ile Glu Val Glu Asp Tyr Leu Pro Lys Gly Val Phe
                165                 170                 175

Ser Phe Glu Lys Leu Leu Lys Tyr Cys Glu Glu Lys Thr Leu Cys Pro
            180                 185                 190

Tyr Phe Ile Val Arg Arg Met Ile Ser Leu Cys Asn Ile Ile Ile Tyr
        195                 200                 205

Ser Tyr His Tyr Leu Leu Asp Pro Lys Ile Ala Glu Arg Val Ser Asn
    210                 215                 220

Glu Val Ser Lys Asp Ser Ile Val Ile Phe Asp Glu Ala His Asn Ile
225                 230                 235                 240

Asp Asn Val Cys Ile Glu Ser Leu Ser Leu Asp Leu Thr Thr Asp Ala
                245                 250                 255

Leu Arg Arg Ala Thr Arg Gly Ala Asn Ala Leu Asp Glu Arg Ile Ser
            260                 265                 270

Glu Val Arg Lys Val Asp Ser Gln Lys Leu Gln Asp Glu Tyr Glu Lys
        275                 280                 285

Leu Val Gln Gly Leu His Ser Ala Asp Ile Leu Thr Asp Gln Glu Glu
    290                 295                 300

Pro Phe Val Glu Thr Pro Val Leu Pro Gln Asp Leu Leu Thr Glu Ala
305                 310                 315                 320

Ile Pro Gly Asn Ile Arg Arg Ala Glu His Phe Val Ser Phe Leu Lys
                325                 330                 335

Arg Leu Ile Glu Tyr Leu Lys Thr Arg Met Lys Val Leu His Val Ile
            340                 345                 350

Ser Glu Thr Pro Lys Ser Phe Leu Gln His Leu Lys Gln Leu Thr Phe
        355                 360                 365

Ile Glu Arg Lys Pro Leu Arg Phe Cys Ser Glu Arg Leu Ser Leu Leu
    370                 375                 380

Val Arg Thr Leu Glu Val Thr Glu Val Glu Asp Phe Thr Ala Leu Lys
385                 390                 395                 400
```

-continued

```
Asp Ile Ala Thr Phe Ala Thr Leu Ile Ser Thr Tyr Glu Glu Gly Phe
                405                 410                 415

Leu Leu Ile Ile Glu Pro Tyr Glu Ile Glu Asn Ala Ala Val Pro Asn
            420                 425                 430

Pro Ile Met Arg Phe Thr Cys Leu Asp Ala Ser Ile Ala Ile Lys Pro
        435                 440                 445

Val Phe Glu Arg Phe Ser Ser Val Ile Ile Thr Ser Gly Thr Ile Ser
    450                 455                 460

Pro Leu Asp Met Tyr Pro Arg Met Leu Asn Phe Lys Thr Val Leu Gln
465                 470                 475                 480

Lys Ser Tyr Ala Met Thr Leu Ala Lys Lys Ser Phe Leu Pro Met Ile
                485                 490                 495

Ile Thr Lys Gly Ser Asp Gln Val Ala Ile Ser Ser Arg Phe Glu Ile
            500                 505                 510

Arg Asn Asp Pro Ser Ile Val Arg Asn Tyr Gly Ser Met Leu Val Glu
        515                 520                 525

Phe Ala Lys Ile Thr Pro Asp Gly Met Val Val Phe Phe Pro Ser Tyr
    530                 535                 540

Leu Tyr Met Glu Ser Ile Val Ser Met Trp Gln Thr Met Gly Ile Leu
545                 550                 555                 560

Asp Glu Val Trp Lys His Lys Leu Ile Leu Val Glu Thr Pro Asp Ala
                565                 570                 575

Gln Glu Thr Ser Leu Ala Leu Glu Thr Tyr Arg Lys Ala Cys Ser Asn
            580                 585                 590

Gly Arg Gly Ala Ile Leu Leu Ser Val Ala Arg Gly Lys Val Ser Glu
        595                 600                 605

Gly Ile Asp Phe Asp His Gln Tyr Gly Arg Thr Val Leu Met Ile Gly
    610                 615                 620

Ile Pro Phe Gln Tyr Thr Glu Ser Arg Ile Leu Lys Ala Arg Leu Glu
625                 630                 635                 640

Phe Met Arg Glu Asn Tyr Arg Ile Arg Glu Asn Asp Phe Leu Ser Phe
                645                 650                 655

Asp Ala Met Arg His Ala Ala Gln Cys Leu Gly Arg Val Leu Arg Gly
            660                 665                 670

Lys Asp Asp Tyr Gly Val Met Val Leu Ala Asp Arg Arg Phe Ser Arg
        675                 680                 685

Lys Arg Ser Gln Leu Pro Lys Trp Ile Ala Gln Gly Leu Ser Asp Ala
    690                 695                 700

Asp Leu Asn Leu Ser Thr Asp Met Ala Ile Ser Asn Thr Lys Gln Phe
705                 710                 715                 720

Leu Arg Thr Met Ala Gln Pro Thr Asp Pro Lys Asp Gln Glu Gly Val
                725                 730                 735

Ser Val Trp Ser Tyr Glu Asp Leu Ile Lys His Gln Asn Ser Arg Lys
            740                 745                 750

Asp Gln Gly Gly Phe Ile Glu Asn Glu Asn Lys Glu Gly Glu Gln Asp
        755                 760                 765

Glu Asp Glu Asp Glu Asp Ile Glu Met Gln
    770                 775
```

<210> SEQ ID NO 37
<211> LENGTH: 772
<212> TYPE: PRT
<213> ORGANISM: S. pombe

<400> SEQUENCE: 37

-continued

```
Met Lys Phe Tyr Ile Asp Asp Leu Pro Ile Leu Phe Pro Tyr Pro Arg
 1               5                  10                  15

Ile Tyr Pro Glu Gln Tyr Gln Tyr Met Cys Asp Leu Lys His Ser Leu
            20                  25                  30

Asp Ala Gly Gly Ile Ala Leu Leu Glu Met Pro Ser Gly Thr Gly Lys
        35                  40                  45

Thr Ile Ser Leu Leu Ser Leu Ile Val Ser Tyr Gln Gln His Tyr Pro
    50                  55                  60

Glu His Arg Lys Leu Ile Tyr Cys Ser Arg Thr Met Ser Glu Ile Asp
65                  70                  75                  80

Lys Ala Leu Ala Glu Leu Lys Arg Leu Met Ala Tyr Arg Thr Ser Gln
                85                  90                  95

Leu Gly Tyr Glu Glu Pro Phe Leu Gly Leu Gly Leu Thr Ser Arg Lys
            100                 105                 110

Asn Leu Cys Leu His Pro Ser Val Arg Arg Glu Lys Asn Gly Asn Val
        115                 120                 125

Val Asp Ala Arg Cys Arg Ser Leu Thr Ala Gly Phe Val Arg Glu Gln
    130                 135                 140

Arg Leu Ala Gly Met Asp Val Pro Thr Cys Glu Phe His Asp Asn Leu
145                 150                 155                 160

Glu Asp Leu Glu Pro His Ser Leu Ile Ser Asn Gly Val Trp Thr Leu
                165                 170                 175

Asp Asp Ile Thr Glu Tyr Gly Glu Lys Thr Thr Arg Cys Pro Tyr Phe
            180                 185                 190

Thr Val Arg Arg Met Leu Pro Phe Cys Asn Val Ile Ile Tyr Ser Tyr
        195                 200                 205

His Tyr Leu Leu Asp Pro Lys Ile Ala Glu Arg Val Ser Arg Glu Leu
    210                 215                 220

Ser Lys Asp Cys Ile Val Val Phe Asp Glu Ala His Asn Ile Asp Asn
225                 230                 235                 240

Val Cys Ile Glu Ser Leu Ser Ile Asp Leu Thr Glu Ser Ser Leu Arg
                245                 250                 255

Lys Ala Ser Lys Ser Ile Leu Ser Leu Glu Gln Lys Val Asn Glu Val
            260                 265                 270

Lys Gln Ser Asp Ser Lys Lys Leu Gln Asp Glu Tyr Gln Lys Leu Val
        275                 280                 285

Arg Gly Leu Gln Asp Ala Asn Ala Ala Asn Asp Glu Asp Gln Phe Met
    290                 295                 300

Ala Asn Pro Val Leu Pro Glu Asp Val Leu Lys Glu Ala Val Pro Gly
305                 310                 315                 320

Asn Ile Arg Arg Ala Glu His Phe Ile Ala Phe Leu Lys Arg Phe Val
                325                 330                 335

Glu Tyr Leu Lys Thr Arg Met Lys Val Leu His Val Ile Ala Glu Thr
            340                 345                 350

Pro Thr Ser Phe Leu Gln His Val Lys Asp Ile Thr Phe Ile Asp Lys
        355                 360                 365

Lys Pro Leu Arg Phe Cys Ala Glu Arg Leu Thr Ser Leu Val Arg Ala
    370                 375                 380

Leu Gln Ile Ser Leu Val Glu Asp Phe His Ser Leu Gln Gln Val Val
385                 390                 395                 400

Ala Phe Ala Thr Leu Val Ala Thr Tyr Glu Arg Gly Phe Ile Leu Ile
                405                 410                 415
```

-continued

```
Leu Glu Pro Phe Glu Thr Glu Asn Ala Thr Val Pro Asn Pro Ile Leu
            420                 425                 430

Arg Phe Ser Cys Leu Asp Ala Ser Ile Ala Ile Lys Pro Val Phe Glu
        435                 440                 445

Arg Phe Arg Ser Val Ile Ile Thr Ser Gly Thr Leu Ser Pro Leu Asp
    450                 455                 460

Met Tyr Pro Lys Met Leu Gln Phe Asn Thr Val Met Gln Glu Ser Tyr
465                 470                 475                 480

Gly Met Ser Leu Ala Arg Asn Cys Phe Leu Pro Met Val Val Thr Arg
                485                 490                 495

Gly Ser Asp Gln Val Ala Ile Ser Ser Lys Phe Glu Ala Arg Asn Asp
            500                 505                 510

Pro Ser Val Val Arg Asn Tyr Gly Asn Ile Leu Val Glu Phe Ser Lys
        515                 520                 525

Ile Thr Pro Asp Gly Leu Val Ala Phe Phe Pro Ser Tyr Leu Tyr Leu
    530                 535                 540

Glu Ser Ile Val Ser Ser Trp Gln Ser Met Gly Ile Leu Asp Glu Val
545                 550                 555                 560

Trp Lys Tyr Lys Leu Ile Leu Val Glu Thr Pro Asp Pro His Glu Thr
                565                 570                 575

Thr Leu Ala Leu Glu Thr Tyr Arg Ala Ala Cys Ser Asn Gly Arg Gly
            580                 585                 590

Ala Val Leu Leu Ser Val Ala Arg Gly Lys Val Ser Glu Gly Val Asp
        595                 600                 605

Phe Asp His His Tyr Gly Arg Ala Val Ile Met Phe Gly Ile Pro Tyr
    610                 615                 620

Gln Tyr Thr Glu Ser Arg Val Leu Lys Ala Arg Leu Glu Phe Leu Arg
625                 630                 635                 640

Asp Thr Tyr Gln Ile Arg Glu Ala Asp Phe Leu Thr Phe Asp Ala Met
                645                 650                 655

Arg His Ala Ala Gln Cys Leu Gly Arg Val Leu Arg Gly Lys Asp Asp
            660                 665                 670

His Gly Ile Met Val Leu Ala Asp Lys Arg Tyr Gly Arg Ser Asp Lys
        675                 680                 685

Arg Thr Lys Leu Pro Lys Trp Ile Gln Gln Tyr Ile Thr Glu Gly Ala
    690                 695                 700

Thr Asn Leu Ser Thr Asp Met Ser Leu Ala Leu Ala Lys Lys Phe Leu
705                 710                 715                 720

Arg Thr Met Ala Gln Pro Phe Thr Ala Ser Asp Gln Glu Gly Ile Ser
                725                 730                 735

Trp Trp Ser Leu Asp Asp Leu Leu Ile His Gln Lys Lys Ala Leu Lys
            740                 745                 750

Ser Ala Ala Ile Glu Gln Ser Lys His Glu Asp Glu Met Asp Ile Asp
        755                 760                 765

Val Val Glu Thr
    770


<210> SEQ ID NO 38
<211> LENGTH: 760
<212> TYPE: PRT
<213> ORGANISM: Homo sapien

<400> SEQUENCE: 38

Met Lys Leu Asn Val Asp Gly Leu Leu Val Tyr Phe Pro Tyr Asp Tyr
 1               5                  10                  15
```

-continued

```
Ile Tyr Pro Glu Gln Phe Ser Tyr Met Arg Glu Leu Lys Arg Thr Leu
            20                  25                  30

Asp Ala Lys Gly His Gly Val Leu Glu Met Pro Ser Gly Thr Gly Lys
        35                  40                  45

Thr Val Ser Leu Leu Ala Leu Ile Met Ala Tyr Gln Arg Ala Tyr Pro
    50                  55                  60

Leu Glu Val Thr Lys Leu Ile Tyr Cys Ser Arg Thr Val Pro Glu Ile
65                  70                  75                  80

Glu Lys Val Ile Glu Glu Leu Arg Lys Leu Leu Asn Phe Tyr Glu Lys
                85                  90                  95

Gln Glu Gly Glu Lys Leu Pro Phe Leu Gly Leu Ala Leu Ser Ser Arg
            100                 105                 110

Lys Asn Leu Cys Ile His Pro Glu Val Thr Pro Leu Arg Phe Gly Lys
        115                 120                 125

Asp Val Asp Gly Lys Cys His Ser Leu Thr Ala Ser Tyr Val Arg Ala
    130                 135                 140

Gln Tyr Gln His Asp Thr Ser Leu Pro His Cys Arg Phe Tyr Glu Glu
145                 150                 155                 160

Phe Asp Ala His Gly Arg Glu Val Pro Leu Pro Ala Gly Ile Tyr Asn
                165                 170                 175

Leu Asp Asp Leu Lys Ala Leu Gly Arg Arg Gln Gly Trp Cys Pro Tyr
            180                 185                 190

Phe Leu Ala Arg Tyr Ser Ile Leu His Ala Asn Val Val Val Tyr Ser
        195                 200                 205

Tyr His Tyr Leu Leu Asp Pro Lys Ile Ala Asp Leu Val Ser Lys Glu
    210                 215                 220

Leu Ala Arg Lys Ala Val Val Val Phe Asp Glu Ala His Asn Ile Asp
225                 230                 235                 240

Asn Val Cys Ile Asp Ser Met Ser Val Asn Leu Thr Arg Arg Thr Leu
                245                 250                 255

Asp Arg Cys Gln Gly Asn Leu Glu Thr Leu Gln Lys Thr Val Leu Arg
            260                 265                 270

Ile Lys Glu Thr Asp Glu Gln Arg Leu Arg Asp Glu Tyr Arg Arg Leu
        275                 280                 285

Val Glu Gly Leu Arg Glu Ala Ser Ala Ala Arg Glu Thr Asp Ala His
    290                 295                 300

Leu Ala Asn Pro Val Leu Pro Asp Glu Val Leu Gln Glu Ala Val Pro
305                 310                 315                 320

Gly Ser Ile Arg Thr Ala Glu His Phe Leu Gly Phe Leu Arg Arg Leu
                325                 330                 335

Leu Glu Tyr Val Lys Trp Arg Leu Arg Val Gln His Val Val Gln Glu
            340                 345                 350

Ser Pro Pro Ala Phe Leu Ser Gly Leu Ala Gln Arg Val Cys Ile Gln
        355                 360                 365

Arg Lys Pro Leu Arg Phe Cys Ala Glu Arg Leu Arg Ser Leu Leu His
    370                 375                 380

Thr Leu Glu Ile Thr Asp Leu Ala Asp Phe Ser Pro Leu Thr Leu Leu
385                 390                 395                 400

Ala Asn Phe Ala Thr Leu Val Ser Thr Tyr Ala Lys Gly Phe Thr Ile
                405                 410                 415

Ile Ile Glu Pro Phe Asp Asp Arg Thr Pro Thr Ile Ala Asn Pro Ile
            420                 425                 430
```

-continued

```
Leu His Phe Ser Cys Met Asp Ala Ser Leu Ala Ile Lys Pro Val Phe
        435                 440                 445

Glu Arg Phe Gln Ser Val Ile Ile Thr Ser Gly Thr Leu Ser Pro Leu
    450                 455                 460

Asp Ile Tyr Pro Lys Ile Leu Asp Phe His Pro Val Thr Met Ala Thr
465                 470                 475                 480

Phe Thr Met Thr Leu Ala Arg Val Cys Leu Cys Pro Met Ile Ile Gly
                485                 490                 495

Arg Gly Asn Asp Gln Val Ala Ile Ser Ser Lys Phe Glu Thr Arg Glu
            500                 505                 510

Asp Ile Ala Val Ile Arg Asn Tyr Gly Asn Leu Leu Leu Glu Met Ser
        515                 520                 525

Ala Val Val Pro Asp Gly Ile Val Ala Phe Phe Thr Ser Tyr Gln Tyr
    530                 535                 540

Met Glu Ser Thr Val Ala Ser Trp Tyr Glu Gln Gly Ile Leu Glu Asn
545                 550                 555                 560

Ile Gln Arg Asn Lys Leu Leu Phe Ile Glu Thr Gln Asp Gly Ala Glu
                565                 570                 575

Thr Ser Val Ala Leu Glu Lys Tyr Gln Glu Ala Cys Glu Asn Gly Arg
            580                 585                 590

Gly Ala Ile Leu Leu Ser Val Ala Arg Gly Lys Val Ser Glu Gly Ile
        595                 600                 605

Asp Phe Val His His Tyr Gly Arg Ala Val Ile Met Phe Gly Val Pro
    610                 615                 620

Tyr Val Tyr Thr Gln Ser Arg Ile Leu Lys Ala Arg Leu Glu Tyr Leu
625                 630                 635                 640

Arg Asp Gln Phe Gln Ile Arg Glu Asn Asp Phe Leu Thr Phe Asp Ala
                645                 650                 655

Met Arg His Ala Ala Gln Cys Val Gly Arg Ala Ile Arg Gly Lys Thr
            660                 665                 670

Asp Tyr Gly Leu Met Val Phe Ala Asp Lys Arg Phe Ala Arg Gly Asp
        675                 680                 685

Lys Arg Gly Lys Leu Pro Arg Trp Ile Gln Glu His Leu Thr Asp Ala
    690                 695                 700

Asn Leu Asn Leu Thr Val Asp Glu Gly Val Gln Val Ala Lys Tyr Phe
705                 710                 715                 720

Leu Arg Gln Met Ala Gln Pro Phe His Arg Glu Asp Gln Leu Gly Leu
                725                 730                 735

Ser Leu Leu Ser Leu Glu Gln Leu Glu Ser Glu Glu Thr Leu Lys Arg
            740                 745                 750

Ile Glu Gln Ile Ala Gln Gln Leu
        755                 760
```

DNA MOLECULES ENCODING HUMAN NHL, A DNA HELICASE

CROSS-REFERENCE TO RELATED APPLICATIONS

This application is a divisional of U.S. Ser. No. 10/148,806, filed Jun. 5, 2002, now U.S. Pat. No. 6,762,042 which is a national stage entry of PCT/US00/33065, international filing date of Dec. 7, 2000, which claims priority to U.S. Ser. No. 60/169,970, filed Dec. 9, 1999.

STATEMENT REGARDING FEDERALLY-SPONSORED R&D

Not Applicable.

REFERENCE TO MICROFICHE APPENDIX

Not Applicable.

FIELD OF THE INVENTION

The present invention relates in part to isolated nucleic acid molecules (polynucleotides) which encode NHL, a putative DNA helicase. The present invention also relates to recombinant vectors and recombinant hosts which contain a DNA fragment encoding NHL, substantially purified forms of associated NHL, associated mutant proteins, and methods associated with identifying compounds which modulate NHL, which will be useful in the treatment of various neoplastic disorders, given that this gene is located at 20q13.3 and immediately adjacent to M68/DcR3, which is involved in tumor growth. Also included within the present invention is a human genomic fragment representing this portion of the human genome, along with three additional genes (M68/DcR3, SCLIP, and ARP).

BACKGROUND OF THE INVENTION

Naumovski et al. (1985, *Mol. Cell Biol.* 5:17-26; Reynolds et al. (1985 *Nucleic Acid Res* 13:2357-2372) and Weber et al. (1990 *EMBO J.* 9:1437-1447) disclose members of the RAD3/ERCC2 gene family of DNA helicases.

It is known that several chemotherapeutic agents inhibit helicases, including actinomycin Cl, daunorubicin and nogalamycin (Tuteja, et al., 1997, *Biochem. Biophys. Res. Comm.* 236(3):636-640), and a prostate cancer drug, CI-958 (Lun, et al., 1998, *Cancer Chemother. Pharmacol.* 42(6): 447-453). In addition, some topoisomerases have been shown to have anti-cancer activity.

Despite the identification of the aforementioned helicase-encoding genes and chemotherapeutic agents, it would be advantageous to identify additional genes which reside within chromosomal regions associated with a disease state such as cancer as well as a gene which encodes a type of protein which may be associated with that disease. The present invention addresses and meets this need by disclosing a DNA molecule encoding a DNA helicase with a chromosomal location suggestive of association with cancer.

SUMMARY OF THE INVENTION

The present invention relates to an isolated or purified nucleic acid molecule (polynucleotide) which encodes a novel mammalian DNA helicase.

The present invention also relates to an isolated nucleic acid molecule (polynucleotide) which encodes mRNA which expresses a novel human DNA helicase, NHL.

A preferred aspect of the present invention relates to an isolated or purified DNA molecule which encodes human NHL, the nucleotide sequence as set forth in FIG. 1A-B and SEQ ID NO:1.

The present invention also relates to biologically active fragments or mutants of SEQ ID NO:1 which encode a mRNA molecule expressing a novel DNA helicase, NHL. Any such biologically active fragment and/or mutant will encode either a protein or protein fragment which at least substantially mimics the biological properties of the human NHL protein disclosed herein in FIG. 2 and as set forth as SEQ ID NO:2. Any such polynucleotide includes but is not necessarily limited to nucleotide substitutions, deletions, additions, amino-terminal truncations and carboxy-terminal truncations such that these mutations encode mRNA which express a functional NHL protein in a host cell, so as to be useful for screening for agonists and/or antagonists of NHL activity.

The present invention also relates to recombinant vectors and recombinant hosts, both prokaryotic and eukaryotic, which contain the substantially purified nucleic acid molecules disclosed throughout this specification.

The present invention also relates to a substantially purified form of a human NHL protein which comprises the amino acid sequence disclosed in FIG. 2 and set forth as SEQ ID NO:2.

A preferred aspect of this portion of the present invention is a NHL protein which consists of the amino acid sequence disclosed in FIG. 2 and set forth as SEQ ID NO:2.

Another preferred aspect of the present invention relates to a substantially purified NHL protein, preferably a human NHL protein, obtained from a recombinant host cell containing a DNA expression vector comprises a nucleotide sequence as set forth in SEQ ID NO:1 and expresses the respective NHL protein. It is especially preferred is that the recombinant host cell be a eukaryotic host cell, such as a mammalian cell line.

The present invention also relates to biologically active fragments and/or mutants of a NHL protein comprising the amino acid sequence as set forth in SEQ ID NO:2, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for selective modulators, including but not limited to agonists and/or antagonists for human NHL pharmacology.

A preferred aspect of the present invention is disclosed in FIG. 2 and is set forth as SEQ ID NO:2, a respective amino acid sequence which encodes human NHL. Characterization of one or more of these DNA helicase-like proteins allows for screening methods to identify novel NHL modulators that may be useful in the treatment of human neoplastic disorders. The modulators selected through such screening and selection protocols may be used alone or in conjunction with other cancer therapies. As noted above, heterologous expression of a NHL protein will allow the pharmacological analysis of compounds which modulate NHL activity and hence may be useful in various cancer therapies. To this end, heterologous cell lines expressing a NHL protein can be used to establish functional or binding assays to identify novel NHL modulators.

The present invention also relates to polyclonal and monoclonal antibodies raised in response to either the NHL or a biologically active fragment of NHL.

The present invention relates to transgenic mice comprising altered genotypes and phenotypes in relation to NHL and its in vivo activity.

The present invention also relates to NHL fusion constructs, including but not limited to fusion constructs which express a portion of the NHL protein linked to various markers, including but in no way limited to GFP (Green fluorescent protein), the MYC epitope, and GST. Any such fusion constructs may be expressed in the cell line of interest and used to screen for NHL modulators.

Therefore, the present invention relates to methods of expressing mammalian NHL, and preferably human NHL, biological equivalents disclosed herein, assays employing these gene products, recombinant host cells which comprise DNA constructs which express these proteins, and compounds identified through these assays which act as agonists or antagonists of NHL activity.

The present invention also relates to the isolated genomic sequence which comprises SEQ ID NO:1, a 115 kb genomic fragment set forth herein as SEQ ID NO:3. As especially preferred aspect of this portion of the invention is the region of the genomic fragment of SEQ ID NO:3 which comprises the regulatory and coding regions of human NHL, as well as intervening sequences (introns). This 115 kb fragment contains at least the coding region of four genes, NHL, M68/DcR3, SCLIP and ARP. As discussed herein, it has been shown that this region of chromosome 20 is associated with tumor growth. Therefore, an aspect of this invention also comprises the use of one or more regions of this 115 kb genomic sequence to identify compounds which up or downregulate expression of one or more of the genes localized within this 115 kb region, wherein this up or down regulation results in an interference of tumor growth. For example, a transcription element of one of these four genes may be responsible for M68/DcR3 (and/or NHL) overexpression in tumors, and if M68 or NHL overexpression in tumors has a caustic role, blockage of M68/DcR3 or NHL overexpression in tumors by interfering with this transcription site will be useful.

It is an object of the present invention to provide an isolated nucleic acid molecule (e.g., SEQ ID NO:1) which encodes novel form of human NHL, or fragments, mutants or derivatives of human NHL as set forth in FIG. 2 and SEQ ID NO:2. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for selective modulators of human NHL activity.

It is a further object of the present invention to provide the mammalian, and especially human, NHL proteins or protein fragments encoded by the nucleic acid molecules referred to in the preceding paragraph.

It is a further object of the present invention to provide recombinant vectors and recombinant host cells which comprise a nucleic acid sequence encoding mammalian, and especially human, NHL protein and biological equivalent thereof.

It is an object of the present invention to provide a substantially purified form of human NHL, as set forth in FIG. 2 and SEQ ID NO:2.

Is another object of the present invention to provide a substantially purified recombinant form of a NHL protein which has been obtained from a recombinant host cell transformed or transfected with a DNA expression vector which comprises and appropriately expresses a complete open reading frame as set forth in SEQ ID NO:1, resulting in a functional, processed form of NHL. It is especially preferred is that the recombinant host cell be a eukaryotic host cell, such as a mammalian cell line.

It is an object of the present invention to provide for biologically active fragments and/or mutants of mammalian, and especially human, NHL, such as set forth in SEQ ID NO:2, including but not necessarily limited to amino acid substitutions, deletions, additions, amino terminal truncations and carboxy-terminal truncations such that these mutations provide for proteins or protein fragments of diagnostic, therapeutic and/or prophylactic use.

It is also an object of the present invention to use NHL proteins or biological equivalent to screen for modulators, preferably selective modulators, of human NHL activity. Any such compound may be useful in screening for and selecting compounds active against human neoplastic disorders.

As used herein, "substantially free from other nucleic acids" means at least 90%, preferably 95%, more preferably 99%, and even more preferably 99.9%, free of other nucleic acids. Thus, a human NHL DNA preparation that is substantially free from other nucleic acids will contain, as a percent of its total nucleic acid, no more than 10%, preferably no more than 5%, more preferably no more than 1%, and even more preferably no more than 0.1%, of non-NHL nucleic acids. Whether a given NHL DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

As used herein, "substantially free from other proteins" or "substantially purified" means at least 90%, preferably 95%, more preferably 99%, and even more preferably 99.9%, free of other proteins. Thus, a NHL protein preparation that is substantially free from other proteins will contain, as a percent of its total protein, no more than 10%, preferably no more than 5%, more preferably no more than 1%, and even more preferably no more than 0.1%, of non-NHL proteins. Whether a given NHL protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting. As used interchangeably with the terms "substantially free from other proteins" or "substantially purified", the terms "isolated NHL protein" or "purified NHL protein" also refer to NHL protein that has been isolated from a natural source. Use of the term "isolated" or "purified" indicates that NHL protein has been removed from its normal cellular environment. Thus, an isolated NHL protein may be in a cell-free solution or placed in a different cellular environment from that in which it occurs naturally. The term isolated does not imply that an isolated NHL protein is the only protein present, but instead means that an isolated NHL protein is substantially free of other proteins and non-amino acid material (e.g., nucleic acids, lipids, carbohydrates) naturally associated with the NHL protein in vivo. Thus, a NHL protein that is recombinantly expressed in a prokaryotic or eukaryotic cell and substantially purified from this host cell which does not naturally (i.e., without intervention) express this protein is of course "isolated NHL protein" under any circumstances referred to herein. As noted above, a NHL protein preparation that is an isolated or purified NHL protein will be substantially free from other proteins will contain, as a percent of its total protein, no more than 10%, preferably no more than 5%, more preferably no more than 1%, and even more preferably no more than 0.1%, of non-NHL proteins.

As used interchangeably herein, “functional equivalent” or “biologically active equivalent” means a protein which does not have exactly the same amino acid sequence as naturally occurring NHL, due to alternative splicing, deletions, mutations, substitutions, or additions, but retains substantially the same biological activity as NHL. Such functional equivalents will have significant amino acid sequence identity with naturally occurring NHL and genes and cDNA encoding such functional equivalents can be detected by reduced stringency hybridization with a DNA sequence encoding naturally occurring NHL. For example, a naturally occurring NHL disclosed herein comprises the amino acid sequence shown as SEQ ID NO:2 and is encoded by SEQ ID NO:1. A nucleic acid encoding a functional equivalent has at least about 50% identity at the nucleotide level to SEQ ID NO:1.

As used herein, “a conservative amino acid substitution” refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

As used herein, the term “mammalian” will refer to any mammal, including a human being.

BRIEF DESCRIPTION OF THE DRAWINGS

FIG. 1A-B shows the nucleotide sequence which comprises the open reading frame which encodes human NHL, the nucleotide sequence set forth as SEQ ID NO:1. The initiating Met residue (ATG) and the stop codon (TAG) are underlined.

FIG. 2 shows the amino acid sequence of human NHL as set forth in SEQ ID NO:2.

DETAILED DESCRIPTION OF THE INVENTION

Figure 3A:
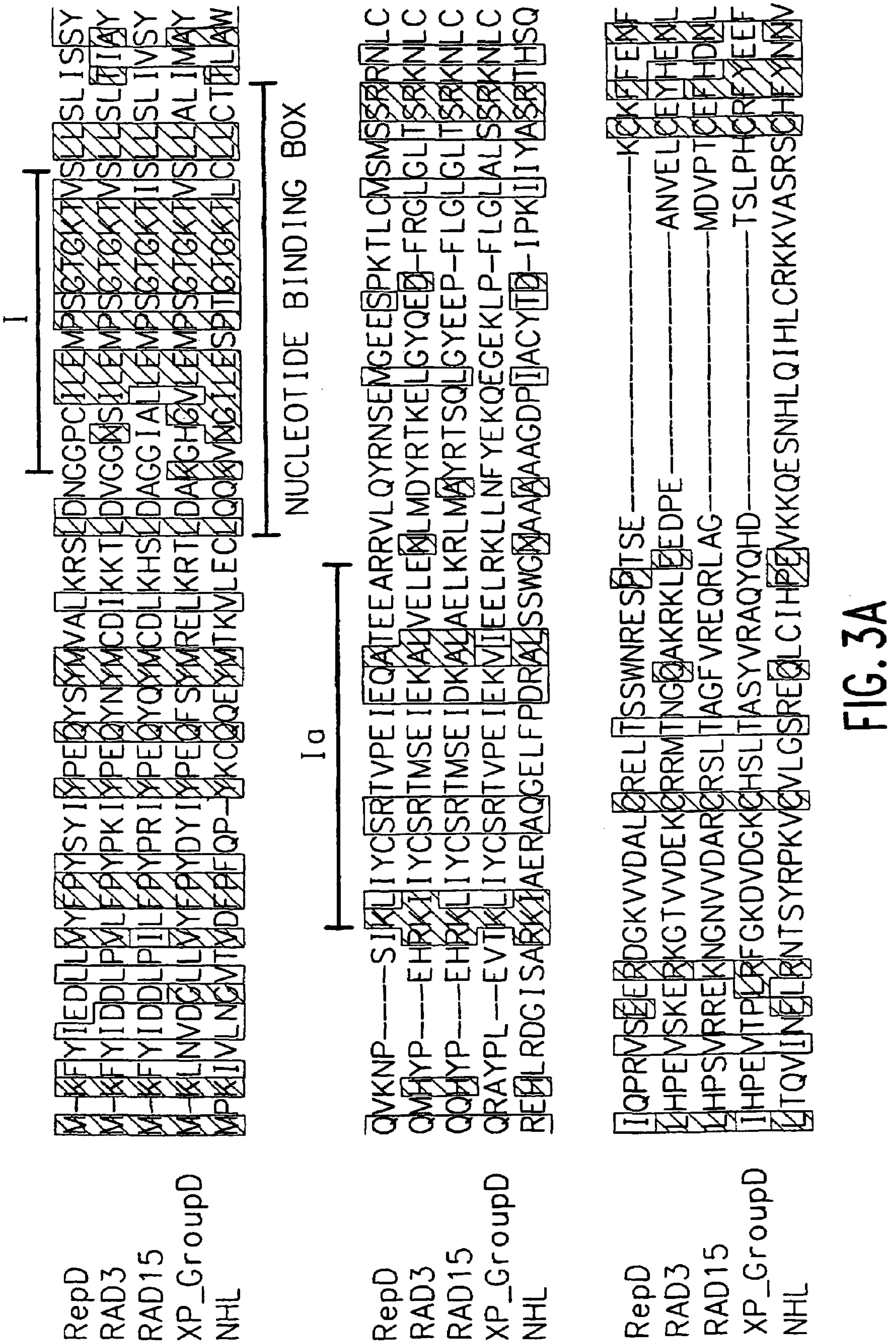
FIG. 3 shows the alignment of amino acid sequences of human NHL to ERCC2/RAD3 gene family members. Rep D (*Dictyosteliem discoideum*); RAD 3 (*S. cerevisiae*); RAD 15 (*S. pombe*) and XP_GroupD (*Homo sapien*).

The present invention relates to an isolated or purified nucleic acid molecule (polynucleotide) which encodes a novel mammalian DNA helicase. An especially preferred aspect of this invention relates to an isolated nucleic acid molecule (polynucleotide) which encodes mRNA which expresses a novel human DNA helicase, NHL.

The gene M68/DcR3 is a secreted TNFR member that is overexpressed in a number of human tumors. M68/DcR3 is located at 20q13.3, a known site that is associated with frequent gene amplification in cancer. M68/DcR3 protein binds to FASL and inhibit FAS mediated apoptosis. Thus, genes tightly linked to M68/DcR3 may be coregulated (e.g. co overexpressed and/or amplified in tumors). During the course of cloning the genomic M68/DcR3 fragment and identifying genes that are linked to M68/DcR3 at 20q13.3, three genes, including a novel gene that is similar to the Rad3/ERCC2 helicase family, were identified (termed NHL) in the immediately adjacent (overlapping) region. Given NHL's chromosomal location and the frequent association of DNA helicases with human genetic disorders (mutations in DNA helicases have been found associated with multiple diseases, including xeroderma pigmentosum, Cockayne's syndrome, Bloom's syndrome, and Werner's syndrome), NHL is a candidate for contribution to certain human neoplastic disorders. To this end, the genomic clone for this gene is disclosed and the complete sequence is determined. The transcript was identified through exon prediction using GRAIL2 and sequence alignment to a contiguous 4.5 kilobase region of chromosome 4 (88% sequence identity). The complete exon structure of NHL was subsequently confirmed by RT-PCR analysis. Multiple sequence alignment of NHL to known helicases showed that NHL contains all the seven critical helicase domains. BLAST analysis of the predicted 1,219 amino acid sequence revealed an approximately 26% sequence identity and 48% sequence similarity to the RAD3/ERCC2 gene family of DNA helicases (Naumovski et al., 1985 *Mol. Cell Biol.* 5:17-26; Reynolds et al., 1985 *Nucleic Acid Res* 13:2357-72; Weber et al., 1990 *EMBO J.* 9:1437-1447). The mRNA expression pattern of NHL was also examined in multiple human tissues. Radiation hybrid chromosomal mapping reconfirms that it is linked to M68/DcR3 locus.

A preferred aspect of the present invention relates to an isolated or purified DNA molecule which encodes human NHL, the nucleotide sequence as set forth in FIG. 1A-B and SEQ ID NO:1, which is as follows:

```
AGTCAGCCCT GCTGCCAGCC AGTGCCGGGT GCTGGGGACT CAGGGAGGCC CGCCGGGACC  (SEQ ID NO:1)

ACTGCGGGAC AGTGAGCCGA GCAGAAGCTG GAACGCAGGA GAGGAAGGAG AGGGGGCGGT

CAGGGCTCTC AGGAGCCGGG TCCTGGGCAA GGCGCAGCCG TTTTCAAATT TTCAGGAAAG

CGGTCGGCTC ACACTCGAGC AGTAAAAAGA TGCCTCTGGG GAGGAGGCCC GTGCAGCTCT

CCGGGCAATG GTGGTGGCTC GGCCTAGAGA GGCGGTAGTG GAACGCAGAC CCTGGTGGGG

GAATGACATC AAGGGAGGAG ACGGGCGGGA CCCCAGATTT CTGCCTGTGG GCGATGGAAG

TGAGGTTCAC TGGCCAGCGG AGCCGGACAC AGAACGCGCA AAACGCCGTG TAGGCCTGGA

GGAGCCGAAG AGCAGGCGGA CCCCCTCCGC GGGGGAACAG TTTCCGCCGG GAGCACAAAG
```

-continued

CAACGGACCG GAAGTGGGGG GCGGAAGTGC AGTGGGCTCA GCGCCGACTG CGCGCCTCTG

CCCGCGAAAA CTCTGAGCTG GCTGACAGCT GGGGACGGGT GGCGGCCCTC GACTGGAGTC

GGTTGAGTTC CTGAGGGACC CCGGTTCTGG AAGGTTCGCC GCGGAGACAA GTGAGCAGTC

TGTGCCATAG GGATTCTCGA AGAGAACAGC GTTGTGTCCC AGTGCACATG CTCGCATCGC

TTACCAGGAG TGCCCGAGAC CCTAAGATGT TCGGAGTGGT TTTTTCGCAC AGACCCGAAT

AGCCTGCCCC TCAGCCACGC TCTGTGCCCT TCTGAGAACA GGCTGATATG CCCAAGATAG

TCCTGAATGG TGTGACCGTA GACTTCCCTT TCCAGCCCTA CAAATGCCAA CAGGAGTACA

TGACCAAGGT CCTGGAATGT CTGCAGCAGA AGGTGAATGG CATCCTGGAG AGCCCTACGG

GTACAGGGAA GACGCTGTGC CTGCTGTGCA CCACGCTGGC CTGGCGAGAA CACCTCCGAG

ACGGCATCTC TGCCCGCAAG ATTGCCGAGA GGGCGCAAGG AGAGCTTTTC CCGGATCGGG

CCTTGTCATC CTGGGGCAAC GCTGCTGCTG CTGCTGGAGA CCCCATAGCT TGCTACACGG

ACATCCCAAA GATTATTTAC GCCTCCAGGA CCCACTCGCA ACTCACACAG GTCATCAACG

AGCTTCGGAA CACCTCCTAC CGGCCTAAGG TGTGTGTGCT GGGCTCCCGG GAGCAGCTGT

GCATCCATCC TGAGGTGAAG AAACAAGAGA GTAACCATCT ACAGATCCAC TTGTGCCGTA

AGAAGGTGGC AAGTCGCTCC TGTCATTTCT ACAACAACGT AGAAGAAAAA AGCCTGGAGC

AGGAGCTGGC CAGCCCCATC CTGGACATTG AGGACTTGGT CAAGAGCGGA AGCAAGCACA

GGGTGTGCCC TTACTACCTG TCCCGGAACC TGAAGCAGCA AGCCGACATC ATATTCATGC

CGTACAATTA CTTGTTGGAT GCCAAGAGCC GCAGAGCACA CAACATTGAC CTGAAGGGGA

CAGTCGTGAT CTTTGACGAA GCTCACAACG TGGAGAAGAT GTGTGAAGAA TCGGCATCCT

TTGACCTGAC TCCCCATGAC CTGGCTTCAG GACTGGACGT CATAGACCAG GTGCTGGAGG

AGCAGACCAA GGCAGCGCAG CAGGGTGAGC CCCACCCGGA GTTCAGCGCG GACTCCCCCA

GCCCAGGGCT GAACATGGAG CTGGAAGACA TTGCAAAGCT GAAGATGATC CTGCTGCGCC

TGGAGGGGGC CATCGATGCT GTTGAGCTGC CTGGAGACGA CAGCGGTGTC ACCAAGCCAG

GGAGCTACAT CTTTGAGCTG TTTGCTGAAC CCCAGATCAC GTTTCAGACC AAGGGCTGCA

TCCTGGACTC GCTGGACCAG ATCATCCAGC ACCTGGCAGG ACGTGCTGGA GTGTTCACCA

ACACGGCCGG ACTGCAGAAG CTGGCGGACA TTATCCAGAT TGTGTTCAGT GTGGACCCCT

CCGAGGGCAG CCCTGGTTCC CCAGCAGGGC TGGGGGCCTT ACAGTCCTAT AAGGTGCACA

TCCATCCTGA TGCTGGTCAC CGGAGGACGG CTCAGCGGTC TGATGCCTGG AGCACCACTG

CAGCCAGAAA GCGAGGGAAG GTGCTGAGCT ACTGGTGCTT CAGTCCCGGC CACAGCATGC

ACGAGCTGGT CCGCCAGGGC GTCCGCTCCC TCATCCTTAC CAGCGGCACG CTGGCCCCGG

TGTCCTCCTT TGCTCTGGAG ATGCAGATCC CTTTCCCAGT CTGCCTGGAG AACCCACACA

TCATCGACAA GCACCAGATC TGGGTGGGGG TCGTCCCCAG AGGCCCCGAT GGAGCCCAGT

TGAGCTCCGC GTTTGACAGA CGGTTTTCCG AGGAGTGCTT ATCCTCCCTG GGGAAGGCTC

TGGGCAACAT CGCCCGCGTG GTGCCCTATG GGCTCCTGAT CTTCTTCCCT TCCTATCCTG

TCATGGAGAA GAGCCTGGAG TTCTGGCGGG CCCGCGACTT GGCCAGGAAG ATGGAGGCGC

TGAAGCCGCT GTTTGTGGAG CCCAGGAGCA AAGGCAGCTT CTCCGAGACC ATCAGTGCTT

ACTATGCAAG GGTTGCCGCC CCTGGGTCCA CCGGCGCCAC CTTCCTGGCG GTCTGCCGGG

GCAAGGCCAG CGAGGGGCTG GACTTCTCAG ACACGAATGG CCGTGGTGTG ATTGTCACGG

GCCTCCCGTA CCCCCCACGC ATGGACCCCC GGGTTGTCCT CAAGATGCAG TTCCTGGATG

AGATGAAGGG CCAGGGTGGG GCTGGGGGCC AGTTCCTCTC TGGGCAGGAG TGGTACCGGC

-continued

```
AGCAGGCGTC CAGGGCTGTG AACCAGGCCA TCGGGCGAGT GATCCGGCAC CGCCAGGACT

ACGGAGCTGT CTTCCTCTGT GACCACAGGT TCGCCTTTGC CGACGCAAGA GCCCAACTGC

CCTCCTGGGT GCGTCCCCAC GTCAGGGTGT ATGACAACTT TGGCCATGTC ATCCGAGACG

TGGCCCAGTT CTTCCGTGTT GCCGAGCGAA CTATGCCAGC GCCGGCCCCC CGGGCTACAG

CACCCAGTGT GCGTGGAGAA GATGCTGTCA GCGAGGCCAA GTCGCCTGGC CCCTTCTTCT

CCACCAGGAA AGCTAAGAGT CTGGACCTGC ATGTCCCCAG CCTGAAGCAG AGGTCCTCAG

GGTCACCAGC TGCCGGGGAC CCCGAGAGTA GCCTGTGTGT GGAGTATGAG CAGGAGCCAG

TTCCTGCCCG GCAGAGGCCC AGGGGGCTGC TGGCCGCCCT GGAGCACAGC GAACAGCGGG

CGGGGAGCCC TGGCGAGGAG CAGGCCCACA GCTGCTCCAC CCTGTCCCTC CTGTCTGAGA

AGAGGCCGGC AGAACAACCG CGAGGAGGGA GGAAGAAGAT CCGGCTGGTC AGCCACCCGG

AGGAGCCCGT GGCTGGTGCA CAGACGGACA GGGCCAAGCT CTTCATGGTG GCCGTGAAGC

AGGAGTTGAG CCAAGCCAAC TTTGCCACCT TCACCCAGGC CCTGCAGGAC TACAAGGGTT

CCGATGACTT CGCCGCCCTG GCCGCCTGTC TCGGCCCCCT CTTTGCTGAG GACCCCAAGA

AGCACAACCT GCTCCAAGGC TTCTACCAGT TTGTGCGGCC CCACCATAAG CAGCAGTTTG

AGGAGGTCTG TATCCAGCTG ACAGGACGAG GCTGTGGCTA TCGGCCTGAG CACAGCATTC

CCCGAAGGCA GCGGGCACAG CCGGTCCTGG ACCCCACTGG AAGAACGGCG CCGGATCCCA

AGCTGACCGT GTCCACGGCT GCAGCCCAGC AGCTGGACCC CCAAGAGCAC CTGAACCAGG

GCAGGCCCCA CCTGTCGCCC AGGCCACCCC CAACAGGAGA CCCTGGCAGC CAACCACAGT

GGGGGTCTGG AGTGCCCAGA GCAGGGAAGC AGGGCCAGCA CGCCGTGAGC GCCTACCTGG

CTGATGCCCG CAGGGCCCTG GGGTCCGCGG GCTGTAGCCA ACTCTTGGCA GCGCTGACAG

CCTATAAGCA AGACGACGAC CTCGACAAGG TGCTGGCTGT GTTGGCCGCC CTGACCACTG

CAAAGCCAGA GGACTTCCCC CTGCTGCACA GGTTCAGCAT GTTTGTGCGT CCACACCACA

AGCAGCGCTT CTCACAGACG TGCACAGACC TGACCGGCCG GCCCTACCCG GGCATGGAGC

CACCGGGACC CCAGGAGGAG AGGCTTGCCG TGCCTCCTGT GCTTACCCAC AGGGCTCCCC

AACCAGGCCC CTCACGGTCC GAGAAGACCG GGAAGACCCA GAGCAAGATC TCGTCCTTCC

TTAGACAGAC GCCAGCAGGG ACTGTGGGGG CGGGCGGTGA GGATGCAGGT CCCAGCCAGT

CCTCAGGACC TCCCCACGGG CCTGCAGCAT CTGAGTGGGG CCTCTAGGAT GTGCCCAGCC

TGCCACACCG CCTCCAGGAA GCAGAGCGTC ATGCAGGTCT TCTGGCCAGA GCCCCAGTGA

GTGCCCACGG AGGCCCCCAG CACACCCAAC GTGGCTTGAT CACCTGCCTG TCCAGCTCTG

GTGGGCCAAG AACCCACCCA ACAGAATAGG CCAGCCCATG CCAGCCGGCT TGGCCCGCTG

CAGGCCTCAG GCAGGCGGGG CCCATGGTTG GTCCCTGCGG TGGGACCGGA TCTGGGCCTG

CCTCTGAGAA GCCCTGAGCT ACCTTGGGGT CTGGGGTGGG TTTCTGGGAA AGTGCTTCCC

CAGAACTTCC CTGGCTCCTG GCCTGTGAGT GGTGCCACAG GGGCACCCCA GCTGAGCCCC

TCACCGGGAA GGAGGAGACC CCCGTGGGCA CGTGTCCACT TTTAATCAGG GGACAGGGCT

CTCTAATAAA GCTGCTGGCA GTGCCC.
```

The above-exemplified isolated DNA molecule shown in FIG. 1A-B and SEQ ID NO:1 comprise 4946 nucleotides, with an initiating Met at nucleotides 828-830 and a "TAG" termination codon at nucleotides 4485-4487. The initiating Met and TAG termination codon are underlined.

The present invention also relates to biologically active fragments or mutants of SEQ ID NO:1 which encode a mRNA molecule expressing a novel DNA helicase, NHL. Any such biologically active fragment and/or mutant will encode either a protein or protein fragment which at least substantially mimics the biological properties of the human NHL protein disclosed herein in FIG. 2 and as set forth as SEQ ID NO:2. Any such polynucleotide includes but is not necessarily limited to nucleotide substitutions, deletions, additions, amino-terminal truncations and carboxy-terminal truncations such that these mutations encode mRNA which express a functional NHL protein in a host cell, so as to be useful for screening for agonists and/or antagonists of NHL activity.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant hosts, both prokaryotic and eukaryotic, which contain the substantially purified nucleic acid molecules disclosed throughout this specification.

The degeneracy of the genetic code is such that, for all but two amino acids, more than a single codon encodes a particular amino acid. This allows for the construction of synthetic DNA that encodes the NHL protein where the nucleotide sequence of the synthetic DNA differs significantly from the nucleotide sequence of SEQ ID NO:1 but still encodes the same NHL protein as SEQ ID NO:2. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the NHL protein in the host. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Therefore, the present invention discloses codon redundancy which may result in differing DNA molecules expressing an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

The present invention also relates to recombinant vectors and recombinant hosts, both prokaryotic and eukaryotic, which contain the substantially purified nucleic acid molecules disclosed throughout this specification. The nucleic acid molecules of the present invention encoding a NHL protein, in whole or in part, can be linked with other DNA molecules, i.e, DNA molecules to which the NHL coding sequence are not naturally linked, to form "recombinant DNA molecules" which encode a respective NHL protein. The novel DNA sequences of the present invention can be inserted into vectors which comprise nucleic acids encoding NHL or a functional equivalent. These vectors may be comprised of DNA or RNA; for most cloning purposes DNA vectors are preferred. Typical vectors include plasmids, modified viruses, bacteriophage, cosmids, yeast artificial chromosomes, and other forms of episomal or integrated DNA that can encode a NHL protein. It is well within the purview of the skilled artisan to determine an appropriate vector for a particular gene transfer or other use.

Included in the present invention are DNA sequences that hybridize to SEQ ID NO:1 under stringent conditions. By way of example, and not limitation, a procedure using conditions of high stringency is as follows: Prehybridization of filters containing DNA is carried out for 2 hours to overnight at 65° C. in buffer composed of 6×SSC, 5× Denhardt's solution, and 100 μg/ml denatured salmon sperm DNA. Filters are hybridized for 12 to 48 hrs at 65° C. in prehybridization mixture containing 100 μg/ml denatured salmon sperm DNA and 5-20×$10^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography. Other procedures using conditions of high stringency would include either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook et al., 1989, *Molecular Cloning: A Laboratory Manual*; Cold Spring Harbor Laboratory, Cold Spring Harbor, N.Y. In addition to the foregoing, other conditions of high stringency which may be used are well known in the art.

The present invention also relates to a substantially purified form of a human NHL protein which comprises the amino acid sequence (1219 amino acid residues) disclosed in FIG. 2 and set forth as SEQ ID NO:2. A preferred aspect of this portion of the present invention is a NHL protein which consists of the amino acid sequence disclosed in FIG. 2 and set forth as SEQ ID NO:2, as follows:

MPKIVLNGVT VDFPFQPYKC QQEYMTKVLE CLQQKVNGIL ESPTGTGKTL CLLCTTLAWR (SEQ ID NO:2)

EHLRDGISAR KIAERAQGEL FPDRALSSWG NAAAAAGDPI ACYTDIPKII YASRTHSQLT

QVINELRNTS YRPKVCVLGS REQLCIHPEV KKQESNHLQI HLCRKKVASR SCHFYNNVEE

KSLEQELASP ILDIEDLVKS GSKHRVCPYY LSRNLKQQAD IIFMPYNYLL DAKSRRAHNI

DLKGTVVIFD EAHNVEKMCE ESASFDLTPH DLASGLDVID QVLEEQTKAA QQGEPHPEFS

ADSPSPGLNM ELEDIAKLKN ILLRLEGAID AVELPGDDSG VTKPGSYIFE LFAEAQITFQ

TKGCILDSLD QIIQHLAGRA GVFTNTAGLQ KLADIIQIVF SVDPSEGSPG SPAGLGALQS

YKVHIHPDAG HRRTAQRSDA WSTTAARKRG KVLSYWCFSP GHSMHELVRQ GVRSLILTSG

TLAPVSSFAL EMQIPFPVCL ENPHIIDKHQ IWVGVVPRGP DGAQLSSAFD RRFSEECLSS

LGKALGNIAR VVPYGLLIFF PSYPVMEKSL EFWRARDLAR KMEALKPLFV EPRSKGSFSE

TISAYYARVA APGSTGATFL AVCRGKASEG LDFSDTNGRG VIVTGLPYPP RMDPRVVLKM

QFLDEMKGQG GAGGQFLSGQ EWYRQQASRA VNQAIGRVIR HRQDYGAVFL CDHRFAFADA

RAQLPSWVRP HVRVYDNFGH VIRDVAQFFR VAERTMPAPA PRATAPSVRG EDAVSEAKSP

GPFFSTRKAK SLDLHVPSLK QRSSGSPAAG DPESSLCVEY EQEPVPARQR PRGLLAALEH

SEQRAGSPGE EQAHSCSTLS LLSEKRPAEE PRGGRKKIRL VSHPEEPVAG AQTDRAKLFM

VAVKQELSQA NFATFTQALQ DYKGSDDFAA LAACLGPLFA EDPKKHNLLQ GFYQFVRPHH

KQQFEEVCIQ LTGRGCGYRP EHSIPRRQRA QPVLDPTGRT APDPKLTVST AAAQQLDPQE

HLNQGRPHLS PRPPPTGDPG SQPQWGSGVP RAGKQGQHAV SAYLADARRA LGSAGCSQLL

AALTAYKQDD DLDKVLAVLA ALTTAKPEDF PLLHRFSMFV RPHHKQRFSQ TCTDLTGRPY

PGMEPPGPQE ERLAVPPVLT HRAPQPGPSR SEKTGKTQSK ISSFLRQRPA GTVGAGGEDA

GPSQSSGPPH GPAASEWGL*.

The present invention also relates to biologically active fragments and/or mutants of the human NHL protein comprising the amino acid sequence as set forth in SEQ ID NO:2, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists of NHL function.

Another preferred aspect of the present invention relates to a substantially purified, fully processed NHL protein obtained from a recombinant host cell containing a DNA expression vector which comprises a nucleotide sequence as set forth in SEQ ID NO:1 and expresses the human NHL protein. It is especially preferred is that the recombinant host cell be a eukaryotic host cell, such as a mammalian cell line.

As with many proteins, it is possible to modify many of the amino acids of NHL protein and still retain substantially the same biological activity as the wild type protein. Thus this invention includes modified NHL polypeptides which have amino acid deletions, additions, or substitutions but that still retain substantially the same biological activity as a respective, corresponding NHL. It is generally accepted that single amino acid substitutions do not usually alter the biological activity of a protein (see, e.g., *Molecular Biology of the Gene*, Watson et al., 1987, Fourth Ed., The Benjamin/Cummings Publishing Co., Inc., page 226; and Cunningham & Wells, 1989, *Science* 244:1081-1085). Accordingly, the present invention includes a polypeptide where one amino acid substitution has been made in SEQ ID NO:2 wherein the polypeptide still retains substantially the same biological activity as a corresponding NHL protein. The present invention also includes polypeptides where two or more amino acid substitutions have been made in SEQ ID NO:2 wherein the polypeptide still retains substantially the same biological activity as a corresponding NHL protein. In particular, the present invention includes embodiments where the above-described substitutions are conservative substitutions.

One skilled in the art would also recognize that polypeptides that are functional equivalents of NHL and have changes from the NHL amino acid sequence that are small deletions or insertions of amino acids could also be produced by following the same guidelines, (i.e, minimizing the differences in amino acid sequence between NHL and related proteins. Small deletions or insertions are generally in the range of about 1 to 5 amino acids). The effect of such small deletions or insertions on the biological activity of the modified NHL polypeptide can easily be assayed by producing the polypeptide synthetically or by making the required changes in DNA encoding NHL and then expressing the DNA recombinantly and assaying the protein produced by such recombinant expression.

The present invention also includes truncated forms of NHL which contain the region comprising the active site of the enzyme. Such truncated proteins are useful in various assays described herein, for crystallization studies, and for structure-activity-relationship studies.

The present invention also relates to isolated nucleic acid molecules which are fusion constructions expressing fusion proteins useful in assays to identify compounds which modulate wild-type NHL activity, as well as generating antibodies against NHL. One aspect of this portion of the invention includes, but is not limited to, glutathione S-transferase (GST)-NHL fusion constructs. Recombinant GST-NHL fusion proteins may be expressed in various expression systems, including *Spodoptera frugiperda* (Sf21) insect cells (Invitrogen) using a baculovirus expression vector (pAcG2T, Pharmingen). Another aspect involves NHL fusion constructs linked to various markers, including but not limited to GFP (Green fluorescent protein), the MYC epitope, and GST. Again, any such fusion constructs may be expressed in the cell line of interest and used to screen for modulators of one or more of the NHL proteins disclosed herein.

Any of a variety of procedures may be used to clone NHL. These methods include, but are not limited to, (1) a RACE PCR cloning technique (Frohman, et al., 1988, *Proc. Natl. Acad. Sci. USA* 85: 8998-9002). 5' and/or 3' RACE may be performed to generate a full-length cDNA sequence. This strategy involves using gene-specific oligonucleotide primers for PCR amplification of NHL cDNA. These gene-specific primers are designed through identification of an expressed sequence tag (EST) nucleotide sequence which has been identified by searching any number of publicly available nucleic acid and protein databases; (2) direct functional expression of the NHL cDNA following the construction of a NHL-containing cDNA library in an appropriate expression vector system; (3) screening a NHL-containing cDNA library constructed in a bacteriophage or plasmid shuttle vector with a labeled degenerate oligonucleotide probe designed from the amino acid sequence of the NHL protein; (4) screening a NHL-containing cDNA library constructed in a bacteriophage or plasmid shuttle vector with a partial cDNA encoding the NHL protein. This partial cDNA is obtained by the specific PCR amplification of NHL DNA fragments through the design of degenerate oligonucleotide primers from the amino acid sequence known for other kinases which are related to the NHL protein; (5) screening a NHL-containing cDNA library constructed in a bacteriophage or plasmid shuttle vector with a partial cDNA or oligonucleotide with homology to a mammalian NHL protein. This strategy may also involve using gene-specific oligonucleotide primers for PCR amplification of NHL cDNA identified as an EST as described above; or (6) designing 5' and 3' gene specific oligonucleotides using SEQ ID NO:1 as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding NHL.

It is readily apparent to those skilled in the art that other types of libraries, as well as libraries constructed from other cell types-or species types, may be useful for isolating a NHL-encoding DNA or a NHL homologue. Other types of libraries include, but are not limited to, cDNA libraries derived from other cells.

It is readily apparent to those skilled in the art that suitable cDNA libraries may be prepared from cells or cell lines which have NHL activity. The selection of cells or cell lines for use in preparing a cDNA library to isolate a cDNA encoding NHL may be done by first measuring cell-associated NHL activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding NHL may also be isolated from a suitable genomic DNA library. Construction of genomic DNA libraries can be performed by standard techniques well known in the art. Well known genomic DNA library construction techniques can be found in Sambrook, et al., supra. One may prepare genomic libraries, especially in P1 artificial chromosome vectors, from which genomic clones containing the NHL gene can be isolated, using probes based upon the NHL nucleotide sequences disclosed herein. Methods of preparing such libraries are known in the art (Ioannou et al., 1994, *Nature Genet.* 6:84-89).

In order to clone a NHL gene by one of the preferred methods, the amino acid sequence or DNA sequence of a NHL or a homologous protein may be necessary. To accomplish this, a respective NHL protein may be purified and the partial amino acid sequence determined by automated sequenators. It is not necessary to determine the entire amino acid sequence, but the linear sequence of two regions of 6 to 8 amino acids can be determined for the PCR amplification of a partial NHL DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the NHL sequence but others in the set will be capable of hybridizing to NHL DNA even in the presence of DNA oligonucleotides with mismatches. The mismatched DNA oligonucleotides may still sufficiently hybridize to the NHL DNA to permit identification and isolation of NHL encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO:1 either for the purpose of isolating overlapping 5' and 3' RACE products for generation of a full-length sequence coding for NHL, or to isolate a portion of the nucleotide sequence coding for NHL for use as a probe to screen one or more cDNA- or genomic-based libraries to isolate a full-length sequence encoding NHL or NHL-like proteins.

This invention also includes vectors containing a NHL gene, host cells containing the vectors, and methods of making substantially pure NHL protein comprising the steps of introducing the NHL gene into a host cell, and cultivating the host cell under appropriate conditions such that NHL is produced. The NHL so produced may be harvested from the host cells in conventional ways. Therefore, the present invention also relates to methods of expressing the NHL protein and biological equivalents disclosed herein, assays employing these gene products, recombinant host cells which comprise DNA constructs which express these proteins, and compounds identified through these assays which act as agonists or antagonists of NHL activity.

The cloned NHL cDNA obtained through the methods described above may be recombinantly expressed by molecular cloning into an expression vector (such as pcDNA3.neo, pcDNA3.1, pCR2.1, pBlueBacHis2 or pLITMUS28) containing a suitable promoter and other appropriate transcription regulatory elements, and transferred into prokaryotic or eukaryotic host cells to produce recombinant NHL. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. To determine the NHL cDNA sequence(s) that yields optimal levels of NHL, cDNA molecules including but not limited to the following can be constructed: a cDNA fragment containing the full-length open reading frame for NHL as well as various constructs containing portions of the cDNA encoding only specific domains of the protein or rearranged domains of the protein. All constructs can be designed to contain none, all or portions of the 5' and/or 3' untranslated region of a NHL cDNA. The expression levels and activity of NHL can be determined following the introduction, both singly and in combination, of these constructs into appropriate host cells. Following determination of the NHL cDNA cassette yielding optimal expression in transient assays, this NHL cDNA construct is transferred to a variety of expression vectors (including recombinant viruses), including but not limited to those for mammalian cells, plant cells, insect cells, oocytes, bacteria, and yeast cells. Techniques for such manipulations can be found described in Sambrook, et al., supra, are well known and available to the artisan of ordinary skill in the art. Therefore, another aspect of the present invention includes host cells that have been engineered to contain and/or express DNA sequences encoding the NHL protein. An expression vector containing DNA encoding a NHL-like protein may be used for expression of NHL in a recombinant host cell. Such recombinant host cells can be cultured under suitable conditions to produce NHL or a biologically equivalent form. Expression vectors may include, but are not limited to, cloning vectors, modified cloning vectors, specifically designed plasmids or viruses. Commercially available mammalian expression vectors which may be suitable for recombinant NHL expression, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAIamp (Invitrogen), pcDNA3 (Invitrogen), pMCIneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565). Also, a variety of bacterial expression vectors may be used to express recombinant NHL in bacterial cells. Commercially available bacterial expression vectors which may be suitable for recombinant NHL expression include, but are not limited to pCR2.1 (Invitrogen), pET11a (Novagen), lambda gt11 (Invitrogen), and pKK223-3 (Pharmacia). In addition, a variety of fungal cell expression vectors may be used to express recombinant NHL in fungal cells. Commercially available fungal cell expression vectors which may be suitable for recombinant NHL expression include but are not limited to pYES2 (Invitrogen) and *Pichia* expression vector (Invitrogen). Also, a variety of insect cell expression vectors may be used to express recombinant protein in insect cells. Commercially available insect cell expression vectors which may be suitable for recombinant expression of NHL include but are not limited to pBlueBacIII and pBlueBacHis2 (Invitrogen), and pAcG2T (Pharmingen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines. For instance, one insect expression system utilizes *Spodoptera frugiperda* (Sf21) insect cells (Invitrogen) in tandem with a baculovirus expression vector (pAcG2T, Pharmingen). Also, mammalian species which may be suitable and which are commercially available, include but are not limited to, L cells L-M(TK⁻) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCC CCL 171) and CPAE (ATCC CCL 209).

Figure 5A:
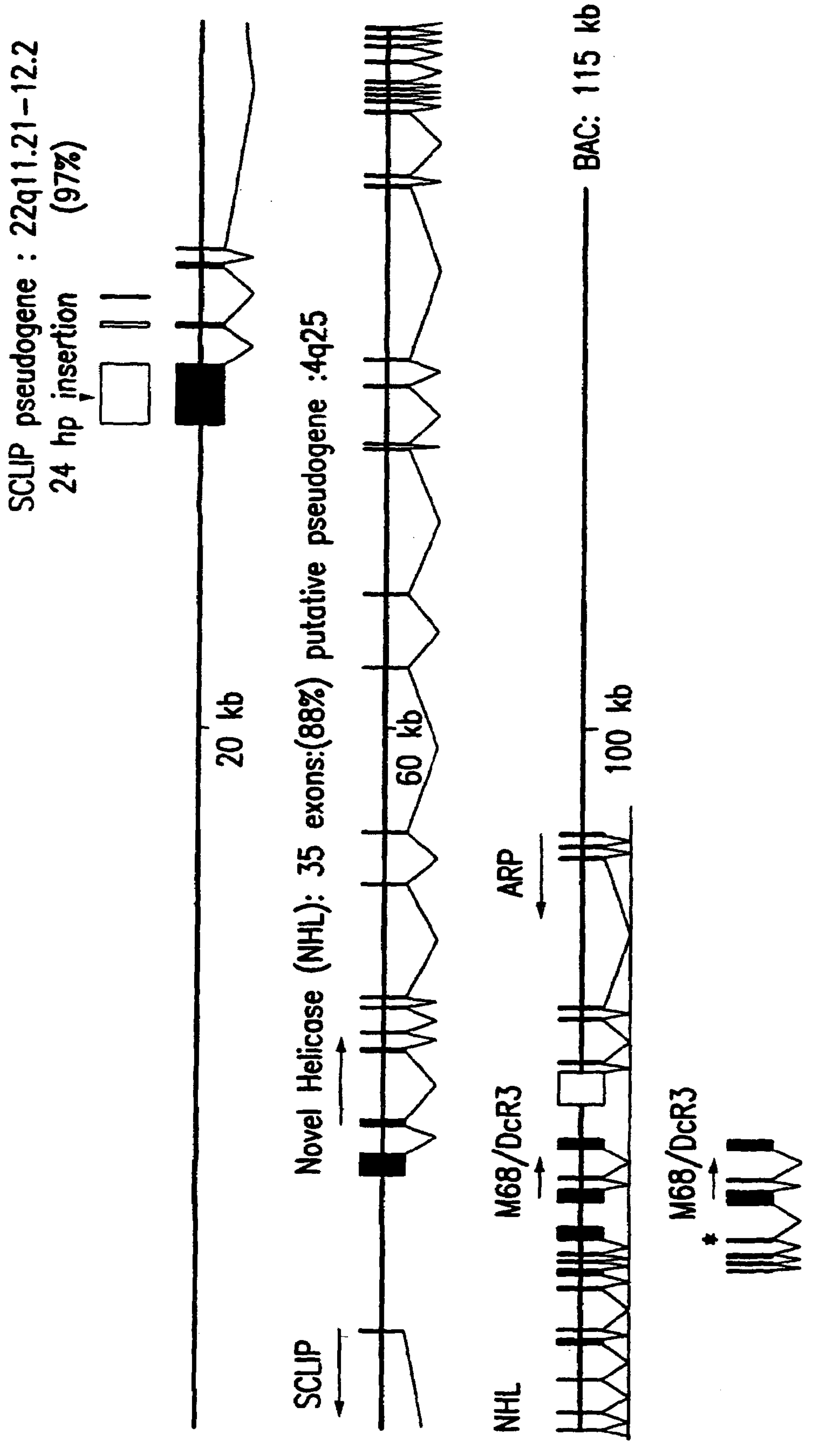
FIG. 5A-B show the genomic structure of the NHL gene (FIG. 5A) and the entire 115 kb genomic region (FIG. 5B) containing the NHL, M68/DcR3, SCLIP and ARP genes.

As disclosed in Example section 1, a 115 kb BAC clone (from Genome Systems) was subcloned and subjected to restriction and sequence analysis. Four genes at chromosome location 20q13.3 were identified, including M68/DcR3, NHL, SCLIP and ARP (FIG. 5A). The nucleotide sequence of this BAC clone, hbm168, is presented as follows:

(SEQ ID NO:3)

```
TGAAGAGCTT TGACCAAGAG GCTGTGACGA GGCCCTACGA GGACTCTGGC TCTCCTCCTG    60

CTAAGCACAC CCAGGCAGGT GTCCTGGCAG ATGAGGACCA CATGCAGAGC CTCGGCCAGC   120

CCACCAATGC CCGGATATGC AAGTGAGCCC AGCCTGGACC CCCCGGCGAG GCCCAGCAGC   180

ACCAGCCCAG GCCCGAAAAC CTTAAGAAAT GACCAGTGTC TGCTGCTTTA AGCCACCAAG   240

CTCTGCGGTG GTTTGTTAGG CTGCAAGCAT GGCTAATTCA GAAACTGCCA GAAACAAGCA   300
```

-continued

```
CTGCTGTCCC CAGCCTGGGA CACACAGGAC CGCCTCTGCG TGGGGAGAGG GCACAGGCTA    360
AGGGCACAAA TGCCATCCCA GACCCGGCTC TTGTGTGTGG AAGGGGCCAC TGTGCCATGA    420
GGCAGAGGAA ACCTTGGCAG GACCTTATGC CACAGCAATT TAAAAGAGAA GAAACAGGCT    480
GGGCGTGGTG GCTCATGCCT ATAATCCCAG CACTTTGGGA GGCCAAGGTG GTGGATCACT    540
TGAGGTCAGG AGTTCAAGAC CAGCCTGGCC AATATGGTGA AACCCTGTCT CTACGAAAAA    600
TACAAAATTT AGGCAGGCGT GGTGGCGGGT GCCTGTAATC CCTGCTATTC AGGAGGCTGA    660
GGCAAGAGAT TTACTTGAAC CCAGGAGGTG GAGGCTGCTG CAGTGAGCTG AGATCATGCC    720
ACTGCACTCC AGCCTGTGTG ACGGAGTGAG ACTTGGTCTC AAAAAAAAAA AAGGAAACAC    780
ATCTGACTAG TGTGATCTCG CAAGGAACAT TCCAGACACA GTGGAGCTAG AAGGTTCTTC    840
TCCAAACAAG GAATCCCCAC GGGATCAAAT TGTTTTGCAT CGGCCAGACA TGGTGGCTCA    900
AGCCTGTAAC CCCAGTGCTT CGGGAGGCTG AGGTGGGAGG ACTGCTTGAG TCCAGGAGTT    960
CAAGACTAGC TTGGGCAACA CAGTGAGAGC CCATTAGCCA GGCGTGGTGG CACATGCCTG   1020
CAGTCCCAGC ACTGTACTAA AAATCTACAC GGGGCCGGGC ATGGTGGCAC ATGCCTGTAG   1080
AGTCCCAGCT ACTCAGGAGG CTGAGGCAGG ACGATTCCTT GAACCCAGGA GGTCACGGCT   1140
GCCATGAGCC GTGACTGTGC CACTGCACTC CAGTCTGTGC AACAGAACGA GACTCTGTTT   1200
CGAAAAACAA AAAATCATTT CATCTCTCCA GTTTCTCCAC TGGCAAAAGA CTCTGTCAAG   1260
GTAAAAAATG GTTCTGACCC ACAGAAATCT AAGAAAGGAA AAAATATAAA AAATAGAAAA   1320
TTTAAAAAAG AGATGGTCTC AGAATAAAGA CCAACCTGGG CTATGGTTGT CACTCTTCCC   1380
TCACACCTTA GAAAGCTTTC TGCCCGCATC TGGCCAAAGG GCCACCCTGC CCCATCTTGG   1440
ATCAGTGAGG TGCCTTCGAA CAAGCCACCT GCCCTGGAGC CCGTCCTGTC TTGTCTGCCA   1500
CCGCACGCTC AGTAGGGGAG GGGAAGTCGC TAGGTTTTAG TTCACCAGTC TCTGGATCAA   1560
GACGTGCCAT AACCAAGAAG CCCCAGCCAC ACCCAGACCC GATGTGGCCA CAAGGGGTCA   1620
GCTGGGAAGG CCCAGGAAAA GGCGGGAGGC GGACGAATGG AAATGTCATT CTGTGGCCAC   1680
AGAAATGATC TCAACGTTTT GTAACTTCCT ACCAAGAGGC AGTCTTAGCT CTGCCCTTGA   1740
ACCAGCACTT GGTGATGTCG CTTGCGTCAA TCAAGGCAAC AGAAGTGAGC AGGAGGCCCA   1800
CTTTCCTCTG CAACTGTGGG CTTACGGGGC AAAGAAGTCC AGGCCTCCAG GTGGAGGATC   1860
ACAGACCGGG CAAAGCAGAG GAGAGCCACC CAGCCGAGCC TACCTGTGCC TCAGACTGCC   1920
TCCCTCCAGA GACCCCTGTG GCCAAGGCCA CCCAGACCAG CAGGTCCTTG CCAAGCTGTC   1980
AGCTGACGAC AGGGGTTGGT GAGGCCGGCC CAGACCAGCA GAACCACGAA CCAACCAACA   2040
GAATTAAAAA TAATAACAAC TATGTCTTGT CTTAAGCCAC TAAGTTTTGG ATGGTTTCTT   2100
TCTTTCTTTT TCTTTTTTTT TTTCGGAGAC GCAGTCTCAC TCTGTTGCCC AGGCTGGAGT   2160
GCAGTGGCGC AATCTTGGCT CACTGCAAGC TCTGCCCCCC GGATTCACGC CATTCCCCTG   2220
CCTCAGCCTC CTGAGTAACT GGGACTACAG GTGCCTGCCA TTGGGTGTTT TCTTAAACAG   2280
CAAAAGAAAA CTGACACAAT CATAAACAGA GCAAGCAAGA GAACTTGGCA ATTATTTCCT   2340
CTCTACTTCT CACTGTTCTT CAAAGAGTTA ACTCAAGCAT AAGATGTGAG CAAATTCTTT   2400
TAACATCCTA GAAAAAAAGC TCCTACTCAG TGTTCATAAA GCAAAGCTAA CCTACAGGAG   2460
CCACCTTCCA CAGTGACCAC AGGAAACCAA GACAGCAAGT GGGACACCAG CCTCCAGGGC   2520
ACTGCGCCAG CCGTGCGCCT GTGTCTGCCA CTGCCCTGGT CCGTCACTGC CACCAGCCGG   2580
CAAGACACCC ACAGAGGAGA GCTCTAAGCC ACAACTGTGT ACGAAGACAA CTGTGCAGGA   2640
TTTTATTACT ACAACATTTT TGTTTTCTTT TTTTTTTTTT TTTGAGACTG AGTCTCGCTC   2700
```

-continued

TGTCACCCAG GCTGGAGTGC AGTGGCACAA TCTCGGCTCA CTGTAACCTC CATCTCCCTG 2760

GTTCAAGCAA TTCTCCTGCT GCAGCCTCCC AACTGGATTA CAGGCGCCCG CCACCACGCC 2820

TGGCTAATTT TTGTACTTTT AGTAGAGATG GGGTTTCACC ATGTTGGCCA GACTGGTCTC 2880

AAATTCCTGA CAAGTGATCC ACCCACCCTG GCCTCCCAAA GTGCTGGGAT TACAGGTGTG 2940

AGCCACTGCG CCTGGCCCAT TTTTGTTTAT CAATAAAAAT GTACTTAATG TTGAACTCTC 3000

CACATTTCAA ATGGGTAACT CCAGTGTCCT TGATGCTCCT GCGACATGTT CGTGAGACTT 3060

CTCTTGGGTG TGAGAGTCTA GCATGTGGGT GGTCTGGACA GGAGGGGGAG GGAAGAGTGC 3120

AGAGCCGGGC AGGGTAAAGA GACCCCCTAG GATGTGAAGG CCGCCCTGCA TTTGTCAGAC 3180

TGGGCAACAC CCACTCCATC AGATGGACCC TGGTATGGGC GGCAAGCCAC CTAGGTGCCG 3240

AGGCAAGAGA CCGAGGGCAC GAGCTGTTCC GGTGTAATAA AATGCATAAA ATAAGAATAG 3300

TTATACTAGA TATAGATCAT AAATATGATT ATATATGAAT ATCATTCATC ATTAGTTTGT 3360

AGCAATTACT CTTTATTCCA ATATTATAAT AATCCTTGCC TAAGCATAAC CTAGGAAAAA 3420

CTAGGAAATC ATAACCTAGG AAAAACTAGG CCATACAGAG ATAGGAGCTG AGGGGACATA 3480

GTGAGAACTG ACCAGAAGAC AAGAGTGCGA GCCTTCTGTT ATGCCTGGAC AGGGCCACCA 3540

GAGGGCTCCT TGGTCTAGCG GTAACGCCAG CATCTGGGAA GACGCCCGTT GCCAAGTGGA 3600

CCGTGGTCTA GCGGTAGCCT CAGTGTCAAG GAAAAACACC CGCTACTTAG CAAACCAGGA 3660

AAGAGAGTCT CCCTTTCCCC GGGGGAGTTT AGAGAAGACT CTACTCCTCC ACCTCTTGCG 3720

GAGGGCCTGA CATCAGTCAG GCCCGCCCGC AGTTATCCGG AGGCCTAACC GTCTCCCTGT 3780

GATGCTGTGC TTCAGTGGTC ACGCTCCTAG TCCGCCTTCA TGTTCCATCC TGTGCACCTG 3840

GCTCTGCCTT CTAGATAGCA GCAGCAAATT AGTGAAAGTA CTGAAAGTCT CTGATAAGCA 3900

GAAATAATGG CGTAAGCGGT CTCTCTCTCT CTCTCCTCTC TCTCTGCCTC AGCTGCCAGG 3960

AAGGGAAGGG CCCCCTGGCC AGTGGGCACG TGACCCACAT GACCTTACCT ATCACTGGAC 4020

ATGGTTCACA CTCCTTACCC TGCCGCTTTG TCTTGTATCC AATAAATAGC GCAACCTGGC 4080

ATTCGGGGCC GCTACCAGTC TCCGCGTCTT GGTGGTAGTG GTCCCCCAGG CCCAGCTGTC 4140

TTTTTCTTTT ATCTTTGTCT TGTGTCTTTA TTTCTACACT CTCTCATCTC CGCATACGAG 4200

GAGAAAACCC ACCAACCCTG TGGGGCTGGT CCCTACACCC TGGCTTTGTA GACTGGAGCC 4260

TAGGCACGAC TCAGCTGCTG TAGTGAATTG CGATCCTCCA AACCCAGCAA GGCACCTGCA 4320

GGACATCTGG CCCAGTCTCC TCGTTGAGCC AGTTCACGAA AAAGAGACTT TTCTGAGTGA 4380

CATGCTAATG GGCAATATGA GGACTAAATG GGATGGTCTC CAACTTGGAC AAACCAACAG 4440

TAAAAGCCAC TTTGCGGGGA AAGAAACTTT TCCTTTTTTC TTTTTTTTGA GACAGGATCT 4500

CACCCTGTCA CCCAGGCTGC AGTGCAGTGG CATGACCTTG GCTCACTGCA GCCTCAACCT 4560

CTCTCAGGCT CAAGCAATCC TCCCGCCTCA ACCTCCCATG CAGCTGGGAC CATAGGTGCA 4620

TGCCACCACA CCCAAATAAT TTTTATATTT TTTGTAGAGA CGAGGTTTCA CTATGTTGCT 4680

CGGGCTGGTC TCAACTCCTG GGCTCAAGCA ACCCTCCCAC CTCAGCCTCC CAAAGTGCTC 4740

AGATTACAGG CAGGAGCCAC CAGGCCTGGC CAACATAGGA AGAAATTTAA ATTTGAATTG 4800

AATATTAGAA GAGATGAAAA TTCATCAACA TGGAAAGACA AAGATCATTA ACTAAAGCCA 4860

AACCAGAATG GAAGCTGTGT GTACAGTGGG GTCTCATGCT GGGAACGCGA GGGGCACGTG 4920

CAGGGCTCCA CGGTGTGGCG ACGCCCCATG CTCCCTTTGT GGGGGTTCAT CCAGCGGAAC 4980

ATGAGGACCT GGGGTGCTTT TCAACATGTA CGTGAGTTTA ATAATAAAAA GGTTTAAGGA 5040

AAGAAAAATT CATATGTTTC TATATAAACA GAACATCTGG AAAGATCTAT TCTAAGGTGT 5100

-continued

```
TGACAGTAGG AATCTCTAGG TAGTAGTAAT ATGGCCTTTT TGAATTTTTG CTTATCAGTA   5160
TTTTCTAATT TTCTTTTTCT TTCTAAATAA TTCTAGCTAT GAAATAATTT TCTACCATAT   5220
ATATTTTGTA ATAAAAATGG TTATATTTAA TTTTTTAAAG GCTGTACAAA CTTCCTGATA   5280
AAATGGCAAA TTAGACACAC ACATGTGGGC CGGGTACAGT GGCTCGCGCC TGTAATTCCA   5340
GCACTTTGGG AGGCTGAGGC AGGCAGATCA CCTAAGGTCA GGAGTTTGAG ACCAGCCTGG   5400
CCAACATGGT GAAACCCCGT CTCTACTAAA TATACAAAAA TGAGCTGGAT GTGGTGGCAC   5460
ACACCTATAG TGCCAGCTAC TTGGGAAGCT GAGGCAGGAA AATTGCTTCA ACCCGGGAGG   5520
CAGAGGTTGT AGTGAGCCGA GATCATGCCA CTGCACTCCA GCCTAGGCAA CAAGAGCGAG   5580
ACTCCAACTC AAAAAAAAAT AAAAATAACA CACACGTGAA TAGGCTCCTC ATGGAAGTCA   5640
TCACAACAAT GCAGAGGGAA GAGCTTCCAA AGTGTAAACC CAGAAGCGAG GAGCAGGAGG   5700
GTGCGCGCAG ACGCAGAGAG CAGCAAGGTG CAGACTGAGA GGCGGAGGCT GGCCGTGGGG   5760
AGATGACTGA TGCTCAGTTT ATACCCCAAA TCCGTAAATC TAGAGGCCTG GCACATCAAC   5820
TACCTCTGCC AGCAGGAATG AGGGAAAGGA GGGCAACCAA AAGATGTCCC ACCCTCACCC   5880
ATCCAGCTAC CTGCCATCCT CAGCCCCACT GGCAGAAGAC CCTGAGAGGT GGAGGCAGGC   5940
CCCTGCCTAC AGGACCCTGA GAGCTAGGGG AAGGCGTTAT CCTGAACTGT GTCCCCCGTA   6000
AAATTCATAT GTTGAAGGCC TCATCCCCAG TGTGACTGTA TTTAAAGATG GGGTCTTCAG   6060
GAGATAATTT AAATGAGGTC ATATAAGTTG GCCCTCATCC AGTAAGACTT TGACCTTCTG   6120
GTGGTTTTTT TTTTTTTGGA GACTGGGTCT CACTCTATCA CTCAGGTTGG AGTACAGTGG   6180
CACGATCACG GCTCACTGCT GTCTCCAACT CCTGGGCTCA GGTGATCCTC CTGCTTCAGC   6240
CTCCTGAGTA GCTGGGACTA CAGGTGCTTA CCACCGCACC CAGCTGGTGG TGCATTGTGT   6300
TTTTTGTAGA GATGGGGTTT TGCCATGTCG CCCAGGCTGG TCCTGAACTG GGCTCAAGTG   6360
ATCTGTCTCC CTCGGCCTCC TGCAGTGCTG GAATTACAGG TATGAGCCAC CGCGCCTGGC   6420
CGACCGTGAC CTTCTAAGAA GTGAAAGAGA AAGATCTTTC TCTCTCCCTC CCTCTCCATC   6480
ATGAGGACAC AGCAAGAAGT CGGCCATCTG CAAGGTAGAA AGCGAGTCCT CCCAACAGCT   6540
GAACCTGGCA GACCCTGATC TTGGACTTCA GCCTTCAGAG CTGTAAGAAA ATAACTCTCT   6600
GCTGTTCAGG CCACGCGGTC TACGGCAGCC CGAGCAGACT AAGACACACG CCATCTGGGG   6660
AGTCAGACCA GATCAGGAAG AAAGGCCTAG AGCTCAGGAT ACTGAAGGTC CCAACCCGGT   6720
GCTGGACCAG ACCACCCCGG CAGCCGCGGC CACGGAGTCA CGGCTCGGGT GAGGTGACCT   6780
GGACACCATC CCGGCAGCCG CGGCCACGGA GTCACGGCTC GGGTGAGGTG ACCTGGACAC   6840
CATCCCGGCA GCCGCGGCCA CGGTGTCACG GCTCGGATGA GATGACTCGG ACACCACCCC   6900
GGCAGCCGCG GCCACGGTGT CAGGGCTCAG GTGAGGAGAG TTGGATATGG GACTGGGCCT   6960
ACCCCGAGGC TGCTTCCACC CAGACGCCTG GGTGGGTGAC ACGAAAGCTG GGCTCAGTTG   7020
GGATCAGAGC AGCCTCTCCC CAGGTCAGAA ATGACCCTGG GCTCCTCACA GTAGCCCTAG   7080
GGCACCATGA GAAAGCTACG TGGACTTCTC TGACCAAGGG TCACTGCTGC CACACTACTC   7140
ATTGCAGGCC ATGTCAGGGC TCAGCTGAGG AGACGTGGAC ACCACCCCAG CAGCCGCGGC   7200
CACGGCGTCC CAAGGGAGGG ACTTGGGCAC TGCCTCTCTG GGCAAGAGTG GGGAGGTGTG   7260
GGGTGGGAGA TGTCTGGAAA CATCATGGAC ACATGCCGGG AAAACACGGA AGCTGTGCAC   7320
CAAGGTGCTG ACAAAGGAAA AAGGAGAATG GAGGTGTGAA CATCCAGCTA GCAGGTCCCA   7380
CTCAGAAACT CCTGCATTTC CAGACATGGC CACCAGCTCT GTGGATGAGA CAGGGGAGGA   7440
CAGGGTACCT CACACCAGGA ACCCACACAG GTCCATGTCT TGCTCTGTGA TCACACAACA   7500
```

-continued

```
GCCTCCACCA CCCTGACATG CAGGAGGGAG GTCAAAGCCT CGGGTCCAAC AACAGGCTCC   7560
ACAGCAAGGG AAGAAAGGCA GGAAGGAACT CAGGGCCAGG TCCTCCCAGG CAGCAGCTGC   7620
CTGCACGCTG TCCACCAAGG GAGGTCTGAC CTACACCGCA CAGGGGTTGG CAGTCTAGAG   7680
TCGTCCTCTG TCAAACGGTG AGAAAGTCAA AAGCTCATGC TCAGTGATAT GCTAGGTCAG   7740
CATGAAGATG CCACACATGA GACACAGCAA GGATGAGACC AACGGGAAGA CTGCCCCAGA   7800
CCAGAGCCCC AGAGCCCTCT GGGGAGGAAG AATAAGGATG GCAGCCTGGG ACTGCCCGGG   7860
GCTGACTCTG CCTTTATTTC ACCCCAGCAG AGGCAGGAGT GACACCGGCT CACACCAGGA   7920
GCAGCTCTGC CACCTCCTAG CAGTTCCACC TACGGGCAGC AAAACAAAGC TGGCAGTTTG   7980
GGCAAATGTT AGCGTTTTTG CCAACTAACA TTTGAATCGG ACATCTGGTA CAGAGATGAG   8040
GAAGAAAACA CTCACAGTTT CATGAAGACT GTCAAGAAAA TCACTGACTC TTCACTTCAT   8100
TTATGAAAGG CCAGCTCTCT GACATCCCTA CCACTCCCTC TCACATGAGA AATCACGGCC   8160
TTTCAGGACG TGGAGCCACG TGGCCATGCA GGTACGGGAG GCCTCCCCGC AGCTGCAGCT   8220
GGGTCTTCTG GTCCCCGTGC CATTTCTGCT TTTCTTCGCT CTCTACTTAC ACACACATTT   8280
GAGTCCAGTC TCAGAAGAAC TGGAACTAGA AAAATCCTGA CACTTGTCCC TTACTACGTT   8340
AATGCCAGCT GTGCCAAGGA CAGCCCAACC CAAGCCCCCA TCAGCCCCAA TGGCACCGAG   8400
GCCCGAGCTT ACCCGTGAGG GGCCAAGTTG GTCGTCACCA ACACGGTCTT CACCCCCTCC   8460
ACACCACTGC CGTCCACTGC AGTGTCCGGA GTTGTCACAA CCACCACCTC CTCCATGTGC   8520
ACACTCACGT CGGGAGTCGC CATGGCTCAG CGGAAGGGGA CGCCCAGGCC AGCAGCGTCA   8580
GTCCTCCAGG GTCCCAAGTC CTGGAGGAAG CAAGGCAGGG CACAGGGATG GAGTCATCTC   8640
CACATCCACA CAACATAGCA CTCACAAAGG CATCTCTAAT CAGCTCCAAA GACCCACCCT   8700
TGAGTCCCAG ACTGCTACCT CCTGACAAAA ACGAGCGGCA ACAGAAGGGC TACTCCAGGC   8760
TCTGGTTCCG AGGGCGGTGT AAGCGCACTC CACCCGTTTT TCCCACTGGA TAAGCCGAAA   8820
CCCTTGGGTA GAAAGCACAG AGCCACTCCC TCCACGTGGG GCTCAGAGCA GGAGGACAGG   8880
AGGGGCCTGG AATTCCAAGC AACTTCCCTG GACGCAGGCT CCCGGCTTGC CAGTTCTTCC   8940
GTCTCTCCTG GCCTGAACTC AAAGCCAGCC CCAATCCCTG AACTGAGTTT CAGGTGCAGA   9000
AAGCACTCCA AGAAGTCCTC GCTGGTCTGT GGAACGGGAA GGGAAACCCA TTCAAGACAG   9060
AAAGAGAGGA GGGAAACGCC CTGGGTTTTT TTGGGTTTTT GGGTTTTTTT TGAGACGGAG   9120
TCTCGCTCTG TCGCCCAGGC TGGAATGCAG TGGCACGACC TCGGCTCACT GCAAGCTCCA   9180
CCTCCTGGGT TCAAGTGATT CTCCTGCCTC AGCCTCTCCA ATTGCTGGGA TTACAGGTTT   9240
CACCATGTTG CCCAGGCTGG TCTCAAACTC CTGACCTCAG GTGATCCACT CACCTCGGCC   9300
TCCCAAAGTG CTGGGATTGC AGGTGTGAGG CACCATGCCT GGCCTGCCCC GGGTTTAAAA   9360
ATTATTATTA TTTTGTCTTT CCTGGCTTTG CCTTCAGCAA GTCCAACCCC TGCTAAAACC   9420
CGGTGATAAT GGCTGTCCTG GCCCAAAAAG CTTGGAGACA GGGGAATCTT CCTCCTGACT   9480
AAAGGAATGG TGCCCCAAGA GTGTGGGGGC TCCCTGTTGC CCTCTCACTC TCCATCCCCT   9540
ACCTAGCACA GCGAACACAA AAGCCCCTGG TTTCCAGCCA GAGGGCAACG AGCCTGGAGT   9600
CAGAGTGTGG GGGAGGCGAC AAGAGGAGAG GGGAGAAGAG AGGATGGCAC ACAGCTGTGT   9660
GTGAGCGCCT GGGTCGTCCC AAGACAGTCT CTACGTGGTC CTGACCCTAA AGGGCAAAGG   9720
GAAGAAAACT GACCTACAGG ATAGGCCACT GCCCAGGTCT CAGATGGGCC CCAGTGGCGC   9780
ATATGGGACA GATCCACAGT GCACTGGAAA GTCTCTAAAA TAAACTGGCC TAAGAACACA   9840
GACACAGGAA CGGGGTGCAA AATTTGCAGC CTGAACCTAA CCAGCTCGAT TTCTTGCTAT   9900
```

-continued

```
GAAAAAAAAA AGTCTACATT CTCTGTGAAA CTTAAAACAA GACCTAGAGT CCATAGCACA    9960
GTAGTCAAAG CATCCAGAAC ACGATCAAAC TTCCTGGCAA AGGGTAGTCT GGTTGATTCT   10020
CAAAGGAACA AATACACAAG AGAAGCTGGC TCTTGAACGC AGAATCCAGA GACTTTCAGG   10080
TGCTATCGGA CCAGCTCCAA GAGGAAAGCA AACATTGTCA ACCAAGTGGA AAGAAAATCT   10140
TGGTATAGAA ACAGGAGTTA TAACCAAACA GAAATGTGAA AATTAAAAAC GACAACCAAA   10200
AGAAAATACA CAAAGCTGGG ATAGTCTCAG CTACTCGGAA GGCGGGGCTG GAGGATCGTT   10260
TGAGCCTAGG AGATTGAGGC TGCAATGAGC TGTGATCACA CCACCGCACT CCAGTCTGGG   10320
CAACAGAGTG AGAACTCTCT CAAAAAACGA AAAAGAAAGA AAGTAGAACA GAAGTGACCA   10380
GGGGCTGGGG GAGGGAGTAC AGGGAGTTGT TCTTTAATGA GTACAGAATT TCTGTTTGGG   10440
ATGATGAAAA GCTCTGGAAA TGGACGGCGG TGATGGCTGC ACAATCACTG TGGCTGTTCT   10500
GAATGGTGCT GAACCACACA TTTAAAAACA GTTAAAATGG GCTGGGCGTG GTGGCTCACG   10560
CCTGTAATCC CAGCACTTTG GGAGGCGGAT CGCCTGAGGT CAGGAGTTCG AGACCATCCT   10620
GGCCAACACA GTGAAATCCT GTCTTGACTA AAAATACTAA AAATTAGCCA GGCATGGTGG   10680
CAGGCACCTG TAGTCCCAGC TACTTGGGAG GCTGGGGCAG GAGACCTGCT TGAACCCAGG   10740
AGGCAGAGGT TGCAGTGAGC CGAGATCGTG CCACTGCACT CCAGCCTGGG CAACAAGAGC   10800
GAAACTCCAT CTCAAAAAAA AAAAAAAAAA AAAAAAAAAA AAGTTTAAAA TGGTTAAATT   10860
TTATGTTATG TATATTTTAC CGTAATAAAA ACACTGTAAT GCTACTATAA TAGAATGACT   10920
CATTAGGATT AGATATAGAC TAGAAAGTAC AGAATATAAA AACTTTTTAA ACAAAGAAAA   10980
ATTTTCATGG CCAGGCATGG TGTCACACCT GTAATCCCAG GACTTTGGGA GGCCAAGGCA   11040
AGAGGAATGC TTGAGCTCAG GGGTTTGAGA CCAGCCTGGG CAACACAGCA ACACCCCATC   11100
TCTGCTAAAT AAATAATAAA AAATAGCCAG GCATGGTGGT GTGCACGCCT GTAGTTGCAG   11160
CTACTCTGGA GGCTGAGGCA GGAGGATCAC TTAAGCCCAG GAGGTCAAGG CTGCAGTGAG   11220
CCATGGTTGT GCCACTGCGC TCCAGCCTGG GCAACAGATC AAGACCTTGT CACAAAAAAA   11280
AGAAAGAAAG AAAAGAAAAA AGAAAGAAAA TAAAATCTTC CAGAACTTTT AAAATCATCA   11340
TTGTTAATAT AAAAATAACA TCACCTGCCC CTAGGACTGT AACAAACAAG TGTGTCTAAG   11400
GACAGGAGTG GGTCCACCCC AACCTGGCAC GCAGTGGTCC CCTGCGGAGA GTCTGGCCCT   11460
GCACTCACTA AGAGGAGGCA CTCATAGCCC AGCCAGGCCT CTGCAATTAT GCCTTCAATG   11520
CCAGAACTAA CTCACCCAAA CTGAACAATC GATCACAAAA TGTGCCTTCA GGTCTCAAGG   11580
TTCTTGCTAA ATCTTACTCA ACCGACATTT TCCAGCATGG GAACATTTTT CTGAATGTCT   11640
TAGGGAGAGG AAGTCCGCAA GAGAACAAAA GGTCCTCAGG CCACCCTAGC TTCTTTTCCT   11700
CCATTCCACA GGCTGTCTTT TGTCTGGGTA TGCACTGGAC CAGGGGGCTC TACTTCTTCC   11760
TACCTGGGCA TGGGTCTCCA CACAACTCCA AGGTAAAGGG CCACAGGCAA GATAAAGGGG   11820
AGAAAAGAAA GCTACGATTT CCTGGGCCAC CAATCGCAAA TGGCAGCCAG TCTCTGAAGT   11880
AACCCTTGAC CAGAGATCCA AGGAACCAAG AAATGTAGGT GATCTGAACA GAGGGGATGG   11940
TGGTTAAACA CCATGAAGGA AAGACCCATT CTCAAAGAAA AGGAAGCAAA AAGAAACCGT   12000
GGGGAGCTGG GTACCACCCG CAGCAAAGAC CCCGCACGCG TTACTGACGC CAGCCTGGCC   12060
TGGGAGAGCA GTGAGTGTGG CGGACGGTGA GTGGCGGGGA GGGCTGTGGT AGGTTTAGGG   12120
TAAGAAGGGG CAGCGCCCAG AGCCCAGAGA ACACCAGTGA GGGCTCCACA GGAACACTAC   12180
TCAAAGTATT CACGGAACAC ATCTAAACAC AAGCACTAAG GACTAAGTGC GAGGGACAAG   12240
AAAATATTCC CCGTTTCCTG TTTCAGGAGG GTATCGAAAA TGAGTGATGG AAGGAAAATG   12300
```

-continued

```
TATTGTTTAA ATGAGGAAAA AAAATTTTTA CAAATTAAGA ACATCCTGGA ACATGATGAG   12360
CCGTTTACTG TCACTCAATT TAAATGGTGG CCATCTAGGA CAGAGCGCCT AAGGGGAAAG   12420
GGGGCTCACA GGTGAACCCC TCCAGCTGCT GGTGGGCAAT TTCCCATTAG GGCATCAGGG   12480
TCTCTGAAGA CTGTCTTCAG ATGCTTTTTA GCCAGGAAAG TTACAATGAT GAATTCGTTT   12540
ACACTGGCGG AATTACTTCG TATTTCTCAA ATATAATGTT TTCACTAGCA TAACTTTGTT   12600
GTTGTAGACT TAGGCTTCAA AATAAAGAAC TTTAAACAAA CATGAATAAA AAGCCACTTT   12660
AGGCCGGGCG CGGTGGCTCA CACTTGTAAT CCCAGCACTT TGGGAGGCCG CGGCGGGTGG   12720
ATCATAAGGT CAGAAGTTCA AAGACCAGCC TGATCAATAC GGTGAAACCC CGTCTCTACT   12780
AAAAATACAA AAATTAGCCG GGCGCGGTGG CAGGTGCCTG TAATCTCAGC TACTTGGGAG   12840
GCTGAGGCAG GAGAATCGCT TGAACCTGGG CAGCAGAGGT TGCAGTGAGC CAAGATCATG   12900
CCACTGCACT CAAGCCTGGG TGACAGAGTG AGACTCTCTC TTAAAAAAAA AAAGCCACTT   12960
TAAAATTTTA CTCAGGCCAG GTGTGGTGGC TCACGCCCAT AATCCTAGCA CTTTGGGAGG   13020
CCGAGGCGAG CAGATCACCT GAGGTCAGGA GTTAGACCAC CCTGGCCAAC ATGGTAAAAC   13080
CTTGTCTCTA CTGAAAACAC AAAAATTAGC TGGGCGTGGT GGTGTGCCCA TGTAATCCCA   13140
GCTACTCAGG AGGCTGAAGT GAGAGAACTG CTTGAACCCG GGAGGCAGAG GCTGCAGTGT   13200
GCCAAGACTG CACCACTACA CTTCAGCCTG GGCGACAGAG CAAGACCCTG TCTCAGAAAA   13260
AAAAAAAATT CAAAAATTTG GCCAGGCGTG GTGGCTCACG CCTGTAATCC CATCACTTTG   13320
GAAGGCCGAG GCGGGTGGAT CACCTGAGGT CAGGAATTCA AGACCAGCCT GGCCACCATG   13380
ATGAAACCCT GTCTCTACTA AAAATACAAA AAAAAAAAAA CAAATTGGCC GGGCATGGTG   13440
GCGGGTGCCT GTAATCCCAC CTACTTGGGA GGCTGAGGCA GGAGAATCTC TCGAACTCCG   13500
GAGGCAGAGG TTGCAGCGAG CCAAGATTGT GCCACTGCAC TCCAGCCTAG ACAACAGAGC   13560
GAGACTCTGT CTCAAAAAAA AAAAAATTAA AATTAAAAAA TAAAAATTTC ATTTAAAATA   13620
CTACTGATCT CCCGTGCTGA CTTCTCGGGG TTTAACTCTC ACTGAGGAGA CGCTGCTTTC   13680
ATAAGGGTAA GCTCAGCAGG GGCAACTAAA GTCATTTAAG CAGAGAGCTG CAAAGAGGCA   13740
ACAGCCTCAC TGCAGGCAGG GGTCCTCGTC ACAGCTTCAG GGCTTTGCAG AGGATTACGC   13800
AATGTACACG CACAAAACTG AATTCCAGCC TCTCCATTGG CAACTGCATA CATACATATA   13860
TTCTTTTTTT GAGACGGAGT CTCGCTCTGT AGCCCAGGTT GGACTGCAGT GGCCCGATCT   13920
CGGCTCAATG CAAGCTCTGC CTCCCGGGTT CAAGCGATTC TCTTGCCTCA GCCTCCTGAG   13980
TAGCTGGGAT TACAGGCGCC CACCACCACG CCCGGCTAAT TTTTGTATTT TTAGTAGAGA   14040
CGGGGTTTCA CCATGTTGGC CAGGACAGTC TCGATCTCCT GACCTCGTGA TCCGCCCGCC   14100
TCTGCCTCCC AAAGTGCTGG GATTACAGGC GTGAGCCACT GAGCCTGGCC TCCAATGGCA   14160
ACTATATTAA AGGTTCAAAG CAATATGCAC AAAAGTTACC TCACAGAAAA TAGTGCAAGT   14220
CCTTGATACA ATGCTCTTTA GACACAGAAG AAGCACTATA GAATAGAGCA CCTCGCCCTA   14280
TTGCCTTCCC AAGGGCGAGC ACCCCCTCCT CTCTCCACAG CTCCTTCTTT GTTTTTTTGA   14340
GATGGAGTCT CGCTCTGTCA CCCAGGCTGG AGTGCAATGG CAAAATCTTG GCTCACTCCA   14400
ACCTCCGCCT CCCGGGTTGA AGTGATTCTC CTGCCTCAGC CTCCCGAGTA GCTGGGACTA   14460
CAGGCACCCA ACACGCCTAG CTAATTTTTG CATTTTTGGT AGAGACGGGG TTTCATCATG   14520
TTGGCCAGGC TGGTCTCGAA CTCCTGACCT CCAGTGATCC TCCCACCTTG ACCTCCCATA   14580
GTGCTGGGAT TATAGGTGTG AGCCACTACA CCTGGCCTCT CCACAGCCCC TTCTGTGTTG   14640
AAGCCAAGAC CCACCCAGCT TTGATCCCAA GGCTTGGGTT CCCCACTACT GTGAAGTGAG   14700
```

-continued

```
TTTCCAAATT ATTAGGTAAA TCAGATATGA GAAAATATTT TATTTTACTT TTTTTTTTTT 14760
GAGACGCAAT CTTGCTCCCT CACCCAGGCT GGAGTGCAAT GGCACCATCT CCACTCACTG 14820
CAACCTCTGC CTTCTGGGTT CAAGCAATTC TCCTGCCTCA GCCTCCCAAC TAGCTGGGAT 14880
TACAAGTGCA CACCACCACG CCCGGCTAAC TTTTGTATTT TTAGTAGAGA CAGGGTTTCA 14940
CCGTGTTAGC CAGGCTGCTC TCAAACTCCT GACCTCATGA TCCGCCCACG TCGGGCTCCC 15000
AAAGTGGTGG GATTACAGGT GTGAGCCATC ACACCTGGCC CAAGAAAATA TTTTTAAACT 15060
AGTATTCTTC ACCGGCACGG TCAACACTGA TGTAATTGAA ACTGTTGTAT TTGAAGTGTT 15120
AGCAAAGAAA GAGAATTCTG GTTCAACAGA AAAGTCAGTC ACGACTTTTC AGTCACGCAT 15180
GAATTACACA GTAACCAAAT AGATAACATG CCATCACTGA CGACGGGCCC ACAACAAATC 15240
AGCTCCGACC AACAGGGTCC ACACCACCAT GGGTCTACAC AGATCCAGGT CCCGCCTGTG 15300
AGCCTACAGT GACGCGGGCC CCTGTGGGGT GGTCCCTGCA GGTCAGGTCC CTGAGAGTGG 15360
GTCCCAGTGG GGTGATCCCT GCGGGTCGCG TCCCTGCGAG TTGGGTGCCT GCCGGGTGGC 15420
CCCTGCGGGT CGGGTGCCTG CGGGGTGGTC CCTATGGGTC GCGTCCCTGC GGGTCGGGTG 15480
CCTGCGGGGT GGCCCCTGGG AATCGCGTCC CTGCGGGTCG GGTGCCTGCG GGGTGGCCCC 15540
TGGGGATCGC GTCCCTGCGG GTCGGGTGCC TGCGGGGTGG CCCCTGGGGA TCGCGTCCCT 15600
GCGGGTCGGG TGCCTGCGCG GTGGTCCTTG TGGGTCGCGT CCCTGTGGGG TGGTCCCTGT 15660
GGGTCGCGTC CCTGTGGGGT GGCCCCTGCG GGTCGCGTGG TGGCCCCTGC GGGTCGGGTG 15720
CCTGCGGGGT GGTCCCTGTG GGTCGCGTCC CTGCGGGTCG GGTGCCTGCG GGGTGGTCCC 15780
TGCGGGTCGC ACCCCTGCGG CGTGGTCCCC CCGGGATGGG TCCACCGAGG AGGCCGCTGG 15840
AGGCCGAGCC CGCGCCCGCC CGCGGCGCCA AGATGGAGGC AGGAAGCGCC GCCGCCCGCG 15900
CCCGCCACCG CCCGCGCCGC CCGCCTGACG CCGCCGTTGC GCCTGACGCC GCCGCCCGCG 15960
CCGCCGCCCC TCCCCCGGCC CTCCCCTCCC CCCGCCGTAA CGTCCTGACG CTCCGCAGGG 16020
ACCCCTGACT GGACGGCGGC GCGTGAGCGC AGCGAGAGGC CTCGCCGCGG GGGGGCCGCG 16080
GGCTCGCCGG CGCCGCTTAC CTGGGGCCGC GCCGGGCCTG CTTAGGCACC CGGCGGGGGC 16140
GGCGGCGTCG GGAGCTGCGG CGGCGGCGGG CGGCGGCGGC GGCCGCGGGC TTCGCTCCTT 16200
GTTGGGGATT CCGCGGCGGC GGCGGCGCGG GCGCGCGCTT CCTAGTGACG CAGGCGGCGG 16260
GGCCGCGCAC GCACGGGGCT GGGAGGGCCG GACACTTATT TGGCGCTCGC GGAGGAGGAA 16320
GGCGGGGCCG TGAAATAAGG CCCGACGGGC CCCGGGGCGC GTGCGCGGAC CGACACTGTC 16380
AGCTCCTAAC GCCGCAGGTT CCTCCTGGTC CCCGAGGCCC CCGGTCGGGC GTTGCCTGCC 16440
CCGCGCGGGC GGCCGGGCCG AGGGACGATG GTCAGTGGAC GGACGGCGCC AGGGAGCAGT 16500
GCCCACGCGC GGCAGGGCGG TACCTTCAGG CCTCCAGGTA CGGGCGCTCC TCGCCCGGAC 16560
GCTGCTGTGT GTGAATGGGC GCGAGGGGAC TCCCCTGCGG GGCGGACGCC TGAACACGAG 16620
GCTGTGGAGG AGGACGCTGT AGGGTGCGCG GACTCACGCG GAACATGCCA GAGGCTCAGC 16680
CAGCCACGGC GCTCCCAGCG TGGAGGGCGA GGGGCATCCG GGAGCGGCCG GGAGGGCTCG 16740
GTCACCCCTC AAGCTGTCAC CCCAGTCCCA CAACCAGCAC CCCGATCCTA TCGCAGTCCC 16800
ACAGCCGACA CCCCGATCCC ACCCCTGCCC AACAGCCGGC ACCCACCCCA ATCCCATAGC 16860
TAACACCCCG GTCCCACCGC TGTCCCACGG CCGGCACCCC GATCCCACCC CAGTCCCGCA 16920
GCTGGCACCC CGATCCCACC CCAGCCCAAC AGCTGGCACC CACCCCGATC CCACCGCTGT 16980
CCCACAGCCG GCACCCCGAT CCCACCCCAG TCCCGCAGCC GGCACCCCGA TCCCACAGCC 17040
GGCACTCACC CCGATCGCAT AGCATAGCTG ATACCCCGAT CCCACCCCAG TCCCATAGCC 17100
```

-continued

AGCACCCCGA TCCCACCCCA GTCCCATAGC CAGCACCTCG ATCCCATAGA TGACACCCCG 17160

ATCACGCCCC AGTCCTATAG CCCGCACCCC GATCCCACCC GAGTCCCGCA GCCGGCACCC 17220

CATCCCACCC ATGTCCCACA GTCGGCACCC CGATCCCACT CGGATCCGGC AGCCAGCTTG 17280

GATCCTGTGG CCCTCCTCCA GCCCCCAGGG CTCATTTATA TGTTTTATTG GCAGAGGCTG 17340

GGGCTGGCTC TGTTGGCCTC TGTGCTGGGT TTCTTCCTCT GCACCGCAGG ACTGGCTCTC 17400

CTGACCTCTC CAGGTGTCAT CGAACACCCT TGTGCTTGCT GTCACCCGCT GCCTGTCTGC 17460

AGGATCCCGG ATTCCGTATC AGGGGACCGA AATTAGTCGG AAAATAGGAA GCAGGTGCTC 17520

GCTTGGATGG AACCCTGACC CTGTGCTCAC ACTTGTAGGA GGAGGGCTCT GCAGGCCGCC 17580

TCCCGGAACG GGAGGTTCCC AAGCCACTGC ACTTCGGAGG GGCTGTAATT AGAGTTGCAC 17640

ATTCATTCAG TTCCCAGTAA AGTAGAACGT GCTCCAGCCA GTGAGGAAAA GGTGTTTTTA 17700

AAAATTAGAT TGGCCGAGTG CGGTGGCTCA TGCCTTTTAC CTCAACACTT TGGGAGACAA 17760

AGGTGGGAGG ATCACCTGTG GCCAGGAGTT CAAGACCAGC CTGGGCAACA GAGCCTGTCT 17820

CTGGGGAAGA ATAAAAAAAA AAATTGAGCC TTTGTCAGTG CTACTATTTT ATTATCTGGT 17880

AAATATGAGA GGGTTCACGC GGTCTATGTG TGTCATTTAT CTGAGTTTGC CTATCGTCAC 17940

GTTTTGGAAA TAAATGTCAA TAAAGTCGAA GAGGAGTGCT GAGGGGGGCC TGGGGATGGG 18000

AGGGTGGCTA CATCATGCCT GTGTGTTGCG CAAGCCCACC GAGGTCGGCC TGGCGTGAGC 18060

CCTGGGGCCT GTTCTGCCTC CTTCACTCTG GGGCTCCAAG AGACAAACTG GGCAACAAGA 18120

GAGAAACTCC ATCTAAAAAA AAAGAAAAAT CACCTCCAAG ATAACTTAGC TTTCTTCTGC 18180

TGGCATAACA AATTATCTCA AACTTAGTCG CTTAAAAATG CAAATTTAGG CTGAGTGCGG 18240

AGGCTCACGC CCATAATCCT AGCACTTTGG GAGGCCAAGG CAGGATTGCT TGAGGCCAGG 18300

AGTTCGAGAC CAACATGGCC AGAACTGTCT CTTTTTAAAA AATGCAAATG TGTCCGGCAC 18360

GGTGGCTCAC GCCTATAATC CCAGCACTTT GTGAGGCCAA GGCGGGCAGA TCACGAGGTC 18420

AGGAGATAGA GACCATCCTG GCTAACACTG TGAAACCCCC TCTCTACTAA AAATACAAAA 18480

AATTAGCCTG GCGTGGTGGC AGGCGCCTGT AGTCCCAGCT ACTCGGGAGG CTGAGGCAGG 18540

AGAATGGCGT GAACCCAGGA AGCGGAGCTT GCAGTGAGCC GAGATGGCGC CACTGCACTC 18600

CAGCCTAGGC AACAGAGCAA GACTCCGTCT CAAAAAATAA ATAAATAAAA CTGCAAATGT 18660

ATTCTCTAAC TGTTCTGTAG GTCGGAAGTC CAGCCCAGCC TCACTCCGCC AAAATCAGGG 18720

TGTCTGCAGG GCCGATTGCT TTTGGAGCTC CAGGGGAGAA GCTGTTCTGG CCTTTCCAGT 18780

TTCTGGAAGC ACTTGAGCCC CTTGTCTCGT GGCCTATCCC ACACCTGAAA GCCAGCCAAA 18840

GCCAGTTGAG TCCTCACCCT GTTGGCCCCG ACACTGATCT CCTGCCTCCC TCATCTGCTG 18900

TCAAGGCCCC TTGTGATGAC ATGGGGCCAC CAGCTGGCCC AGGGCACCTC CTGTCAGAGT 18960

CCGCCGACCA GTGACCTTCA TTCCATCTGT CGCTGTAATT CCCCTTTGCT TGGAACCAAC 19020

GTTCACAGAT CCCAGGGGTT AGGATGTGAA TATCTTGGGC AGGGCTGTGG GGGGGCTATT 19080

CTTCCTTCTA AAATATTTAT CATTTTTGTT TTGGGGATTT TTTTGGTTTG GTTTTTTTTG 19140

AGACAGAGTC TCGCTCTGTC GCCCAGGTTG GAGTGCAATG GTGCAATCTC AGCTCACTGC 19200

AACCTCTGCC TCCGGGCAGA CGTGAGCCAC TGCACCAGGC CTGTTTTTGT TTTTGTTTGT 19260

TTTGTTTTGT TTTTGAGATG GAGTCTCGGC CGGGCGCGGT GGCTCACGCC TGTAATCCCA 19320

GCACTTTGGG AGGCCGAGGC GGGCGGATCA CGAGGTCAGG AGATCGAGAC CATCCTGGCT 19380

AACACGGTGA AACCCCGTCT CTACTAAAAA TACAAAAAAT TAGCCGGGCG TGGTAGCGGG 19440

CGCCTGTAGT CCCAGCTACT CGGGAGGCTG AGGCAGGAGA ATGGCGTGAA CCCGGGAGGC 19500

-continued

GGAGCTTGCA GTGAGCCGAG ATCGCGCCAC TGCACTCCAG CCTGGGCGAC AGAGCGAGAC 19560
TCCGTCTCAA AAAAAAAAAA AAAAAAAAAA AAAAAAAGAG ATGGAGTCTC ACTTTGTCAC 19620
CCAGGCTGGA GTGTAGTGGC GGGATTATAG GTACGCGCCA TCATGCCCAG TTACTTTTTG 19680
TATTTTTAGT AGAGACAGGG TTTTACCATG TTGGTCAGAC TGGTCTCAAA CTCCTGATCT 19740
CAGGTAATCC ACCCGCCTCA GCCTCCCAAA GTGCTGGGAT TACAGACGTG AGCCACCGTG 19800
TCTGGCCATA TTTATTAACT ACAAAGGGAA AGATGATAAT TTTTTTTTTT GAGATGGAGT 19860
CTCACTCTGT CACCCAGGCT GGAGTACAAT AGCGTGATCT TGGCTCACTG AAACCTCTGC 19920
CTCCCAGGTT CAAGCGATTC TCCTGCCTCA GCCTCCCAAC TAGCTGGGAT TACAGGCGCA 19980
CGCTACCAAG CCCAGCTAAT TTTTGTATTT TTAGTAGAAA CGGAGTTTCA CCATGTTGGT 20040
GAGGCTGGTC TCGAACTCCT GACCTTGTGA TCTGCCCACC TCGGCCTCCC AAAGTGCTGG 20100
GATTATAGGC ATGAGCCACT GCAACCGGCT GAAAGATGGT AATTTTAAAG TAGAGAAACT 20160
GGGTTGGCTG GGCATGGTGG CTTATGCCTG TAAGCTCAGC ACTTTGGAAG TCCAAGGCAA 20220
GAGGATCGCT TGAGTCCAGG AGTTTGAGAC CAGCCTGGAC AATATAGCAA GACCCCATCT 20280
CCGCAAAAGC TAAAAAGTTA GCCAGGTGTG GCGGCACATG CCTGTAGTCC CAGCTACTCA 20340
GGAGGCTGAC GTGGGAGGAT CACTTGAGAC CAGGAGGTCA AGGCTGAAGT GAGCTGTTAT 20400
TGTGCCACTG CACTCAGCCT GGGCAACAGA GCGAGAGTCT GTCTCCAAAG GTAAAAAAAG 20460
GTCCAGGCAC AGTGGCTCAC ACCTGTAATC TCAGCACTTT GGGAGGCCGA GGCGGGCAGA 20520
TTCGTTGAGG TCAGGAGTTC AAAACGAGCC TGGCTAAATG GTGAAACCCC GTCTCTACTA 20580
AAAATACAAA AAAATTAGCC AGGCATGGTG ACGGGCGCCT GTAATCTCAG CTACTTGGGA 20640
GACTGAGGCA GGAGAATCAT GTAAACCCAG GAGGCTGAGG TTGCAGCGAG CCAAGATCAT 20700
GCCACTGCAC TTCAGCCTGG GCGACAGAGC AAGACTGTCT CAAAACAAAA CAAAAGAATC 20760
TTGAGTCCTG AGTTCCTCTA AGGGAAATTC CAGGCACCTC GCCACCCTTG ACAGGCAAAG 20820
GAACAATCTG ATGAGGAAGA AGATAGAAAC AGCTTAAACA ATAGTCTCCC GGCCGGGGGC 20880
AGTGGCTCAC GCCTGTAATC TGAGCACTTT GGGAGGCCGA GGCGGGTGGA TCACAAGGTC 20940
AAGAGATCAA GACCATCCTG GCTAACATGG TGAAACCCCG TCTCTACTAA AAATACAAAA 21000
AATTAGCCGG GCGTGGTGGT GGGTGCCTGT AGTCCCAGCT ACTCGGGAGG CTGAGGCAGG 21060
AGAATGGCGT GAACCCAGGA GGCGGAGCTT TCAGTGAGCT GAGATCGCGC CTCTGCACTC 21120
CAGCCTGGGC GACAGAGCCT CGAGACTCCA TCTCAAAAAA AAAAAAAAAT TAGCTGGGTG 21180
TGGTGGCTCA CACCTGTAAT CCCAGCTACG TGGCAGGCTG AGGCAGGAGA ATCGCTTGAA 21240
CCTGGGAGGC GGAGGTTGTA GGGAGCTGAG ATCGCACCAC TGCACTCCAG CCTGGGCAAC 21300
AGAGCGAGAC TCTGTCTCAA AAAAAAAAAA AAAAAACAAA AAAACAATAG TCTCCCAAGT 21360
AAGTCAGAGT CACAAGGTGT TTTGATTCCC TGTGGAAACT AAAATATAAC AGCTTAACAT 21420
ATGTTCTTGA GTTATTTTTC AGAAACTTGG ACATCCACCA GGTGGAAAAT GCTGAGCTAG 21480
GAACAGTGGC TATAATTTCA GCCTTTTGAG AGGCCAAGGT GGAAGGATCA CTTGAGGCCA 21540
GGAGTTAGAG ACCAGCCTGG CCAACATGGT GAAACCCCGT CTCTAGTAAA AATACAAATA 21600
TTAGCTGGGC ATGGTGGTGC AACCTGAAAT CCCAGCTACT TGGGAGACCT AGCTGGGAGG 21660
ATCGCTTGAA CCTGGTAGGA GGAGTTTGCA GTGAGCTGAA ATTGTGCCAC TGCACTCTAG 21720
CCTGGGCAAC AGAGTGAGAC TCTGTCTCAA AAAATAAATA AATAAAAAGA GAAAAAAGTG 21780
TTGCCTGCAG GCCGGGCACA GTGGCTCACG CCTGTAATCC CAACACTTTG GGAGGCCGAG 21840
ATGGGCAGAT CACCTGAGGT CAGGAGTGCA AGAACAGCCT GGCCAACATG GTGAAACCCC 21900

-continued

```
ATCTCTACTA AAAATACAAA AGTTAGCTGG GTGTGTACAT GTAGTCTCAG CTACTTGGGA 21960
AGCTGACCCA GGAGAATCTC TTCAACCGGG GAGGTGGAGG TTGCGATGAG CTGAGATCAC 22020
GCCACCACAC TCCATCCAGC CTGGGTGACA GAGTGAGACT CCATCTCAAA GCAAAAAAAG 22080
AAACATAGGT GGGACCCTTG GTGTGTCCTT AGGGCATGAT GGTTGAGGTA TACTGCTGGT 22140
CCTGTCATGT AAAAGAAAAC GAGCCGACTC TGTGTCTACT GGAGAAAGCA CTGCATATAT 22200
CAGCCACAGT CAATACCTCG CTTCTGCAGG GACGGTGGCT GCCAGAGTGG GAGGCTTTGG 22260
TAGCACCCAT GTCGTGGAAT CACAATGTTG TCGATAGCTC TGGGGTCTTG TACAAAATGC 22320
CAGATCCTCC CATTTGGTTT CCTTATGGGA AGGATCGCAG TACTATAATA CATGGGCTTG 22380
TGCAAGGGAT CATTATACCC TTTTCTCTTT TTTTGCTTTT CTTTGAGACA GAGTTTCACT 22440
CTCGTCACCC AGGCTGGAGT GCAATGGCGC GATCTTGGCT CACTGCAACC TCCACCTCCT 22500
GGGTTCAAGT GATTTTCCTG GCTCAGCCTT CTGAGTAGCT GGGATTACAC ATGCCCGCCA 22560
CCAGGCCTGA CTTATTTTTG TATTTTTAGT AGAGACAGGG TTTCACCAAG TTGGTCAGGC 22620
TGGTCTTGAA CTCCTGACCT CAGGTGATCC ACCCACCTCG GCCTCCCAAA GTGTTGGGAT 22680
TTCAGGCATA AGCCACCAGG CCCAGCCTTT CTTTCTTTTT AAAATTAATC TTTGTTTAAA 22740
AATACTCTCA TTTTTTATTT AATTGTAGCA CTCCTAGATC CCGAAAGCAG ATACACTCTT 22800
GTTATGGGTC TGATTCTTTT CATTGCTTCA CGCCTTAGAG GATATTGTCC AATACTGGAT 22860
AAAAGTTTAC TCAGGTCTAC TTCCACTTTA ACGGGGATGG CTGAATATCT CTTCCACTTG 22920
GCTGTTTGTT TATAATGAAC TGACAAACAT ACAAATTTTC TTGAGTTCTG TGAGACATTC 22980
TAGTAAATCA TCTAACCTGA AGAGCAGGTT GTGAGAACCC CTGATTTAGA AAGCCCAGTG 23040
GTCATAAATA TAAGTGGCTC TGGACTGGCT CCCGGGGTCT GAAGTGTGGG CAGTCGGTTA 23100
GGATTGAGCC CTTGTAATTT GTAGGATCTC ACACACACTC CAGGAAGGCA GTGTCAGAAT 23160
TTACCTGTAT TATATTGGAC ACCCAGTTAG CGTTTGGAGA ATTGGTTGCT GGTATAGAAA 23220
AATACCAAAT ATTTTATGTC AGGGGAGTGA AAGAAAAAAC AAAAACCCGG CCGGGCGCGG 23280
TGGCTCACGC CTGTCATCCC AGCACTTTGG GAGGCCGAGA CGGGCGGATC ACGAGGTCAG 23340
GAGATCGAGA CCATCCTGGC TAACACGGTG AAACCCCATC TCTACTAAAA ATACAAAAAT 23400
TAGCCGGGCG TGGTGGCGCG CGCCTGTAGT CCCAGCTACT CGGGAGGCTG AGGCAGGAGA 23460
ATGGCGTGAA CCCGGGAGGC GGAGCTTGCA GTGAGCCCAG ATCGCGCCAC CGCACTCCAG 23520
CCTGGGCGAC AGAGCGAGAC TCCGTCTCAA AAAAAAAAAA CAAAAAAAAA AAACAAAAAA 23580
AAAAAACCCA TACACTTTAA GGAAAGCAAC TGACAGCATT TGTTACCAGT GATAAAATTT 23640
GAGCTTTGAA GTAAGAATAA CAATTTTGCC ATTGTGCCCC GGCCAAGAAA AAAAAAAGAA 23700
TTTTGCCATT GTGAAAGGCT TCCCAGTACT TTCTGATGAG CTTGACGGTG ATATTAACAA 23760
ATAACTTTTT TTTTTTTTTT TTGAGATGGG GTCTTGCTCT GTCACCCAGG CTGGAGTGCA 23820
GTGGTTCAAT CTCAGCTCAC TGCAACCTCC GCCTCCCAGG TTCAAGCGAT TCTCCTGCCT 23880
CAACGTCCCA AGTCGCTGGA CTACAGGTGT GCGCCACCAC GTCCAGATAA TTTTTGTATT 23940
TTTAGTAGAG ATCGGGTTTC ACCATGTTGC CCAGACTGGT CTCAAACTCG TGACCTCAGG 24000
CGACCCGCCC ACCTCGGCCT CCCAAAGGTG GGAGGCCTTG CTGGGATTAG AGGTATGAGC 24060
CGCTGCACCT GGCCTCTTGT CCTTGTGTTT TGCAGTGATG CAATGACCAT GTCTTACATT 24120
TGCAACCAGA AAAAAAGGTT AGTGTAACAA TGTTTATCCT GTTTTTCCCA GACTAGACAT 24180
TATGAAGATT AAAAAAATTT GAAAGTGTTT TGAATATAAT AAACTATGCT ATACACACAA 24240
CATTTTGGTG ACTAGAAATA CAAGTTTATT GTTTGTTGTT TGTTGAGACA GGGCCCTGCT 24300
```

-continued

```
CTGTCTCCCA GGCTGGGTGG CACAATCATG GCTCACTACA GTCTTGAACT CCTGGGCTTA   24360
AGCGATCCTC CCACCTCAGC CTCCAGAGTA GCTGGGACTG CAAACGAGCA CCACCACGCC   24420
TGGCTAATAT TTGTATTTTT TGTAGAGATG GGGTTTCACC ATGTTGCCCA GACTGGTCTC   24480
AAACTCCTGG GCTCAAGCAA TGCTCCTGCC TCGGCCTCCC AAAGTGCTGG GATCACAAGT   24540
ATGAGCCACT GCACCCGGCT GAGTTTCTGT TGTTTTAAGC CGCTTCATTT GTGGTACTTC   24600
TTACAGCAGT CCCAGGAAAC TGAGCAACTG CAGAACATCA AAATTGTTTT TCTTCAGCAA   24660
AAGGAGAAGC ACTTGTGGTT GGCACCAGCT TTTCCTGTGC TCACTTCTGC ATGGCCGCAC   24720
CTTTGCCCGA CACGAGTGCA CAGCAGGCTG TGGGGGAGCA ACTGGTTGAG TCAGGCCTCC   24780
ACTTGTGCCG TATCCCCACC TGCTTTGCTG GACACCCCTG TTTGGGGGGC ACCCACTGCT   24840
GCCCCAGACA CCAAGCAAGC ACCAGCTGTG TCCAAAACTT ACAGTCACTG TCTTGGCCCG   24900
TTTTGTGCTG CTGTAACAGA ATGCCACAGA CTGGGTAATT TAATACAGAA CAGAAATTTA   24960
TTTCCTCAAA GTTTTGGAGG CTGGGAAGTC CAAGAGCAAG GGGCCATCAG GTCAGGGCCT   25020
GGTCTCTGCT TCCACGATGG CACCTTGACC ACCGTGTCCT CACGTGGTCA GAGAGAGCCC   25080
ACTCCCAGGA GCCCTTTTAA TAGAGCAGAA CACTGCTGCG CTGCGGTTAA GTTTCCAACA   25140
CGTGAACTTC GGAGGTGACA CATTCAGATC ATAGCAGTCA CTCTAGGCAC AGTGTCTGAT   25200
GTGGTTTTAA AATACGTTCA CAGACTGGCC GGGCACTGTA GCTCACGTCT GTAATCCCAA   25260
CAGTTTGGGA GGCCAAGGTG GGTGGATCAC CTGAGGTCAG GAGTTCAAGA CCAGCCTCAC   25320
CAACATGGTG AAACCCCATC TCTACTAAAA ATACAAAATT AGCCAGGTGG TGCATGCCTG   25380
TAATCCCAGC TACTCGGGAG GCCGAGGCTG GAGAATCGCT TGAATCCAGG AGGTGGAGGT   25440
TACAGTGAGT CGAGATCATG CCATTGCACT CCAGCCTGGG CAACAAGACC GAAACTCTGT   25500
CTCAAAAAAT AAAATAAAAT AAAATACATT CACAAGGCCG GGCACTGTGG CTCACGCCTG   25560
TAATCCCAGC TACTTGGGAG ACTGAGGCAG GAGAATCGCT TATAACCTGG GAGGTGGAGG   25620
TTGCAGTGAG CTGAGATCAC ACCGCTACAC TCTAGCTTGG GCAACAAGAG TGAAACTCCG   25680
TCTCAAAAAA GTAAAATAAG GCCCTGCAGG CATGGTGGCC CACACCTGTA ATCCCAGCAC   25740
TTTAGGAGGC CAAGGCGGTC GGATCACGAG GTCAGGAGTT CGAGACCAGC CTGGCCAACA   25800
TGATGAAACC CCGTCTCTAC TAGCCTAGCC AACATGGGGA AACCCTGTCT CTACTAAAAA   25860
TACAAAAATT AGCCGGGCAT GGTGGTGCGT GCCTGTAATC CCAGCTACTC AGGAGGCTCA   25920
GGCAGGAGAA TCGCTTGAAC CCAGGAAGCA GAGGGTGCAG TGAGCCAAGA TTGCGCCGCT   25980
GCTCTCTAGC CTGGGCGACA GAGCGAGACT CCATCTCTAA ATAAATAAAT AAAATAAGAA   26040
AATAAAATAT GTTCACAAAT CCTTTGACAT TCCTCACCTC AAAAGCTGGA ACCCAACTCC   26100
CTCCTAAGCA TGAGTCTTCT CAGTGACTCA CTTCTAACAG CAGAACTTAC ATGGTTCCCC   26160
ACACCCAGAG GACATTGGGT TCCTCCCAAT ATCCCCCCAC CCAGCGACCC CCACCCAGGT   26220
CGCTGGCTTT GGGTCCCCCA GAGCCATGTT TCAAGGACAC TCAGGCAGCC CCTGGATGTC   26280
CATGTGGTAA GGAATGAAGG CCTCCTGCCT GCAGCCTCGG GAGGGAGCAT TCTCAGAAGA   26340
GGATGCCCCA CCTCCTGCCC AGCCTTCAGA TGGCCAGGAC CTCGTCCAAC GTCCTGACTG   26400
CAACATCATG AGAGACTCCG AGCCAGAAAC CCCCAGGTTT TGTACTCCTG ACTTATGGGA   26460
ACTGACAGAT AATGTTCGTT GTTAATTAAG GGGTGACTTG TCACACACAA TAGGTCACTA   26520
AACAGCTCTG TCTGGCCTCC CAGGAGGAGC CTGCCTTTCC TTTTCTTCAT GGGAAAAGTG   26580
CGATCAGTTT GTGAAGGAAT GTCCGCCCCC ACTTGATGCC AGAGGCTCCA CATGGTGACT   26640
GTCATAAACT CCATCTGCCC TCAGTGCCTT GCCAGCACCC GGCCTGCGAT CAGCTTGGTC   26700
```

-continued

TTGCGGGAGG CCAAGGCCCA CGTGTGTTTG TGTGTGGTGT CTGTGTCTGC GTGCCCATGC 26760

ATGCCCAGGG TACAGGGATG CCATATACAA ATTCTTTCAA TGTTGTATGT GGCATGTGTG 26820

TGTCTGTATG CCCAGGATAC AGGGATGCTA TATACAAACT CTGTTTTTTC GTTTTTTTTT 26880

TTTTGAGACA GAGTCTTGCT GTTTCGCCCA GGCCGGACTG CAGTGGCGCT ATCTCGGCTC 26940

ACTGCAAGCT CCACCTCCCG GGTTCACGCC ATCCTCCTGC CTCAGCCTCC TGAGTAGCTG 27000

GAACTACAGG CGCCCGCCAC CACACCCGGC TAATTTTTTG TATTTTTAGT AGAGACGGGG 27060

TTTCACCATG TTAGCCAGGA TGGTCTTGAT CTCCTGACCT CGTGATCCAC CCGCCTCAGC 27120

CTCCCAAAGT GCTGGGATTA CAGGCATGAG CCACCACGCC TGGCCTACAA ACTCTTTCTT 27180

TTTTTTTTTT TTTTTTTTGA GATGGAGTCT CACTGTCTTC CAGGCTGGAG TGCAGTGATG 27240

CGATCTCAGC TCACTGCAAG CTCCACCTCC CGGGTTCATG CCATTCTCCT GCCTCAGCCT 27300

CCCAAGTAGC TGGGACTACA GGCACACACC ACCACGCCCA GCTAATTTTT TGTGTTTTTA 27360

GCAGAGATGG GGTTTCACCA TGTTAGCCAG GATGGTCTCG ATCTCCTGAC CTCGTGATCC 27420

GCCCGCCTCG GCCTCCCAAA GTGCTGGGAT TACAGGCGTG AGCCACTGCG CCCAGCCTGC 27480

AAACTCTTTC AATGTCTTTC TTTTCTCTCT CCTGCCATCT TCTCCCTTGC AGATTTCTTT 27540

TGTCTCTACG TCTTCCCCAG CTGAGTCCGA GGTCCTGACT TGCCCACGCT CCCTGGACTG 27600

GAGGAGAGGT GATAGCAAGA GCTCCTTCAA GCCCAGGAAT GCCACCAGGG CTGCCCCGGG 27660

AGAGGAGGAA GCTGGGTCTC TCGGGGTTGT GGGGACCAGA CACCCTTCTA AGACATGGAC 27720

TCAGCACAGA AAGTCTAGAC ATCCACTACA AACACATCTC CCTCCTAACA GGGGGCCCCT 27780

GGGCACCCCA AGTGGCTGTT TGGTGGGACA GGCATGTCCA TCAGTCAGAA TATCTTTATT 27840

TTTTATTTTT TATTTTTTAT TTTTGAGAGA GTTTCACTGG AGTGCAATGG CACGATCTCA 27900

GCTCCCTACA ACCTCCGCCT CCCAGGTTCA AGCGATTCTC CTGCCTCAGC CTGCCACGTA 27960

GCTGGGATTA CAGGTGTGAG CCACCACACC CAGCTAATTT TTTTTTTTTT TTTTTGAGAT 28020

GGAGTCTCGA GGCTCTGTCG CCCAGGCTGG AGTGCAGAGG CGCGATCTCA GCTCACTGAA 28080

AGCTCCGCCT CCTGGGTTCA CGCCATTCTC CTGCCTCAGC CTCCCGAGTA GCTGGGATTA 28140

CAGGCATGAG CCACCGCGCC CGGCCAATTT TGTATTTTTA GTAGAGACAG GGTTTCACCA 28200

TGTTGGTCAG GCTGGTCTTG AACTCCTGAC CTCAGGTGAT CCACCTCCCT CGGCCTCCCA 28260

AAGTGCTGGG ATTACAGGCC TGAGCCACCA CGCCCAGCCC AGAATGTCTT CTTACTTTTT 28320

ATTACTCTGT CCCCCATCCT GGGTCCAGAC CTGTGACCGT GAACAACCGG CTGCCCAGGG 28380

GTGAATGGGG TGAGTGGGGT GAGTCCACAG AACAGTGGGG TGCAGCCCCA GGGGTCTCGT 28440

AGCACCTGCC CCCAGGTCAG GAAGTCCCAC AGCCTAGAGG CTCCAGCCTC AGATGCATAC 28500

ATATGTAGGC CCTGCCCTTT CCTCCTGAGC GGCGGGCCAC AGAGTCCTGA ACAACAGGAA 28560

GCCCCTGAGG AGGGCTCCGC CCTGAGGGAG GGCAGGGGAG CCCCCGCCAG CCCCACCCAC 28620

AGCAGCGGGC CCTGCCACCC CCCACCCTGA CACCTCACCC CTTGGATTCC AGAGAGGAAA 28680

GTGGGCTTGT GTGTAGTTTA CATGCTCATA TCTTAAAATC ACCGTTGTCA ATAGAACAAT 28740

TCATAATAAT GATGATAAAA TAAGATTTAT AACCAGCTTC AGTCTGGAGA TACACACAGA 28800

GCAGATCTTC ACTCCCAGAC AGGGAGCCCG CAGCTGCCCC CGACCCCACA GGTGCAGGAC 28860

ACACACAGAC AGTTCAACCA TGTCTTAAAC ACACAGGTGT TTATTTAATT GTTCATTTGA 28920

TTGAATTTTT AAGTTCACTT TACTACGTGG ATGAGATGGG TGCATATTAC AGTAGGCTTT 28980

CGCTATGAGC GCTGCCACCA TGAGGAATAT CCCAGCCCTC AGTTCTGCTT CCCTTTCTGA 29040

GTCCCACAAA AGCCAGATGT GGACAGCCTT GGGTTCCCAT CCCAGCTGGC TGCTCCTTCT 29100

-continued

```
GGGGCTGTCT TGGTGGGGAG AGGGAGATGG GGCAGTGGGT CCCTGCTGAC CCCTGAGCCC  29160
TGCAGGGGTC AGGATCCTCC CGTGGTCCCT GGGTGTGGCT CTGGAAGACA CTGGCAGTGC  29220
CCGGCCAAGG CCTCCCGCAG GATGGAAGTT GAGGGCCCTG GCTCTGGGTC CTAAGAGAAC  29280
TCAGCCGCCC CCTTCACACT TTACAGCAAG GGGCCAGGCA GCAGCTTTGG GATGGGGCTT  29340
CCGTGGAGAA GTGGGGGATG CTGCAGTGGT ACAAAGACAG CCTCCCCCAC CGCCATCCTC  29400
CAGCTGACCG TCCTCCAAGG CCAGCACTGG GCGTCCAAGG GAAAGAAGGA ACTCAGCCCA  29460
GAGGGTGTGG GCAGGAGAGG CCTGGAGTCA GGCCTCCACC CACAGCCCCC TCTGGGTGCC  29520
AAGTGGGAAG GGTGTTGGGG CTGGCTTGGG AACCTTACCC GCTGCCCTTC CAACACCTGG  29580
ATCTGTGGGC AGCGGTCCCA CAAAATCCCC CTTGGGGCTC CCTGAGGAGG ACTTCTGGCT  29640
GCCGCTTCCA CCAGGGCAGA GGGCACAGGA GGGGCCAGCA CTCCAAAGGG CTCTAGGGTG  29700
GGTCTTTCAA GGACATCTGC AAAGCCCTGG TGGGGAGGGG CCTGGGCCAG AGGCTCTTTG  29760
GAACTCTTGC ACTTCTGAGT GGGGGACTGT CCATGCTGCC CACAACCTCT AGACCATGCA  29820
GCCTGCTCAT GGGTCCCTGG CAGAGAATGC CCACTCCCCA GCAGACTCAG GGCAGGCCCC  29880
CAACTGCAGG CTTCCAGGAA GGCCCAGGGT GTCCACCTCA CGCCAGGTGG TCTCAGAGGA  29940
CCCCTGTGCA ACCACATTAA GGAAAGCTGC AGCCCCCACC CACCCGCCTG CCAGTTCAAC  30000
AAGCACCGGC TGCACACGCA GGCTCCCAGG CACCATCACC CCCCTCCCCC GTCGCCCCTC  30060
CCTCACGGGG AGCCCCTTCC CCCTGGAAAG ACAGCAGGTA CTGTAGCCTC GCCTGCTGGC  30120
CAGGGGCGCC GGCTCAGAGG ACCTGCCCTG ACCTGCACCT GCTGACCAGA CAGCCCAGCG  30180
TAAGGACCCG CGATCCCACG CCACCGCCCT GGGTTTACCA CGGTCACCAC CACCTCTCTC  30240
ACAGGGCCCC CGGGGGACCC AGCCGCGCCC GGCCTGGTGT CTGCACCGAG GGACCGCGTC  30300
TCACGCCCGG CGGCTCCTGC AGGGGAAGCC GTGGTCAGCG ACTCACCACG AGGACAGGGC  30360
AGGGCGGCTG AGTGCGGAAG AGAAGCATCA AGCTGGGGGC GGGGGTGGGG GAGGAGGAAC  30420
AAAAGTTGCA TCTAGACAGA GGTGAACGAA ACAAAACCAA AACCCGAACG TGTTCCGTCG  30480
CAGGATGGGC GCCGCCCGTC CCGGGCCCTT AGCCCGACAT CTCTTCTCGC TGCTCCTTGT  30540
TCCTGCGCAC CTCGGCCGCG TGCAGCTCCT GCAGGACAGG GGGCGGGAGG GCCTGAGGGC  30600
GGGGGTGGCT TGGGGCGACT CCGGGAACCC CCAGGCGCGC AGGCCGTGGC GCCCTGGCAC  30660
CCGCCCGGCC TCATCCGGGC TGGCCTTCGG CAGGACCCTG ACTGAGTTGA GGGGGCGGGA  30720
GCACCGGGGA GGCGCAGAGC AAGGCCAGGG ACCAAGGACG GGTTTCCTGG GAGCTGGCTG  30780
GGCCCCGCTT CTAGCTCGTA CCGGAGCCGA GCTTCCTTCA GGGCACTTTC AATATAATGA  30840
ATTTAGCCAT CTATTACTGC GGCTAGTTAC TGTCCCGCCA GGACCAGACT CTGGACCTGC  30900
CTCGTGCGCT GCTGGGGACG CCCAGTAAAC ACGGGAGGAG CCCCCGACCC CCACCCCAGC  30960
TCAGCGCCTC GGAGTCCCCG GCCCCGCTCT GCGCCCCTCC GAGCTCCGCC CTAGCCCCGC  31020
CCCCGCCCAG TGCCCCGCCC CCTGCCTGCT GCTAGCCCTG CCCCCGCCCC GGCCCCTGCC  31080
CGCTCCGAGC TCCGCCCTGG CCCCGCCCCG GCCCCTGCCC GCTCCGAGCT CCGCCCTGGC  31140
CCCGCCCCCC GCCCAGTGCC CCGCCCCCTG CCTGCTGCTA GCCCTGCCCC CGCCCCGGCC  31200
CCTGCCCGCT CCGAGCTCCG CCCCGGCCCC GCCCCGGCCC CTGCCCGCTC CGAGCTCCGC  31260
CCTGGCCCCG CCCCCGCCCA GTGCCCCGCC CCCTGACTGC TGCTAGCCCT GCCCCCGCCC  31320
CGGCCCCTGC CCGCTCCGAG CTCCGCCCCG GCCCCGCCCC GGCCCCTGCC CGCTCCGAGC  31380
TCCGCCCCGG CCCCGCCCCG GCCCCTGCCC GCTCCGAGCT TCGCCCCGGC CCCGCCCCGG  31440
CCCCTGCCCG CTCCGAGCTC CGCCCCGGCC CCGCCCCCGC ACCTTCTCGC GCAGCCGCTC  31500
```

-continued

GCGCAGTGCG GCCAGGTGTG CCTCGCGGAT CTCCTTGCTG AGCTCCATCT TGTAGTTGAG 31560

CTTCTCCTCC GCCTGGCGGC TGAAGTTGTT ATTCTCCTCC AGCGCCTTGT GCAGCACCTC 31620

GCGCTCGTGC TCCCGCCGCT CCGCCAGCTG CTTCAGCACC TGCGCCTCCT GCCTCTGTGC 31680

GGGGCCGGCG GGCGCGCGTG AGCGGCAACC CCGGGCCCTG CCCGGCCGGA CTCCTCCCTG 31740

CTCTCCGCCT CCCGCCCAGC GCCCGCTCGC CTCACCTGGC GCCTCCACCT GCCCAGGCCT 31800

CGGTGGGCGC CGGGACCCCC GGGCGCTGCC CTGGGAACCC TCGCCTGCCA TCCGGCCTGT 31860

GGTCGGGGCA GGGCCAGGGG GTCGCGATCC GCCGCCCCCG CCCCCGTCCC TGCCTCGCGC 31920

GCGGGTCCCG CGCTCCTGGC TGCGCCCAGG GCCCCCGCCA TACCCTGCCG CCACTGCACA 31980

CCCTGCCCTG CGCGTCTGCC CCTCCAAGGA CCAGCAGCAA GAAACCCTAA ACTTGTGGGC 32040

GGTCTCTGAG CTTTGTCTCT TCCTCGGACA TCCGCCCACT GAGCAGAGTA GCTGCTTGTT 32100

ACACACCGGG TTCCCAGCTC CCAATTAGGT GCCCAGGAGC GGAGGGTCCC CAGGGATGCT 32160

GGGGGAGGGG CCGGCTGGTG ACCCCTGGGA GGAGAGCGGG GCAGCAGGAC CCGCACCCAC 32220

ATGCCAGTCC CTACTAGTCA GCCCTGTGAA CCCTGGTCTC TGGCCTCACC GGGAAGGGAA 32280

CGGAGCCGCT TCCCCTGCCC AATGCGTTGG CCTCCAGGGT GGCACCCCCA AAAGGACATT 32340

TTTATCTCTG TTTCAGTCTC AGAGGGGCTG GTGGGAGGGG AGGCTGCAGG GAGGGGACCT 32400

GGAGCCCACA CCCACCTCTC CCAGGGCCCC TCCGCCCTCC AGCAAGCCTC AGGGTCTTCA 32460

CACATGAGGC CCTTCCTCCA GCTTCCCTGT CTGGGAGAGG GATGCCCCAC CCGACGTCCC 32520

CAGGGCCCAT CTGGGGACCA CCCCCTAGCA TCCTGCTGGC CCTGACAAGG GTGCCTCCCA 32580

CCCTCACCAG AGGCTCCTGC TCCTTCCAGG TGGCCGCCTC GGAACCCTTC CTCCTCTCCA 32640

TCCCTTTCTT TTTTTGTTCT TGTTTGTTTT TTGAAATGGA GTCTCACCCT GTCGCCCGGG 32700

CTGAGGAGTG CAGTGGCGCA GTCTCGGCTC ACTGCATCCT CCACTTCTTG GGTTCAAGCA 32760

ATTCCCCTGC CTCAGACTCC CTAGTAGGTG GGATTACAGG TGTGCACCAC CACACCTGGC 32820

TAATTTTGTA TTTTTAGTAC AGATGGGGTT TCACCATGTT GGCCAGGCTG ATCTTGAACT 32880

TCCAACCTCA AGTGATCTGC CTGCCTCAGC TTCCCAAAGT TCTGGGATTA CAGGCGTGAG 32940

CCACCACACC CGGCCTCTCC CCATCCCATT CTTATCTCTC AGAAAGAGCC CCAGGGAGCC 33000

ACAGCCCCTC CTGCTCCAGG CCAAGGCACT GACCAAGCCT GTCCGGGAGC ACCCTGCTTC 33060

TTGCAGGCCC TGTCCCCGTG GGCCGCCTCC GTTGAAACTC CTGGGGGGTG GGGGATGGAG 33120

GACTCCTTGC CTTCCTCCGC TCCTCGGCTG CCTCCAGCCG CTTTTGCAGC TCCTCCAGGG 33180

AGGTGTCCTT CTTCTTGGGT GGGGAGGAGA GCATAGGGCT CTCTGGGGAC AGGTCAGAAG 33240

GGGACTTGAG GATGACCTCG AAGCTCTGGC CTGAGGCCCG CTTGTCCAGC TGCTTCACCT 33300

CCATGTCTGC AGGGCAAGAC CAGAGTAGAG CTTCAGAGGC CCGGCCAGGG CATGGCGTGG 33360

GCTGAGCGGG ATGCTCCCAG CACACATCCA ACCCCAGGGC TGGGCGAGAG GGGGTGGCTG 33420

CTCCCGCAGG AATCCCAGGC TTCAGCCCCC AGGATGGGCC CCTTCCCCCT AGAACCTCCC 33480

TCTCCAGAGG CAGCCAGGAC GGGAGTTCAG AGAGACTGCC GGAGGCCGGG GGAAAAGGTG 33540

AGGTGGGCAG GCACCGCAGG GAAGGGCAGG CGGCAGCCAG GCACTCACCC CCGTACTGGT 33600

AGACGGTATT GGGGTGCGGC TGTGTGTAGA AGCAGGAGCA GATGAGCGAC AGCACCGACA 33660

GCTCCTTCAT CTTCTCCTTG TAGGCTGTGG GCACAAGGCT GGGCTGAGCA AGCACCACTG 33720

GGGCCTGCCC ACCTGGGCCC CCGTTTTCCC TCCCCATGGC TGCCTCTATC ATGTCTCTGT 33780

GAGACACGGA GCTGCCCAGC ACGCTCTCTT GTGTGTCTCC ACACCGCCGG CCCCTTCGTC 33840

TCTCCAGCTC TCTCGCTTCC AGACGTCGGC ACTGTCTCCG TGGTGTGTCC CCTGCCTTCT 33900

-continued

```
GTCTCTCTCG CCCTCTGCCT CTCCCCGCTT TTCCTCTCTC TCGGCATTAA TGTCTGTCTC  33960
ATCTTCCACA CTGACTTGTT TCTCCATCCT TCTCCTGCCT GCTGTGGTCT GAATGTTTCC  34020
ATTACCCAAA ACTCATGTGT TGAAATCGTA ACCCCAAGGT GCCGGTGTGC GGAGGTGAGG  34080
CATTCGGAGG GAATTAGGCC ATGAGGATAG AGCCCTCCTA AGTGGCCCCA GAGTGGGGCT  34140
TCAGAGAACT CCCTCACCTT CCATCATGTG AGGACACAGC CAGAAGACGC CACCCGTCTA  34200
TGTACCAGGA GGCGAGACCT CTCCAGGCAC CGACTCTGCC GGCACCTTGA TCCTGGACTT  34260
TCTGGCCTCC AGAGCGATGG GAAATAAGTT CCTGTCGTCT ATAAACCACT CAGTCTCAGG  34320
TACCTGCCCA GACTGACAAA GTGGCTACCC CTGCCTGTCT GGGTCTCTGT TTACCTTCTG  34380
TGTGTCTGAC TCTGTCACTG TCATTGTATC TTTCTGTGTC TCTGGGGGTA GCCCCTGACT  34440
CTGTCTTTCT CCCTGAGTGC ATCTTTCTGT GATTCCTTGT CACTGTGTGT CTTTCTGACT  34500
CTTACCTCCC TCTGTCCCGC TACTTCTCTC TCCCCTCCTC CTCCTTCCCA CTCCTCGCCA  34560
GCTCAAGCAG GCAAGATTTA CTCATGACGG GACCAGCACA GATGCAAACC CTCTGTGGGC  34620
AGGACTTTCT TGGGCTGTAA ACCTGGATGA AGCCCTCAGA CCCTCCTTTT TCCTTCCCAA  34680
TGATTGTGTG GTCACCTTGA GATGAAACCA GGCCCTCTCC AGGCACATGC TCTCTGTCTA  34740
TCTAGGGCTG GGCTTGGGCC ACTGATGCCA CCAAGGAGCA AGGGAGGGAA GCTGTCCGTT  34800
CAGGACCACA GCCAGCCCTC TTGCCCATTC AGGTCAATCA AGTGCCCACC AGCCAGTGTC  34860
CCTGCTGCCC AACCCAAACC AGAAGCAAGC CGGGCTCCTG TGGCCCTGTG CCCTGTCAGG  34920
GGAAGAGGAA GGCGCCTGCT GTCACAGTGA AAATAATTTA GCTCTTTTGG TCTATTCAGG  34980
GCGAACCTCA TTCCTAAGCA GACACGCTGG CCCGGTTTCT CACTAGTGCT CGATAATCCT  35040
TTTGGCTGGG TGCAGTGGCT CATTTAACTG TAATCCCAGC ACTTTGGGAG GCCAAGGCAG  35100
GTGGAACACC TGAGGTCAGG AGTTTGAGAC CAGCCTGACC AACATGGTGA AACCCGATCT  35160
CTACTAAAAA TATAAAAATT AGCCAGGCGT GGTGGCAGGC ACCTGTAATC CTAGCTACTT  35220
GGGAGGCTGA GGCAGGAGAA TCGCTTGAAC CTGGGAGGCG GAGGTTGCAG TGAGCCGAGG  35280
TCGCGCCATC GCACTCCAGC CTGGGTGACA GTGTGAGACT CCGTCTCAAA ACAGAAAGAA  35340
AAAGAGAGAG AGGAAGAAAG GAAGGAGGGA GGGAGGGAGG AAAAGAAGAA AGGAAAGGAA  35400
AGGAAGACAG ACAAGGCAGA AGTAATCAAG CCTTTCATGG TGAGCTGGGT CTTCTGGTGA  35460
CAGTGCAGAG AATGGTCTGT CCTGACTTAA ATTTCCTGGT GACCTACACT TTTCTGGACA  35520
GAGCAGCACA GAGCCCAAGA GGGTGTAAGG AGGAGCAGAA AGGAATCCCA GGGTGGGCAG  35580
GCCCGTGCGA GAGCCTTTGG GGGAAGGAAT GAGACTTTGA GCCGGGAAGC GAGGCAAAGC  35640
TACCTGTCTT GGTCATTGTC TTCAGGGAGG GAGATGGAGG GGGACCAGGT GGGGGAGCCT  35700
CACAGGGGAC TTTGGTCTGA CTTGTCAAGT TTTCTTTTTT TCTTTTTGAG ATGGAGTCTT  35760
GCACTGTTGC CCAGGCTGCA GTGCAGTGGT GCGATCTCGG CTCACCGCAA GCTCCGCCTC  35820
CTGGGTTCAC ACCATTCTCC TGCCTCAGCC TCCCGAGTAG CTGGGACCAC AGGCACCGCC  35880
ACCACACCCA GCTAATTTTT TGTATTTTTA GTAGAGACGG GGTTTCACTA TATTAGCCAG  35940
GATAGTCTCG ATCTCCTGAC CTCGTGATCC GCCCGCCTCG ACCTCCCAAA GTGCTGGGAT  36000
TACAGGTGTG AGCCACTGTG CCTGGCCTAC TTTATTTTTT AGAAACAGGA CTGTGCTCTG  36060
TTGCCCATGC TGGAGTGTAG GGTGCAGCTG TGCGGTTCAC TGCAGCCTTG AACTTCTGGG  36120
CTTGACGGAT CCTGCCATCT TAGCAGCTGG GACTACAGGT GCATGCCAGC ACACCAGTTT  36180
TCTTTTTTTT TTTATCTCTG CTCACTGCAA TTCCGCCTCC TGGGTTCTAG CGATTCTCCT  36240
GCCTCAGCCT CCCAAGTAGC AGGGATTACA CGCACATGCC ACCACACCCG GCTAATTTTT  36300
```

-continued

GTATTTTTAG TAGAGACAGG GTTTCACTAT GTTGGTCAGG CTGGTCTTGA GCCACCGCGC 36360

CCGCCCGGCC TACACACCAG CTTAAAAAAA AGAAAAAAAT AGCTGGGCGT GGTGGCTCAT 36420

GCCTGTAATC CCAGCACTTT GGGAGGCTGA GGCAGGCAGA TCACCTGAGG TCAGGAGTTC 36480

AAGACCAACC TGGCCAACAT GGCGAAACCC TGTCTCTACT ACAAATATAA AAATCAGCCA 36540

GGCGTGGTGG CGGGCTCCTC TAATTCCAGC TACTTGGGAG GCTGAGGCAG GAGAATCACT 36600

TGAACCCGGG AGGTGGAGGT TGAAGTGAGC CAAGATCGAG CTACTGCACT CCAGCCTGGG 36660

AGCAAGACTC CCGTCTCAAA AAAAAAAAAA AAATTTGTAG TGGTATGGAG GCCGGGCATG 36720

GTGGCTCACG CCTGTAATCC CAGAACTTTG AGGGGCCAAG GCGGGCAGAT CATGAGGTCA 36780

GGAGTTCGAG ACCAGCCTGA CCAACATGAT GAAACCCTGT CTCTACTAAA AATAACAAAA 36840

ATTAGCCAGG CATGGTGGCG GGCACGTGTA GTCCCAGCTA CTCGGGAGAC TGAGACGGGA 36900

GAATCGCTTG AACCCAGGAG GCAGAGGTTG CAGTGAGCTG AGATCACGCC ACTGCACTCC 36960

AGCCTGGGTG ACAGAGTGAG ACTCTGTCTC AAAAACAAAC ACAAACAAAC ATATATATAT 37020

ATACATGTAT ATATATAATA TATATATACG TATATATACA CGTGTATATA TATAATATAT 37080

ATACGTATAT ATACACGTGT ATATATAATA TATATACGTA TATATGTATA TATTAATATA 37140

TATACGTATA TATACACGTG TATATATTAA TATATATACG TATATATACA CGTGTGTATA 37200

TATTAATATA TATACGTATA TATGTGTGTG TGTGTATATA TATATGTATA TATATATATA 37260

TATATACATA TATATATACA GAGAGAGAGA GAGTAGTGAT AGGTCTTGCT GTCTTGTCCA 37320

GGCTGATCTT GAACTCCCGG CCTCAAGAGA CCCTCCCACC TCAGCCTCCC AAAGCACTAG 37380

GATTATAGGT GTAAGCCACA GTACCTAGCC TATTAAAAAT TAATGTTAAA CAAGAGGATG 37440

TGATGAGGGA GTTAGAGGGT GTGCCAGCCA TGTGTTCCAC AGCAGCAGGT CAGGAGACAT 37500

TGGGGACATT TAGAGGAGCT GAAGAGGTGG CCAACCCTGT GCTCAGGAGG ACGGGGGAGG 37560

GAGAGAGCAA GAGGGAGTTT GGGCTGGGGC AGAACGTACC TGGGTCCTGA GAGGATAAGA 37620

AGGTAGGGAC TTGGCCCCTC CAGGCCTGAC TCTGCCAGCA ACCAGCTCCC TATCAGCAGA 37680

CTCCAGGCCC CTACCCTTCA GCTCATCCTT CCTTATCACA CATCCAAAAC TCTGAATGTG 37740

GCCGGGCGCA GTGGCTCACG CCTGTAATCC CAGAACTTTG GGAGGCTGAG GCAGGAGGAT 37800

CGCTTGAGAA CAAGAGTTTG AGACCAGCCT AGGCAACATG GTGAAACCCC ATCTCTACTA 37860

AAAATATAAA AATTAGCTGG GTGTGGTGGC ACATGCCTGT TGCCCCAGCT ACTCAGGAGG 37920

CTGAGGCAGG AGAATCACTT GAGCCTGGAA GGCGGAAGTT GTAGTGAGCA GAGATTGTGC 37980

CACTGCGTTC CAGCCTGGGC AACACAGCGA GACTCTGTCT CAAAAAACAA AAACTGGAAT 38040

GTGTTTACCA TAAAGGCCAG AAAATGTGAT TAACAGCTGC TCAAAGCCCC TGTCTGCCCT 38100

AAGCCTGAAA TTTTCACCGA AAAAAAGATC TGTAGGCTCA TACAGAGGAA GGACAAACAC 38160

CAGGGAGGCT CTCTTCCAGT TTGCTTCACC TCAGCAAGCA GACGGCTGGC AGCAATTTGG 38220

GGGCAGGTGT GAGCACCTGC ATCATCAGGA AAGAAGGGGC ACGGTGGGGA CGCAGGTCAG 38280

ACCTCTCACA GGTCTTGGCT CTGCCCAGGA GACACGTGTC CAACTGAGAG GTGAGGAACT 38340

GGGTTCTGCA GCTGCAGACA CAGGTGCGGC TCAGCATCTG ATGGCCACGG AGACCCCCTG 38400

GCTTGGCTTC TCCCAGCTGG TGGCCCATGA GGAGCTTCTA TCCCAAGAGA CTGTCCCTCA 38460

AGGAGCAAGT GGGACCAGGT ACCCACAGGA CGGAGCCTGG GAGTGAGGCC TGCCCTGTGG 38520

TCTGGCTACA GGGAGGAAGG GCAGATTGGA GGGGGCAGGA CAGCAGGTCA GGAATTGGCC 38580

AACTCTGGAG AGAGCAAGCA AGGGGAAGTC TGCGCACAGG GCAGGGCTGG TCAGGGGCGA 38640

GGCAGGGCAT TGGACCAGTA TTTTCAGAGC TGGTGAGGCT TAAAGAGCAT GTCTACTGCC 38700

-continued

```
TCTTATTACA GAGAGAGGAT GCCGAGGCCC AGACCCATCC AGGCCACCTC TCCACAGACA   38760
CAGCTGGTGC CAGGGAAGCC CCTCCCAGAG CCTCAAGGCA TTGCTCCCTC TCTCTCTCTC   38820
TTTTTGTTTT TTTGGAGACG GAGTCTCACT CTGTCTCCCA GGCTGGAGTG CAGTGGTACA   38880
ATCTCGGCTC ACGGCAAGCT CCGCCTCCCG GATTCACGCC ATTCTCCTGC CTCAGCCTCC   38940
CGAATAGCTG GGACTACAGG CGCCCGCCAC CACGCCCAGC TAATTTTTTG TATTTTTAGT   39000
AGAGACGGGG TTTCACTGTG TTAGCCAGGA TGGTCTCGAT CTCCTGACCT TGTGATCCGC   39060
CCGTCTCAGC CTCCCAAAGT GCTGGGATTA CAGGTGTGAG CCACCGCGCC TGGACTTTTT   39120
TTTTTTTTTA AGACGGGGTC TCACTCTGTC ACCCAGGCTG GAGTGCAGTG GCGCGATGTC   39180
GGCTCACTGC AACCTCTGCC TCCCCAGTTC AAGTGATTCT CCTGCCTCAG CCTCCCAAGT   39240
AGCTAGAATT ACAGGCACAT GCCACCATGC CCAGCTAATT TTCTGTATTT TTAGTAGAGA   39300
TGAGGTTTCA CCATGTTGGC CAGGCTGGTC TTGAACTCCT GACCTCCGGT GATCTGCCCA   39360
CCTCAGCCTC CCAAAGTGCT GGGATGACAG GCGTGAGCCC CCGCGCCTGG CCCCCCGCAG   39420
TGCTGGGATT ACAGGCGTGA GCCCCCGCGC CCGGCCCCTC CCTCTCTTTG ACTCCCTTCT   39480
TTCTCACCGC CCCCTCCCCA CCATCCTTCC CCTTCACTGA CTTCAGGGAG TTAAAAACAA   39540
TTCTCGCAGT GAGCTGGGCT TGTTTTGTCT CCCTGCTTCT CTTTGTACTA AACATTAGAT   39600
ACCGAGGAAA TGCGGATTGG CCTTTGGATG ATTCATGAGC AGGAGTCAGA AAAAGGCACC   39660
AGGTTGGCCT CAAGCAGCAG GGTATAGTAG TGCCCGCTCC CAGGGTCACA CCTCACGCCC   39720
ACCCCTCCCG CCGTCCAGGT GGATGGTGCC CACTCCCAGG GTCACACCTC ACGCCCACCC   39780
CTCCCGCCGT CCAGGTGGAT GGTGCCCACT CCCAGGGTCA CACCTCACGC CCACCCCTCC   39840
CGTCGCCCAG GTGGATGGTG CCCACTCCCA GGGTCACACC TCACGCCCGC CCCTCCCACC   39900
CACCCGGGTG GATGGTGCCC GCTCCCAGGG TCACACCTGA CGCCCACCCG GGTGCATGGT   39960
GCCCGCTCCC AGGGTCACAC CTCACGCCCA CCCCTCCCGC CCGCCCGGGT GGATGGTGCC   40020
CGCTCCCAGG GTCACACCTC ACGCCCACCC CTCCCGCCGT CCAGGTGGAT GGTGCCCACT   40080
CCCAGGGTCA CACCTCACGC CCACCCCTCC CGCCGCCCAG GTGGATGGTG CCCACTCCCA   40140
GGGTCACACC TCACACCCAC CCCTCCCGCC CACCCGGGTG GATGCCCTTA TCAGCTCTCC   40200
TTCTCCTTCT CTTTCGTCTT CTTCGTCTTC CTCCTCTTCT TTCTTCTTTT TTTTTTTTTT   40260
TAGAAAGAGT TTCTACTCTT GCTGCCCAGG CTGGAGTGCA ATGGCACAAT CTCAGCTCAC   40320
TGCAACCTCC CTCTCCCCGG GTCAAGCAAT TATCCTGCCT CAGTCTCCCA GATTGCTGGG   40380
ATCACAGGAG TGTGTCACCA CACCTGGCTA ATTTTGTACT TTTAGCAGAG AGGGGGGATT   40440
TCACCATGTT GGCCAGGCTA GTCTCGAACT CTTGACCTCA GTTTATCCAC CGGCCTCAGC   40500
CTCTCAAAGT GCTGGGATTA CAGGCATGAG CCACCCTATC TGCCTCACTT CTACAGAGGA   40560
GGAATGAAGG CTCAGAGAGG GCAAGCATTC CACCCAGCAT CACACAGAGT GCCGGGTGAG   40620
AGCCCAGTCA TGAGCCTGGG CCTGACTGCA GGCTCCTGTT GGGAGCTCGC GGAGGTGGGG   40680
GATCTGTCCA GAACTGAGAG GCCAGGGGAC CACAGTGGCC TCTGACCCCT GGAGGGCCCT   40740
GGAGGCTGCT GCCGGCTCCC CCCGGGGGCA GATGGAGGTC ACTGTCACCC AGGCTGCTTC   40800
TCATGGTGCC AGGAGCACAG CATGGCAGGA GCCACCAGCC GATTTGCCTT TCCCTGGGCA   40860
GGAAACTCAG AAATGTGGCT ACCACAGTCA GGCTGCTTGA CGTGCGGTGA GCACTCATCT   40920
CTTAGCAGGC AAGCGGCCAA GCACCTTTCC TGAAATATTG AGGCCTCAGA ACAAGCCCCA   40980
GGAGAGGTGC CAGCACCGTC ATCTCTACCC AGATAAGGAG ACCCAGGTCC TGAGAGGTTA   41040
GGCAGCTCGG ACAACACCAC ACAGCTGGAG GAGGTCAGAC TCTGGGTTGC AGAAGGAGAA   41100
```

-continued

```
TGTGAGCAGA GGCCACAAAA GAGCGAGGAG CCAGTGCCCA GATGCCGAGA TGCCCTCGCC  41160
CTCCCAGCTC AGCCCCAGGA ACCGAGCCCA TGGGGAGGGA CCGTCAGGGA AAGGCTGTCA  41220
GGAAGGGCAG GAGGCGGCCC TGGAGAGGAC GGCGCTGCCC TCAGGGGCAG GAGGGGAGTC  41280
CCCTCCGCTG AGAGCCCCCC CACCCCCAGT ATCCCCGGGG GTGTCCAGGA GGAGGCGGAG  41340
GGAGGAAGCG CAGATGGACA GGACTCCCAG ATAGGGTGGG GAGGTGTGGC CGGTGACACA  41400
CACGGTCCCC TCCTGGCAGG TGCTGAAGTC ACCTGGAGCC TCCAAGCCCG TGGGGCCTGA  41460
GGGGCGGGGT CAGGTCGGGC ACGCGTGGGT GGGCGGAGTT CTGCGCCCCG GGCCAAGGCG  41520
CCCGAGTTGA ACCAGTCAGC TCGGGAGAGG GACCGCGGCG ACCTGTCCCG GGGGCGTAAG  41580
AAAAGGTGGG AGGGAGTGCG GCTCGTGAAC GGGGGCGGCG ATGGGAAGGA GGTGCGGCCC  41640
TTCGTCCTGT CCTCCCAAAC GTCGAGTGAA AAACGAAGCG GGTTCTGCGG CCTCGCGGCG  41700
GAGCAGAGCG TTTCGGGAAG GGCGGGCCCA GCGTCCTCGC GCCCGAGGTC GCCCGGCAGC  41760
TCCCCTGCGT CCACAATCCG CCCCCCGCCC GGGCCTGCGC CCGCCCCTCC GCCTGAGCTC  41820
CGCGCGGGAC GGGCCGGGAG GCCGGGGTGG GCGCTACCTT CGAAGGCGGT GGGTCCGCCC  41880
CGCGGGAGGT GGAGGGGCGG GAGGGGCGGA GCCCTCTGGT CTCCGGAGGG TTTGGGGATC  41940
GCAGTCGCCC CTCCCCCATC CAGACCCCGC GGCGCAAAGG GCAGTGGCTT TTCTGGCCAG  42000
AGCAGGTGGC GCGGGCGTCG CAAAGGGTGG TCCCCGAGGC CGCAGCGGTG TGGGGGGAGG  42060
GCGCGGTCCC CCTCACTCCG GGCTCCGCCG TGTCTGGCCC GCCCCCCTCC TTCAGCGCCC  42120
CCTCCAGCCC CTGTGCTGCA CTGGCGCGGG GAGCGCCGGG TTCCCGGCTG GGGCTTTGGC  42180
AGAGGGTCCC ACCCTCTCCC CGCCTCCCCA CGAAGGCTCT GGCGGACCCA GATCTCGGGT  42240
CGCCGGACGC CCCAGGGACC CCGCCCGCAC ATCGCGAGCG CGCCCACCCG GTCGCGAGCC  42300
CACGCCCGGG TCTGGGAGCC ACCCTGCGGC AGTCGCGCCC TGCGTGGCAC GCTGCTCCCC  42360
CAGGGGCGAG GCGCCCCCGC CCGACGTCCC GGTCCCGAGC GCTCCCCGCC GCGGCGCCTC  42420
GCAGCCCAGC GCCCCACCAG CCCCGCCGGC GCCGCAGACC CCAGCCTCGG GCGGGTCGGG  42480
CCCAGGCTTG CAACGCGCAG GGTAGGAGAA GGGAAATTGG CGTCCGCTGC CGGCCGCTGC  42540
CCCAGGCGAG GCCAGACGAG GCCTCTGCTC AGATCCCGCC GCCCCACAAA GCCCGTGGCC  42600
CCGGAGCCTA CCGGAAATGG TGCTGGCCAT GGTGCTGGCG GCGGTTGGGC CTGCGGAGGC  42660
TGGAGAGGCG CAAGTGGCGG CCGGAGCTGC AGACGGCTGG TGCTGCAGTG CCGGGGAGGG  42720
GAGGGGAGAG GAGTGGAGGG AGCGAGGGCG GGCGGGAGGC GGGCGCGGCG GGAGAGAGAG  42780
AGGGAGGGAG ACAGAGGGAG AGAGAGAGAG GGTTGGGGGA AGGAGCGGGG GGAGGAGGGA  42840
GGGAGGGTTG GGGGAAGGAG AGAGAGAGAG AGAGAGACTG CGGGGGCGGG GGAAGGAGGG  42900
AGGGAGGAAG GGAGGGAGGA AGAGAGAGAG GAGCAAGCGC CTGGCTGCGG AAGGGGCCGC  42960
GGCTCTCAGG GGGAGAGGGC GGAGGAGGGG GGCTACCCGA ACTGCAACAA GACCCCCCAC  43020
CCTCCAACCG CTCACAGCGG GACAGCTGCT TCTCCAACTT GGCTTTGTGA GGCCTGAGAG  43080
TGGGGTGGGG GTGGAGATGA GCCCCCATTC CCCAGGGCAG GCGGGGCAGG GGCAATGCCG  43140
GAGGAGCAGG TCCCACCCAT GGGGTGGGGC CGCAGAGCTC TTCGCCGCCA AGGCCGCTGT  43200
AGGCTGGGCT GGCGCCAACA GGGTCCAGGT CTGTGCCTGC CATCGGAGAG GATGCCACAG  43260
CCACAGGGGT GGGCGCTGGC CTGGAGGCCT CCAAGGGGCA TCTCCTGTGA GCCCAGGGGA  43320
TGGGCAGGAT CTGAGCGGAG AAGAGTGAAA GTGGAGGAGT GAGGCCAGAA CAAAGGCTTT  43380
GCCGTGAAAG AGGTGGTTTC CCGCCTGGGC TCAGACCTTC ACTCACTGTG TGGCCCAGGC  43440
CAAGGGCAAG CGTCTGACCT CGCTGGGCCT TTGTTTCTCA GGGGTAAGAT GAAACAATGA  43500
```

-continued

```
TGCCCCCAGA CGATGGAGAG GAGGGGTGCC AGGGTTGTGC GCACTTACTG AGTGGGGGGC  43560
AACCTATCCT GCCTCCCCCT CTCCTCATAA CTCCCAAAGG GAAACCCTGG TAGGCAAACG  43620
GAGCGTCTTT GCCATTGCAG GGATGAAGCC ACCGAGGCAG GGAGAAAAGT GCTTTGCCCT  43680
ACAAGCAACT AAGTCATAGG GCCAGGAGCA AAACCCTGAA AACCTCAGGA GACTTGCAGA  43740
GCCATGAGGC TGGCTCAGCA ACACAAAAGC CAGGGGCAAG CCTCAGCTCT AGCAGTGCGG  43800
TGGGAGCACC CAAGGCCAGT CACATCCTAG GGTGGCCTGG AGAGTCCTGA CCCCTGACGT  43860
GCAAGCCGGC ATCATCCCCG GGACTGTGAG TCTGGTGGGG GTGATGCCCA GGAATGTGAC  43920
ATTGTGTGGC CCAGAGGTAC CCTTAAGACT GGAGGATCAC CAGGCGGGCC CTGACCTCAT  43980
CACAGGAGCC CTTTAAAAGC AGTTTCCTTT GCCTGGTTGA AGAAATCGGA GGGATCAAAC  44040
CAAAGAAGGT TTTCTGTTGT TGAGATGAGG GGGCCACGTG GCAAGGATCT GAGAACTGCT  44100
CCCAGCCAAC AGCCAGCAAG ACAACAAGAC CTTAACTGCA AGGAAGTGAG TTCTGCCAAC  44160
AAGAAGAGAA TGGGCTTGGA GGCAGGTTTG ACCCCAGGGC CTCCACACAA GAACTGAGCC  44220
CAACTGCCCA CTTGGTTTCA GCCTTGGGTT ACTAAGAATT AGGAGGTAAT GAATGAGAGT  44280
TGTTTTAAGC TGTTGGTTTT GTGGTGATTT GCTATGAAGC CATATCAAAC TAATATACAC  44340
ACAGAGGTGT TGGCCCCTGG GCCATTCCTA GGAAGCCAGC TCTGCGAAGG AGGAAGAAGG  44400
GCAGAGAGGC ACACAGAGCT GCCCACCACA GCAGCTGTGT CCTCCCTGTT GGCCACCACA  44460
GTAGCAGTTG GGGATGGTCA GCATCCTTCA GGCAGACTCC AGCCCCGGGT GCTGGAGCTC  44520
AGGTGCTAGG GATCAAGAGA AGTAGCCCTC TCTGGGACCT CCAGAGTCTT CTCATGTGGG  44580
TGGGGTAGGA CCCACCCAGT CAGGCTCAGA GCACCGCAAT GCCTCACACT CATTGTGACT  44640
CTGGCCAGGC CCTCTCTGAG CCTCTGTGTC CTCATCTGGA GCACAGGGAC CAGGTGTGTG  44700
GAAGCCCGTG GCATAGTGCC AGGAACACAG TAGATGTGCA CAGTGTGCAC TAGCAGGAAC  44760
ACACAACAGG GGTACTGACT GTCAGCACCT AGGCAGGCAC ACGCAATGGG CTACTGACTG  44820
TCAGCCATAC TGACTGTCAG CGTGCTAGCA GGCATACACA ACAGCTGTAC TGACAGCACA  44880
CTAGCAGGCA CATGCCATAG GTGTACTGAC TCTCAGTGCA CTGGCAGGCA CACGCAATAG  44940
GAGTAATGAC AGCATGCTGG CAGGCACACA ATAGCTGTAC TGACTGTTTG CCCCAATATA  45000
GTGCCAGGTC TTGGAGCAGA TTTTGACTTC TCACCAAGAT CAAATGCAGA AAGTGCACGA  45060
GCATTTCAAA GATGTTTTTC ACATGCACAT TAGTGCTAGT TAAAAAAATG TTTTGACTGG  45120
GTGCAGTGGC TCACAACTGT AATCCCAACA CTTTGGGGGG CCGAGGTGGG CAGATCACCT  45180
GAGGTCAGGA GTTTGAGACC AGCCTGGCCA ACATGGTGAA ACCCCATCTA CCCTAAAAAT  45240
ACAAAAATTA GCCAGGTGTG GTGGCAGGTG CCTGTAATCT CAGCTACTTT GGAGGCTGAA  45300
GCAGGAGAAT CACTTGAATC CAGGAGGCAG AGGTTGCAGT GAGCCGAGAT CCCACCACTG  45360
CACTCCAGCC TGGGCAACAA TATCAAGACT CCACCTCAAA AAAAAAAATG TTTTTCATAA  45420
AGTGTGACTT TTATCAGACC TCTGCATTCT TGAAATTAAC TCTGGCTTGG CTGGGCGTGG  45480
TGGCCCACAC CTGTAATCTT AACACTTTGG GACGCTGAGG TGGGCAGATC ACGAGGTCAG  45540
GAGTTCAAGA CCAGCCTGAC CAACATGATG AAACCCCATC TCTACTAAAA ATACAAAAAT  45600
TAGCCGGGCG TGGTGGCATG CACCTGTAAT CCCAGCTACT CAGGAGGCTG AGGCAGGAGA  45660
ATCGCTTGAA CCCAGGAGGT GGAGGTTGCA GGGAGCCCAG ATCGCACCAC TCTATTCCAG  45720
CCTGGGCGAC AGAGCAAGAC TCTGTCTCAA AAAAAAAAAA GAAAGAAAGA AATTAACTCT  45780
GGCTCCTAGA AGGAGCCCTA TATCTCAGCA GGACACTCAG TCATTCAACA GACATCTGTC  45840
AAGCACCTGC TGTATGCTGG AGCTGTGGGT ACGTCAGCAA TTAGAGGAAG AGGGCAGGGG  45900
```

```
TACAGGAGTT CCTGACCACC CCAGGCCAGC ACGCTCCTAT AGCAGCTGGC AAGGAGCAGA    45960

TGACTCAGAC TTCAGCTCAG TCCACAGGAC AGCCTTTTCT GGCCACTGCT CTCAGGAGAT    46020

GAGATGTGTG GCTGCAAAAG GTAAACTCCT GGCTCCTGAG CAGGCTCTGG GCAATCTGCT    46080

CAACGCTCTG TGCCTCACTT TCTCACCCAG AAAGTGTGGA CAATGAGAGG ACTTATCTGG    46140

CTGGGCGCGG TGGCTCACGC CTGTAATCCC AGCACTTTGG GAGGCCGAGG CGGGTGGATC    46200

ACCTGAGGTC AGGAGTTCAA GACCTGCCTG GCCAACACGG TCAAACTCCA TCTCTACTAA    46260

AAATATAAAA AATTAGCCGG GCTTAGTGGT GCACACCTGT AATCCCAGCT ACTTGAGAGG    46320

CTGAGGCAGG AGAATCACTT GAACCCAGGA GGTGGAGGTT GCAGTGAGCC AAGATTGTGC    46380

CACTGCACTC CAGCCTGGGC AAAAAGCCAA AACTCTGTCT CAAAGAAAAA AGAATCATGG    46440

CAGAAGGTGA AGTCTATGTT AGTCCCAGTT CCCAGGTCGT ACATGGCGGC AGGAGAAAGA    46500

GAGAGAGAAG GGGAAACTGC CACTTTTAAA CCATCGGGTC TCCTGAGCAC TCACTGTCAG    46560

AACAGCCTGG AGGAAACTGA CCGCATGATC CAACCACCTC CCTCCAGGTC CCTCCCTCCA    46620

CACGTGGGGA TTACAATTCG AGGTGAGACT TGGGTGGAGA CACAGAGCCG AACCATATCA    46680

GCATGTATGG GGGGCACTGA AACTTGTGCT TGGTGCCCAT TCATTCAACG AGTGTGTGTG    46740

GCTGGTCTCC TCATCTTCAA CTCCCTGCCG AGTCTCAGAT AGGCAGCCTG CAGTTCCTTC    46800

ACCACAACAG GCACATGGGG CTGGGTGCCA GTGAGTGCTG GGGCTTCTCC GAGCACTATC    46860

TCACACCCAG GAGCGTGGGC ACGCATGGCA TTCGCATGTG CCGTCAGTGG ACATTAAACA    46920

CAGCCATGAA GAAGCCACGA AGAAGTGCTG CCTGCCGGCC GTGCGCGGTC ACGCAGCGCC    46980

AACTCCCTCC TGGGGCCTTC TGGGGCCTTC TGGGGCATGG GAGCTGGGGC CGCCTGAGAC    47040

AAACATCCGT GACGCTGGGC TGACCCCACA GAACGGTGCG GGCCTCGCTC TTGGAGTCAG    47100

CCCTGCTGCC AGCCAGTGCC GGGTGCTGGG GACTCAGGGA GGCCCGCCGG GACCACTGCG    47160

GGACAGTGAG CCGAGCAGAA GCTGGAACGC AGGAGAGGAA GGAGAGGGGG CGGTCAGGGC    47220

TCTCAGGAGC CGGGTCCTGG GCAAGGCGCA GCCGTTTTCA AATTTTCAGG AAAGCGGTCG    47280

GCTCACACTC GAGCAGTAAA AAGATGCCTC TGGGGAGGAG GCCCGTGCAG CTCTCCGGGC    47340

AATGGTGGTG GCTCGGCCTA GAGAGGCGGT AGTGGAACGC AGACCCTGGT GGGGGAATGA    47400

CATCAAGGGA GGAGACGGGC GGGACCCCAG ATTTCTGCCT GTGGGCGATG GAAGTGAGGT    47460

TCACTGGCCA GCGGAGCCGG ACACAGAACG CGCAAAACGC CGTGTAGGCC TGGAGGAGCC    47520

GAAGAGCAGG CGGACCCCCT CCGCGGGGGA ACAGTTTCCG CCGGGAGCAC AAAGCAACGG    47580

ACCGGAAGTG GGGGGCGGAA GTGCAGTGGG CTCAGCGCCG ACTGCGCGCC TCTGCCCGCG    47640

AAAACTCTGA GCTGGCTGAC AGCTGGGGAC GGGTGGCGGC CCTCGACTGG AGTCGGTTGA    47700

GTTCCTGAGG GACCCCGGTT CTGGAAGGTT CGCCGCGGAG ACAAGTGAGC AGTGAGTCGC    47760

AGTGACCCTA CAAGTGGTTC TTTTACCCGA GCGGCTCGTA GGCGCGTTGC GGTTTTTCGA    47820

AACTACAGCT CCCGGCAGGC CCCAAGCCGC CCTCGGGGCC GCGGGTCGGC GGATTGGCCG    47880

CGCTGCATTT TGGGACCTGT AGTTTCCTGC GCTCGTGGCG CTGGCGCCGC GGCCTTGGCT    47940

GAGCCCTTGA CCGGGGCTGG AGGGAAGGGC CGACATTCAG TGTGTCCGCG TCTGTTCTGT    48000

TAGTCCCAGT TCCCGGGCGG GATTGAGGCT TAGAGAAGTT GAGTGATTTG CTGAGGGCTG    48060

CACGGGTTGG CATCCCGGCA TGCTCTTTCG CTACTTTGGC TGCATCTGGT TGCCCACCCG    48120

GGCGGATGGG GAATGGACTC CAGCCAGCCA GGAGGGCAGA GGGCTGGAGA GGCAGGGCCG    48180

GAGGTTCAGA CCCTCCGCTC TGACGTTGCG CCTGGTGAGG CCGGGAGGGG TGCCGCTTGC    48240

CTCTTCAGCC CTCACGCTCT TGTGGAAGTC GCGGAATTAC TGCAGGCGGA ACTTGCAGCA    48300
```

-continued

CTGTGGGCGT CTTTTCCAGA GAAGGACGGA GTTGTGGGGC GGGAGGATAA GGCAAGGCCC 48360
AGCCACTTCG CATCTTCGCC CCGCCAGCTC CTCGAGATGG GATATACCAG GGTTGCTCTC 48420
CAACCCTCTC CGCAGGAGGG ACTGATGGAA ACGCCTGGGA AAGTAGCCCG GTACCCACAA 48480
AGGCTGTCTA CAAACAGAGT CTTACTGTCT TTCCCAGGTC TGTGCCATAG GGATTCTCGA 48540
AGAGAACAGC GTTGTGTCCC AGTGCACATG CTCGCATCGC TTACCAGGAG TGCCCGAGAC 48600
CCTAAGATGT TCGGAGTGGT TTTTTCGCAC AGACCCGAAT AGCCTGCCCC TCAGCCACGC 48660
TCTGTGCCCT TCTGAGAACA GGCTGATATG CCCAAGATAG TCCTGAATGG TGTGACCGTA 48720
GACTTCCCTT TCCAGCCCTA CAAATGCCAA CAGGAGTACA TGACCAAGGT CCTGGAATGT 48780
CTGCAGCAGG TAGAGCACAG GCCCCGAGGA AAGGACTGCG GGTGGGTGGA GCTTCAGCCA 48840
GGACGGGGTG TGCTTCCCTC TCCCGGCCCA TTCCAGCCAG GCCCCTCCGG GCCAGAGGCA 48900
GCGTCTGTCA TAAAAAGGGC TGGTGTTCCA GGTGGGGTCA GAGAGAGGAT TGACAAGTAA 48960
AAACGATCGT CCTTTGAAGG GGGCCGGCCC CTCCACACCT GTGGGTATTT CTCATCAGGC 49020
GGGACGAGAG ACTGAGAAAA TGAATAAGAC ACAGAGACAA AGTATAGAGA GAAAAGTGGG 49080
CCCAGGGGAC CGGCGCTCAG CATACAGAGG ACCTGCACCG GCACCAGTCT CTGAGTTTCC 49140
TCAGTATTCA TTAATTACTA TTTTCACTAT CTCAGCAAGA GGAATGCGGC AGGACAGCAA 49200
GGTGATAGTG GGGAGAAGGT CAGCAAGAAA ACGTGAGCAA AGGAATCTGG GTCACAAATA 49260
AGTTCAAGGG AAGGTACTAT GCCTGGATGT GCACGTAGGC TAGTTTTATG CTTTTCTCCA 49320
CCCAAACATC TCGGTGGAGT AAAGAGTAAC AGAGCAGCAT TGCTGCCAAT ATGTCTCGCC 49380
TCCTGCCACA GGGCGGCTTT TCTCCTATCT CAGAATTGAA CAAATGTACA ATCGGGTTTT 49440
ATACCGAAAC ATTCAGTTCC CAGGGGCAGG CAGGAGACAG TGGCCTTCCT CTATCTCGAC 49500
TGCAAGAGGC TTTCCTCTTT TACTAATCCT CACCACAGAC CCTTCACGGG TGTTGGGCTG 49560
GGGGACTGTC AGGTCTTTCC CATCCCACGA GGCCATATTT CAGACTATCA CATGGAGAGA 49620
AACCTTGCGC AATACCCGGC TTTCCAGGGC AGAGGTCCCT GCGGCTTTCC GCAGTGCATC 49680
GTGCCCCTGG TTTATCGAGA CTGGAGAATG GCGATGACTT TTACCAAGCA TACTGCCTGT 49740
AAACATATTG TTAACAAGGC ATGTTCTGCA CAGCTCTAGA TCCCTTAAAC CTTGATTCCA 49800
TACAACACAT GTTTCTGTGA GCTCAAGGCT GGGGCAAAGT TACAGATTAA CAGCATCTTA 49860
GGGCAAAGCA ATTGTTCAGG GTACAGGTCA AAATGGAGTG TGTTATGTCT TCCCTTTCTA 49920
CATAGACACA GTAACAGTCT GATCTCTCTT TTCCCTACAG TCCTTGAGGG TGACAGACTT 49980
AGGAGTGCCT TGGGGGCCTC TCTGAGGAGC AGCTGATATT CACGGGTCAG GAGGAACCAT 50040
TTCCATTAGA GGGGCAGCCG GTGGCCAGCC TCACTTGGAA GGTCTTTGAA CCTCGGGGGT 50100
GCAGGGAGGT GGCAGTGGTG CAGGTTGCCT TCTCCTGGGT TCCTTGAGGT GCCCTCTTGT 50160
ACCCGGCTCA CACCCTTCCC CTCCCCGAGT TTCCTGCTCA GGTTCCCGTC TGAGAGCTTG 50220
TATGTAGGAC GTCAGATAGG ACAGCATAAA TGTTTGGATC CAGAAACGCA GAACAGTTTC 50280
CTATTTTGAG ACTTGACACC TAATTAGTCA TCTTACTATT TAAGCTGAAA AATAGTGTCG 50340
TGTTTTGGGT AACGTTCTGC AAATCGTTTG CTAATGGCGG CTGAGTTGCT TCACGCCCTT 50400
TAGGGCAAGA GTGGGACTTG CCTGTGGACT TCTCCGCGGT CCCACAGGGC TCTCGCCACC 50460
TGGCAGTGGC CTCTGCATCT GCAAAGAGCT GCCCGCTGGC TGCCGAAGCT TGTCTCAGGG 50520
CAGCTTGTGT GGCCTCGCCT CTTCCTGGCT TCCCCGTAAC CCTTGCTCCG AACTCCGTTC 50580
AGAAGGTGAA TGGCATCCTG GAGAGCCCTA CGGGTACAGG GAAGACGCTG TGCCTGCTGT 50640
GCACCACGCT GGCCTGGCGA GAACACCTCC GAGACGGCAT CTCTGCCCGC AAGATTGCCG 50700

-continued

AGAGGGCGCA AGGAGAGCTT TTCCCGGATC GGGCCTTGTC ATCCTGGGGC AACGCTGCTG 50760
CTGCTGCTGG AGACCCCATA GGTGACCCTA GTTCCCAGGC CTCTCCTGGC CTCCTGTGGG 50820
GATGGTTGGC AAGGGATGGC GCTGAGGGTG GGGTGGGCCC ATGGGGACTC CTGCCGTCTC 50880
TCAAGCAGAA CTCAAGGAGA ATTTTTTAGC TGCTGTATAA TTTCTCGCCA TCGTGGGTGT 50940
AAACCTAGGG TTGGGCTTTT TTGCTGAATT AGGGCACGGC AGATGCCCAC TTCACCCATT 51000
TTTGATAAAC CAGTATCTGG GGTGTCAGAT TCTTGGCTGT CTGCAGGGCC GAGTTAGCCG 51060
AATGCCACCT GCCTTTGATA CGTGAGAACG TTGTCTGAGA ACCGTGACTT CTGTGCTTGC 51120
TTGTGTCTGG TCAGCTTGCT ACACGGACAT CCCAAAGATT ATTTACGCCT CCAGGACCCA 51180
CTCGCAACTC ACACAGGTCA TCAACGAGCT TCGGAACACC TCCTACCGGT GGGTCAGACG 51240
AGTTTACACC TGTCTCGGGG TCCTCAAGAG AACCAGCTTG GCATGGTGCT GAGTCCACAG 51300
CCCCATGCTG TGCTGTGGTG GAGGGTGGTG GTCTTTCTAG ACGCTCCCCC GAAGTGTGCA 51360
GAGCGCTGGT GCCCAGGGGT GGGGTGCGGC CTGGGCTGCC TCCAATGCCC ATTACTTGTG 51420
AGGAAGCAGC TTTGCATCTG TGTGCTGACC TTGGGCGGGC GTCCTGAGCT CCTCGCAGGT 51480
GCTGTTGTAG CAGCTGTGCA GTAGGTCAGG GCTGGCCCCC AGTGCAGCTT TGCACATGAA 51540
GTAGGAGGAG GCCCTGCTGC TTGTCAGAGC CCAGCAGAGT CTTGGTGTTC TGTCGGGTTC 51600
CTGTGGCCGG ACCAGTGGCA GGGTGCTGTG GAAGCTGTCG AATCTCCTCC CTCTGTCCAG 51660
TACCCCCGCT CGTCTTCTAG CTCCCTCCTA CGCCCGGGCC ACGTTTCAGT TATGCTCACT 51720
TCCTCTGACC GCCGAGGCTC CTGCCTGTCT CCATACAGCT CACGCTGCAG GGCCACGCTG 51780
TGGGTGTTGG AGACAGCTCC TCCTCGACCC ACGGTGCTCT CTCCCACCAG GCCTAAGGTG 51840
TGTGTGCTGG GCTCCCGGGA GCAGCTGTGC ATCCATCCTG AGGTGAAGAA ACAAGAGAGT 51900
AACCATCTAC AGGTAGGCTC CTGGGCTCCC GCTCCGGCTC AGTGTCCGAC AGGCGAGTGC 51960
TGCTGGGTGT CCAGAGCCCC AGGCTGCCCT CCCGCTGGGC TAGGGTTTGA AGTTCACTGG 52020
GGGACTGCAG GGGAGGACCT GGTGGGGGTG GGGACTGGCT TCGGTCCTTT CTTGGCCGTG 52080
CTTCAGCTGC GCACTCTGCC CTTCCTCCCA CAGATCCACT TGTGCCGTAA GAAGGTGGCA 52140
AGTCGCTCCT GTCATTTCTA CAACAACGTA GAAGGTACAA GCAGCTGGGT GGGACCAGGG 52200
TCGGGTTGGA GTGTGTGCAG CCTCTCAGGG TGGAGCTCAG TGGTGTCACA GCCTGGTTGT 52260
GCTTGCCCGG TGGGGCGGCC AGTGCGGCCA TGTACCTGGG CCCTGTCTTC TGACTCGGGG 52320
CCACCCATGT TAGACTTCTG TGTGGAAGAG CTCACACAGT GGTCTGAGAC AGCCAGCCGG 52380
CAAGACTGCC TCTGGCTGGT GCCTGGGGCC TTGGATTTTG GGAAGGCTCC CTCCATTTCC 52440
TGATGAGAGG GTCTCCCTGC ACCTAACCTG CTGGTGCAAA CAGTAGGGGT TTTGCTGAAC 52500
ACCGGCTTTC TCTTCGGGGA CTTTGTTGCT TGCCCAGCAG CAGGTGCTCC AGTGACCGGC 52560
CCTCATACCA TCTTGGGAGG GTGTCCTGGA AGCCGTGTCT GGCCTCCCGC GACCCTGCCC 52620
CGTGTGTCTT TTTCCTGTGC TGACCTTGCT GCGGAAAATT ATGGCCCTGA GTGTGACTCC 52680
AGGCTGAGTC CTGTGGGTCC AACACGGGAT GCCTTGGGGC CTCTTCTGGA GACGGGATGT 52740
GAGTGACAGG AGCCGGCCGG GGCAGCTTGC CCTGTGACTG CACGTGGCCA CAGCCTGTGA 52800
GGGCCGGGGG TGCTTCTCCA CCCACGTGGC TGCCCCTCGG GTATGTCAAG GCCTTCTGGG 52860
GCTCATCACG GGGTCCTAGA GACAGTGGCA GGGTGCACCC CCGTTGGCTG CCCTTACAGT 52920
TTCTGTGACC TGAGGGTGGC ATCTGTGCAG TCGGCGCGGT CTGTGCTTCT GTGGGATCAG 52980
GGTTCCCTCT GTTTCCTGCC TCAGTTGGGG CTCAAGCCTC AGGTGAGGTG GCCCCGGAGC 53040
ACTCAGAAGG CATCGGCGGT CCTGTGGGCT GCTTTCTGCA CTCACGTTTG CTGAGTGCTC 53100

-continued

```
AGTGTGCCAG GACTGAGGAC CCTGAAGCTG CTCTTGTATT TAGGGCGGCG CTCCCCTGGC   53160
AGAGACTGAG CCAGGTGGTC CCGCATGACC CACTACCAGG CGTTTCTGGG CCCTGGCCCT   53220
TGGAGGGACA GGGTGGGCGG AACATGGGCC TGCAGGGAGG CTCCCGCTTA CTGGAGGCAT   53280
GTGCTGTGTT GCTGGAGACA TCCTCTGTGT TGCTTCTTGT TCGCTGTGGT TTTTGGTCTG   53340
GTGGCACCAA GGACCCTCAG TCATCTTGAT GTGTGGTTGT CCAGGCCTTT TTGTTGGTCC   53400
TAAGAAGGGG CTCTGCCTTT GTGCCCCCAG GTTCCCTGAC AGGAGCTGCC GGCTCGTCCC   53460
GGTGATGCCT GCAGGACGTG ACTCTGGGAC GGGGGGTTGG GCAGATGTGC TGATGGAAAT   53520
TCTCAACCAG GCGTCATTTC CGAGGTCCTC ACCTGGATTT CCAGGACAGG AGTGCCTGCT   53580
GGGTGTCCCC AGTCCCATGC AGCGGGGGTC CTTGGGATAG CATGGAACGC TGAGCATGGG   53640
CCTGGCCGGC CGTGGTCCTG GACAAGGGCA GTGCCCCGGT GGCTGCTGGG CCTGGGACCT   53700
GGTGGGGACG CTGGGCCTGG TACCTGGTGG GGATGCTGGG CCTGGGACCT GGTGGGGAGG   53760
CCTCTGACTG CCTCCTGGTG CTGCTTCCGT CTGTGTTAGG CCTCTGGGTA TTGGGGCCCC   53820
CATCTGTCTC CTCCTCCAGG CCTGTGGACT CAGACCAGGA AGACACAGGC CAGCCCCTGC   53880
CTGTCCCCCT TGGCTTGGGC TCTCACTGCC CGACCTGGCG GGAGGTTGCC TAGCCGTGAA   53940
CCTTCGCACC CTGTCTGCCA CCGGACAGGC TGTGAGGGGG TGTCTGCAGC ACCTGCACCG   54000
GCCTGAGCAT CTTCAGAGTG GGCTGCAGCT CCTGGAGGGG TCTGAGAGGA AGGGAGGCAG   54060
GTATTTTGGG CGAATGAGGA GACAGCTGGA GAGCTGGCAC CCTTCCTGGC CTGCGTCCTG   54120
TGAGGACTCT GGTTGGGGAC AGCAAGCTTG GGGTCAGCCT GGGGCAGAGC CTCTGGGACG   54180
GCCCCGCCCC TCGTGCCCCT TCCCCTCGCA GCTCCTGTCC TCGCCCCGCC CTCAGCTCTC   54240
CGCCAGGCAA GGTTTGGCAA GTGCCGCTGT GCGGCAGTGC CTGCTGATTG GCTGGTCTGT   54300
TGCTATGGTG CTGCCCAGGG GTGTGCTTTT CCTCCCCTGC CTTCCCTGCT ATCCCTGGGA   54360
GTATCTGGGG TTGGGTCATC GCTGGTGTGT GTGAGTGTGT GTGTGTGTGT ATGTGCACGT   54420
GTGCATATGT GTGCGCTTCT GGCCTCTGCA GCTGAGTCCT GGCCCTCGGG GGGCCTGGCA   54480
CCTCCTGGGG ACAGGCACAA AGCAGCCATG ATGGAGTCGG GAGCTGGGGG AGGCCCCATT   54540
GCCCCACGTG GCTGCCCTGT GACTCTGGGG TGCTTGTTAG AAGAGGTATC TGGTTCTGTC   54600
TGTGTTTAAG CAACTCCCTA AGGAATTCTT GTGGTTCCAG TTTGGGGGGC CTGTACTGTA   54660
GAGGCAAGGG AGGGGCAGGA CATCCCCCAG ACTCTGACTT CTGAAGCCTT TTCTGCCCGG   54720
GGCCTCTCCG CCAGTACAGG CAGTGTCCTT TGCCAGGGCT GCCATGCTGC AGAGGGGAGT   54780
GGGCCACTGT TTAGCCCAGG AAAACCTGGC TCTCCCTTAG CTGGAAGTTC TGGGCCTGTT   54840
GTGGTTGGCA GGGAAGCTGA GTGACGGTGC TAATCACAGG GGCACCTGCA GGGGTTTGTG   54900
GGAGATGCCT CTGTGGGTTG GGGCGATAGG CTGAGGGGCT GTTCTTCCCT GCCCTGAGGA   54960
GGGCTGAGTG TAGCCGCCAC TCCTGTCCTG TCTTGGGCTG TCTCGGAGAG GATGCGTAGA   55020
ACCCTCGGGA TCCTGCTGGC CTCCGTCTGG TCCACCCTGA ACCTCAGGCC TTCTGGGGGC   55080
AGAGGAGGAT TCCCTCAGGA TCACTCGGGT GGGGGCCTCT CTTGGGCACC TGAGACCCTC   55140
AGTGGGTGCT TTGTGGCGCG TTCACGGTTG GTGGGGGACG CCCAGCCCTG CCCGCCGTGT   55200
AGGAGCCGTT CTGTCCTGGG CATCCCCCTG TGGTCTGGGA CTTAGTGGAC CCTGAGGGTG   55260
TGTGTTTACC CCTGCCTCAC ACCTGCAGAA AAAAGCCTGG AGCAGGAGCT GGCCAGCCCC   55320
ATCCTGGACA TTGAGGACTT GGTCAAGAGC GGAAGCAAGC ACAGGTGAGA CCCCTCAGTG   55380
AGGCCACGAC CACTGTCCTT CCATGGCCCA GCTCTCCTGT GACCTGTGGA GGCCCGGATA   55440
TATTTCTTCA CTTTTCTTTG TTCCTTTTTA AATTATGAAA CTAACCACCA TTCAGTACGA   55500
```

-continued

AAAAGTTTAA GCAGCTCTGA GGAAGATAGA GTAAAAAATT GTCTCCCTCT TCCCTGGCCC 55560

TCAGCCATCC CCGGTGGCCA CCGTGGAGTG TGGACGGAGC CCTGCAGGCC TGTGTCTGTG 55620

CGGAAGCACG CGCAGTTTTG TCTGCACAGA CTGTCCTGCA GTTGGCTGTT TTCACTCAGC 55680

GTTGTGGGTA TAGCTTCCCA TGCTGGTGCT GGCAGCTCGG CCTTGTTCTT TTGAGGACAG 55740

CAGATGTCTC CTATGTCTAC CTCTTACAGC TTCAGAGATT CAAGTTATAA TAAAGCTCTT 55800

CTTATATTGA GGGGGAAACC TCCCTCCCCC TTTTTTTTGA AACAGGGTCT CGCTCTGCTA 55860

CCCAGGCTGC AGTGCAGTGT CACAGTCTTG GCTCACTCCA GCCTCAGCCT CCCAGGCTCA 55920

AGCGATTTTC CCACCTCAGC CTCCCAAGTA GCCGGGACTG CAGGCACGCA CCACCATGCC 55980

TGGTTAATTT TTGTATTTTT TGTACAGACA GGGTCTCACT CTGTTGCTCA GGCCAGTCTC 56040

CTCAGCTCGA GAGTTCCACC TGCCTTGGCC TCCCAAAGTG CTGGGATTAC AGGCGTGAGA 56100

CCCCATGCCT GGCCAGCTCT TTTTTTTTTT TTTTTTTTTT TTGAGACGGA GTCTCGCTCT 56160

GTCGCCCAGG CTGGAGTGCA GTGGTGCGAT CTCGGCTCAC TGCAAGCTCC GCCTCCCGAG 56220

TTCACGCCAT TCTCCTGCCT CAGCCTCCCG AGTAGCTGGG ACTACAGGTG CCCGCCACCA 56280

CGTCTGGCTA ATTTTCTGTA TTTTTAGTAG AGACGGGGTT TCACCGTGTT AGCCAGGATG 56340

GTCTCGATCT TCTGACCTTG TGATCCGCCC ACCTCGGCCT CCCAAAGTGC TGGGATTACA 56400

GGAGTGAGCC ACCGCGCCCG GCCCAGCTCT GCTTTTTCTT AGTGGTTCTG CCTTGTGTTT 56460

GTTTCTATCC AGGAATAGGG TTGGTTTTAC TTTTCCATCG AGTTTTTAAA GAGACGACGA 56520

TTTACATGGT CGGAAACTCA CGAGGACTCC CCATCCCTTG GTCGGAAACT CACATGGACT 56580

CCCCATCCCT TGGTCAGAAA CTCACGTGGA CTCCCATCCA TCCCACGCAG CAGCTTCCCA 56640

CCTGGGCCCT ACGTGCAGGA TGAGGGCTCC TTCCGGGTCA GAAGACATGG CGGCCTCGGG 56700

GCACCGTCCC CTGCATGGGG TGCTCACAGG ATCTTCTCCT CTCTCCTTCC CAGGGTGTGC 56760

CCTTACTACC TGTCCCGGAA CCTGAAGCAG CAAGCCGACA TCATATTCAT GCCGTACAAT 56820

TACTTGTTGG ATGCCAAGGT GGGGGCTCAG TCCTGTAGCT GACGACTCCT GATGTCCAGG 56880

GGTGTCCCTG GGCTTGGGAA CAGCTGTCCG AGCCTTTGCT GCTTCAGGGC CTTAGATCAG 56940

CAGGCCTGGG TGGGAGGACT CACCTCTGTC ACTGGGCAGG GGCTCAACCT GGCCAGACAC 57000

ACTTGTGAGC AGCCCCAGGC CACAGGTCAG TTTTCTGAGC AGTCTGGGAG CGGGCAGGCT 57060

GGTGGGAGTG AGGAGAGACC TCCAGGCTGT GGTCCATAGG CCAGTGCCCG CTCTTGATCC 57120

TGACAGCTCA GGTTCTCTCC TTCACGTCAG GCCATGGGAG GCACCGAGAA CACAGGAAGC 57180

CCACTGACTC CCCTCTTCCC AGCGCGTGCC CGGCCCCACA CTCACTCCCC CTCCCAGCAT 57240

GTGCCCGGCT TCACACTCAC TCCCCTCTTC CCAGTGCATG CCCGGCCCCA CACTCACTCC 57300

CCCCACAGCA TGTGCCCGGC CTGACACTCA CTCCCCTCCT CCCAGTGTGT GCCCAGCCCC 57360

ACTCCCTTCC GCCCCGTGTG CCCAGCCCCA CGCTCACTCC CCCCGCCAGC ATGTGCCCGG 57420

CCCCACACTC AACTCCCCTC CTCCCAGTGT GTGCCCGGCC CTGCTGCCCT CCTCCCCATG 57480

TGCCCTGCTT TTGTGCCCCA CACTTTTTAC TTAGTGCAGG TGGGATCACA CGCCACGGGT 57540

CAATGGTTTG TGTGTTCACG TGACGATGGC GTGGTGACGT TTCCAGATCC CGTCGTTGGT 57600

TCGCTCATTC TCGGGGTGTA TATTTATTGA GAGCTCATCA TGCTGGGTGC TATTCCAGGC 57660

ATAGCAAGAC TGGCTTCACT CACATGGAGC TTTGATTCTA GTGGTGGGGA CAGGTGGACA 57720

GCAAAAGAGT AAGCACGTGA GCTGACGATA CTGAAGGGAA ATAGAGCAGA GGGAGGAGGC 57780

GGAGACCGAG CCAAGCGGGC CCAAGTGCGA TGTCGGCGGG AGGTGGGGAA TGCTGGTGGG 57840

TCTGAGGGGA GCCTCAGCAG GTGCAGCAGA GCAAGGGAAG AGGTGAGTGG GGGCGGCTGG 57900

-continued

GGGGCCGACT CCTGGGAAGC TGTAGCAGAA CCCCACAGAG AGCTGGTGAG GTTTGCCGTG 57960

GTTGTGGGTG ACTCGGTGCT TTGAGCCCTG GCTGCCCCTG GGAACCATCT GGAGAGCTTC 58020

TAACCCAACC AGGCCCCTCC CTGGGACAGT TATATCACAG CTGGTAAGCC GAGTCTAACA 58080

CTTTCACGGA AACGCAGAAC ATCTAAAACA GCAAGATGAC CGTGAAGAAG AACAGAGCTG 58140

GAGGACTCAC CTCGCTGGTT TCAAGACTCC TCTAAAGCTG CAGGAGTGGA GGTGGAGATG 58200

GCCCAGCTCA GGCACAGGCC TGCAGGCCAT GGAGAAGGCA GCAAGCTCAA GCTGACCCAC 58260

ACGCATGTGG TCATTGTTTT TTTTTTCAGT TGGAATCTCA CTCTGTCACC CAGGTTGGAG 58320

TGCAGTGGCA CCATCTCGGC TCACTGCAGC CCCCGCCCCT AGGTTCTAGC GATTCTCCCA 58380

CATCAGCCTC CCGAGTAGCT GGGATTACAG GCGTGCGCCA CCATGCCTGG CCCTTGGTGA 58440

TTGTTTTTTG ACAAACATGC CAATTTAATT GAGAGAGGAA ATGAAGGTTG ATTTCTGGTT 58500

TTCTGAAAAA ATGGTGCTAA GAACAGCTGG ATATCTGTTC GGAAAACAGT GAATCTTAAC 58560

TCTTGTTTTA CCCTGTATAA ACCTAAATGT AAAAGCTAAA CTAAAAGTTA TAGAAAGGAA 58620

CATGGGGGAG GTCTTTGCAA CTTTGGGGTA GGCAGAGATT TCTTAGTATG GATACACAAG 58680

GCACTAGCCA TGAAGAAAAA CATTAAAATT TAGACTTCAC CAAAATTTAA AGCTTCAACT 58740

CTGTGGAAGA GTTGAGAAAA TGAAAAAGCA GTTAAAGAAA GGGAGAAAAT ACTTCTTTCA 58800

AAGGACTTAA AAAATTTTTT CAGCCCTCCT CTGATTTGAA AGGACCTTTG ACCAGAGTAT 58860

GTAAAATTCT CCCATAACTA AGCAAACAAC CCACTTAACC ACTGGGAAGG GATCTGGACA 58920

GACGTTTCAC CAAGATGGGT GGAATGGCCA GTTAACCACT GGGAGAGCAT CCGGACAGAC 58980

GTTTCGCCAA GATGGGTGGA ATGGCCAGTT AACCACTGGG AGAGCATCCG GACAGACGTT 59040

TCGCCAAGAT GGGTGGAATG GCCAGTTAAC CACTGGGAGA GCATCCGGAC AGACGTTTCG 59100

CCAAGATGGG TGGAATGGCC AGTTAACCAC TGGGAGAGCA TCCGGACAGA CGTTTCGCCA 59160

AGATGGGTGG AATGGCCAGT TAACCACTGG GAGAGCATCC GGACAGACGT TTCGCCAAGA 59220

TGGGTGGAAT GGCCAGTTAA CCACTGGGAG AGCATCCGGA CAGACGTTTC GCCAAGATGG 59280

GTGGAATGGC CAGTTAACCA CTGGGAGAGC ATCCGGACAG ACGTTTCGCC AAGATGGGTG 59340

GAATGGCCAG TTAACCACTG GGAGAGCATC CGGACAGACG TTTCGCCAAG ATGGGTGGAA 59400

TGGCCAGTTA ACCACTGGGA GAGCATCCGG ACACACGTTT CGCCAAGATG GGTGGAATGG 59460

CCAGTTAACC ACTGGGAGAG CATCCGGACA GACGTTTCGC CAAGATGGGT GGAATGGCCA 59520

GTTAACCACT GGGAGAGCAT CCGGACAGAC GTTTCACCAA GGTGGATGCA ATGACCAGTT 59580

GAGCACATGG AAAGTCGCCC AGCATCTCCA GTCATAGGAG AAGGCAGATT AAAGCCACGG 59640

GGAGCCGACA CTGTGGTCCC ACTGGCATGG CTGAAATTCA GAAGCCCTGA GTGTGGCATG 59700

AGGATGTGGA ACAGCTGGAT CTCATCCATC GCTGTGAAGT TGTCTAGCCA CTCCACAAAC 59760

GTGTGGCAAA CAGCCGAGCC GGGAGAAGGG AAGACGTGTT CAAAGATTCA TATGTGGCCA 59820

GGCTCAGTGG CTCACGCCTG TAATCCCAGA ACTTTAGGGG CCAAGGCTGG GGGATCGCTT 59880

AAGCCCAGGA GTTTGAGACC AGCCTAGGCA ACATACGGAG ACCCCATCTC AAAAAAAAAA 59940

AAAAAGAAAA AAGAAAAGAC TTCAGTGTGC AGGTTTACCA GAGTTTTGTT TGCAGTTGCC 60000

AAAACTGGGA AGCAGCCCGC GTGAGCCCAT CCACAGGTGA ATGGACAGAC CGTGGTACCC 60060

GAACACTAAC AGCAGCCACG GGCGTGGACT GTGGTCACAC AGCAGCAGGG AGCCGATGAG 60120

TCTCGGACAT GCTAACCCAG AGAGGCCCAT TGAGGAGGAC CTACTGTTTT TTGTGTTTTT 60180

GTTTTTTGTT TTGAAATGGA GTCTCGCTCT GTGGTGCAGG CTGGAGTGCA GTGGTGTGGT 60240

CTTGGCTCAC TGCAGCTTCC GCCTCTTGGG TTCAAACAGT TCTCCTGCCT CAGCCTTCCG 60300

-continued

```
AGTAGCTGGG ACTACAGGCA CCCGCCACCA CACCCGGCTA ATTTTTGTAT TTTCAGTAGA   60360
GACGGCAGTT CGCCATGTTG GCCAGGCTGG TCCCAAACTC CTGACCTTGT CATCCACTCA   60420
CTTTGGCCTC CCAAAGTGCT GAGGTTGCAG GCATGAACCA CCGCACCCGG CTGGACCTAC   60480
TGTTTTATTC CATTTATGTG ACACTCTATT AATAGAAAAG GCAGGGGTGG GGCTGGTGGT   60540
TATATGGTGC ACATAACTGC CAGAACTCAG TACACTTAAA ATGAACATCT TAATGTGTGA   60600
AATTTTTTTT TTTGAGACGG GGTCTTGCTC TGTCACCCAG GCTAGAGTGC AGTGGTGCGA   60660
TCTCCACTCA CTGCAAGCTC TGCCTCCTGG GTTCACGCCA TTCTCCTGCC TCAGCCTCCC   60720
GAGTAGCTGG GACTACAGGC GCCCGCCACC ACGCCTGGCT AATTTTTTTT TTTTTTTTGT   60780
ATTTTTAGTA GAGACGGGGT TTCACAGTGT TCGCCAGGCT GGTCTCGATC TCCTGACCTC   60840
GTGATCCGCC TGCCTCGGCC TCCGAAAGTG CTGGGCTTGC AGGCGTGAGC CACCATGCCC   60900
GGCCAATGTG TGAAAATTTA AAAGTACCAA AGCTGGACCC CACCCCAGAT TGCTCCCATG   60960
ACACTCTGTG GGTGGGACCT GGGAGTTGGG TTTTGTTTTG TTTTGTTTTG TTTTTGAGAT   61020
GAAGTCTCAC TCTGTCGCCT AGGCTGGAGT GCAGTGACAC AATCTCGGCT CACATTAACC   61080
TCTGCCTCCC AGATGAAAGC GATTCTCCTG CCTCAGCCTT CTGAGTAGCT GGGATTACAG   61140
GCACACACCA CCACCCCCTG CTAATTTTTG TATTTTTAGT AGAGACGGGG TTTTACCATG   61200
TTGGCCAGGC TGGTCTTGAA CTCCTGACCT CGTCATCCGC CCGCCTCGGC CTCCCAAAGT   61260
GCTGGGATTA CAGGCGTGAG CCACCGCGCC TGGCTGGGAG TTGGGTTTGT AAATCTCCCT   61320
GAGTGGGGCT GGGGCAGGGA ACTGCTGGGT CTGGGTCTTC CTGGCTCCTC TGGTCTGTGG   61380
CTTCCTGACT GCGGTGGCCG GGGGCTCCCA GGGCATCGTG GCCGTCTGTC TTGCTGAGCG   61440
TGGCACGTGC CTTTCCATGC TGTGGAGGAG CGTCTCCCGG TATGGCGAAC TGCTGGTTAG   61500
GGTGGGGCGG TGTTGCCAGG TCATCCAGGT CTGGCCTCTG CTCTCGACAT CGCCGGCGCT   61560
GTTGCTCATC TGCGCTTGTG ATGTTCGATG CCTGCTGCAC ATGTCTTGGC TTCCCTCTTT   61620
CCCGGCCTCT GTGAGCTCCA GCGCTGCGTC CCTTCTCTTC CTCCTGTAGA GCCGCAGAGC   61680
ACACAACATT GACCTGAAGG GGACAGTCGT GATCTTTGAC GAAGCTCACA ACGTGGTGAG   61740
TCTCCGCTGG CCTCCTAAAC ACCTCCTATT GCTTCTGGCC TTTTTGTCAA GAGCCACGCA   61800
AACCTTTCTG GAGGGGCTCT GGCCAAACTC CTGAAGCCCT AGGTGCCCAG GACTGGGGAC   61860
TGAGCACACC AGGAGCTTCT GCCACCCCCT CCCGCCCTGA TCCGATGCCT CTGCTGGGGC   61920
TGGAGACTGG CCAGCTGGGC CAGGGACCTG CCCGTCAGGC GCAGGGCCCC CACAGGCCGC   61980
TCACCAGACC CTTTCCCTCC AGCCAGCTCG GGGTCAGCCT GGGCCAGGGC TGTCTCCTCT   62040
GCCCTCGGCA GCAGCAGGCT TGTGGTCTTG CCTGCAGTGT CTCTGCCCTT CCGGCCACAT   62100
GGCTTGAGAC TGAGGCAGGA GAATCGCTTG AACCTTGGAG GCAGAGGCTG CAGTGAGCCA   62160
GGATCACACC ACTGCATTCC AGCCTGGGTG ACAAAGCGGG ATTCTGTGTC AAAAAAAAAA   62220
ATGTTGACTG GGCGCGCTAG CTCATGCCTA TAATCCCAGC ACTTTGGGAG GCTGAGGTGG   62280
GCGGATCACG AGGTCAAGAG ATCAAGACCA TCCTGGCCAA CATAGTGAAA CACCGTCTCT   62340
ACTAAAAATA CAAAAAAATT AGCTGGGCGT GGTGGCGTGT GCCTATAGTC CCAGCTACTC   62400
AGGAGGCTGA GGCAGGAGAA TCACTCGAAC CCAGGAGGTA GAGGTTGCAA TGAGCCAAGA   62460
TCACACCACT GTACTCCAGC CTGGTGACAG AGCAAGACTC CGTCTCAAAA AAAATAAAAT   62520
CAAAAAGAAT AATTGGCAAT TCCAGTGAAA TAATTGTTTG TTTGTTTGTT GAGACAGGGT   62580
CTCCTTCTGT CGTCCAGGCT GGAGTTCAGT GGTATGATCT TGGCCCACTG CAACCTCCAC   62640
CTCCTGGGCT CAAGCCATCC TCCCACCTCA GCCTCCCGAG TAGCCGGGAC TACAGGTGCA   62700
```

-continued

```
CACCACCACG CCCGGCTAAT TTTTGTATTT TTTGTAGAGG CGGGGTTTCC CAGCGTTGCC   62760
CAGGCTGGTC TTGAACCCCT GAGCTCAAGT GATCTGCCCA CCTTGGCCTC CCAAAGTGCT   62820
GGGATTACAG GTGTGAGCCA CCGCGCCCGG CCTGAAACAA TCGTTTCTAA ATATTGGTGT   62880
GGGCCACACA GTCATGTTTG GACCTACTTG TGGCCTTTTA CAGACCCCAG GCCAAGGCTT   62940
TGGGAACTTG GCTGTCAGCC TCCTGTGCCT TCTGCACCCC CACCCCATTT CTGCTTTCTG   63000
GAACCCCCGA TCCTGTCCTG TTCTGTGGTG ATTCGGGTGT GCTTGGGCTC TAGGAGAAGA   63060
TGTGTGAAGA ATCGGCATCC TTTGACCTGA CTCCCCATGA CCTGGCTTCA GGACTGGACG   63120
TCATAGACCA GGTGCTGGAG GAGCAGACCA AGGCAGCGCA GCAGGGTGAG CCCCACCCGG   63180
AGTTCAGCGC GGACTCCCCC AGCCCAGGTG CGTTCATAGC CAGACTGCTT GGTCCTGAGG   63240
CCTGCGCTGC TGCAGGGTGA GCCCCACCCG GAGTTCAGCA CGGACTCCCC CAGCCCAGGT   63300
GCGTTCATAG CCAGGCTGCT TGGTCCTGAG GCCCGTGCTA CTGCAGTGGG CAGCCTGCCC   63360
TGTGGCTGTG TGTGGTCGGC CTGGGCACCA TCTATTCAGG CTGGCACTGC AGGGCATCCG   63420
CTTCTCTCAG AGGCTTCTTG GGTGTGAATT CTTCAGGCTC CTGTAGCCTG TGGAAGGGCT   63480
GGTATTGTTC AGTAGTTCTG GTATTTTCCA AAGACCTATG TCTTCTCCCA GCCAGTATCA   63540
ACTTGGCCTC TACTGTGTAA AACTGGAAAA CTCTACTTTG TGAAGCTGAG TTGGGAGCAT   63600
CGCTTGAGGC CAGGAGTTTG AGACCAGCCT GGGCAACATG GCGGAACCTC GCCCCTGCCA   63660
AAAAATTAGC CAGGTGTGGT GGTGTGCTCC TGTGGTCCAA GCTTTTCTGG AGGCCGAAGT   63720
GGGAGGCGTG CTTGAGCCTG GGAGGCAGAG CTTCCGGTGC CCCAGATGAC TCCACTGCAC   63780
TCCAGCCTGG GCGGCAGAGT GAGGCCATCT CAAAAAAAAA AAAAAGGAAA ACTAAATATA   63840
TTCACTCTAA GGGCATTTTG CATCTTTAAA TGACCCACAA ATCTGGCATG CATCAGCTGC   63900
TCTGCCTGTA GGTTCCTTCC CAGTGTTTGT CCAGAGGTGT ATTTCCACAC AGCGCTAGTC   63960
ACGGCATATG TGGAAAACGT GGAAACCCTT CATGGATGTT GTCAGTTGCT CTATATTTTC   64020
TTTCTTTTTT TTTTTTTTGA GATGGAGTTT CACTTTTGTT GCCCAGGCTG GAGTGCAATG   64080
GCGCGATCTT GGCTCACTGC AACCTCCGCC TCCTGGGTTC AAGCAATTCT CCTGCCTCAG   64140
CCTCCCAAGT AGCTGGGATC ACAGGCGTGC ACCACCACGC CCAGCTAATT TTGTATTTTT   64200
AGTAGAGATG GTTTCTCCGT GTTGGCCAGG CTGGTCTCGA ACTCCTGACC TCACGTGATC   64260
CACCCGCTTC GGCCTCCCAA AGTGCTGGGA TTACAGGCGT GAGCCGCCAC GCCCGGCCTT   64320
TGTCCATATT TTCTACATGG CTTCTGTAAA CAGCTGACTA GGAGTCTGTG TGAATATCTT   64380
CATAGGTTCT GCTGTGACAC TACTTGCTCG TGAGCATCTC CAGGTGTAAA CAGCATCAGC   64440
TTCCCCCATT TTCCTTTAAA ATCGCACATG TGGACGGACA CCACGGGGAC CCTGGACCCT   64500
GGGGAGCCCC GTCCTCACCC TTCTCACCAG GATGGCTGCT TGGTAGAGAG TGAGTTTGCA   64560
AAGTTGGCAT TTGTTTAGTA CAGAAGTTAT CAGGTGTTCT GGCTTTAGAA TCCCTTTATA   64620
TATATATATA TATACATATA TTTAAGTGAC AGGGTCTCAC TCTGTTGCCC AGGCTGGAAT   64680
GTGGTGGTAC AATCAAAGTT CCCTGTAGCC TCGGCCTCCT GGGCTCATGG GATCTTCCCG   64740
TCTCAGCGTC TTAAAGCGCC GGGACCACAG GTGTGCACCA CTGCCACCGG CTCTCAAGAT   64800
TGCCACGCAG GGAGTTGCAG TGGGGGAAGG GGTTCCTGGG ACTTTGAACG CTCCACCTCC   64860
CTCCTCTCCA CAGTCCCCCA ACCCCACCTC TCTAACGGGG TGGACGGCCG CCTCTTTCCA   64920
TCCTTCGCTT GGCGCAGGGT GGGGAGAGTG ACAGGTCTCC TTCCCTCATC TCGGCAGCTG   64980
CCATTTCATC GCTTACATAA CGTGGGAGAA ACATCCACCC ACCCCCAGGC CTGTGTGAAC   65040
ATCACCACGG GGCCTTCTCC ACTCTTCAGT TTTGTTAGTT ACTTGATGTG CAGGGCTTTT   65100
```

-continued

```
TGTTGTAACT AGTGGGGGAC GTGTGGTGGG GTGGGCTTCT GCCATCTCAT TCAGGACCAG   65160
AACTTCAGTT TTCATCCCTA TCTGTTCCCC CACCCCTTTG GAGATGGGGT CTCACTCTGT   65220
CACCCAGGCT GGAGAGCGGT GGTGCCATCA CGGCTCACTG CAGCCTCCAC CTCCTGCAGC   65280
CTCCACCTCT TGGGCTCAAG TGATCCTCCT GCCTCGGCCT CCCAAGCTCC TGGGACTACA   65340
GGCGTGTGCC ACTGTGCTTG GCAGGGTCCA TTCTTTTCCT CACACTTTAT TTATTGAAGA   65400
GCCCAGGCCG TTTACCCTGC AGAGTCGGAA TCTGTACAGG AGGGGCAGCC ACACGAGTTC   65460
CCCGGTTTAC TCTGAACTTA GGTGGCTTGA GGGCCCCAGT TAGACTGCGG CCACCGTTTG   65520
CCGGGCTCCA GATGGGACGT CCTTTCTATC AGAAGGCTCA CAGTATCTCC TTTCCCGTTT   65580
CTTCCCATGT GAACATTGTT GCTGCTGAAC ACCTGAATAT GTTAATCACT GGGGGCTTGC   65640
AAGATGGCAG TGTGCTAATT CCATCATCTA GTCAGTTAGC AGGAATAACT TAGGACCACG   65700
CCCTGCACCA TATCAGCTAT GTGGTGATCC CATTCACACA GGAAAGGTGG GACAAATGCT   65760
GGGGGTGGGC CGGGTGTGCT GTCTCACACC TGTCATCCCA GCACTTTGGG AGGCCCAGGC   65820
AGGCGGATCA CGAGGTCAGA GATTGAGACC ATCCTGGCCA ACACGGTGAA ACCCCGTCTC   65880
TACTAAAAAT ACAAAAAAAT TAGCCAGGTG TGGTGGTGCA TGCTTGTAAT CCCAGCTACT   65940
TGGGAGGCTG AGGCAGGAGA ATCACTTGAA CCCAGGAGGC GGAGGTTGCA GTGAGCCGAG   66000
ATCGCACCAT TGCACTCCAG CCTGGCAACA GAGCGAGACT CCGTCTCAAA AATCAATCAG   66060
TCAATCAAGT GTCATCACTG AATGTTTGTG TGTGAACGTG GGGATTGGTC CTGCCCCATG   66120
CTCCCTCCTG AATCTCACTC CTGACCTCAG TTGCTGCACC TTGAGGTGTT TTCTGTGGGC   66180
TCTTGTGTCC TGACCCCGGC GGTTGTGGCC TCTGCTGTCT GGGAGTCAGG ATTTTTCACA   66240
CTCATGTCCT GCTCCAGACC TGGAATCAGC CAAGTCTCCA AGAAGCCCTG CTTTCTTTTC   66300
CTGCAAGACG GTATTTCAAG ACCCGCCGTG CGGCAGCGGG TTGGTCATGG TTACTGGGTT   66360
GGTCGTTGTG ACTGGGTGTT TTCGTGGAGA TACAGCCATA CGCACAGGTG TGTTCACAAA   66420
TGTTAATTCT AAAGGTCAAA CACCCGGCCA GGCATAAGGG CTCAGCGGTA ATCCCAGCAC   66480
TTTGGGAGAC CAAGACTGGT GGATCACCTG AGGTCAGGAG TTTAAGACCA GCCTGAGCAA   66540
CAGGGTGAAA CCCCATCTCT ACTAAAAATG CGAAAATTAG CCGGGCATGG TGGCGCACAC   66600
CTATAGTCCC AGCTAGTCGG GAGACAGACA CGAGAATTGC TTGAACCTGG GACATGGAGG   66660
TTGCAGTGAG CAGAGATGGC GCTGCTGCAC CCCTGCCTGG GTGACAGAGT GACACCCTGT   66720
CTCAAAAATG AATAGATAAA TAAAGATAAA ACACCTGCTC CTCTTGGTGT CTCCAGTTTG   66780
GATTTGGCCT GTGTAGCCTC TTCCTTCGCC TGTTGGTGGA TTTGGCCTGC ACGGATTCTG   66840
TGTGGCCTCT TCCTTCCCCT GTTGGTGGAT TTGGCCTGCA CGGATTCTGT GTGGCCTCTT   66900
CCTTCCCCTG TTGGTGGATT TGGCCTGCAC GGATTCTGTG TGGCCTCTTC CTTCCCCTGT   66960
TGGTGGATTT GGCCTGCACG GATTCTGTGT GGCCTCTTCC TTCCCCTGTT GGTGGATTTG   67020
GCCTGCACGG ATTCTGTGTG GCCTCTTCCT TCCCCTGTTG GTGGATTTGG CCTGCACGGA   67080
TTCTGTGTGG CCTCTTCCTT CCCATGTTGG TGGATTTGGC CTGCATGGAT TCTGTGTGGC   67140
CTCTTCCTTT CCATGTTGGT GTCCTTTTTT CCATGCCAGG AATCCTGGTT CTCAAGGGCG   67200
GGGTTGTTGG CACGAGCGTG ATGCAGACTG CCTTTGCTGC CTTTCTCTTG CCCAGGGCTG   67260
AACATGGAGC TGGAAGACAT TGCAAAGCTG AAGAGTAAGT GTTGCCCTCC CCGCCTCCTT   67320
GCAGCTGGGT GGGGCCTCCT CCTTGCGAGG AGGTGGGTGA CACCTCCTCG ACCCACAGTG   67380
ATCCTGCTGC GCCTGGAGGG GGCCATCGAT GCTGTTGAGC TGCCTGGAGA CGACAGCGGT   67440
GTCACCAAGC CAGGGAGGTG AGAGGCGGGG AGCCAGCCCC TTCACTGCAG GCCCAGCCTA   67500
```

-continued

GAGCTAGAAA CGGGCCATGG TGCAGTCCTG GGCTGTCACA TCACGAGTGA GGCCTGTTTT 67560

CAGGCCTGTT TTCCCTTTTT GAGACCTGGG AGGAGCACCT GCTTTGCATG ATCTGGTTGC 67620

TGAGATGTTG AGAGGAGCAG CACACACTCC CACGGGACAG CACACAGCCC CCCACGGAAC 67680

GGCACACACA CCCATGGAAC AGCACACACA CTCCCACGAA CAGCACACAC ACTCCCACGA 67740

ACAGCACACA CACTCCCACG GAACAGCACA CACACCCACG GAACGGCACA CACACCCACG 67800

GAACAGCACA CACACTCCCA CGGAACAGCA CACACACCCA CGGAACGGCA CACACTCCCA 67860

CGGAACAGCA CACTCTCCCA CGGAACAGCA CACTCTCCCA CGGAACAGCA CACACACTCC 67920

CACGGAACAG CACACACACC CACGGAACGG CACACACTCC CACGGAACAG CAGACTCTCC 67980

CACGGAACAG CACACACACT CCCACAGACA GCACACACAC ACCCACGGAA CAGCACACTC 68040

TCCCACGCGG GGCCGCTGGG TTTCCTGCAG TTTCTCCTCC TCCAGGCCTT TCCCTGGACC 68100

CTGGTCCACT CCGTCATTTG AGCACAGGTG CCTGTTAGAA CGAGACCTTC TTGTTAGGAC 68160

GATGAGTGTC CCACCCACCA CCTCTTTTGG ACTCCGGGAG GCCTGGAACG TTCTGAACGC 68220

TCCGTGGGGC TCCAGTCTTC TCCGCAGCCA GGGCAGCAGG GTTTGCTGTC TGTCCTGCAG 68280

GCAGATGAGG AGTCAGGGCT GGGGCCTGTG TGGGGGCTCT CCTGAGCGCG CAGCCGCCGA 68340

GGTGGAGCGT GTTCTGCCTG AGCGCCGACC TGGTCGGGGG AATCCCAGTT GCTTCCAGGT 68400

GGAGCCACTG TCCTCAGCGT AATGCTCAAG GCTCTGGCCT GGCTCCTCGG CCACCCTGCA 68460

CCCTCAGGGT CCCCTCCTGT AGCTTCTGCT GCCCCATCAC TGTCACTCTC CAAAGCTTTG 68520

GGGACTCTGC CCAGAGCCAC CGCCTCCCAG AAGCCCCTGA CAACCTCTTG ACGACCCCCT 68580

AGTGACCCCA TCCCTCCCCT CTGACGGCGG CCCCTGCTCT GAGGCGGCTT CTTTTCCTCG 68640

GTGCTGTTCT CGTGCTGGCC AGGCCTCCTC TCCCCACCTG GAGGCTCCTG AGGGCGGAGG 68700

CCTCTCACCT CCAATGCTGG CGTCCCCTGG AGGGCTGAAT TTGTTTCCGA GGGAAGGAAA 68760

CTTCCACAGT TGTTGCCTTC AGTTCCAAAG CTGCAGCCTG ATTTCCCCCT CCAGGCTCGA 68820

GCCTGTTTTC TTCTCGGCAG CTACATCTTT GACCAGTGTC GTCCCCCCTC AGGCCCGAGC 68880

CTGCCTTCTT CTCCTCAGTT CCCAAAGCTG CAGTCTGGTC CCCCCGCCAG GCTCGAGCCT 68940

GCCTTCTTCT CCTCGGCAGC TACATCTTTG AGCTGTTTGC TGAAGCCCAG ATCACGTTTC 69000

AGACCAAGGG CTGCATCCTG GACTCGCTGG ACCAGATCAT CCAGCACCTG GCAGGACGTG 69060

AGTGCTGGCA CGGGGTCTTT GGTGCGGGCA AATGTGGCGT AGGGGGTGCA GCAGGCCTCC 69120

ATCTTGGCAG TCAGGGCTCC CCTGGCCGTC ACCTGGCCGT CAGCAGGAAC AGGCCCACAG 69180

AACCTCATCT TCTGATCGGG GCGTGGAGGC GTTAGTGCCA CTTGCCAGCT GCCGTAGAGC 69240

CTGTCCCAGT TCTGCAGCTG GCGGCTTCGT CCTACAGCCT CATCCCATTA TTCTGCTTTT 69300

GAGAAAGAGC AGCCCAAGGC CCTAGCTGGC TTGTGGGGCC TCTGGCTTCT CCACACCACC 69360

CCGAGTTCTG CTTCTCAGAG TTGTGGGGTC CAGAGGCTTT GCCCAGAGGC GGTCTCCCCA 69420

TGGGCTGCTC TGGTTTGAGA CGCCGGGCCC AGCGGGGTCT CTCCTCTGCT GCGCTCCCGG 69480

GTGCTGGGGA GGGTGGCTTT TGCTGCTTCA ACCCTTAGGC GACCATAGAG CCTCTTTTCA 69540

AGTCCCACTG ACCCCCTTGG AGACTCTGTC CCTGCCTGGC TTCTCTCCTG GCTGCTGGGA 69600

AGAGCAGGCG AACTGCCCGC CCTGAATGGA TGCTGCGCTC CACCCTGGGC CCCCCATTGG 69660

GCAGGAGATG GAGCTTGGCA GTCGGGCTGA GCGGGCTCAT GCTGGAAGGG CCGGGGCTGG 69720

GGTCGGGGCC TCCCCTGCCT GCAGTGTGGG TGTCAGCGCC CTGCTGCCCT CCAGGTGCTG 69780

GAGTGTTCAC CAACACGGCC GGACTGCAGA AGCTGGCGGA CATTATCCAG GTGGGGCCTG 69840

CTCCTCTGTG GCATCTCCTT CCCTGATGGA AGCCGGGCGG GTGCCTTCTC CTGCTGTATT 69900

-continued

```
AGTTAACTGA TTCTAGACTT GGGGATGGGA GAAAGGCCCC TACACCACCT GTTTCTGATT   69960
GGCAAACTCT CGGCTCCTTT CCAGTGCCCT AAACCCACAC TGGGCCTCCT GCAGGGATGG   70020
GGGAGGACGA GGTCTGGTGG CACATGCCCA GGGTGATGCT GGTGAGGGAG GACGCAAAGG   70080
ACAGTGGGGG CCGGGGAGCC GCTCCTGCCC TGTCCGGGCC CTCAGGCCAG GGGGGACCCA   70140
CTGCTGGCAG CCCCAGCAGC CCCAGCTGCA CGCAGATGAA GAGCTCTGGA CACACGCGGC   70200
TTCCTGAACA GCTTCTCCAG GGACAGACAA ATGGGGACCC TGCAGGTTCC CGGCAGGGGT   70260
GTCCCTGGGA GCCCATGATT GGGGGTGCGA CCCTGGCCCC CTTCTCATTG GCCCCGTCCT   70320
GTCCTGCAAT GCCCGTCCCA TGTGAGGTCT GCTTCTGGCT CCATGCCTAT GGCAGCACCT   70380
GCTTTCCCTG GCGTAGAGGT GCTTGTCCGG TTTGTGGAGG GCACGCCCCA TTTTGGGTGC   70440
TCTGGGCACG TTGCCTCTCC GGGGCCTCGG TGGCTTTTTT AGAAGCAGAC TCAGAAGTCC   70500
CTGACTGGGG AAGCCAAGGC ACAGGTGGCT GTGTGGAGCC CTGTGAGCCC TCCTCTGTGC   70560
TGCCCACGCT GTACCTGCTG GCCACACGAG ATCATGGCAG GGTTAGGCAG GGCTGCCCAG   70620
CGCTATGACA GCTTCATGAG TGTCCATCTG GCCTGTGGGG TGCTTGAGCT GGGGGAGGCC   70680
GCAGAAGAAC CCTGGGATGC ATGGCTGGCC TGTGCATGCT GCTGGGCATG GAGCTGCAGA   70740
TCCCGGAACA AGCAGGCACT GCCTTCTCCT TCACAGACGC AGCTCTGAGC GGGGGCGAGA   70800
CCTGGGCAGG GACCAGGTGG GGTGGGCACA GGGTGGTGGG GCCCAGGCTC AGCCCTCCCT   70860
CCACTGTGGC CGTCTCTGTG GCCAGTGACG CCACAGCCTG TGTCTTCTCT GTGCGGTAGC   70920
TGGGGCTGGA AGGACAGCAC TGCCTTGTCC TCCCAACTCC TCCCCAAAGG CACGGTGGGC   70980
ATCCCAGGCC CAGACCCCTC TGTCTGTGGC TCCTGCCTGC CAAGGGCTGC TGTGCTGTCC   71040
CGCATGGAGT GTGGTTGGCT CTTCAAGCAG GAGGCCGTGC ACCTATCAGG CGGACCTGCT   71100
TCCATGTCCC TGATGGGTCA CTGCAAAGCA CCTCCAGCAC ATGGCCAGGC GAGGTAGCCC   71160
TGCAGCCCAG GGCCTGGAGG GCAGGTGTGA GCTGGCCCGG GCCTGTCCCT CCCTGGAATA   71220
CAGCTTCCCA GGCTCCCACT TATGGAGAAG TCTCCTCCAC ACTATGGAAC TGAATCCTAG   71280
AATGTGGCTT CTGAGGTTCC TACACTCGAA CTGAATCCTG GAATGCGGCT TCCAAGGCTT   71340
CCAGCTATGG AGAAGACTCC ACACTCTGGA ACCGAATCCT GGAACGCGGC CTCCCAGGCC   71400
CCCAGCTATG GAGAAGACTC CACACTCTGG AACCGAATCC TGGAACGCGG CCTCCCAGGC   71460
CCCCAGCTAT GGAGAAGACT CCACACTCTG GAACCGGATC CTGGAACGCG GCCTCCCAGC   71520
CTCCCACTTA AGGAGAAGTC TCCACACTCT GGAACCGGAT CCTGGAACGT GGCCTCCCAG   71580
GCCCCCACTT AAGGAGAAGA CTCCACACTC TGGAACCGAA TCCTGCACAC TCCATCGGTT   71640
TGGAATTTCC TTTGGCTGCT GCTCTAAGTA GCCGCTGGTG GATGACTCAG CTTCTGCCAG   71700
CCCTCGGGTG CCTGGAGGAT GAGGGACTGC ACACAGTGCT CACCCGCGTT GGCTCCTGAG   71760
CCCCTGCAGG TGTGGGCGGT GCCCATAGGG CTGGTGCTGG GTTGGGCCTG CAGCCCTGAG   71820
TCACAGGTGA CCCTGGGGGC AGAGTGGGGC CAGTGGCCCC AGGAAGAGGA TGTGGGATGC   71880
ACAGCTCAGC TGGAGGCGAA CTCCAGGCAG GGTCAGGCCG TGTGCTCGGA AGTCAGGGCT   71940
TAGCTGGAGG CAAACTCTGG GCAGTGCTGG CCCGTGTTCG GGAACCAGTT GCCCCTGGGC   72000
CCCCGTGAGA CTGCTGGGTC CTCATCCCTC TCTGCCTGAG GCCGGAGCTG CCCTGGGCTG   72060
AGGCACAGGG GGATTTGTGG TGCTGTTTTT TTGAGAAAGG GTCTCGCTTT GTCACCCCGG   72120
CTGGAGTGCA GGGGCTTGAT CACAGCTCAC TGCAGCCTCA ACCTCCTGGG CCCAAGTGAT   72180
CCTCTTGCCT CAGCCACCCG AGGAGCTGTG AACACAGGTG TGCACCACCG CACTCAGCTA   72240
ATTTTTAAAA TTTTTTTGTA GAGATGAGGT CTTGCCATGT TTCCCAGGCT GGTCTCAAAC   72300
```

-continued

TCCTGGGCTC AGGCAGTCTG CCCGCCTTGG CCTCCCAAAG TGCTGGGATT ACAGGCAAGA 72360

GCTTCCATGC CTGCCCAGCA GAAGGCTTTT CGAAGGAAGC TGTTTCCTGA GGCAGACTCA 72420

GCCCTGCTCA TGGCAGCCAC CAGCGTGGGG GTGAACTTCT TCTGTTACTT CCATCCCCGT 72480

GGGCCAAATG CTTTGGTAAA ACACAAGGCC CTGTGTTTAG CTGTCTTGAC AGTGAAAATG 72540

GCTGGGAAGG AAGGAAGGAA CGGAAGGAAA TTTCTCTCTC CTTCTGTGCG TACCCAGGCA 72600

CGTGCACATG CATGCAGAGT ACGCACACAC GCACGCACGC CTGCACAAAT CCACGCATGT 72660

TGCCAAGTCT CTGTGTTCCA GCCGTGGTGT CTGCCCCCCG GTGTTCTCTA GTTCGGCTTC 72720

TCCGCATTTC TGTGAATGAT TCCGGCTTCT TGGTGTTCCC AGCAGAACTC CCTCAAGTCT 72780

GCGGCGGGGC TCTGACGGCG GTGGCTTGGC TGACATGGCC ACATTGCTGA GCCTGTTGGG 72840

GGCTTTGCGT TCCTGTTCTG GCCGTTTTTG GCTCGTTTTC CAGGAACGGT CGTCACGCGC 72900

TCCTCTCCTA GTGCAGGCAT CATTCCTTTC CCATTGATTT GCAGGGTTCT CTGTAAGTTC 72960

TGAGGATCCC ATATACATAT ACTCTCTGTA AGTTCTGAGG ATCCCATATA CATATTCTCT 73020

CTCTAAGTTC TGAGGATCCC ATATACATAT TCTCTCTCTA AGTTCTGAGG ATCCCATGCC 73080

GACATACATA TTCTTTCCTT GTCTCATGCT GGTCATTTTT TCCATTTTCA TGACAGGTTT 73140

GGTGAACACA TGTTTCCTTG TCAGATTTTT GTTCTGAGCT TGTGCCTCCC GACCAAGATG 73200

CTAAACCGGG TCTTGTGTAT TCTCCAAACT GCACTGTAGA GTGACGGAGC TTTGTGTCTG 73260

GGCCTCCATG CCTTCTGACG TCACCTGTGG GGGTGTGAAA GGCAGACTCT ACCTTGATTT 73320

TTCCCAGCAC GCCACACCGG TGGTTCTGTG CGCTGACCGA GCGGCTCGGC TTCCCCCAAC 73380

TCCACTGGGC ACCTGCCACA CTTTTCCTCA TGTTTTTGTT CACTGTGGTT TTGTCGTAAG 73440

TCCTGGTGTT GGCCTGAACC AATTTCTTTT TGTTTGTTTT TGAGACAGAG TTTTGCTCTT 73500

GTTGCCCAGG CTGGAGTGCA GTGGCGCGAT CTCGGCTCAC TGCAAGCTCC GCCTCCCGGG 73560

TTCACGCCAT TCTCCTGCCT CAGCCTCCCA AATACCTGGG ATTATAGGCA CCTGCCACCA 73620

CGCCTGGCTA ATTTTTTGTA TTTTTAGTAG AGACGAGGTT TCACCGTGTT AGCCAGGATG 73680

GTCTCGATCT CCTGACCTCG TGATCCGCCT CCCAAAGTGC TGGGATTACA GGCATGAGCC 73740

ACCGTGCCCA GCCTGATATT TTTAGTAGAA ATGGGGTTTT GCCATGTTGG CCAGGCTGGT 73800

CTCGAACTCC TGACCTCAGG TGATCCTCTC ACCTTGGCCT CCCAGAGTGC TGGGATTACG 73860

GGTGTGAGCC ACCACGCCCG GCCTCTTGTT CTTTTGAAAC CTGCCCTGAC GTTTTTTCCA 73920

TAGTGCATCT TGGAGTCAGC GTGTCTACTT CCTGTAAAAA TCTTACTGTG ATTTTGACTA 73980

GAATGTGTTG AATTCCTGTT TTTTTTTTGA GTCAGGGTCT CTCTGTTGCC CAGGCTGGAG 74040

TGCAGTGGGA CCATCACAGC TCACTGCAGC CTCAACCTCC TGGGCTCAGG GGATCCTCTC 74100

AGCTCAACCT CCCAAGTAGC TGGGACCACA GGCACATGCC ACCATGCCCG GCTAGGTTTT 74160

TTTTTTTTTT TTTTTGGTGA ACACCCTGGG GTTGCACCAT GTTGCCCACG CTGGTCTCGA 74220

ACTCCTGGGT TCGGGCAGTT TGCTCCTCTC AGCCTCCCGG AGTGCTGGGA TTACAGGCCT 74280

GAGCCACTGC ACTAGGCCAT GTTGAATTTC TAGATTAATT TGGGGCCCTC AGGGGCACAG 74340

AGAGGAGGGC TGGGCCAGTT GGCGGGAGGA GAGGCCCCTC GGGCTGCCGC ATTTTCAGTG 74400

CATGGAGATG GCCTATGTTG GGGGAACACA GAGCTCACCG GGGGTCCCTG CAGGGAGGAG 74460

AAAGGGTCAG GCAGGTGCCA GCTCCTGTCC ATTGGCCTGG GGCTGCATGA TGGCAGGGGC 74520

CGGTGAACCG ATGACCCCTG GGTGTCCTGT GACCTTCTGT GTATGCGGCT GATGCTGCAG 74580

AAAGTCGGGT GGCCTCAGGC TCCTGACGGG GCTGCACTTC CTCTGCCTTT CAGATTGTGT 74640

TCAGTGTGGA CCCCTCCGAG GGCAGCCCTG GTTCCCCAGC AGGGCTGGGG GCCTTACAGT 74700

-continued

```
CCTATAAGGT AGGGGCCACC TCCAGGAGGC AGGTGGAGGG CAGCCCTTGT TCCCCGGCAG   74760
GGCTGGGGGC CTTACAGTCC TATAAGGTGG GGGCCACCTC CAGGAGGCAG GTGGGGCTGG   74820
GGCTCTTCTG GTCCTAAAAG GTAAGGGGCT GCCCCCAGGA CATGGGCGGG GCCTCCACAC   74880
TCCTGGTCCT GTCCCCTCCA GGTGCACATC CATCCTGATG CTGGTCACCG GAGGACGGCT   74940
CAGCGGTCTG ATGCCTGGAG CACCACTGCA GCCAGAAAGC GAGGTACAGA CCTGGGCCCA   75000
CACGCTCCCC GCCCGCCCGG GTGCAGTGCC CGGCACCACC ATGCCACAGG CTAGGCACAT   75060
GCCCAGCCGT GGATCTCCTG CCCCCATGGG CCTGGCCACC TTCTCCATAT CCAGGCCAAT   75120
CCAGAGCATT CTCCTCACTG TCCCTCTGAA GATTGGAGTT ACTGAGAGAC GTAGGAGATG   75180
GCCTGATGGC ACCGTGACCT GCCCAGAGTC ACCTGGTTGG TGGTGGCAGA GCCACAGCCC   75240
AGCCAGGCCT CCCTGCTGGG ACACGCTCGT TTATGCCGAG GCCGTCAGCA CAGAGCCTCC   75300
ACAGTGAGGC ACGGCTCTGC CTGCTGCCTC CACGCAGCGC CTGGCCGGGC CAAGCCTCAG   75360
GGTCACATCT GAAGGGGGCC CGGCTGGCCC TGTTGTCCGA AGCCCCTGGT GCGCTCAGCC   75420
CCGAGGCCCC ACGTGCCTTC TTGGCTTCCT GTCCTCCGTG GCGTCTTCGA GTCGGTGCTG   75480
CCGGGGACGC TGTGTGGATG GGGTCTGTGA GTGTGCCCTC GGCTCCGTGT CCGGAGCCCT   75540
GTGGTTCTTG GGGTGTATCT GGCCCCACCC CCACTGCGTG GTGTCCAGGG TGGGGCTTCA   75600
CGGCTGCAGC TGCGGGAGCT GCTGCCCCTG CCTTGTGCTC CAGTGGGGCC TTGCCTCTGG   75660
GCTTGGTTCG TCCCTCTCTG GAACATTCTT TCTCAGCTGC TGTCCGACCC ATGGTGGCAT   75720
GACGTGGCCC TGGCTGAAGC AGCCCTTGTG CGGTTGCTGT GGTTGGGTCT GCCTGGCCGA   75780
GCCGGAAGGG AAGGGCTGGG AGGGCGTCAG GGTGGCGTGG CTTGACCCCC GCTCGGTGAT   75840
GGTCCTGCAG CAAGGCCTCT CCCAGCAGGA AGCGTCCATC CCGGGGGGAG GCCGGCGCCC   75900
CTCACGCAGT TGGGGTTGCG GGAGGCAGTG CGTGCCTGAG GCAGCCGGTG CACAGATTCC   75960
AAGGGCCTGG AATCTGTTTG TTCCATTGAC CTCTGATGTC ACTTGACTTC TCAGAAGCAG   76020
CCACTCCCTG CACTGGGCGT TTGTAGGAAA TGAGCTCCTG GAGGAGGGGG TGGGGAAGTT   76080
CCCCCATTGC AGGGCACACT CAGCCCCAGG AAGGAAACGT GCCTCGTCCC TGCTGACTCC   76140
GAATCGCAGT CAGAGTCGTT CTGCTTGTGC CGTGTTGAAT TCCCGGCATC CGGCATCCAG   76200
ACTCAGCCTC CTCCCCAGGC CACGGCCGCC GTGGCCAGTC GGTCAAGCCC TTCTAGGAAC   76260
TTCCTTTGAG CTGGCGCCCT TGTTCACTGC TGACGCCACT CAGAGGCTTG TGCACGTGTC   76320
CTGCTTCCAG GCAGAGCTGG GAACTCGCAC CCCGTCTTCT GCACGCGGCC GTGGAATGTC   76380
GGGATGCCGG CGCTTCCTTC CCCTGTGCTC TTGGCGGGGT GGGCTTCTTG CCCTGAGCCG   76440
CATGTCACAG TTTCTGCAGA AGTTTAGGGT TGGAGTGGGC TGACCTCTCT GCAGGTGTCC   76500
CCAGCCTCTG CCTGGGGTCT GCCTCCTACT CCCAGGACCC CCTGTCCCCC AGAGGGGCCC   76560
CAAGCTGGCA GGCTCACACT CAGGGCAGCC TCCTTTGTTC TGACTTCTGC ACAGTGGGCC   76620
TGGGTGGCTG CCCGCGGCTC GCTTGCTTGA TGCCAGTGGG TGGAGAGGGT GATGGGCAGA   76680
GAGGCAGGTG GTCAGGCCCC CAGTCCCGTC CTCACACTCT GTGCCCTCTG CCGCCCCCCG   76740
CCCCACAGGG AAGGTGCTGA GCTACTGGTG CTTCAGTCCC GGCCACACCA TGCACGAGCT   76800
GGTCCGCCAG GGCGTCCGCT CCCTCATCCT TACCAGCGGC ACGCTGGCCC CGGTGTCCTC   76860
CTTTGCTCTG GAGATGCAGA TGTACGGGCC ACCCCTGCCA GGGCCTGAGC ACCGGTGACA   76920
CCTCTGACAT CAGCGGGGTG GAAGTGGTGG GGGTCCCCAT GAGCCGGGTG CTGGGGGTCT   76980
CGGGCCTCGA GGGCTAAAGG GGTGCTGGTG CACTTCCCCA CTGTCTGCTC CCTCTGGCCA   77040
CGCTCAGCCC TTTCCCAGTC TGCCTGGAGA ACCCACACAT CATCGACAAG CACCAGATCT   77100
```

-continued

GGGTGGGGGT CGTCCCCAGA GGCCCCGATG GAGCCCAGTT GAGCTCCGCG TTTGACAGAC 77160
GGTGAGGGCC TGTCCCTGGG CCCTGCTGGG GTGGGAGGTG GGGGAGCACT GAGGCCTGAG 77220
GCCCTGAGCA GTGGCCTCTC CGGCTCTAGG TTTTCCGAGG AGTGCTTATC CTCCCTGGGG 77280
AAGGCTCTGG GTGAGTGCCC TGAATGCCCC AGCTGTGCGC ATCCTGGATC CTGGACCCCT 77340
GCTCCCAAGA GCTGGTAGGG ACCCCTGCAG ACATCCTGCC CCTGCCTTGA CCCCGGCCCC 77400
TGCACTTCCA GGCAACATCG CCCGCGTGGT GCCCTATGGG CTCCTGATCT TCTTCCCTTC 77460
CTATCCTGTC ATGGAGAAGA GCCTGGAGTT CTGGCGGGTG CGTCTCCCCT GTGTTCTGGG 77520
CGGGGTGGGT GAGGGCAGGG CTGGAGCATG AAGCAGGCAG TGGTCACAGC TCCTGCTTGC 77580
CCTCATCGGA TCGGCGGCGT GACCAGGGCT GCCGTGTCCC TGCCTCTTCC TCCCACAGGC 77640
CCGCGACTTG GCCAGGAAGA TGGAGGCGCT GAAGCCGCTG TTTGTGGAGC CCAGGAGCAA 77700
AGGCAGCTTC TCCGAGGTCG GCACTTGGCC GGGGCTCTGG GCCTGCTGCC CCCTCGTGCC 77760
TCCCCTGCCT CTCACAGCTT CCCCAAGGCT GACCACTGGC CCTGACCATG GGCTCCGGCG 77820
GCTCCCGCTG CCTCTTCAGG GCTCCTGCGT TTCCTTCCTG GCCCTGAGTG TTGCCTCTTA 77880
TCTTACAAAG CCCCCAGCAC CGGGTGGGTG TGGTAACAGT GGCCCTCCTC TCTGAGTAGC 77940
CCTAGTCGGC CACCCTGGCC CTGGGGTTCC CCGTGTTTTC TGGGAAGCAC TGAGCAGGCG 78000
TGGGGTCAGC CTGGGATCCG TGCCAGGAAG AAGCTTCCAG AACCCGATTG GCCTTCCTGG 78060
CTAGGACGAT CCTTCATCTT GGAGCATGAG ACCTGGGTCT CCCTCATGGG GGAGGAAGGG 78120
GCTGGGGGGG GGCTCCAGGC TCAGCCTCAC CAACTTTCCT TCCAGACCAT CAGTGCTTAC 78180
TATGCAAGGG TTGCCGCCCC TGGGTCCACC GGCGCCACCT TCCTGGCGGT CTGCCGGGGC 78240
AAGGTGAGCT CTCCAGGGCC CTCTGCCCTG ACCTGGTTGC CTGTTCCCTG GTGGGTGCTT 78300
ATGGCTCCCC AGCAGACTCT GGGCCCTGGG GGCTGCCCGG TCCCCTCCTT GGGTCCCACG 78360
AGAGCGACTG CTGGCCCTGC TGGGAGCGTG TCCTGCTCTG GCCCTGGGCA GGCAGGATGG 78420
GAGTTTCCTG GCCACAAGAG TTGGAGGTGG CGTCTGGGAG CTGTGGACCC CAAGTGGGGT 78480
CCTGACCCAC AGATGGAGCT TCCTCCCACC CCTGGTTGGG GACGGAGCCT CGGGGAAGGT 78540
GGCTGGGCTG GGTGTGGGCA CCAGGGAGAG GAGCCCCCAC GGCCCCAGGC AGCTCCCTGG 78600
TGTGTCCCCT AGGCCAGCGA GGGGCTGGAC TTCTCAGACA CGAATGGCCG TGGTGTGATT 78660
GTCACGGGCC TCCCGTACCC CCCACGCATG GACCCCCGGG TTGTCCTCAA GATGCAGTTC 78720
CTGGATGAGA TGAAGGGCCA GGGTGGGGCT GGGGGCCAGG TGAGTTACAG CAGGGTGGGG 78780
CTGGGGTAAG GCGGTCTGGT GACTGAGCCC CCGCCCCGTG GCCAAGGGAG CCCCCGTGAC 78840
CGAGCCGCCT CGCCCCACAG TTCCTCTCTG GGCAGGAGTG GTACCGGCAG CAGGCGTCCA 78900
GGGCTGTGAA CCAGGCCATC GGGCGAGTGA TCCGGCACCG CCAGGACTAC GGACCTCTCT 78960
TCCTCTGTGA CCACAGGTGC GTGCAGTCCG GTGGCAGGCG CGGCGCCAGG GGACACGCCC 79020
ACACCCCACT GGGCCCCTGG ACTCTCCTTC CCCACATGAG GCCCCGTCTC CTCCAGAGCC 79080
TCTCCGGCTA CTCGGGGTCA GCGTGGGGCC CCTGCAGCAG ATGAGGGTCT TCACTTCGGT 79140
GAACTGAACC CTTGAAGCGG CTGTGGGCAG GGCAGCAGGG CTATGGCCAC CCCCCAGGTT 79200
CGCCTTTGCC GACGCAAGAG CCCAACTGCC CTCCTGGGTG CGTCCCCACG TCAGGGTGTA 79260
TGACAACTTT GGCCATGTCA TCCGAGACGT GGCCCAGTTC TTCCGTGTTG CCGAGCGAAC 79320
TGTGAGTTCC TGCCCAGGGA GGGGATGAGG GTGTTGTCCC CAGAGGAGCC AGAAATGGGT 79380
CCACCCACCC CCATGGTTCT GCAGATGCCA GCGCCGGCCC CCCGGGCTAC AGCACCCAGT 79440
GTGCGTGGAG AAGATGCTGT CAGCGAGGCC AAGTCGCCTG GCCCCTTCTT CTCCACCAGG 79500

-continued

AAAGCTAAGA GTCTGGACCT GCATGTCCCC AGCCTGAAGC AGAGGTCCTC AGGTGCGGAC 79560
GGGCAGCGCT GGGTGGGCGG TGTGGGGGTG GCGGAGCGGG CGGCGTGGGG CGGGCAGCAC 79620
CAGGCGCCCA GGGCGGAGGC GACTCACCTG GCTTTGTGCG CTTCCCCTCC CACCTCCAAA 79680
GGCTGCCTCT CCCTCCTAGG GCAGGGCCCC CACGGGCTCC AACCCTCCCC TACAGGCAGA 79740
GAACGCCCCA GGCAAGGATG CCCCCCGAGG CTGAGACTCC CCCCAATAGC AGGGAGGACA 79800
CCCACAGGCA GGACCCCAAG TGCTGGGACT CTCCCCCAAG AGGGGCTTTG CCACAGGCAG 79860
GGACCCCAGC TGGGGCCCCC CGTGGGCTTC ACTGCGCACT CGGGTGCCCC TGCAGGGTCA 79920
CCAGCTGCCG GGGACCCCGA GAGTAGCCTG TGTGTGGAGT ATGAGCAGGA GCCAGTTCCT 79980
GCCCGGCAGA GGCCCAGGGG GCTGCTGGCC GCCCTGGAGC ACAGCGAACA GCGGGCGGGG 80040
AGCCCTGGCG AGGAGCAGGT ACAGTTCCAG GGCCTTGGGA TGGACACAGA CCCTCTGTCT 80100
CCTGAGGCCA ACCCGACCCC GCCCATCTGG CCTCAGGCAC CTCCCCACAC ACCCCTGTAA 80160
ATCCCCTGCC TGGCAGGCAG GCGGGCAAGC GGGCGGGGGA TCCCAGCTGC CTGGCTGTCT 80220
GTGGGTCCTC CACCCCACCT CACCCACAGG CTGCTGGCTC CCAGGTGGTG CATGCCCTGG 80280
CCCTCCGCGG GTGCCCCCCA CATCACTTTG GTTCTCTGGC GGGTCAGCTT GGCTCAGTGC 80340
ACTCAAGGTC GGGTGCCCCT GCCACTGGCT GCGCTTGAGG CTGGCCTTTC TCCACCAATG 80400
TGCTGCGGGT GGAACCCAGG TTCCTTCTTC CTTGGGGCCT TTTGCCCCAG AAGCCCATAA 80460
TTCCTCAGGC CAACCCGAAA TTTTCTCCCT GCTTCCTGCT GGGAGCCATT CCCCTCTTCC 80520
TGCCCATCCC TGCCCTTCAG GCCCCTGGAG TGAGCTCCAG GTGCAGGCAC CAGGCACCTG 80580
TGTCCCCTTC CTGCCAGCCC CTCGCTGTGG TCGGACTGTC TTCCCTGGAC CTGCTCTTAC 80640
AAGTCACCAC CTGCGAGCCT CATGAGCCCC TGGTGTGACT TGGACAGGAC CAAGTTGTGG 80700
CACTGTCACC GGGGTGTGCT GTGCCCCCCT CCCCCGACCT CCATCTTGGC TCAGGGCTCC 80760
TTGGGACCAT CTTCCCTGTG CGTCCAGGTG CTTTGGGACC CCAGAGTGTG TGGTTGGGGT 80820
CTGTGTGTGG TTGTGAGCTG TGTCCTCCTC AGGCCCACAG CTGCTCCACC CTGTCCCTCC 80880
TGTCTGAGAA GAGGCCGGCA GAAGAACCGC GAGGAGGGAG GAAGAACATC CGGCTGGTCA 80940
GCCACCCGGT GCGTGAGCTG TCCCTGCACC TGTGCCGACC ACCATAGACA CGCATGGGAA 81000
CGCAGCCGTG GGTGCCCCCA GCCACGGCTG GTCCCGATGG GACCAGGGAA TCCACCCCCA 81060
GGAGCTGATG TCCAGGGCAG CTGTGATGCT GACGGCCAGG GGCTCAAGTG TGTGGTTTCT 81120
TCTGCAGGGG GCTCATGAGT CCCAGCTGGA ATCAGGCCCC ACCCTTGGGC AGGTTTGGCA 81180
TGGGGCCTGC AGCACTGGGC TTGGCCCTGG CATTTCCCTC AAGTGTGGAT GCACACCTGC 81240
CTCATGTGAG GGACACAGCC CATTCCTAGC CTTGGATCAA AGAACGGAGT TATAGCCGGA 81300
GCCAGGAAGC CCCCTGCCTG CTGGAAAACC CCAAGTGTGG CGGCCTTTGT CCATGTCCCT 81360
TGGCTTCTGG GAAGAACTGG GTGGTGCCCA GGCAGGGCTG GTGCCATCAG GAAGTGGGTG 81420
GCTGCTGAGG GGCCTGGGCT GGCGAGGGCC TGGGTGGGGA GTGCCTGGGC CGCCCCTGCC 81480
TTGGTTTCCA CGTTTCCGTG TTGGTCTGGG GTGTGTAGAG AGATGGGCAC TGCTCATCCG 81540
GAAGCCCCTC CTTGTGCGCT GCCATCCTGG GAGCCTCAGC CGCATCCGCT GTGGGGCAGG 81600
GGGCTTGAGG GAGGAGGAGA GAGACGGGCC ATGCAGGACC CCTGGCTTGA GGCAGAGCCA 81660
ATCTACCCTT TGCCCATTCA CTGCTCTCAG TTCCCTGCCA GCCTCTCACT GTGTGACCTC 81720
AGACGGGCCC AGCCCCACAG CTTTCTTCCC GCAGCCCCTC CCTATGTCCA TCCAGCCAGC 81780
CAGTTTCTCA GGCAGCAGCC CCACCTCGGC AGTCACTGTC CCAGGGAACG CTCAATGTTC 81840
CAAGGAAGGC TCTGCAGCCC CAGGGACCAG ATGATGAGGC TGGCCCTGAT GGAGCCTCGG 81900

-continued

```
GCCTGTGTCC TGCAGGAGGA GCCCGTGGCT GGTGCACAGA CGGACAGGGC CAAGCTCTTC  81960
ATGGTGGCCG TGAAGCAGGA GTTGAGCCAA GCCAACTTTG CCACCTTCAC CCAGGCCCTG  82020
CAGGACTACA AGGGTTCCGA TGACTTCGCC GCCCTGGCCG CCTGTCTCGG CCCCCTCTTT  82080
GCTGAGGACC CCAAGAAGCA CAACCTGCTC CAAGGTGCCC TGGCTTGCAG AGGCCACCCA  82140
CCCTGAGGGC AGTGCTGCCG CCGCGTGTGG GGTGGGGGCC ATCTGGGTCC AAGGTGGTCT  82200
CTGTTCTCTA GAGAAAAAGG GGCACATGGG GACAGACGCC CCTTCCTCTA CAGGCTTCTA  82260
CCAGTTTGTG CGGCCCCACC ATAAGCAGCA GTTTGAGGAG GTCTGTATCC AGCTGACAGG  82320
ACGAGGCTGT GGCTATCGGC CTGAGCACAG CATTCCCCGA AGGCAGCGGG CACAGCCGGT  82380
CCTGGACCCC ACTGGTAAAT GGGGCCCCAG GTGGGACCCT CAGACTCCTG CGTGGAAGGC  82440
AGTGTGGGCC AGAGTCCTGG GCTGCTTGGG GTGGGCATCC TCGGGCCCTG CTTGGCCCCG  82500
CCTCTCTGTT CCCCTATGGG AGTGATGGGG GCCTCCACCT CCACCACCAG CACCAGCAGC  82560
ACCACCTCCA CCTTCACCAC CACCACCTCC ACCACCACCA CCTCCACCAC CTCCACCTCC  82620
ACCACCTCCA CCACCTCCAC CACCTCCACC ACCACCACCA CCTCCACCAC CACCACCACC  82680
ACCACCTCCA CCACCACCAC CACCACCACC ACCTCCACCT CCACCACCTC CACCACCACC  82740
TCCACCTCCA CCACCACCAC CACCTCCACC TCCACCACCT CCACCTCCAC CTCCACCACC  82800
ACCACCTCCA CCACCACCAC CACCACCTCC ACCTCCACCA GCAGCAGCAT CACTTGTTGG  82860
GGAGACCCTG TGCAACTCCA TGCACAGCCC TGTCCCTGCC ATAGCCCCGA CCCCTAAGCA  82920
CAGCCCTGTC CAACTGCCAC ACGTCCCCTG CCTCCCATGC ATGGTCCTGG GGGGTCAACT  82980
GCACACGCCA GGGTCCTAGG GTCCTAGACC CCTGTCCTCC CTGTTTCTGC CTCTGTTTGG  83040
GGTGGAGTCC AAGTCTCCAG AGGCGGAAGC ATCTGTGTTC GTGTGTTAAT GAACAGCCCC  83100
TACAGAGTTC CCCTAGTTCA CCCAGGGGGG AACCTAGCCT GTTGGGACGA CCCCAGATCC  83160
CTTCTGGGCT TGGTACTCAC TGGGATATCC TCATGCCTGC ACCCAGCCTA CGGCTCTGAG  83220
CTCCTGAGTG GGGCTTTGGC CTGCCCGCCA CTGTTCCAGC CCCCATCCAG CAGGCTGGTG  83280
TCTCCTCTGA TGCCCCCAGC ACCCAGGCGT GTACCTGCCT GGGTTTTCCC GCCCTGGTCT  83340
GAGGTGGGTG AGGCCTGGCC TCCCTAGCCA GCCCTGCCCC CCCACCCCAG GGAACTTTCC  83400
AGATGCTCCC GACCAGCTTT GTGGCTCTAC ATCTCTTCAT CAGGAAGAAC GGCGCCGGAT  83460
CCCAAGCTGA CCGTGTCCAC GGCTGCAGCC CAGCAGCTGG ACCCCCAAGA GCACCTGAAC  83520
CAGGGCAGGC CCCACCTGTC GCCCAGGCCA CCCCCAACAG GTAGCTGACT CCTGAACCGT  83580
GTGCAGCCTA CGACTTGGTG GGTCCCTCAG TGGCTTCACG AGGCTAACTC TTGAGTGTGG  83640
CCGGGGCTGC CCCTGTGGGG AGCCATCTCA TGGTGGGGAC TGCTCCCGGT TCTGCACCCC  83700
GCAGTTGTCC TGAGCAGCTC TCCAGGAGTT CCTGGAGGAA GGGCGGGCAG GGCGGTGGGA  83760
CTCTCAGTCC TCCACCCCAG CGCCACTCTG AGCCATGCTA CTCCCACACC AGGAGACCCT  83820
GGCAGCCAAC CACAGTGGGG GTCTGGAGTG CCCAGAGCAG GGAAGCAGGG CCAGCACGCC  83880
GTGAGCGCCT ACCTGGCTGA TGCCCGCAGG GCCCTGGGGT CCGCGGGCTG TAGCCAACTC  83940
TTGGCAGCGC TGACAGCCTA TAAGCAAGAC GACGACCTCG ACAAGGTGCT GGCTGTGTTG  84000
GCCGCCCTGA CCACTGCAAA GCCAGAGGAC TTCCCCCTGC TGCACAGCAA GTGGCCCTGG  84060
CGTGGGGAAC AGCCGGTGGG GTGGGGGCCA GGGGACAAAA TGGGGGCTGT GCCGGGTCTG  84120
ATTGAAGCTC CCCGCAGGGT TCAGCATGTT TGTGCGTCCA CACCACAAGC AGCGCTTCTC  84180
ACAGACGTGC ACAGACCTGA CCGGCCGGCC CTACCCGGGC ATGGAGCCAC CGGGACCCCA  84240
GGAGGAGAGG CTTGCCGTGC CTCCTGTGCT TACCCACAGG GCTCCCCAAC CAGGTAGGGC  84300
```

-continued

ACCTGCCTGG CTGCTCCTGG CAGCGCCCCA ACCGCACGCA GCCCTGGGAG TGAGCAGCAA 84360

AGCCCCAGGC CCCCCTCAGA CTCAAGTCTC TGTCTCCAGG CCCCTCACGG TCCGAGAAGA 84420

CCGGGAAGAC CCAGAGCAAG ATCTCGTCCT TCCTTAGACA GAGGCCAGCA GGGACTGTGG 84480

GGGCGGGCGG TGAGGATGCA GGTCCCAGCC AGTCCTCAGG ACCTCCCCAC GGGCCTGCAG 84540

CATCTGAGTG GGGTGAGCCT CATGGGAGAG ACATCGCTGG GCAGCAGGCC ACGGGAGCTC 84600

CGGGCGGGCC CCTCTCAGCA GGCTGTGTGT GCCAGGGCTG TGGGGCAGAG GACGTGGTGC 84660

CCTTCCAGTG CCCTGCCTGT GACTTCCAGC GCTGCCAAGC CTGCTGGCAA CGGCACCTTC 84720

AGGTTGGTGC CTGGCCACTA CAGTTCCTGC TGGGTGTAGC CCCAGGTGAT GGGCTGAGGG 84780

GGAAAGGGCA GGCCCTTGTC CTGGTGGCAA CGCCTGGCAG ACGTGTGCAG TGGGCCGGTT 84840

GTCTCACAGG CCTCTAGGAT GTGCCCAGCC TGCCACACCG CCTCCAGGAA GCAGAGCGTC 84900

ATGCAGGTCT TCTGGCCAGA GCCCCAGTGA GTGCCCACGG AGGCCCCCAG CACACCCAAC 84960

GTGGCTTGAT CACCTGCCTG TCCAGCTCTG GTGGGCCAAG AACCCACCCA ACAGAATAGG 85020

CCAGCCCATG CCAGCCGGCT TGGCCCGCTG CAGGCCTCAG GCAGGCCGGG CCCATGGTTG 85080

GTCCCTGCGG TCGGACCGGA TCTGGGCCTG CCTCTGAGAA GCCCTGAGCT ACCTTGGGGT 85140

CTGGGGTGGG TTTCTGGGAA AGTGCTTCCC CAGAACTTCC CTGGCTCCTG GCCTGTGAGT 85200

GGTGCCACAG GGGCACCCCA GCTGAGCCCC TCACCGGGAA GGAGGAGACC CCCGTGGGCA 85260

CGTGTCCACT TTTAATCAGG GGACAGGGCT CTCTAATAAA GCTGCTGGCA GTGCCCAGGA 85320

CGGTGTCTTC GTGGCCTGGG CTTGGTGGTG GGAGTTGAGG GACAGGGAGT TGGCAGAGGC 85380

CCCTCCCAGC CTGCCATGTG ACACTGTACT TCCTCCACGG TGGGCTCAGC CCTGCCCTCA 85440

TCCTCACAGC CGCAGCCAAG CTGCAGTTGG TAGGGGATCC ACCGACACAC CAGGCTGCCT 85500

GGGCTGGTCT CTGGGTTGGG AGCTGCCCCA GGTGCTGAGG AGGGCAGCTC CCTGGCTGGT 85560

GAGGCCCCTC CCAGAACCAC CCTTGGACTG AGCTCTGGGG AGGGATGGTA CCAGGTGGGT 85620

GAGGGGGGCT GCCTGGGGAG GGAGGGGTTC CTATGGGGCG TGGCGAGGCT GGCCCAGCCC 85680

TCTCCCCGCC CATATATGTA GGGCAGCAGC AGGATGGGCT TCTGGACTTG GGCGGCCCCT 85740

CCGCAGGCGG ACCGGGGGCA AAGGAGGTGG CATGTCGGTC AGGCACAGCA GGCTCCTGTG 85800

TCCGCGCTGA GCCGCGCTCT CCCTGCTCCA GCAAGGACCA TGAGGGCGCT GGAGGGGCCA 85860

GGCCTGTCGC TGCTGTGCCT GGTGTTGGCG CTGCCTGCCC TGCTGCCGGT GCCGGCTGTA 85920

CGCGGAGTGG CAGAAACACC CACCTACCCC TGGCGGGACG CAGAGACAGG GGAGCGGCTG 85980

GTGTGTGCCC AGTGCCCCCC AGGCACCTTT GTGCAGCGGC CGTGCCGCCG AGACAGCCCC 86040

ACGACGTGTG GCCCGTGTCC ACCGCGCCAC TACACGCAGT TCTGGAACTA CCTGGAGCGC 86100

TGCCGCTACT GCAACGTCCT CTGCGGGGAG CGTGAGGAGG AGGCACGGGC TTGCCACGCC 86160

ACCCACAACC GCGCCTGCCG CTGCCGCACC GGCTTCTTCG CGCACGCTGG TTTCTGCTTG 86220

GAGCACGCAT CGTGTCCACC TGGTGCCGGC GTGATTGCCC CGGGTGAGAG CTGGGCGAGG 86280

GGAGGGGCCC CCAGGAGTGG TGGCCGGAGG TGTGGCAGGG GTCAGGTTGC TGGTCCCAGC 86340

CTTGCACCCT GAGCTAGGAC ACCAGTTCCC CTGACCCTGT TCTTCCCTCC TGGCTGCAGG 86400

CACCCCCAGC CAGAACACGC AGTGCCAGCC GTGCCCCCCA GGCACCTTCT CAGCCAGCAG 86460

TTCCAGCTCA GAGCAGTGCC AGCCCCACCG CAACTGCACG GCCCTGGGCC TGGCCCTCAA 86520

TGTGCCAGGC TCTTCCTCCC ATGACACGCT GTGCACCAGC TGCACTGGCT TCCCCCTCAG 86580

CACCAGGGTA CCAGGTGAGC CAGACGCCTG AGGGGGCACC ACACTGCAGG CCAGGCCCAC 86640

TTGTGCCCTC ACTCCTGCCC CTGCACGTGC ATCTAGCCTG AGGCATGCCA GCTGGCTCTG 86700

-continued

```
GGAAGGGGCC ACAGTGGATT TGAGGGGTCA GGGGTCCCTC CACTAGATCC CCACCAAGTC   86760
TGCCCTCTCA GGGGTGGCTG AGAATTTGGA TCTGAGCCAG GGCACAGCCT CCCCTGGGGA   86820
GCTCTGGGAA AGTGGGCAGC AATCTCCTAA CTGCCCGACG GGAAGGTGGC TGGCTCCTCT   86880
GACACGGACA AACCGAGGCC TGATGGTAAC TCTCCTAACT GCCTGAGAGG AAGGTGGCTG   86940
CCTCCTCTGA CATGGGGAAA CCGAGGCCCA ATGTTAACCA CTGTTGAGAA GTCACAGGGG   87000
GAAGTGACCC CCTTAACATC AAGTCAGGTC CGGTCCATCT GCAGGTCCCA ACTCGCCCCT   87060
TCCGATGGCC CAGGAGCCCC AAGCCCTTGC CTGGGCCCCC TTGCCTCTTG CAGCCAAGGT   87120
CCGAGTGGCC ACTCCTGCCC CCTAGGCCTT TGCTCCAGCT CTCTGACCGA AGGCTCCTGC   87180
CCCTTCTCCA GTCCCCATCG TTGCACTGCC CTCTCCAGCA CGGCTCACTG CACAGGGATT   87240
TCTCTCTCCT GCAAACCCCC CGAGTGGGGC CCAGAAAGCA GGGTACCTGG CAGCCCCCGC   87300
CAGTGTGTGT GGGTGAAATG ATCGGACCGC TGCCTCCCCA CCCCACTGCA GGAGCTGAGG   87360
AGTGTGAGCG TGCCGTCATC GACTTTGTGG CTTTCCAGGA CATCTCCATC AAGAGGCTGC   87420
AGCGGCTGCT GCAGGCCCTC GAGGCCCCGG AGGGCTGGGG TCCGACACCA AGGGCGGGCC   87480
GCGCGGCCTT GCAGCTGAAG CTGCGTCGGC GGCTCACGGA GCTCCTGGGG GCGCAGGACG   87540
GGGCGCTGCT GGTGCGGCTG CTGCAGGCGC TGCGCGTGGC CAGGATGCCC GGGCTGGAGC   87600
GGAGCGTCCG TGAGCGCTTC CTCCCTGTGC ACTGATCCTG GCCCCCTCTT ATTTATTCTA   87660
CATCCTTGGC ACCCCACTTG CACTGAAAGA GGCTTTTTTT TAAATAGAAG AAATGAGGTT   87720
TCTTAAAGCT TATTTTTATA AAGCTTTTTC ATAAAACTGG TTGTAGTTGC ACAGCTACTG   87780
GGAGGGCAGC CGGGGACACC TGAGCCGCCC GCTGTGCCCA GATCCCTCAG GCTGCCTGCC   87840
ATCAGAACTG CTGCCCGGGG CTTCCCCTAC CTCAGACAGA CCCTCCCTGG GAGGATCAGT   87900
GGGGAGTGCC ACCTCTGCCC CCAGTGGCTG TGGCACGTGG CAGGGGCCCC TGAAGCTCAG   87960
CGAGGGTCAG GGCCTGGGAG GGTATCATTG CTGGAAGAAC AGGATGGGGC TCAGGCCAGC   88020
CCTAGTCGCC GGGGCCCACA CTAACCCCCC ACTTATGAAT TCCTCCCACT CCCAACTCAC   88080
AGGGGATTTC CCGAGAGGGG ACCTGCCAAA GACCTCCTCC AGGCCTCCCA TGCTTCCCGG   88140
GAAGTGAAGC TTCTCCCCCT CTGGGGCAGG CTCTGAAGCC TCCCGATGCA CCCAGAGCAA   88200
CCAGGGCGCT GCACCAGCCA CTCGCCTCCC CAGCACGGCC AGCTTCCCGG GGCTGGAGGT   88260
CCCCCCCAGG TCCTGGGAAC CAACCTGCAG AACACACACA GGGTCCCCTG GAGAGGACGC   88320
GGGGACTTCC AGGGCCCGAC TCCTGTGAGT CACAGCCCCG CAGCTGCTGC GCCACCCCCA   88380
CCCTGACTCA TGCCCCTTCC CAGCAGCTCC TCCCAGGACC CCATGTCCTT CCCACATCCG   88440
CAGGAAGGGA GTGCCTGGAC TCTCCAGGCC CACCTGGGGA GCCCCTCACC TGCCCACCAG   88500
CCCCTGAGCA GCCCAGTAAC ACCATCACCG TGTCCAACAG CCAGGAGCCT CCACCCTCCA   88560
GGAGGGAAGG GATGGACAGA GCCACACTCG CCGTCTTTAT TTTGCACTCA CCCTGGGTGA   88620
CACTGGGCAG GCCGCTCCTG CCCACAGCCA GACTGAGGAA GAACACACCA CTCGGCAGGC   88680
CCAGTGGGGT CCGTGCAGGG AGGACCCCAG GACCAGCCTT ACTCCCGAGC AGGGGACACA   88740
GGGCCCCACA GAGAACCCCT CCGGGAGGTT CTCTCCTGGC TGGGGGAGGG CTCTGGACCC   88800
CCACAAACAC TCCCCAACTT GCGGGGCTGG GGCATAAAAA CAGCCACTCC CAGCAGGCCC   88860
CCTCAGCTTT TTGCATCAGT CAGCTCCCTC CCGGGGGATT AGGGTGAGGT GAAGCCAGGC   88920
CCAGGCGTGG GGTATAGGTC TTCCCCCGCA GGCCTCAGCC CTGTCCCGAG GCTGCATCAC   88980
AATCCAGGGC CCCCGCTGGC CTTTGGGAAC ATGGCCTGGG TCTTCCTCAA GGCAAGATCA   89040
GCCCCAGACC ACTTCCGGGG TCACGGGGTC ACAGGGCAGA AGCCAGATGG CAGCCATGGC   89100
```

-continued

```
TGACGGGCCT CCTCCTCGAT GGGGCGGAGA CAGCCACGGG GTCTCCCGAG GGTCCCACAG   89160
GGCTGTCCTC ATGCAGCCCA AGCCAGCCTG AGCACTGGAG CCCCAATTCC CAACCAGGTC   89220
TCCCTCAGAC CCCCCAGAAA GGGCCTCGAA AGCCCGCCGC TGCGCCCTGT GGAAAGGCTG   89280
CCGCTGCAGG GCCTGGGCCA GCCGGGCTGC CAGACTCCCC TCCAAAGCCT CCGCATGCCT   89340
ACGCTTTTCC AGACATAGAG GAAAGTTTGT CTTCGAGAAA ACAAAGTAAA TAGAAGAACC   89400
CCAAAGCAAA GCAAACCCAC CCCCCAGATC AGCAGCATGG GAGCCAACAG GAGGCCACTC   89460
CTCCAGCACC AGGGGACCAG CCGTCCCGAC GGCAGCGCGG CTGCGCCTAC GTGATGTCCC   89520
TCTGCCGCGG CGGCCGGTGC ACATTCCGCA CGACACACTT CACCATCCAC TCGATGCCCT   89580
CGCGCACCCC TTTGCTGTGA AGACAGCGGG TGTGAGGCGG GGGGTCTCGG TCCCCAAAGC   89640
CCCCGCAGGT GCAGCCCCCA CTCACCCTGT GAGGGCCGAG CAGGCCTGGG TCAGGCAATC   89700
GCGCCTGCCG ATCTTGCTGG TGCAGTCGCT GAAGGCCGTC TTGATGTCAG GGATTGAGAG   89760
GCACGTCTGG GGGAGGTAAG GCCGTGAGGA GCAGCCCCCA CCTCTGGCCC TGTCCTGCCT   89820
GTGGGCCCGG GACTCTCAGA AGGGCGTATG CCCTTCACCC CAGGGAAACA GCCAGAGCTC   89880
CACCAGGGTC CCAGTGTCTC CCACAGAGAC CACAGCAGTG AGGACCCTGT GCTCAGCCCG   89940
AGGCTGAACA TGGCTGGTAG TGCCTGAGAC AAACTAGACG TCCACACGGC TCCAAGGAGT   90000
CCACCCCCCA TCCCCTCCCT GGGGGACACC CTGAGCCCCG AGGTGGGGCG CTGAGGACTG   90060
AGGCCTCCTG GGCAGTGGCG GAGGCAGGTC CCAGGGGCCC ACACAGCCGG GGATGATGGA   90120
GAGGTGGGAG CCCTGCATCA GTGATGGGGG CAGTCTGCAG TCATGGTGGC TTCTGCTCAC   90180
AACCACCTGC CCAGTCTTCA AAAAGCAGCC CTCCCCTCCC CTTTTCCTCC GAGGGGAGAC   90240
CCCTGCCCCG TACCAGATGT CCCTCTTGTC GGCTGAGATT GTAGGGGAGG CCAGCCTTAC   90300
AGGCTGGGGG CAACAGAGCC ACCCCAGAGA AGGCAGGAAG TGAAGATTCA CCCGGCCCTC   90360
TGGACGCCCG GCTGCTTCTG TGCAAACCCA CTCCAAGAGA ACAGCTAGAA CTCAGCGTGG   90420
CCAGTGCTCC CGGGGGCAGT GGCACCTCAG AGGGGTCTTG AGGGGCTGCC CTGGGGGTGG   90480
GGCTGGCACA GATGCCACCT CCAAGGGTAG CAGGAACAGG TAAGGGTCAG AGCTGACTCC   90540
CACCAGGGCC CCAGCATCAC TTCTTTGAGC TCTGAGTTTC ACCTGGGTGT CCCCACAGCT   90600
TGGCCACACA CTCCTGAGAC ACGGCCGCCC TCCTGGGGAG AGGTGCCCTG CATACCAGGA   90660
AGAGGCCTCT GGGCGCCTGC CCTGAGGTGG GAGAACCTCC AGGGCTGGCA GCAGCAGGTC   90720
TGGAGAGGAA CCAAGCTTGG GAAGCTGCTG GGGGCAGGGC AGGCCTTGAG AATGGCTCTG   90780
TACCCCCTGG GCAGTCACTG GGCCTGGGGT GTCTGGGTGC ACACCTACTC CCCTTGCTGT   90840
GGGGGAGGCT GGGGACTCGG GAAGCTGCTG CGGGAGGCAG GGGTGGGGCT CACCTCCACA   90900
TCCTGCTTGT TGGCCAGCAC CAAGACGGGG ACACCGCACA GCGCCTCGCT GGTCACCACC   90960
TTCTCTGGGG AGGGCAGGAG AGGCAGCGCC TCACACCCAG CATCCTGCCT CTGACTGCCC   91020
AGGGGCCCAC AGGCGTGGAC ACTGTGACAG CCACTCCCTC TGCCCCCCCC CCGTCACCCA   91080
CTAGGCAGGA GCACTTCTGA CCAGACACTG AGCCTGCCCC AGGCACAGAG CTGCCCAAGC   91140
TGGACCTGCC CCCACTCACC ATCCATCCCT CCCAGAGCAG CCAGGCCGCA CTCACCAAAC   91200
GCCTGCTTGG ACTCAGCCAG CCTCTCCTCG TCGGTGGAGT CAATGACGTA GATGACGCCG   91260
TGACACTCCG CATAATACTG GGAGGAAGCA CCAGGAGTTG GGGCTCAGTC CCCACCCTGC   91320
CAAGGGCCAG CAGAGCCAGG CCTGTGTCAT GGCCACAGTG AGGGGCTCAC ATGAGGAAGG   91380
GGCAAGAGGG CAGCCCCCAA CTGCAAGACC CTTCTGGGAT GCATTCTGGG GTTGCGGGGA   91440
GATCTGGTGG AGGTGTCCCC AGACGCTGCT CCTGAGAACC TGCCGGCAAC CTTTGGCCTG   91500
```

-continued

ATGGTGGCCA AAGGTGAAAG ACAGGGATTG GGCCAGGCGT GGTGGCTCAC ACTTATTATC 91560
CCAACACTTT GGGAGGCAGA AGCAGGAGGA TCACCTGAGC CCACTTCACG GCCAACCTGG 91620
GCAACACAGT GAGACTCCGT CTGTACAAAA GCTTATGGTA ATGTGCGCCT GCAGTCCTAG 91680
CTACTCGGGA GGCTGAGGTG GGAGGATGGC TTGAGCCTGG GAGGTTGAGG CTGTAGTGAG 91740
CTCTGATCAC ACCACTGCAC TCCAGCCTGG GTGAGAATGA GAGACCCTGT CTCAAAAAAA 91800
AGATAGGGTT TGGGGGCTGG AGGAACCTAG ACCACAGCCT GGCCCGTTGA GGGAGTGCAC 91860
CTGTGGGGCT CTGTGCCAGC ACCTCGCACA GGGAGGGAGT GTGGCCATGC GGATAAGACT 91920
GACCAGCACC ATCTACGAAG CGAGCCTTCC CTGCCAGGAC AGGGCCAGAG TCACTGAGCT 91980
CAGACCTCTG CAGCCTGGGC TGGTCAGTCC TGGGCTCGCT GGCAACACTC CTGGGCAAGA 92040
CAGGGCACAG CCCCTGCAGC CTCAGGTACA AGTGCTGAGC CCTGGACCAG ATGAGTGCAC 92100
CTCTATCTCA ATCAGAAAAA AACACAGCAA ACTCCGCGTC CACGTGGAGC AGACAACAGC 92160
TCACATTTGC CACTTTGCCT CCAGGCTGTG CCAGCTCTCC TGTCCAGGCA TGAGTGCCCA 92220
GAGACCTAGA ACTGGATGCT GACCAGGTAG GACAAGCTGG TGGTCAGTGT GTTAAGACAC 92280
ACACACCCGA GAGCATGAGA AGCCAGGAGG CACAGCCCAA CTCTCCGAAA TCCTTAGGGT 92340
GTCTGAGCAG GGAGTACCAG ACAACCCCAT CCCAGTGCCA GACAAGCTTG TGCACCTGCA 92400
CTTCCCACAG AGGAGAGAAG CCTGTGCACC TGCACTTCCC ACAGTGGAAA GGAGGAGGCC 92460
CAAGGCCAGG CCCCCCCACC CCCAGGAACT TCCCACAGTG GAGAGGAGGC CCAAGGCCAG 92520
GCGCCCTCCA GGGTTCTGCA GGTAGCGAGG CCCCCCCACC CCCAGGAACT TCTCTGGCCT 92580
ACAGACAGGT CCCACACAGA GGCCGCCAAC CCCTCAAGGG ACCCTGCAGT GTGCCGGCTG 92640
TCTGCTGCTG ACACAAGGGA GCAGGCGGAC CCTAAGGTGG AGACCTCTGT GGCAGGAGGG 92700
GCGGCTCTGT GGAGGCTGCA GCAAGCCCAG TGAGAGAATC TCCACGTGGC TCCTGGGGCT 92760
TCTGAGCAGG GTGGCAGAAG GTTCATGTGC AACCGGGTCC TGGACCATGG GACCACGTGG 92820
CCAGAGCCAC CCATCACACC TACCAGGCAC AAGGTGCACA GCCCAGCAGG GCCGCAGTGG 92880
ACGGGAGCGA CACCTCAGGG CTGAGTGCGG GCAGGACCCA GAGCCCCACG CCCCAGTGGA 92940
GGCGTCACAG CAGTGGTCAT TGTGGGGTGC CCCACAAGGA GGGGGAAGAG GGAGGTGTCC 93000
CAGCGTGGCT CCTGGCTGGC CAGCTGACCC CAGTGGAGCA GTCAGAGGGA CTGTGGGTCT 93060
GAGTTTTTCT CCCCAGCAGC AATGGGAGCT CCCCAACTGC AAAGTGCCAG CCAGCCTGAG 93120
AGACTAGTGT TACAGCAAAG AACCCAGGAG CTGAGGTCCT GGCACATGCC ACACATGTGG 93180
ACACCAACCC AGGGTCCAGC CCCAGGACGA GGCCAATTCG CAATGACGCC CCTTTCTGTG 93240
GTGCTGGCTC TGCACAAGGA TGCAGGATAC AGGAACCAGG GTGGGAGCAG GGGCCTCCCT 93300
TCCGGTCCCT CCCAGTGACC TAGGGGGGTC CCTGCAGCTG ATCCTCCCAG CTCTGAGCTC 93360
AGCAGGGTCA GGGGTCCCGG CCACTAGAGC AGCACATACT CAGCAGACAC GCTGAATGAC 93420
GAGCCACAGC TGCCTCATGG GCATGACTTG CACCTCATGT CTAGGAGACC CTGGTGGGCA 93480
GGAGATGGGG CTGCCATCCC ACAGCTGTCC CACAGCTGGG GACCCAGGGA GCCACTGGCC 93540
CCACCACGGT GGTGTCTGGA GAAGGGCTCA GACTGCCAGG AAGTCGCACC CCAGCAGAAG 93600
TGGTAGTGAA TTGGGAGGGC ACTCAAGGAA GGGCTGTGCA GCCCCAAGAC CAGCAGCAAG 93660
GATGGGCTAC AGTGGCCCCC TTAAGTCTCC CTCTTCCAGT TTCGCCTTAA GAGAGGCCCT 93720
CAGGACCTTG GAGGAACCCC TCTCCAACGT GGAAGTGTGG GTCCACATAG GGCTGCAGCT 93780
GTGGCCAGTG CAGGCATCTC TGGCCCCACT GTATTCTTGC TTCATGTTGG AGAACACTGC 93840
ACCACCAGAT GGTCTCATTT TGGTTTCTGT GGGACCCACT TTGGCTGCAA AGAGCCACAC 93900

-continued

TGCCAGGTCA CACCTGCCCA GGGCAGCCCA CACTGGGGAC CCACCAGGCC ATGGTGTGAA 93960

GTCCCGGCCA GCCTGGCCCC ACATGGCACA GCATAGCCAG TTCTCCTCCA GGGCTCCCTG 94020

CTGGGCCAAC CACAGCTCTG CGGATCCTGC TGCCTGAGTC GACCTCTCCT CTCCCGTCCT 94080

CCCTGCCTTC CTGGTGCCGA CCCCCAGTGT GCATCCTGTA CCTCGACCTG TCTCAGCATC 94140

TGTGCCTGAG ACACCGGCCT GTGACAAGAT CATCATCATC TGTGTCACTC CCCAAGCATG 94200

CTGCGCACTG GACACACAGG CCCTGACTCA ACTTGTCCTG TCTGACTTCA GTGGTCCTAC 94260

AGGATCTATC AGAGATCACT TGGCCATGGG AGAAATGTCT TCTTGGCTAG AAGTCACAGC 94320

AGGAGGGGAC ACTTTGGGGG CGCCTAGGAA AGGGGAACTA GGATCAAAAA AGAGATCAGG 94380

ACCTGGGCAC TCAGCTCTAG AGATGGCATC AGGGCAGCCA AGGCACTGGG GACACCCCAC 94440

ACCCACTGTG CCAGCCTAGG GCAGGGAGCC CGAGGAAGCC ACAGGCTCTG CCCTGCTCAG 94500

TGCTGGACTC AGTGCCTGGC CCAGGCTGAG AAGGAGATAA ACTGCAGCCT TGGGGGTGTG 94560

GGGAAGGGGC ACCACACTGG GATCTCAGAA ATGCCCAAAA CCTGTGTCAA AATAGGAGAC 94620

TGCCCCTGTG ACACCCTGAG GAGTCTTCTG GTGATCATGG AAGAACAAAT GTTAAGCTAG 94680

AACTGAAGGA ACCTCATCAG GGGAGAGGCA GCCATCCTGC CGTCCCCACA TCTGGTCTTT 94740

GCCATTTCTG TGTCCTGTGG TGGTCAGCAG CAAGGTCTCT GAGCCGAAAG GAGGCACTCA 94800

CTTTGGAGGA GTGCAGGGTC CCCAGGTCCC CACACTTTGT CTTGTCCTGA CTGAGAAAGA 94860

AACAGACTGC CCTGACCTCT CTGACTTGGC CAGCGAGGTT GCCCTTAGGC TCAAACCCAA 94920

GCCAGGGTTT GAACATTCCC AGACACTTGT AAGATGTTTA GGTTGTTAAC ATAATGTTCA 94980

GGTTTCAAAA CATTGAAAGA AACTAGCCCC AGCCCTGAAC CCAGATCCCC CCCGGCTTCA 95040

GGCATGACCA GTGAACACGC CCTTCTCTCA CTGGTCACCT GAGGATGCCG CACTCTGTCA 95100

ACAGGTTCCC CTAATACATG CTCTGATCTG ATCGCCTTGG CATTTAGTGA TTCTTTCCCT 95160

GGAATTCTCC ACTGGCCCCA TCGCAGGGAA CTCCCAAGTG GGAAACTCCC CTACCACCAC 95220

TTTTGGGGCA ACTTCAGCTA AGGGTTCAGC TGGGACAAAA CAGGGAGCCA CTCGGGAACC 95280

TGGGACAGGA CCAGAGAGAA AACCCGAGGG ACAGAGTGGG TAAGGAAAGC TGCTGAGGAA 95340

GGGCCCAAAG GGCACTCTGG AAAGAAGTGG CACTGGAGGG CTGGGGTGGG GGTGGTCCTG 95400

GCCAGGGAGT CTTACCTTGT CCCACAAAGA CTGCAGCTCT TCCTGCCCTC CTAACTCCCA 95460

GAACATGAGC CGAGCCTTTC CCACATCCAC AGTGCCGACT GGGGAGAGGA GGAAACAGGC 95520

AACGCTCATG ACCTTGGTCC TCGACACACC CAGTCCCAGC TCTCCCAGGG GATGGGGCAA 95580

ACCATGCTGG TGCCACTCAA ATGAGACTTG AGAGGGGCCC GACAGGGCTG TGGCCACGGG 95640

CCAGCTGGAC TGTGAATATC ACGGCATCCT CAAGGCCCCA AACCCACAGC CTGCTATTGA 95700

GACCCTTACT GTTTAGGCCC ACGGTGGTGG TGATTTTGGA TAGACTCATC CCCTTGTAGT 95760

TCTTGTTAAA TCGGGTTTTC GACTGCTCCA GGAAGGTCTG AGGAGAGAGG CAGAGGCGAA 95820

ACACATCAAG GAGGGGCTAT ACTGGCTTCC AAATATCCTT ACTCAGGTCT GTTCTTTAAA 95880

AGACAGAAAC AGAAACAGAG CAACACTCTG CTCTTCAGGA GGCTGGTGGT GACTATCCTG 95940

CCGTCTCAGG TGAAATTTGG CTTCCGTCTG GGTAGTGAAC GTGCAGCTGA CAGCACAAAA 96000

CCGAAGGGGG CGCCGCCAGG CCGTGGGAAA GGTGCGCGCA AGGGCGTGGG CACTCACCGT 96060

CTTCCCAGCA TTGTCCAGGC CCAGGATCAG GATGCAGTAC TCGTCCTTCT GAAACATGTA 96120

CTTGTACAAG CCCGACAGCA GCGTGTACAT CCTGCCCTGG GCACCCCAAC ATAGGTCAGT 96180

GTGCAGCCAG AAAGCACCTC CCCTCCCCCG GGCTTCTCCA CGGTGGTCAG TGGCGCCCCA 96240

CGTCCAGCCG ACCGCTCAGG ACGAGAGCCT GGGGGCCATT CCCGACTCCT CGTCCCTCTC 96300

-continued

CCACCCCGTC CCTCTGTAAC TTCTCCCAGG TCAGCCGCCA CTGTGTCCTG CTCACAGCAA 96360

TGACTGCGAC CTCTCCGCAT ACACATCGGT TCCGGCCCCT CCCCTGCTCG CGGGACTACC 96420

CAGCCGGGTG TTCACAGTGA GCTCACCCGC GCTCCCGCCC TCCCCCGAGG CTTCGCTCCC 96480

ACGCTTCACG CGCGCGGAAC GGGGAACACA CTCGCTGCAG CCCCGCCTGG GCCACGGCAC 96540

CCTCGAGCGC CAGCCCCGCG CCCCACCCGG GAGCAGCGAG CCACCGGCGC GCTCCCCAGG 96600

AGCCCCTGCA GGCGCCGGGT AGGGACGCCC CATCACCCCA TTTCTTAAAA CGGGGACGGC 96660

CCTGGGGGGA GCGGACTACA GGGCGGGTGA GCAGCGGCGC GGCTGCTCCT GGAGTGCACC 96720

TGGAGGCGGC GCGCGGCTGG CAGGGAACGA CTGCGAAGGA AGAACCTGGG TCGCGGCCCC 96780

CGGCTACGTC CGCCCCAAGC CGCCGCCGCC AGGTCTGAGG CTCCCCGACA AGCAGCCAAA 96840

GCTGGCTCCT GTCACACCCG CGTCCCACCT CGAGTCCTGG GCCGCCCCTC GGGCCTCGCG 96900

CCTCACCGCA CAGCCTGCGG CCTACCTGCG TCCGCCGCGC CCTCGGAGCC GCTGCTGCTG 96960

ACCCCCGCTG ACCTCCGCTG ACCCCGCGCT AACCCCGCGC GGCGCCTGAC GGGACGCGGG 97020

CCGGCCTCAG GGAATGAGCT GAACCGCGTC CCAGCGGCCT CCGCGCTCCG CTTCCCGGCT 97080

GCCCCCGCGC GCCAAGCACT TCCGGAAGCG GCGGCGCTCG GGAGGAAGTG CCGATCGGCT 97140

GCTGGGGCGA AAAGGGGGCG CCGGGCCGCT CTAGCCGGTG AGGCCGGCGG GCTCTCTGTG 97200

GCTGCGGCTG GGAAACCGCG CGGAGGAGGT GCCCGCCCGG GGACCACGTG GCCGCGGTTT 97260

GCGGGGACGC GGCCCTGGCC AGACAGAAGA GACGCCGGGC GGGGGGGCGC GGCCGGCCTG 97320

GAAGGCGGCG GGCGCGGCGG GTGGGCTCGG CGGAGGGTGA GGCGGCGGGG CGCCCCGCGG 97380

GGAAGGGGCT CCGGAGTGAC GCGGGACCCG GCTAGCGGCG AGCCCACGGC GGCTCGGAAG 97440

GGAAGCGCGG AGCCTGAGCG GGGGTACCCG GGCTGCGACC TCTGCGCTGG GAGCTGTGCC 97500

TCTGAGCCGG TGTCTCCCCG AGGGAAAGGG GACGTGCCCG TGCCCGTCCC CGCCCTCAGG 97560

CTGTGGGGTC GGTCCCGAGA CGCGGGGCTC AGCTGGCTTC TCTTCTTGCA GCCCTGGTCC 97620

AGCGCCTCCC TCTCTCAGCA TGGACGAGGA GAGCCTGGAG TCGGCCTTGC AGACCTACCG 97680

TGCGCAGCTG CAGCAGGTGG AGCTGGCCTT GGGCGCCGGC CTGGATTCGT CTGAGCAGGC 97740

TGACCTGCGC CAGCTCCAGG GGGACCTGAA GGAGCTCATC GAGCTCACCG AGGCCAGCCT 97800

GGTGTCTGTC AGGAAGAGCA GGTTGTTGGC CGCGCTGGAC GAAGAGCGCC CGGGCCGCCA 97860

GGAAGATGCT GAGTACCAGG CTTTCCGGGA GGCCATCACT GAGGCGGTGG AGGCACCAGC 97920

AGCGGCCCGT GGGTCCGGAT CAGAGACCGT TCCTAAAGCA GAGGCGGGGC CAGAATCTGC 97980

GGCAGGTGGG CAGGAGGAGG AAGAGGGAGA GGACGAGGAA GAGCTGAGTG GGACAAAGGT 98040

GAGCGCGCCC TACTACACCT CCTGGGGCAC TCTGGAGTAT CACAACGCCA TGGTGGTGGG 98100

AACGGAAGAG GCGGAGGATG GCTCGGCGGG TGTCCGTGTG CTTTACCTGT ACCCCACTCA 98160

CAAGTCTCTG AAGCCGTGCC CGTTCTTCCT GGAGGGAAAG TGCCGCTTTA AGGAGAACTG 98220

CAGGTAAAGC CCTTTGTTGT CAGATGCCAA CCTTAGGGGC GTAAGGGGCA CGCACACAGG 98280

GTCGGGTCAG GATCGGCCCT CCCTTTGCTT TGCAGTTTTG TCTCAGCTTC CTGGGGCAGG 98340

CGTGCTTTGA CAGCTGTGTC TGTGTTCAGG CGTCTACGTC TTCCTTCTGG GGTGAATCAA 98400

GAAGCATGGA AGGAGGCCAG GCGCGGTGGC TCACGCCTGT AATCCCAGCA CTTTAGGAAG 98460

CCGAGGCGGG CAGATCACCT GAGGTCAGGA GTTCAAGACC ACGCTGGTCA ACATGGTCAA 98520

ACCCCATCTC CTTAAAAACA CAAAAATGAA CCGGTCGTGG TGGCGCGCAC CTGTGGTCCT 98580

GGCTACTCAG GAGGCTGAGG CAGGAGAATT GGTTGAACCC AGGAGGCCGA GTTTGCAGTG 98640

AGTGGAGATG CAGCCACTGT ACTGCAGCCC GAGCAGCAGT GCAAGGCTTA TGTGGAAGAG 98700

-continued

```
AGTAGGTCTC CAGCCTATCG TCAGTTTTTT TTTGGTCGTT GTTTTAATTT TTTTTGAGAC   98760
AGGGTCTTAC TTTGTCAACC AGGCTGGAGT GCAGTGGCAT AGTCCTGGCT CACTGCAGCC   98820
TGGACCTCCT GGGCTCAACC GATCCTCCTG CCTCAGCCCC CCTAGGAGCT GGGCTACAGA   98880
CTCACGCTAC TACACCCAGC TAATTTTTAT ATTACTATAA TTTTTTATCT TTTTTTTGAG   98940
ACGGAGTCTT GTTCTGTTGC CCAGGCTGGA GTGCAGTGGC GTGATCTCGG CTCACTGCAA   99000
GCTCCGCCTC CCGGGTTCAC GCCATTCTCC TGCCTCAGCC TCCCGAGTAG CTGGGACTAC   99060
AGGCGCCCGC CACCATGTCT GGCTAATTTT CTGTATTTTT AGTAGAGACG GGGTTTCACC   99120
ATGTTAGCCA GGATGGTCTC AATCTCCTGA CCTCGTGATC CGCCCACCTT GGCCTCCCAA   99180
AGTGCTGGGA TGACAAGCGT GAGCCACCGC GCCTGGCCTT TTTTTTTTGG AGACAGAGTT   99240
TCACTCTCCT CACCCAGGCT GGAGTGTAGT GGCGCAATCT CAGCTTACCG CAACCTCTGT   99300
CTCCCGGGTT GAAGTAATTC TCTACCTCAG CGTCCAGAGT AGCTGGCATT ACAGGCGCCC   99360
GCCACCACAC TCGGCTAATT TTTTGTATTT TTAGTAGAGT CGGAGATTCA CCATCTTGGC   99420
CAGGCTGGTC TTGAACTCCT GACCTCGTGA TCCACCCACC TTGGCCTCCC AAAGTGCTGG   99480
GATCACAGGC GTGAGCCACT GCGCCTGGCC CTGTTGTTAG TTTTATTCTC TAGAGTTCAA   99540
CTTTTAAATT TTACTTTCAT GGAGATTTTC AAACATACCC CAAATTAGAG AGTTTAGCAT   99600
AATCACCGCC CACGGTCCAT CATCCAATGT CGTCATTTAT TAATATTTTC CCAGTCTCAT   99660
TTTGTCTGTT CTCCCTGCCC TATTTTTTTC TTTCCTGGGC CATTTTAAAG CAAATTCCAG   99720
AAGTTACTGG TTTTTTCCAA TTATGAATAC TTCATAGTTG CATCTCTAAT CTAACTGATT   99780
AGGAAATTAC TTAAAAAGTA ACTTTTTGGA AGTCCAAGTC CGATGTGAGG ACAAAAAAGA   99840
GTAACTTCTG TGTCATAATA GGTAACACAT TTAATGGTAA TACCTCTTCC ATATTCAAAT   99900
ATGAACAATT ATTACTGTAA TGTCTCTATT TCCCTAAGCG CATAGCTTTA TTTTTCCTCC   99960
TTTTTACTTT TCTCTTAGAA GAAATATTTA CCAAGCCTTC TAGTAGGTAA TTTTCTTTTT  100020
TAGCCAATAG TTCAGGCTGA CCGTGTAACC ATCCCTAGTT CTAGTTCTAG TTCTTTGAAT  100080
GTCTTCCTTT TTTTTTTTTT TTGAAACAGC GTCTTGCTGC TCTGTCACCC AGGCTGGAGT  100140
GCAGTGGCAC AATCTCGGCT CACTGCAATC TCCGCCTCCC TGGCCCAAGC CATCCTCCCA  100200
CCTCAGCCTC CCTAATAGCT GATACTACAA GTGTGCACTG CCACGCCCAG CTAATTTTTG  100260
TATTTTTTGT AGAGACGGGA TTTCACCATA TTACCCAGGT CTCGAATTCC TGATCCCTTT  100320
GATGAGAGAT CTGACACATC CCTGTGGTGC TCCCTCTGGA CCAGGCACTG CTCCAAGGGT  100380
TTCATATACT TTCATTCATC TGTGCAACAG CCCTGTAGGT AGGCCCTGCA GTCACACCAT  100440
CTGACAGAGG AGGAAACAGG AGTAGAAGAA CTGAGTGGTC CAGGGCTTCA AGGCTCAGAG  100500
GGCTCCAGTT GCCCCCAGCC CTCGTTCCGT CCCCTGCTCC ACCCAGTGCT GCTTGCCATG  100560
TCGGCATCAG GCCTGATCTG AAAGCTTCCG GAGCATCTTA CAGACGTCCA CCTTCCCACC  100620
ATTCAGGACT GATAAGTTCT CTTGGATTTG CGTTGGACCT TTTTTTTTTT TTTAAGATGG  100680
AGTTTCACTG TTGTTGCCCA GGCTAGAGTA CAATGGCACG ACCTCCACCT CCTGGGTTCA  100740
AGGGATTCTC CTGCCTCAGC CTCCCAAGTA GCTGGGATTA CAGGCGCCTG TCACCACGTG  100800
GTGCCCAGCT AATTTTTATA TTTTTAGTAG AGGCAGGGTT TCACCGTGTT GGCCAGGCTG  100860
GTCTCGAACC CTTGACCTCA GGTGATCCCG CCTTGGTTTC CCAAAGTGCT GGGATTACAG  100920
GCATGAGCCA CCACACCCGG CCCAGGATTT CTTTATATAT TCTGGATATC ATCCCTTATG  100980
AAGTATATAG TTTGCAGATA TTTGCTCCCA TTGTTTGGGT TGTCTTTTCA CTTGATATAG  101040
TGTCCTTTGA TGCACAAACA TTTTAAATTT TGATGCAGTG CAATTTATTG TTTCTTTATT  101100
```

-continued

```
GCCTATGTTT TTGTCATCAG GTTTAAGAAA CCACCTCATC CATAGTTATG AGGATTTTCA  101160
CCTATGTTTT CTTCTAAGAG TTCTGTAGTT TTAGCTGTTA AATTTAGGTC TTTGATCCAT  101220
TTTGAGTTAA TTTTTGTATA TGTTATTAGG TGAGGGTCCA CTTTATTCTT TTGCATGTGG  101280
ATTTCCAGTT TTCCCAGCAC CATTTGTTTA AAAGACTGCT TTTTCTCCAC TGAATGGTCT  101340
TGGCACTTTT GTCCAAAATC AATTGGCAAT ATATGTAAGG GTTTATTTCT GAGCTCTCTC  101400
TCCTGTTCCA TTGGTGTATA TGTGCCAGTA CCACACTGTT CTGATTATTA TAGCTTTGTG  101460
ATAAGTTTTA AACTCAGGAA GTGGTAGTTA TTCACCATTT GCTCCTCTTT TTCAAGTTTG  101520
TTTTGTTTCT GGATCCTTTG CAATTTCATA TGAATTTTAG GATCGGCTTG TCCAATTCTG  101580
CATAAAAGAC AGTTTGAATT TTGATATGGA TTGCATAGAA TGTGTAGATC TGTTTGGGGC  101640
ACATTGTCAT CTTTACAATA TTAAGCCTTC TGGCTGGGTG TGGTGGCTGA CGCCTGTAAT  101700
CCCAGTACTT TGGGAGGCTG AGGCGGGCAT ATCACTTGAG GTCAGGAGTT CAAGACCAGC  101760
CTGGCCAACG TGGTGAAACC CCGTCTCTAC TAAAAATAAA AAACAAATTA GTCGGAGGTG  101820
GTGCACACCT GTAATCCCAG CTACAGGAGA GGGTGAGGCA GGAGAATCGC TTGAACCTGG  101880
GAGGAGGAGG TTGCAGTGAG CTGAGATCAT GCCACTGCAC TCCAGCCTGG GTAACAGAGG  101940
GAGACTCCAT CTTAAACAAC AACAATAACA GAAGAAAAAA ACAGTATTAA GTCTTCCAAT  102000
TCATGAATGA AGGATCTGTC CATTTATTTA CGTCTTTAAT TTCTTTCAAC AGTATTTTGT  102060
ACTGTTCAAG TCTTGCACAT TCTTGGTTAA ATAAGTATTA TTTTTGATGC TTCTCTAAGG  102120
AATTGTTTTT CTTTTCCTTT TTTTTTTTGA GACAGAGTCT TGCTCTGTCA CCCAGGCTGG  102180
AGTGCAGTGG CACAATCTTG GCTCACTGCA ACCTCTGCCT CCCGGGTTCA AGCAATTCTT  102240
CTGCTCACCC TCCCAAGTAG CTGGGATCAC AGGTGCCTGC CACCACACCC AGCTAATTTT  102300
TTTTTTTGAG ATGGAGTCTT GCTCTGTTGC CCAGGCTGGA GTGAAGTGGC CCAATCTTGG  102360
CTCACTGCAA GCTCCACCTC CCGGGTTCAC ACCATTCTTC CGCCTCAGCC TCCTGAGTCG  102420
CTGGGAATAC AGGTGCCTGC CACCACGCCC AGCTAATTTT TTGTATTTTT AGTAGAGATG  102480
GGGTTTCACC ATGTAGCCAG GATGGTCTCG AACTCTTGAC CTCAGGTGAT CTGCCTGCCT  102540
CGGCCTCCCA AAGTGCTGGG ATTACAGATG TGAGCCACTG TGCCCGGCTC GAGTTGTTTT  102600
CCTTAGTTAC ATTTTCAGGC TGTTTGTTGC TAGTATATAG AAATACAAGC TGGGCACCGT  102660
GGCTCACGCC TGTAATCCCA GCACTTTGGG AGGCCAAGGC GGGTGGATCA CCTGTGGTCA  102720
GGAGTTCGAG ACCAGCCTGG CCAACATGGT GAAATCCAGC CTCTATTAAA AATACAAAAA  102780
TTAGTCTGGC ATGGTGGCAG GTGCCTGTAA TCCCATCTAC TCAGGAGGCT GAGGCAAGAG  102840
AATTGCTTGA ACCTGGGAGG CGGAGGTTGC AGTGAGCTGA GATCGCGCCA TTGCACTCCA  102900
GCTTGGGGAA CAAGAGTGAG ACTTCATCTC AAAAAAAAAA AAAAAGAAAT ACAGTGGATT  102960
TTTTTATGTT AATCCTGTAT TGATTGCTGA ATTGGTTTAT TAGTGCTAAT AGGATTTTTT  103020
ATGCACTATT TAGGATTTTC GATATATACA ATCATATATA TTCAATATAT ACAATTAATA  103080
TATATGTGAA TAGAGATAAT TGTAGTCTTT GTTTCTAGTT TGCATGGCAT TTATTTCTTT  103140
TTCTTGCTTA ACTGCCTTAG CTAGAACTTC AAGTACGATG TTGAATAAAA GTGACTAGAG  103200
CGGGCCGGGG GTGGTGGCTC ACACCTGTGT TCCCAGCACT TTGGGAGGTG GAAGTGGGCA  103260
GATCACTTGA GATCAGCAGT TTGAGACCAG CCTGGCCAAC ACGGCGAAAC CCCATCTCTA  103320
CTAAAAATAC AAAAATTAGC TGGGTGAGGT GATGTGCACC TGTAGTCCCA GCTACTTGAG  103380
AGGGTGAGAC ATGAGAATTG CTTGAACCTG GGGGGCGGAG GTTGCAGTGA GCCAAGATCA  103440
TGCCACTCCA CTCCAGCCTG GAGGACAGAG CAAGAACCCT GTCTTTAAAA AAAAAAAAAA  103500
```

-continued

AAAAGTGGCT AGAACAAACA TCTTTATCTT GTTCCTGATC TTAGGTGGAA AACTTTTTTG 103560

TTCCTGATAT TAGGTGGAAA ACTTTTAGTC TTTCACTGTT GAATATGATG TTACTTGTAG 103620

GTTTTCTGTA GATTCCCTTT ATCGAGTTGA GGAAATTCTC TTATATTCAT AGTGTGTTGA 103680

GTGTTTTTTA TCATGAAAGG GTGTTGATTT TTTTTTTAAA GATAGGGTCT TGTTCTGTCA 103740

CCCAGGCTGG AGGGCAGTGG CATGATCATG GCTCACTGCA ACCTCGAATT CCTGGGCTCA 103800

GGGGATCCTC CTACTTCATC CTCCTGAGTA GGTGAGACTA CAGGCATGAG CCACCATGCC 103860

CAGCTAATTT TTTAATTTTT CTGTAGAGGT AGGGTCCTGC TTTGCTGCCC AGGCTGGTCT 103920

TAAACTCCAG GGCTCAAGCA ATCCTGCCTC AGCCTCCCAA AGTGCTGAGA TTACAGGGGT 103980

GAGTCACTGC ACTGCACCCA GCTGTGTGGG ATTTTTCAAA TGCTTTTTTC CTTTAGATGA 104040

TCATGTGTGG TTTTTTTCCT TTCATTTTGT TAATGTGGTA TATTGATTTT CGTATGTTGA 104100

ACCATCCTTG AATTCCTCAG ATAAAGCACG CATATTCATG GCGTATTATC TCTTTATTAT 104160

TATTTTTTTT GTAGAGATGA GATTTCACTC TGTTGCCCAA GCTGGTCTCA AACTCCTGGG 104220

CTAAAGTGAT CCTCCTGCCT CAGCCTCCGA AAGCGCTGGG ATTATAGGCA TGAGCCACTT 104280

GGCCCTATCT TTTTTCTTTT TCTTTTTTTT TTTTTTTTGA GACAGAGTCT CACTCTGTCG 104340

CCGGGCTGGA GTGAGTGGCG CGATCTCGGC TCACTGCAAC CTCCATCTCC CGGGTTCAAG 104400

CAATTCTCCT GCCTCAGCCT CCTGAGTAGC TGGGACTACA GGTGCCCGCC ACTATGCCCA 104460

GCTAATTTTT TGTGTTTTTA GTTGAGACGG TGTTTTGCCA TGTTGGACAG GCTGGTCTTG 104520

CACTCCTGAC CTCGTGATTC ACCCACCTTG GCCTCCCGAA GTGCTGGGAT TACAGGCATG 104580

AGCCACCGCA GCGAGCCTTA TCTTTTTAAC AGTTAAAAGT TTAAGGCCTT ATCATGTAAT 104640

AACATTGCTG GATTTGATTT GCTGCTGTTT TGTTGAGAAT ATTTGCATCT GTATTGATAA 104700

GGGATATTGG TCTGTAGTTT TCTTTTCTTG GCATGTCTTT GTATAGCTTT GATGCCAGCA 104760

TAATATTGGC CTCATAGAAT GAGTTAGGAA GTATTCTTTA TATTATGGGA AGAGGTAAAA 104820

AGGGATTGGT GTTAATTCTT CTTCAAATGT TTGATAGAAT TCAACAGTGA AGTGATATAT 104880

ACAATCATAT ATATAGAGAG AGAGAGAGAG AGAGATGGAC TTTTCTTTTG TTGGAAGTTT 104940

ATTGACTATT GATTCAATTT CCTTATTGAA ATTGACTTTT CTTTTTGGAA GCTAAAATGT 105000

ATAACTGTAG TGAAAGTTTC TGAACTTTTC TTTCATTGGA AGTTTTTTGA CTACTGATTC 105060

TTTATTTGTT ATAGGTCTAT TCAGATTTTC TGTTTCTTCT TGAGTCAGTT TGGTCTCGCT 105120

CTGTCGCCCA GGCTGGAGTG CAGTGGTGCC ATCTTGGCTC ACTGCAACTT CTACCTCCCG 105180

AGTTCAAGTG ATTCTCCCAC CTCAGCCTCC CCAGTATCTC GGACTACAGG CGCACGCCAG 105240

CATACCTGGC TAATTTTTGT ATTTTTAGTA GGAACAGCAT TTCACCATGT TGGCCAGGCT 105300

GGTCTCGAAC TCCTGACCTC AGGTGATCCA CCCGCCTCGG CCTCACAAAG TGCTGGGACT 105360

ACAGACATAA GCCACCGCGT CCAGCCTTGA GTCAGTTTAG ATAGTTTGCA TGCATGTTTC 105420

TAGGAATTTG TCCATTTTGT TTATGTTATC TAATCTGTTA CCATACAATT GTTCATAGTA 105480

TCCTTTTATA GCCCTAGTTA TTTCTGTAAG ATCAGTAGTA ATAGCTCCAC TTTCTCTCTT 105540

GGTTTTAGCA ATTTGAGTCA TCTCTTTTCT TCTTCTTTTT TTTTTTTTGA GATGGAGTCT 105600

CACTGTGTCA CCCAGGCTGG AGTGCAGTGG CATGATCTTG GCTCACTGCA ACCCCTGCCT 105660

CCCAGGTTCA AGCAATTCTG CCTTAGCCTC CTGAGTAGCT GGGATTACAG GTGTGAGCCA 105720

CCACACCCAG CTAGTTTTGT TTTGTTTTTT TGTTTTTGAG ACGGAGTCTG TTTCTGTCTC 105780

CCAGGCTGGA GTGCAGTGGT GCAATCTCAC TCATTGCAAC CTCCGACTCC CAGATTCCAG 105840

CAATTCTCCT GCCTCAGCCT CCCGAGTAGC TGGAACTATA GGCGTGCACC ACCACGCCTG 105900

-continued

```
GCTGATTTTT ATATTTTTAG TAGAGATGGG ATTTCACCAT GTTGGCCAGG CTGGTCTTGG  105960
ACTCCCTACC TGAGGTGATC CGCCCACCTT GGCCTCCCAA AGTGCTGGGA TTATAGGCAT  106020
GAGCCACCAT GCCCAGCCAG TTTTTGTATT TTTAGTAGAG ATGGGGTTTC TCCCTGTCGG  106080
CCAGGCTGGT CTTGAAATCC TGACCTCAGG TTATCCACCA GCCTTGGCCT CCCAAAGTGC  106140
TAGGATTACA GGCATGAGCC ACCACGCATG GCCTGTCTTT TCTTCTTGGT CATTTTCGCT  106200
AAAGGTTTGT CAATTTTGTT GATCTTTTTT GTTGCTGATC TCTATTGTTT TCCCATTCTG  106260
TTTCATTTAT TTCCATTTTA ACCTTTGTTT CCTTTTTTCT GCTGGTTTGG GTTTAATTTG  106320
CTCTTTTTTT CCCCTAATTT TTCAAGGTAT ACAGTTAAGT TATTGATTTG AGATCTCTTT  106380
TTTCTTTTCT TTTTTTTTTT TTTTTTTTTT TTTGGTTGCT GTTGAGATGG AGTCTCCCTC  106440
TGTCACCCAG ACTGGAGTGC AGTGGCATGA TCTCAGCTCA CTGCAGCCTC CGCCGCCCAG  106500
GCGATTCTCC TGCCTCAGCC TCCTGAGTAG ACGTTTCCCG GCCAAGGTGT TTCTTTTTGA  106560
ATGTAAGCAT TTACAGCTAC AGATTTCCCT CTAAACACTG CTTTCACTGC ATTCCATAAG  106620
ATTGTTTTTT GTTGTTTTTT GTTGTTGTTT TGTTGTTTGA GACACAGTCT CACTCTGTTG  106680
CCGTTTGGAG AGCAGCGATG CGATCATAGC TCTGTAGCCT TGAGCTCCTG GACTCAATCA  106740
GTCCTCCTGC CTCAGCCTCC CAAGTAGCTG GGACTACAGG TGTACACCAC TGCACCTAAC  106800
TAATTTCTTT TATAAGTTTT TGCAGAGGCC AGGCACAGTG GCTCACACCT GTAATCCCAG  106860
CACTTTGGGA GGCCAAGGTG GGTGGATCAC CTAAGGTCAG GAGTTCGAGA CCAGCCTGGC  106920
CGACAGGGAG AAACCCCATC TCTACTAAAA ATACAAAAAT TAGCTGGGCG TGGTGGCAGG  106980
TGCCTGTAAT CCCAGCTACT CAGGAGGCTG AGGCAGGAGA ATCGCTTGAA CCTGGGAGGC  107040
AGAGGTTGCA GTGAGCCAGG ATCACACCAT TGCACTCCAG CCTGGGTAAC AAAAGCAAAA  107100
CTCCATCTCA AGAAAAGAAA AAAAAAAGTT TTTGCAGAGA CAGGGTATCA CTTTGTTGCC  107160
CAGGCTGGTC TCAAACTCCT GACTTGAAGG AGTCCTACTG CCTCAGCCTC CCAAAGTGCT  107220
GAGATTATGG GCAAGAGCCA CCGCACCCTG CCACTTGGCT GTTTTGTTCT GTTGTATTTC  107280
CATTTTCATT GATCTCAAGA CATCCTAATC TCCCTTTTGT TTTTTTGTTC GACTTACTGG  107340
TTATTCAAGA GTGTCTTTAT TTCTGCATAT TTGTAAATTT TCCAAAAAAG TTTTTCTTTC  107400
TTTTTTTTTT GAGAAAGGGT CTTGCTCTGT CGCCCAGGCT GGAGAATGGT GGTGCACAAT  107460
CTTGCCTCAC TGCAACCTCT GCCTCCCGGG TTCAAGTGAT CCTCCCACCT CAGCCTTCCC  107520
AGTAGCTGGG ATTACAGGCA CACACCACCA CACCTGGCTA ATTTTTGTAT TTTAGTCTTA  107580
ACGTGCTGGT CAGACTGGTC TCGAATTCCT GACCTCAGGT GATCTGCCCG CCTTGGCCTC  107640
CCAAAGCACT GGGATTACAG GCGTGAAACA CCATGCCCAG CCCCCAATTT TTTTTTTTTA  107700
ATAGAGAGAA GGTCTCACTC AAGCCCAGGC TGGTCTTGAA CTCCTGAGCT CAAGCTGTCA  107760
TCCCTCCTCG GCCTCCCAAG GTGCTGAGAT TACAGGTGTG AGTCACAGTA CCTGGCCTTC  107820
TTTCAAGACT TTAAAAATGC CATCTTGGCT GGGCACGGTG GCTCACGCCT GTAATCCCAG  107880
CACTTTGGGA GGCCGAGGTG GGCAGATCAC GAGGTCAGGA GATCAAGACC ACCCTGGCTA  107940
ACATGGTGAA ACCCTGTCTC TACTAAAAAT ACAAAAAATT AACCAGGTGT GGTGGCAGGT  108000
GCCTGTAGTC CCAGCTACTC GGGAAGCTGA AGCAGGAGAA TGGCGTGAAC CCGGGAGGTG  108060
GAGCTTGCAG TGAGCTGAGA TCACACCACT GTACTCCAGC CTGGGCAACA GTGCGAGACT  108120
CCGTCTCAAA AAAAAAAAAA AAAATGTCAT CTCACTGCCT TCTGGTCCAA TAGTTTCTGA  108180
TGAGAAATTG GCTGTTAATC TTATTGAGGA ACATTTATAT ATTGACTAGT CACTTGTCTC  108240
TTGCTGTTTT AGGAGATTCT CTATCTTTGG GTTTCAGCAG TTTGATTATA ATGTATCAGT  108300
```

-continued

```
GTGGATCCCT CAATTTATAA GCTACTTGGA GTTCATTGGA CTTCTTGGAT GTGTAAATTC  108360
ATGTCTTTCA TTAAATTTGC AAAGTTTCAG CTACTATTCT TTGCATCTTG AAATACTAGT  108420
TTTGTTTCTT TCTGTCTGTT TGCCGCTTAT GGAACTTTAT GCATACATTG ATGTGCTTCA  108480
TGGTGTAGCA CAGGTCCCTT GGGCTCTAGG CATTTTTCTT TGTTCTTTTT TTCTTTCTGC  108540
TCCTCATTTT GGATAAATTC AGCTGACCTG TCCTCAAGTT CACTGTTTCT TTCTTCTTCC  108600
TTCTCAAATC TGCTGTTGAA ACTTCTGGTG AAATTTTCAC TACAGTTACT GTACTTTTTA  108660
GCTCCAAAGT TTCTATTTGG TTTCTTTCTG TAGTAATTAT CACTTTACTA GTATTCTCTA  108720
TTTGGTTACA CATGGTTCTT TTGTTTTCCT TTAGTTCATT ATCCATGGTT TCCTTTATTT  108780
TTAAATTTCT TTTTATTTAG TTATTAATTT TTTTTTTTTT TGAAGCGGGG TTTCACTCTT  108840
GTCACCCAGG CTGGCAGGCA ACGTCACAAT CTTGGCTCAC TACAACCTCC GCCTCCTGGG  108900
TTCAAGTGAT TCTCCTGCCT CAGCCTCCCA AGTAGCTGGG ATTATAGGCA TGTGCCACCA  108960
CACCCACCTA ATTTTTGGTA TTTTTAGTAG AAACTGGGTT TCACCACATT GGCCAGACTG  109020
GTCTTAAACT ACTAACCTCA GGTGATCTGT CCGCCTCAGC CTCCCAAAAT GCTGGGATTA  109080
CAGATGTGAG CCACTGTGCC CAGCCTCTTT TTTTAGTGTA TTTAAGGTAA TTGATTGAAA  109140
GTTTTTGTCT AGTCATTCAA ATGTCTAGGC TTCCTCAGGA ACAGTTTCTA TTAATTTCTT  109200
TATTTTTAAA AAATTTTTTT TAATTTTCTT TTTTTTTTAG ATGGAGTCTC ACTCTATAGC  109260
CTAGGCTGGA GTGCAATGGC TTGATCTTGG CTCACTGCAA CCTCTGCCTC CTGGGTTCAA  109320
GCGATTCTCC TGCTTCAGCC TCCTGAGTAG CTGGGACTAT AGGTGCGTGC CACCACTCCT  109380
GGCTAATTTT TTGTATTTTC AGTAGAGACA TGGTTTTGCC GTGTTAGCCA GGATGGTCTC  109440
GATCTCGTGA CCTCATGATC CTCCTGCCTC GGCCTCCCAA AGTGCTGGAA TTACAGGTGT  109500
GAGCCACCGC GCCCAGCCTA TTTTTTATTT TTTGAGACAA AGTCTCCCTC TCTCACCCAG  109560
GCTGTAGTGC AGTGGCACAA CCCTGGCACA CTGCAGCCTT AACCGTCCAG GCTTAAGTGA  109620
GTCTCCCACC TTAGTCTCCT GAGTAGCTAG AACTACAAGC ATGTGCCACC ATGCCTGGCT  109680
GGTTGTGTTG TTACTGTTTT AGACACAGGG TCTTGCTACA TTTCTCTGAC TGGTCTTGAA  109740
CTCCTGGGCT CAAGCAGTCA TCCCACCTTG GCCTCCCAAG GTGTTGAGAT TACAGGTGTG  109800
AGCCACCGCA CCCGGCCTGT TAATTTCTTT ATTTCCGGTG AATGGGCCAC ACTTTCTTGT  109860
TTCTTTGCAT GCCTTGTAAT TTTTTGTTGA AACCTGCACA ATTTGAAGAT GATAATGTCG  109920
TTACTTTGAA AATCAGATCC TCCGCCCTCT GCAGGGTTCA TTGTTGCTGT TTGTTGTGGA  109980
TTGTCGTTTC TCGTTTGTTT AGTTACTTTC CTGACCTTTT TAAATAAAGA CTATATTCTG  110040
TCAGGGGTGC TTGTTTCTGT TCTTTTAGGT TAGTGGTTAG CTTGTGCTTT GAAAGAGATT  110100
TCTTTAAATA TCTAGTGGCA AAAAGGATAA AGAGGCCGGG CGCAGTGGCT CACGCCTGTA  110160
ATGCTAGGAC TTTGGGAAGT GGAGGCGGGT GGATCACTTG AGGTCAGGAG TTTAAGATCA  110220
GCCTGGCCAG TATGGTGAAA CCCTGTCTCT ACTAAAAATA CAAAAATTAA CCGGGCATGG  110280
TGGCACCTGC CTGTAGTCCC AGCTACTGGG AAGACTGAGG CAGGAGAATC GCTTCAATCC  110340
AGGGGGCGGA GGTTGCAGTG AGCTGAGATT GCGCCATTGC ACTCCAGCCT GGGCAACAGA  110400
GCGAGACTCT GTCTCAAATA AAAAAAAAAA AAAAAGGATA AAGAGTGTCT TCCATCCTTT  110460
CCAGGTTGCC TCTGTACTGG GGCAAGTCCT TCAGTGTCCG CCAGGCTGTT CACGGCTTTT  110520
CCTCAGCCTT TACTTCTCGC TCCCATGGAG CCTAAGGATG AACCAGAGGT GAAAGTTGAG  110580
GGCCTCCTCA GGTGTTTCTG AGCCCCTGTC TAGCCCCAGC TGTGTGCATG GCCTTCTGGA  110640
TTTCCAAGCA TGAACAGGAG CTTTCCAAAG CCCTTAGACC TTCATGTAGC TCTTTTCCCA  110700
```

-continued

```
GCCTCTTCCT TCCTAGGCTT TTCTGTCAGC TCTTTGCCCA TCTGTTGTTG TCCCTCCCCC 110760
ACAACTTCAG GTAGTATCTA CCTGTAAATG CCTTCAGGCC AGGCGCGGTG GCTCATACCT 110820
GTTATCCCAG CACTTTGGGA GGCCGAGGCG GGTGAATTGC TTGAGGTCAG GAGTTCGAGA 110880
CCAGCCTGGC CAACATGGTG AAGCCCCGTC TCTAGTAAAA ATACAAAAAT TAGCTGGGCG 110940
TGGTGGGTGC CTGTAATCTC AGCTACTCGG GAGGCTGAAG CAGGAGAATT GCTTGAGCCT 111000
GGGAGGCGGA GGTTGCAGTG AGCTGAGATC GTGCCATTGC ACTCCAGCCT GGGCGACAGA 111060
GTGAGACTCC ATCTCGGGGA AAAAAAAAAA AAAAAAATGC CATCAACAGC ACGACCCTGG 111120
AGGCTGCCCC AGCCCTGAGA GAGTTCGAGG GGGTGAAACA AACGCAAGCC CTTCAGGGAG 111180
ACACTAGAAA GATCCAAATC CATAAGCAGG ATTCCTTGAG AAAAGGTCTG TATCATCCCT 111240
TCTGACACCA GCAAGCCACA TCAGAAATAC AGGTTGCCTT CCCCATGGCT ACATGTGAGC 111300
TGGTAGTAGT GGCTGAGCAG AAATAGCCCA GCTGTCCTCC TGAAATTTAG CAGGGTCTTA 111360
CTTCATTGAG CAGTCATCTG GTTCGTAGAC ACCAGAGTTA CAGAAAAGTT TATTGGGAGG 111420
TTTTGACAGT TTAATAGAAA AAAGTTTATT GTGACAGTTT TGACAGCTGA ATAGAAAAAA 111480
GTTTACTGTG ACAGTTTTGA CAGCAGAATA GTTGCTTTGC TGGAGAGACG GATCTTTGGA 111540
GCTGCCAACT CCATCATTTT GGTGATATCC AGCTCTGTTG CTGAATTTTT AGCTATGCTG 111600
TTTTAAGTTA TTTTCTTAGT GGTTGCTCTA GAGATGACAA TGTGCATCTT TAACTTACCA 111660
CAATGTACTT CAGATTATTA CTAACTTAAC ACTTAAAGTA CAGCATTTTT TTTTTTATGG 111720
AGTTTCACTC TGTCACCCAG GCTGGAGTGC AATGGTGTGA TCTCGGCTCA CTGCAACCTC 111780
CGCCTCCCAG GTTCACGCCA TTCTCCTGCC TCAGCCTCCT GAGTAGCTGG GACTACAGGC 111840
ACCCCCACCA CACCCGGCTA ATTTTGTATT TTTAGTAGAG ATGAGGTTTC ACCATGTTGG 111900
TCAGGCTGGT CTCGAACTGC TGACCTCAGG TGATCCGCCC ATCTTGGCCT CCCAAAGTGC 111960
TGGGATTACA GGTGTGAGCG ACTGCACTGA GCCTAAGTAT GGCAACGTGT CTATAACATA 112020
GATCTACTTC CGTTGTACTA TGACATAGTT CCCCCTCCAT TTTCCTATAG CACAGTCCCA 112080
ACCTCCCTTT TCCTCTGACA TAGTTCCATC CTCCCTCCTC CTATGACGTC CTCCCTTCTC 112140
CTCTGGCATA GCTCCATCCT CCCTTCTCCT ATGACACAGC TCCATCCTCC CTTCTCCTCT 112200
GACACAGCTC CATCCTCCCT TCTCCTATGA CACAGCTCCA TCCTCCCTTC TCCTCTGACA 112260
TAGCTCCATC CTCCCTTCTC CTATGTCATA GCTCCATCCT CCCTTCTCCT CTGACACAGC 112320
TCCATCCTCC CTTCTCCTCT GGCATAGCTC CATCCTCCCT TCTCCTATGA CACAGCTCCA 112380
TCCTCCCTTC TCCTATGACA CAGCTCCATC CTCCCTTCTC CTATGACACA GCTCCATCCT 112440
CCCTTCTCCT ATGACACAGC TCCATCCTCC CTTCTCCTCT GGCATAGCTC CATCCTCCCT 112500
TCTCCTCTGA CATAGCTCCA TCCTCCCTTC TCCTCTGACA TAGCTCCATC CTCCCTTCTC 112560
CTCTGACATA GCTCCATCCT CCCTTCTCCT CTGACATAGC TCCATCCTCC CTTCTCCTCT 112620
GACATAGCTC CATCCTCCCT TCTCCTCTGA CATAGTTCCA TCCTCCCTTG TCCTCTGACA 112680
TAGCTCCATC CTCCCTTCTC CTCTGACATA GCTCCATCCC CTCTTCTCCT TCATGTATTA 112740
TTGCCATATA TACATTTATG TATGTTATAA CTTCAGCTCT TCAGCGTTAT AATTATTGCT 112800
TCAAAAGTAT TTTGAAAGAA GTTGCCTGGA GGCACTGGCT TATGCCTTTA ACTCCAGCAC 112860
TTTTGGGGGC TGAGGTGGGC AGATCGCCTG AGCCAGGGAG TTGGAGACCA GCCTGGGCAA 112920
CATGACGAAA CCCATCTCCA CCAAAATTAC AAAAAATTAG TCTGGCATGG TGGCACGCGC 112980
CTGTAGTCCC AGCTATTTGG GGGAGGATCC CAGCTAAGGT GGGAGGATCA CTTGAGCCTG 113040
GGAAGTCAAG GCTGCAGTGA GCTGAGATTG TGCCACTGCA CTCCAGCCTG GGTGCAGATC 113100
```

-continued

```
TTATCTCAGA AGTAAAGGGA CTAGGAATGG TGGCTTTTAT CTCTAATCCC AGCACTTTGG  113160

GAGGCTGAGG TGAGTGGATC ACCGGAGGTC AGGAGTTTAA GACCAGCCTG GCCAACATGG  113220

TGAAACCCCG TCTCTACTAA AAATACAAAA AGTAGCCGGG TGTGGTGGTG GGTGTCTGTA  113280

ATCCCAGCTA CTCGGGAGGC TGAGGCAAGA GAATCGCTTG AACCTGGGAA GCGGAGGTTG  113340

CAGTGAGCAA GATCGCACCA CTGCATTACA GCCTAGATGA CAGAGCGAGA CTCTGCCTAA  113400

AAAAAAAAAA AAAAAGAAAA GAAAAGAAAT TAAGATCTAG ACACTGTGGT TCATGCCTGT  113460

AATCCCAAAG CCTTGGGAGG CCAAGGCAGG AGGATCACTT GAGGCCAGGA GTTCAACACC  113520

AGCCTGGGCA ACATAGCGAG ACTCCATCTC TATTTAAAAA AGAAAGAAAT TCAAAGAGAA  113580

AAAAAGTATA CTTGTTTTTT TGTATCATCC ATATTTTACC TTTCTTTTTT TTGCCCCTTT  113640

TTCTTTCCTG TGAATTTGAG TTACTGTCTA GTGTCATTTC CTTTTAGTCT GAAGAACTTC  113700

ATTTAGAATT TTTTTTTTTT TTTGAGACAA AGTCTCACTG TGTTGCCCAG GCTGGAGTGC  113760

AATGGTGCAG TCTCAGATCA CTGCAACCTC TGCCTCCCTG GTTAGAGTGA TTTTCCTGCC  113820

TCAGCCTCCC AAGTAGCTGA GACTGCAGGC ACCTGCCACC ACCCCCAGCC AATTTTTTTG  113880

GTATTTTTAG TAGAGACAGG GTTTCACTAT GTTGGCCAGG CTGGTCTCGA ATTCATGACC  113940

TCATGATCTG CCTGTCCTGG CCTCCCAAAA TGCTGGGATT ACCATGAGCC ACCACGCCCA  114000

GCCCATTTAG AATTTCTTTT TTTTTTTTTT TTTTGAGATG GGGTCTCGCT CTTGTTTCCC  114060

AGGCTGGAGT GCAGTGGCAC GATCTCGGCT CACTGCGAGC TCCGCCTCCC GGGTTCACGC  114120

CATTCTCCTG CCTCAGCCTC CCGAGTAGCT GGGATTACAG GCGCCTGCCA CCACGCCCAC  114180

CTAATTTTTT GTATTTTTAG GAGAGATGGG GTTTCACCAT GTTAGCCAGG ATGGTCTTGA  114240

TCTCCTGACC TCGTGATCCG CCCGCCTTGG CCTCCCAAAG TGCTGGGATT ACAGGCGTGA  114300

GCCACCGCGC CCGGCTAGAA TTTCTTGTAG GACAGGCTTG CTAGCAACCA ATTCAGTGTT  114360

TATTTGGGAA TGTCTTTATT TCAGCTTCAT TTTTTGAAGG ATAGTTTAGC TGGCTATAGA  114420

ATTATTAATT GATCATTCTT TTCAGTGTTT AAAAGTGTCA TCATGCTACC TTCTGGGTTC  114480

CATTGTTTCT GATGAGAAGT CATCTGTCAA ATTGTCCCTT TGTACTTGAA GAATTATCTT  114540

TTTTTCTCTT GATGTTTTCA AGATTTTCTC TTTGTCTTTG GCCTTTAGTA GTTTGTGATG  114600

TATCTAGGTG TGGATCTCTT GGTGTGCATC GTATTTGGGC TTCAGTAAGC CTCTTAGATT  114660

CATAGATTAA TGTTTTGTTT TGTTTTACCA AATTTGGAGA GTTTTTACTC ATCATTTCAA  114720

CAAATTTTTT TCCTGCCCCT CTCTCATCTC CTTTTGGGAG TACCACTGCA TGTATGTTGG  114780

TGTGCGTTCT CTA.                                                    114793
```

Figure 5B:
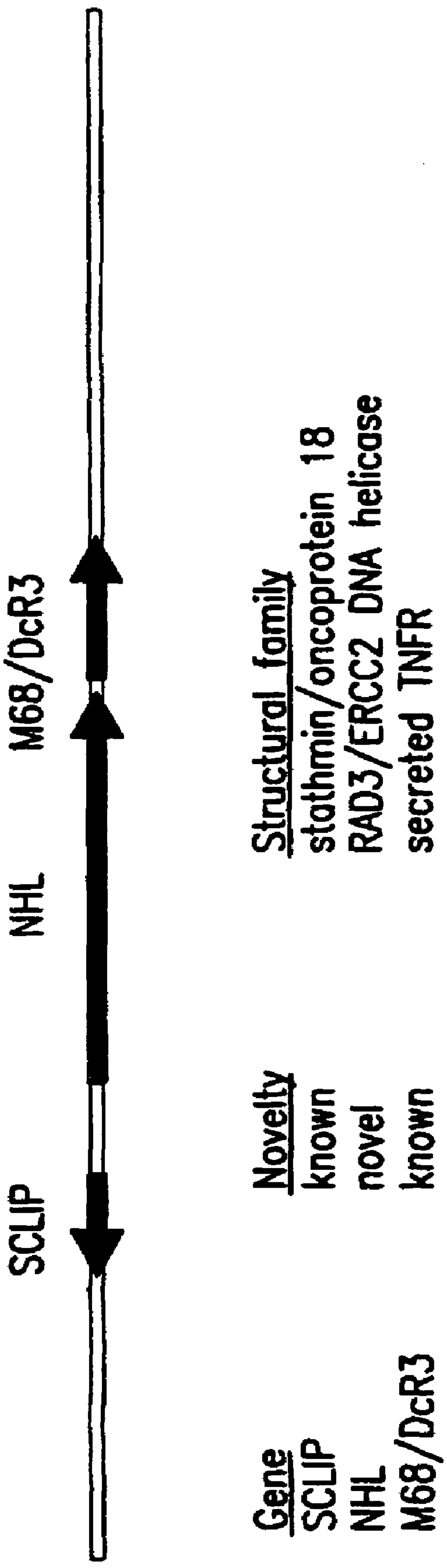

The present invention also relates to a portion of SEQ ID NO:3 which comprises 5' regulatory regions, exons, introns and 3' non-translated regions which comprise the human NHL gene of the present invention. Such regulatory sequence may be found within the various regions of this 115 kb fragment. The 5' portion of SEQ ID NO:1 begins at nucleotide 47095 of SEQ ID NO:3, the initiating ATG of human NHL is from nucleotide 48687-48689 of SEQ ID NO:3, the termination 'TAG' codon is from nucleotide 84855-84857, while the 3' terminus of SEQ ID NO:1 as disclosed herein (GCAGTGCCC) corresponds to nucleotides 85308-85316. To this end, one preferred aspect of the invention is an isolated genomic fragment or fragments which comprise from about nucleotide 470000 to about nucleotide 85500 of SEQ ID NO:3), which comprises the portion of the genomic clone encoding the mRNA transcript responsible for human NHL (see FIG. 5A-B). The genomic sequence encoding NHL contains 35 exons (FIG. 5A). An especially preferred aspect of the invention is a human genomic fragment or fragments which comprise from about nucleotide 47095 to about nucleotide 85316 of SEQ ID NO:3. As noted in regard to SEQ ID NO:1, the present invention also relates to DNA vectors and recombinant hosts which comprise at least a portion of SEQ ID NO:3. Portions of the 115 kb genomic fragment may be housed in multiple vector/hosts so as to optimize handling of the DNA sequences within SEQ ID NO:3. Therefore, the present invention relates to the isolated genomic sequence which set forth as SEQ ID NO:3, a region of SEQ ID NO:3 which contains the coding and non-coding region of human NHL, as well as cis-acting sequences within SEQ ID NO:3 which effect regulation of transcription of one or more of the genes localized within this 115 kb human genomic fragment, including regulatory regions effecting levels of NHL, M68/

DcR3, SCLIP and ARP. As noted above, this region of chromosome 20 (20q13.3) is associated with tumor growth. Therefore, an aspect of this invention also comprises, as one example, the use of one or more regulatory regions of this 115 kb genomic sequence as a target to antagonize the effect of a transcriptional factor(s) which normally upregulate expression of a gene which has a caustic role in tumor growth. Alternatively, compounds may be selected which interacts with a specific cis-acting sequence to upregulate a gene within this region, where upregulation results in a decrease in tumor growth.

The present invention is also directed to methods of screening for compounds which modulate the expression of DNA or RNA encoding a NHL protein. Compounds which modulate these activities may be DNA, RNA, peptides, proteins, or non-proteinaceous organic molecules. Compounds may modulate by increasing or attenuating the expression of DNA or RNA encoding NHL, or the function of the NHL-based protein. Compounds that modulate the expression of DNA or RNA encoding NHL or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing NHL, antibodies to NHL, or modified NHL may be prepared by known methods for such uses.

The DNA molecules, RNA molecules, recombinant protein and antibodies of the present invention may be used to screen and measure levels of NHL. The recombinant proteins, DNA molecules, RNA molecules and antibodies lend themselves to the formulation of kits suitable for the detection and typing of NHL. Such a kit would comprise a compartmentalized carrier suitable to hold in close confinement at least one container. The carrier would further comprise reagents such as recombinant NHL or anti-NHL antibodies suitable for detecting NHL. The carrier may also contain a means for detection such as labeled antigen or enzyme substrates or the like.

The assays described above can be carried out with cells that have been transiently or stably transfected with NHL. The expression vector may be introduced into host cells via any one of a number of techniques including but not limited to transformation, transfection, protoplast fusion, and electroporation. Transfection is meant to include any method known in the art for introducing NHL into the test cells. For example, transfection includes calcium phosphate or calcium chloride mediated transfection, lipofection, infection with a retroviral construct containing NHL, and electroporation. The expression vector-containing cells are individually analyzed to determine whether they produce NHL protein. Identification of NHL expressing cells may be done by several means, including but not limited to immunological reactivity with anti-NHL antibodies, labeled ligand binding, the presence of host cell-associated NHL activity.

The specificity of binding of compounds showing affinity for NHL is shown by measuring the affinity of the compounds for recombinant cells expressing NHL. Expression of human NHL and screening for compounds that bind to NHL or that inhibit the binding of a known, radiolabeled ligand of NHL provides an effective method for the rapid selection of compounds with high affinity for NHL. Such ligands need not necessarily be radiolabeled but can also be nonisotopic compounds that can be used to displace bound radiolabeled compounds or that can be used as activators in functional assays. Compounds identified by the above method are likely to be agonists or antagonists of NHL and may be peptides, proteins, or non-proteinaceous organic molecules.

Accordingly, the present invention is directed to methods for screening for compounds which modulate the expression of DNA or RNA encoding a NHL protein as well as compounds which effect the function of the NHL protein. Methods for identifying agonists and antagonists of other receptors are well known in the art and can be adapted to identify agonists and antagonists of NHL. For example, Cascieri et al. (1992, *Molec. Pharmacol.* 41:1096-1099) describe a method for identifying substances that inhibit agonist binding to rat neurokinin receptors and thus are potential agonists or antagonists of neurokinin receptors. The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the substance, and then measuring the binding of the radioactively labeled known agonist of the neurokinin receptor to the neurokinin receptor. If the amount of binding of the known agonist is less in the presence of the substance than in the absence of the substance, then the substance is a potential agonist or antagonist of the neurokinin receptor. Where binding of the substance such as an agonist or antagonist to is measured, such binding can be measured by employing a labeled substance or agonist. The substance or agonist can be labeled in any convenient manner known to the art, e.g., radioactively, fluorescently, enzymatically.

Therefore, the present invention includes assays by which modulators of NHL are identified. As noted above, methods for identifying agonists and antagonists are known in the art and can be adapted to identify compounds which effect in vivo levels of NHL. Accordingly, the present invention includes a method for determining whether a substance is a potential modulator of mammalian NHL levels that comprises:

(a) providing test cells by transfecting cells with an expression vector that directs the expression of NHL in the cells;

(b) exposing the test cells to the substance;

(c) measuring the amount of binding of the substance to NHL;

(d) comparing the amount of binding of the substance to NHL in the test cells with the amount of binding of the substance to control cells that have not been transfected with NHL or a portion thereof; wherein if the amount of binding of the substance is greater in the test cells as compared to the control cells, the substance is capable of binding to NHL.

The conditions under which step (b) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C.

The assays described above can be carried out with cells that have been transiently or stably transfected with NHL. Transfection is meant to include any method known in the art for introducing NHL into the test cells. For example, transfection includes calcium phosphate or calcium chloride mediated transfection, lipofection, infection with a retroviral construct containing NHL, and electroporation.

Where binding of the substance or agonist to NHL is measured, such binding can be measured by employing a labeled substance or agonist. The substance or agonist can be labeled in any convenient manner known to the art, e.g., radioactively, fluorescently, enzymatically.

Therefore, the specificity of binding of compounds having affinity for NHL shown by measuring the affinity of the compounds for recombinant cells expressing the cloned receptor or for membranes from these cells. Expression of the cloned receptor and screening for compounds that bind to NHL or that inhibit the binding of a known, radiolabeled ligand of NHL to these cells provides an effective method for the rapid selection of compounds with high affinity for NHL. Such ligands need not necessarily be radiolabeled but can also be nonisotopic compounds that can be used to displace bound radiolabeled compounds or that can be used as activators in functional assays. It is also possible to construct assays wherein compounds are tested for an ability to modulate helicase activity in an in vitro- or in vivo-based assay. Compounds identified by the above method again are likely to be agonists or antagonists of NHL and may be peptides, proteins, or non-proteinaceous organic molecules. As noted elsewhere in this specification, compounds may modulate by increasing or attenuating the expression of DNA or RNA encoding NHL, or by acting as an agonist or antagonist of the NHL receptor protein. Again, these compounds that modulate the expression of DNA or RNA encoding NHL or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample.

Expression of NHL DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of NHL in a host cell, NHL protein may be recovered to provide NHL protein in active form. Several NHL protein purification procedures are available and suitable for use. Recombinant NHL protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant NHL protein can be separated from other cellular proteins by use of an immunoaffinity column made with monoclonal or polyclonal antibodies specific for full-length NHL protein, or polypeptide fragments of NHL protein.

Polyclonal or monoclonal antibodies may be raised against NHL or a synthetic peptide (usually from about 9 to about 25 amino acids in length) from a portion of NHL disclosed in SEQ ID NO:2. Monospecific antibodies to NHL are purified from mammalian antisera containing antibodies reactive against NHL or are prepared as monoclonal antibodies reactive with NHL using the technique of Kohler and Milstein (1975, *Nature* 256: 495-497). Monospecific antibody as used herein is defined as a single antibody species or multiple antibody species with homogenous binding characteristics for NHL. Homogenous binding as used herein refers to the ability of the antibody species to bind to a specific antigen or epitope, such as those associated with NHL, as described above. Human NHL-specific antibodies are raised by immunizing animals such as mice, rats, guinea pigs, rabbits, goats, horses and the like, with an appropriate concentration of NHL protein or a synthetic peptide generated from a portion of NHL with or without an immune adjuvant.

Preimmune serum is collected prior to the first immunization. Each animal receives between about 0.1 mg and about 1000 mg of NHL protein associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of NHL protein or peptide fragment thereof in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of NHL in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with NHL are prepared by immunizing inbred mice, preferably Balb/c, with NHL protein. The mice are immunized by the IP or SC route with about 1 mg to about 100 mg, preferably about 10 mg, of NHL protein in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of NHL in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using NHL as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2\times10^6$ to about $6\times10^6$ hybridoma cells about 4 days after priming. Ascites fluid is collected at approximately 8-12 days after cell transfer and the monoclonal antibodies are purified by techniques known in the art.

In vitro production of anti-NHL mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of NHL in body fluids or tissue and cell extracts.

It is readily apparent to those skilled in the art that the above described methods for producing monospecific antibodies may be utilized to produce antibodies specific for NHL peptide fragments, or a respective full-length NHL.

NHL antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing full-length NHL or NHL protein fragments are slowly passed through the column. The column is then washed with phosphate buffered saline until the optical density ($A_{280}$) falls to background, then the protein is eluted with 0.23 M glycine-HCl (pH 2.6). The purified NHL protein is then dialyzed against phosphate buffered saline.

Pharmaceutically useful compositions comprising modulators of NHL may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified NHL, or either NHL agonists or antagonists including tyrosine kinase activators or inhibitors.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The present invention also relates to a non-human transgenic animal which is useful for studying the ability of a variety of compounds to act as modulators of NHL, or any alternative functional NHL in vivo by providing cells for culture, in vitro. In reference to the transgenic animals of this invention, reference is made to transgenes and genes. As used herein, a transgene is a genetic construct including a gene. The transgene is integrated into one or more chromosomes in the cells in an animal by methods known in the art. Once integrated, the transgene is carried in at least one place in the chromosomes of a transgenic animal. Of course, a gene is a nucleotide sequence that encodes a protein, such as one or a combination of the cDNA clones described herein. The gene and/or transgene may also include genetic regulatory elements and/or structural elements known in the art. A type of target cell for transgene introduction is the embryonic stem cell (ES). ES cells can be obtained from pre-implantation embryos cultured in vitro and fused with embryos (Evans et al., 1981, *Nature* 292:154-156; Bradley et al., 1984, *Nature* 309:255-258; Gossler et al., 1986, *Proc. Natl. Acad. Sci. USA* 83:9065-9069; and Robertson et al., 1986 *Nature* 322:445-448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, *Science* 240: 1468-1474). It will also be within the purview of the skilled artisan to produce transgenic or knock-out invertebrate animals (e.g., *C. elegans*) which express the NHL transgene in a wild type background as well in *C. elegans* mutants knocked out for one or both of the NHL subunits. These organisms will be helpful in further determining the dominant negative effect of NHL as well as selecting from compounds which modulate this effect.

The present invention also relates to a non-human transgenic animal which is heterozygous for a functional NHL gene native to that animal. As used herein, functional is used to describe a gene or protein that, when present in a cell or in vitro system, performs normally as if in a native or unaltered condition or environment. The animal of this aspect of the invention is useful for the study of the retinal specific expression or activity of NHL in an animal having only one functional copy of the gene. The animal is also useful for studying the ability of a variety of compounds to act as modulators of NHL activity or expression in vivo or, by providing cells for culture, in vitro. It is reiterated that as used herein, a modulator is a compound that causes a change in the expression or activity of NHL, or causes a change in the effect of the interaction of NHL with its ligand(s), or other protein(s). In an embodiment of this aspect, the animal is used in a method for the preparation of a further animal which lacks a functional native NHL gene. In another embodiment, the animal of this aspect is used in a method to prepare an animal which expresses a non-native NHL gene in the absence of the expression of a native NHL gene. In particular embodiments the non-human animal is a mouse. In further embodiments the non-native NHL is a wild-type human NHL which is disclosed herein, or any other biologically equivalent form of human NHL gene as also disclosed herein.

In reference to the transgenic animals of this invention, reference is made to transgenes and genes. As used herein, a transgene is a genetic construct including a gene. The transgene is integrated into one or more chromosomes in the cells in an animal by methods known in the art. Once integrated, the transgene is carried in at least one place in the chromosomes of a transgenic animal. Of course, a gene is a nucleotide sequence that encodes a protein, such as human or mouse NHL. The gene and/or transgene may also include genetic regulatory elements and/or structural elements known in the art.

Another aspect of the invention is a non-human animal embryo deficient for native NHL expression. This embryo is useful in studying the effects of the lack of NHL on the developing animal. In particular embodiments the animal is a mouse. The animal embryo is also useful as a source of cells lacking a functional native NHL gene. The cells are useful in in vitro culture studies in the absence of NHL.

An aspect of this invention is a method to obtain an animal in which the cells lack a functional gene NHL native to the animal. The method includes providing a gene for an altered form of the NHL gene native to the animal in the form of a transgene and targeting the transgene into a chromosome of the animal at the place of the native NHL gene. The transgene can be introduced into the embryonic stem cells by a variety of methods known in the art, including electroporation, microinjection, and lipofection. Cells carrying the transgene can then be injected into blastocysts which are then implanted into pseudopregnant animals. In alternate embodiments, the transgene-targeted embryonic stem cells can be coincubated with fertilized eggs or morulae followed by implantation into females. After gestation, the animals obtained are chimeric founder transgenic animals. The founder animals can be used in further embodiments to cross with wild-type animals to produce F1 animals heterozygous for the altered NHL gene. In further embodiments, these heterozygous animals can be interbred to obtain the non-viable transgenic embryos whose somatic and germ cells are homozygous for the altered NHL gene and thereby lack a functional NHL gene. In other embodiments, the heterozygous animals can be used to produce cells lines. In preferred embodiments, the animals are mice.

A further aspect of the present invention is a transgenic non-human animal which expresses a non-native NHL on a native NHL null background. In particular embodiments, the null background is generated by producing an animal with an altered native NHL gene that is non-functional, i.e. a knockout. The animal can be heterozygous (i.e., having a different allelic representation of a gene on each of a pair of chromosomes of a diploid genome) or homozygous (i.e., having the same representation of a gene on each of a pair of chromosomes of a diploid genome) for the altered NHL gene and can be hemizygous (i.e., having a gene represented on only one of a pair of chromosomes of a diploid genome) or homozygous for the non-native NHL gene. In preferred embodiments, the animal is a mouse. In particular embodiments the non-native NHL gene can be a wild-type or mutant allele including those mutant alleles associated with a disease. In further embodiments, the non-native NHL is a human NHL. In a further embodiment the non-native NHL gene is operably linked to a promoter. As used herein, operably linked is used to denote a functional connection between two elements whose orientation relevant to one another can vary. In this particular case, it is understood in the art that a promoter can be operably linked to the coding sequence of a gene to direct the expression of the coding sequence while placed at various distances from the coding sequence in a genetic construct.

An aspect of this invention is a method of producing transgenic animals having a transgene including a non-native NHL gene on a native NHL null background. The method includes providing transgenic animals of this invention whose cells are heterozygous for a native gene encoding a functional NHL protein and an altered native NHL gene. These animals are crossed with transgenic animals of this invention that are hemizygous for a transgene including a non-native NHL gene to obtain animals that are both heterozygous for an altered native NHL gene and hemizygous for a non-native NHL gene. The latter animals are interbred to obtain animals that are homozygous or hemizygous for the non-native NHL and are homozygous for the altered native NHL gene. In particular embodiments, cell lines are produced from any of the animals produced in the steps of the method.

The transgenic animals and cells of this invention are useful in the determination of the in vivo function of a non-native NHL in the central nervous system and in other tissues of an animal. The animals are also useful in studying the tissue and temporal specific expression patterns of a non-native NHL throughout the animals. The animals are also useful in determining the ability for various forms of wild-type and mutant alleles of a non-native NHL to rescue the native NHL null deficiency. The animals are also useful for identifying and studying the ability of a variety of compounds to act as modulators of the expression or activity of a non-native NHL in vivo, or by providing cells for culture, for in vitro studies.

As used herein, a "targeted gene" or "Knockout" (KO) is a DNA sequence introduced into the germline of a non-human animal by way of human intervention, including but not limited to, the methods described herein. The targeted genes of the invention include nucleic acid sequences which are designed to specifically alter cognate endogenous alleles. An altered NHL gene should not fully encode the same NHL as native to the host animal, and its expression product can be altered to aminor or great degree, or absent altogether. In cases where it is useful to express a non-native NHL gene in a transgenic animal in the absence of a native NHL gene we prefer that the altered NHL gene induce a null lethal knockout phenotype in the animal. However a more modestly modified NHL gene can also be useful and is within the scope of the present invention.

A type of target cell for transgene introduction is the embryonic stem cell (ES). ES cells can be obtained from pre-implantation embryos cultured in vitro and fused with embryos (Evans et al., 1981, *Nature* 292:154-156; Bradley et al., 1984, *Nature* 309:255-258; Gossler et al., 1986, *Proc. Natl. Acad. Sci. USA* 83:9065-9069; and Robertson et al., 1986 *Nature* 322:445-448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, *Science* 240: 1468-1474).

The methods for evaluating the targeted recombination events as well as the resulting knockout mice are readily available and known in the art. Such methods include, but are not limited to DNA (Southern) hybridization to detect the targeted allele, polymerase chain reaction (PCR), polyacrylamide gel electrophoresis (PAGE) and Western blots to detect DNA, RNA and protein.

The following examples are provided to illustrate the present invention without, however, limiting the same hereto.

EXAMPLE 1

Characterization of DNA Molecules Encoding NHL

M68/DcR3 identification—The human osteoprotegerin (OPG) sequence (Acc. #U94332), which is a member of the TNFR-related family, was used to searched Genbank using the programs TBLASTN and TFASTX3 to identify novel gene family members. Two EST sequences (GenBank Acc. #AA155701 and AA025672) were identified that showed sequence similarities to the cysteine repeats of the OPG sequence. These EST sequences were then used to identify additional EST sequences, which formed a single EST cluster (GenBank Acc. #s aa577603, aa603704, aa613366, aa158406, w67560, aa325843, aa155646, aa025673, aa514270, m91489). Two clones were further characterized, which were derived from colon tumor and germ cell tumor libraries (Research Genetics, Inc). DNA sequence analysis revealed two alternatively spliced forms of the 5'-end UTR of M68/DcR3. The M68/DcR3 open reading frame was confirmed by sequence analysis of clones obtained by PCR cloning from a normal human cDNA library (Clontech).

M68/DcR3 BAC identification and sequencing—To further delineate the gene structure of M68/DcR3, genomic DNA was obtained using a human "Down to the Well"™ genomic bacterial artificial chromosome (BAC) library (Genome Systems, Inc.) according to the manufacturer's protocol. Two sets of PCR primers, C68.36F: 5'-CACAGGTTCAGCATGTTTGTGCGTC-3' (SEQ ID NO:4) and C68.275R: 5'-CACAGTCCCTGCTGGCCTCTGTCTA-3' (SEQ ID NO:5), and E68.715F: 5'-CAGGACATCTCCATCAAGAGGCTGC-3' (SEQ ID NO:6) and E68.972R: 5'-AATAAGAGGGGGCCAGGATCAGTGC-3' (SEQ ID NO:7), were used to carry out PCR reactions to identify positive wells that contained the full-length M68/DcR3 gene. The PCR conditions used were 94° C. for 9 min, 35 cycles of (94° C., 30 sec., 68° C. 3 min.) followed by 72° C. for 10 min. Two positive BAC clones were identified and characterized by restriction digestion and BAC-end sequence analyses, of which hbm168 was selected for shot-gun sequencing.

A shot-gun library for BAC hbm168 was constructed using a conventional strategy. Briefly, two 150-ml bacterial cultures were combined and purified using a modified protocol of the plasmid-Maxi kit (QIAGEN) followed by CsCl gradient purification. After butanol extraction and isopropanol precipitation, BAC DNA was nebulizied at 10 psi for 60 seconds to generate randomly sheared fragments. Following ethanol precipitation, the fragments were end-repaired using T4 polymerase (Promega) and BstXI adaptors (Invitrogen) were ligated overnight. Removal of excess, unligated adaptors and size selection was performed using a cDNA sizing column (Life Technologies, Inc.) to generate genomic fragments in the size range of 1500 to 3000 bp. Adaptor ligated fragments were cloned into a modified pBlueScript $SK^+$ vector (Stratagene) and transformed in XL2-Blue ultracompentent cells (Stratagene). Approximately 1000 clones were isolated, plasmids were purified using the Turbo miniprep kits (QIAGEN), and both plasmid ends were sequenced with the BigDye terminator kits (Perkin-Elmer). Sequence data were assembled using Phred/Phrap/Consed where single-stranded and gap regions were closed using a directed sequencing strategy.

NHL identification and sequencing—The genomic clone for the NHL gene was obtained and sequenced. The transcript was identified through exon prediction using GRAIL2 and sequence alignment to a contiguous 4.5 kilobase region of chromosome 4 (88% sequence identity). The complete exon structure of NHL was subsequently confirmed by RT-PCR analysis. The exon structure was confirmed by RT-PCR using polyA RNA from a human colorectal adenocarcinoma cell line, SW480 (Clontech). Primers were designed based on the genomic sequence that were predicted to be exons. RT-PCR reaction were carried out with SW480 polyA RNA using standard conditions with TaqGold Enzyme at 94° C. for 12 min, 35 cycles of (94° C., 30 sec., 60C, 30 sec., and 68° C. 2-6 min.) followed by 68° C. for 7 min. Most sequence confirmation was accomplished by RT-PCR, although first junction between exon 1 and 2 was confirmed by 5'RACE and junctions between exon 26-29 were by RCCA. The primers used were as follows:

| Junction of Exons | Confirmed by Primers |
|---|---|
| H01/H02 | hdkw (5'RACE) |
| H02/H03 | hdiy, hdiz |
| H03-H09 | hdid, hdie, hdja, hdjb |
| H09-H13 | hdja, hdie |
| H13-H18 | hdje, hdjf |
| H18-H23 | hdjg, hdjh |
| H23-H26 | hdji, hdjj |
| H26-H29 | hdkv, r543(RCCA) |
| H29-H31 | hdij, hdmu, hdnd, hdne |
| H31/H32 | hdij, hdmu |
| H32/H34 | hdip, hdil, hdmv, hdik, hdli |
| H34/H35 | hdng, hdnh |

HDID - 5'-GTGAATGGCATCCTGGAGAG-3'; (SEQ ID NO:8)

HDIE - 5'-GTCTCCAGGCAGCTCAACAG-3'; (SEQ ID NO:9)

HDIJ - 5'-ACCCTGTCCCTCCTGTCTGA-3'; (SEQ ID NO:10)

HDIY - 5'-AGACCCTAAGATGTTCGGAG-3'; (SEQ ID NO:11)

HDIZ - 5'-GATGACCTGTGTGAGTTGCG-3'; (SEQ ID NO:12)

HDJA - 5'-CGCAACTCACACAGGTCATC-3'; (SEQ ID NO:13)

HDJB - 5'-GGAGTCAGGTCAAAGGATGC-3'; (SEQ ID NO:14)

HDJC - 5'-GCATCCTTTGACCTGACTCC-3'; (SEQ ID NO:15)

HDJD - 5'-GGTCTGAAACGTGATCTGGG-3'; (SEQ ID NO:16)

HDJE - 5'-CCCAGATCACGTTTCAGACC-3'; (SEQ ID NO:17)

HDJF - 5'-CGATGATGTGTGGGTTCTCC-3'; (SEQ ID NO:18)

HDJG - 5'-GGAGAACCGACACATCATCG-3'; (SEQ ID NO:19)

HDJH - 5'-CGTGTCTGAGAAGTCCAGCC-3'; (SEQ ID NO:20)

HDJI - 5'-GGCTGGACTTCTCAGACACG-3'; (SEQ ID NO:21)

HDJJ - 5'-ACAGCATCTTCTCCACGCAC-3'; (SEQ ID NO:22)

HFMU - 5'-AGTCCTCTGGCTTTGCAGTG-3'; (SEQ ID NO:23)

HDKV - 5'-TGTGCGTGGAGAAGATGCTG-3'; (SEQ ID NO:24)

HDKW - 5'-GGCTGGAAAGGGAAGTCTAC-3'; (SEQ ID NO:25)

HDND - 5'-TGGTTCAGGTGCTCTTGGGG-3'; (SEQ ID NO:26)

HDNE - 5'-CGTGAAGCAGGAGTTGAGCC-3'; (SEQ ID NO:27)

HDIK - 5'-ATCTTGCTCTGGGTCTTCCC-3'; (SEQ ID NO:28)

HDIL - 5'-CACTGCAAAGCCAGAGGACT-3'; (SEQ ID NO:29)

HDIP - 5'-ATAAGCAAGACGACGACCTC-3'; (SEQ ID NO:30)

HDLI - 5'-CTATTCTGTTGGGTGGGTTC-3'; (SEQ ID NO:31)

HDMV - 5'-CGTGCCTCCTGTGCTTACCC-3'; (SEQ ID NO:32)

HDNG - 5'-CAGACCCCAAGGTAGCTCAG-3'; (SEQ ID NO:33)

HDNH - 5'-GGAAGACCCAGAGCAAGATC-3'. (SEQ ID NO:34)

Figure 3D:
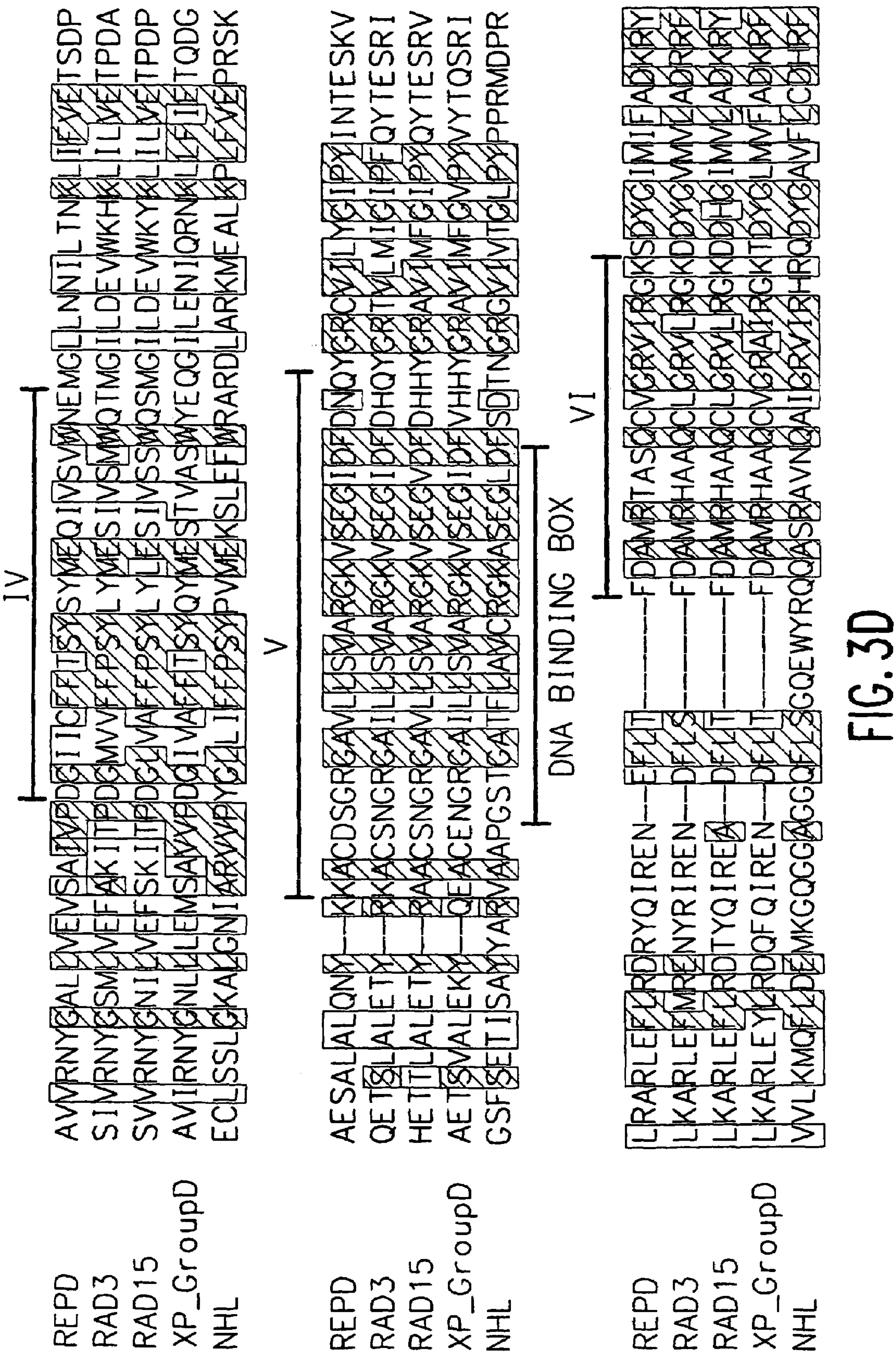

Amplified product were subject to direct sequencing after purification from an agarose gel or cloned into a TOPO PCR cloning vector (Invitrogen) for sequencing. Multiple sequence alignment of NHL to known helicases showed that NHL contains all the seven critical helicase domains. BLAST analysis of the predicted 1,219 amino acid sequence (see FIG. 2, SEQ ID NO:2) reveal an approximately 26% sequence identity and 48% sequence similarity to the RAD3/ERCC2 gene family of DNA helicases (see FIG. 3). Review of this sequence data shows that two partial human cDNA clones (Acc. No. a1080127 and ab029011) are deposited. No. a1080127 covers exon 25-35 while ab029011 covers exons 9-35. Ab029011 starts at amino acid 240 of the full length human NHL protein disclosed herein, but also differs at exon 35 and appears to be a fusion transcript with M68. This cDNA was isolated from brain tissue, which has been known to express rare transcripts.

EXAMPLE 2

Northern Analysis of Human NHL Expression

Figure 4:
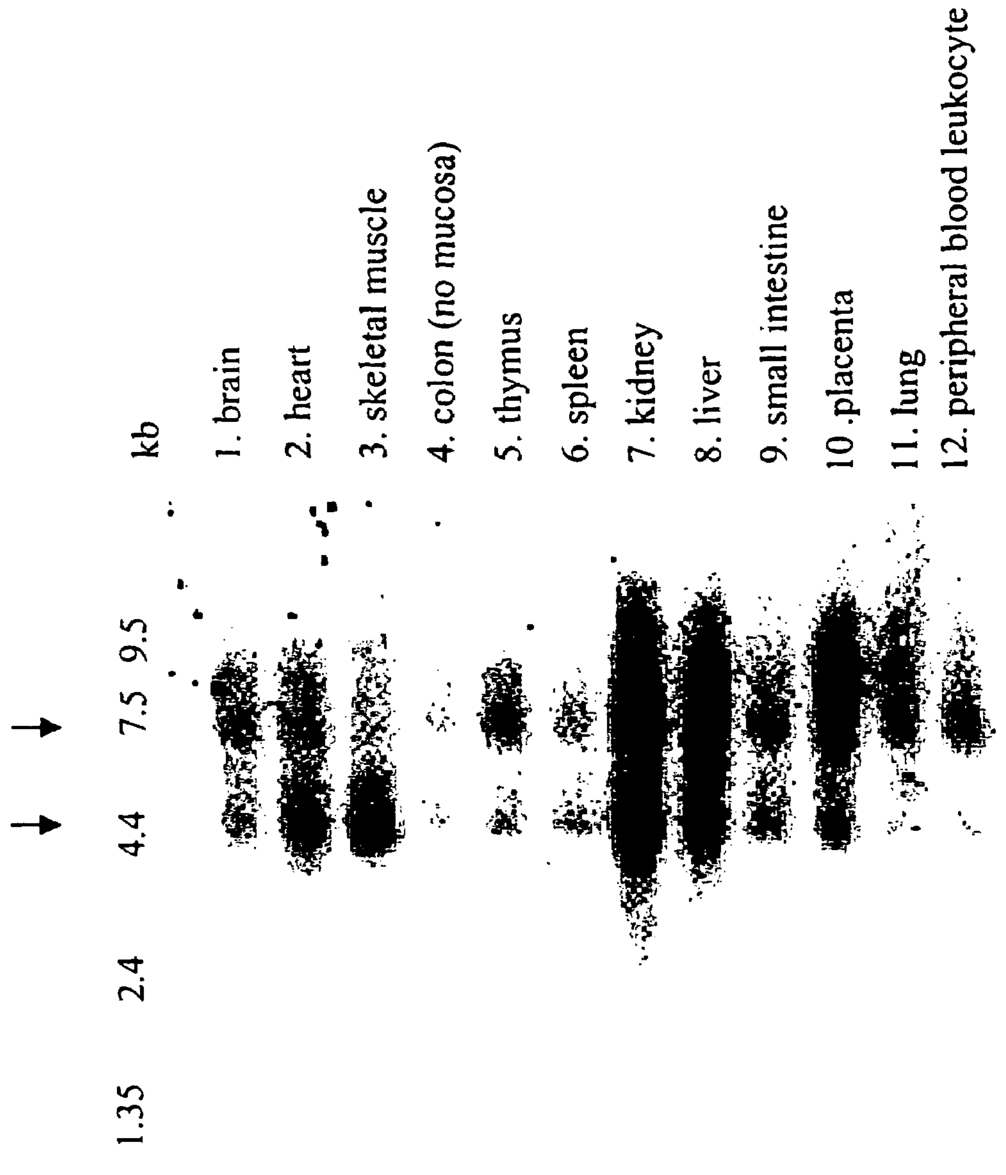
FIG. 4 shows Northern analysis of NHL expression in multi-human tissues.

Messenger RNA (mRNA) obtained from human brain, heart, skeletal muscle, colon, thymus, spleen, kidney, liver, small intestine, placenta, lung, and peripheral blood leukocytes. Two μg of poly$A^+$ RNA were run on each lane a denaturing formaldehyde 1% agarose gel, and transferred to a charged-modified nylon membrane. The probe was made using a 733 bp fragment derived from 1174-1907 nt of the NHL cDNA. This fragment was labeled via the $^{32}$P dCTP random priming method (Ambion). Hybridization was carried in ExpressHyb (Clontech) according to the manufacturer's protocol except for the final wash, which was at 55° C. Membranes were exposed to X-ray film with intensifying screen at −80° C. overnight. The Northern data is presented in FIG. 4. Note hybridization of the NHL probe to an approximately 4.4 kb transcript. The 7.5 kb transcript may suggest an alternative splicing of the NHL RNA.

EXAMPLE 3

Chromosomal Localization

To map the position of M68/NHL in the human genome, primers C68.36F and C68.275R, were used to carry out PCR reactions to 93 clones of the MIT GeneBridge 4 panel (Research Genetics) and results were submitted to MIT for analysis. M68/DcR3 was mapped to the extreme telomere of chromosome 20, at 20q13.3, 28cR from D20S173 with a lod score of 13. An analogous procedure was also carried out with the 83 clones of the Stanford G3 radiation hybrid panel, with PCR results submitted to the Stanford Genome Center for analysis. Analysis using another pair of PCR primers specific to NHL yielded the same result. For fluorescence in situ (FISH) analysis, the normal human male fibroblast cell line, L136 (Coriell Cell Repository, Camden, N.J.) was arrested in mitosis with colcemid (10 μg/ml). A human chromosome 20 α-satellite probe (Vysis, Downers Grove, Ill.) was directly labeled with Spectrum Orange dUTP and was used to identify chromosome 20. The M68 BAC clone was directly labeled with SpectrumGreen dUTP by nick translation (Vysis). Slides were counterstained with DAPI stain and viewed under an Olympus microscope with narrow blue and DAPI/TRITC filters. Fifty metaphase cells were scored to verify that the M68 probe was located on the same chromosome as the Human Chromosome 20 probe. Radiation hybrid chromosomal mapping reconfirms that it is linked to M68 locus, at 20q13.3.

What is claimed is:

1. A substantially purified human helicase protein which comprises the amino acid sequence as set forth in SEQ ID NO:2.

2. A substantially purified human helicase protein which consists of the amino acid sequence as set forth in SEQ ID NO:2.

* * * * *